(12) United States Patent
Zhang et al.

(10) Patent No.: US 10,968,234 B2
(45) Date of Patent: Apr. 6, 2021

(54) COMPOUND CONTAINING TRICYCLIC HETEROARYL GROUP

(71) Applicant: Hangzhou Innogate Pharma Co., Ltd., Zhejiang (CN)

(72) Inventors: Hancheng Zhang, Zhejiang (CN); Shifeng Liu, Zhejiang (CN); Xiangyang Ye, Zhejiang (CN)

(73) Assignee: Hangzhou Innogate Pharma Co., Ltd., Zhejiang (CN)

( * ) Notice: Subject to any disclaimer, the term of this patent is extended or adjusted under 35 U.S.C. 154(b) by 0 days.

(21) Appl. No.: 16/937,119

(22) Filed: Jul. 23, 2020

(65) Prior Publication Data

US 2020/0354376 A1    Nov. 12, 2020

Related U.S. Application Data

(62) Division of application No. 16/468,810, filed as application No. PCT/CN2017/115756 on Dec. 12, 2017, now Pat. No. 10,730,887.

(30) Foreign Application Priority Data

Dec. 12, 2016  (CN) .......................... 201611141395.2

(51) Int. Cl.
| | | |
|---|---|---|
| C07D 498/04 | (2006.01) | |
| C07D 471/04 | (2006.01) | |
| A61P 1/16 | (2006.01) | |
| A61P 35/00 | (2006.01) | |
| A61K 31/5383 | (2006.01) | |
| C07D 519/00 | (2006.01) | |
| A61P 11/00 | (2006.01) | |

(52) U.S. Cl.
CPC ........ *C07D 498/04* (2013.01); *A61K 31/5383* (2013.01); *A61P 1/16* (2018.01); *A61P 11/00* (2018.01); *A61P 35/00* (2018.01); *C07D 471/04* (2013.01); *C07D 519/00* (2013.01); *Y02P 20/55* (2015.11)

(58) Field of Classification Search
CPC .................................................... C07D 498/04
USPC ....................................................... 514/230.2
See application file for complete search history.

(56) References Cited

U.S. PATENT DOCUMENTS 10,730,887 B2 * 8/2020 Zhang .................. C07D 519/00

FOREIGN PATENT DOCUMENTS

| WO | 9719089 A1 | 5/1997 |
|---|---|---|
| WO | 2016197987 A1 | 12/2016 |
| WO | 2017101763 A1 | 6/2017 |
| WO | 2017118438 A1 | 7/2017 |
| WO | 2018108084 A1 | 6/2018 |

OTHER PUBLICATIONS

Int'l Search Report dated Feb. 26, 2018 in Int'l Patent Application No. PCT/CN2017/115756.
Office Action dated Dec. 19, 2019 in U.S. Appl. No. 16/468,810 by Zhang.

* cited by examiner

*Primary Examiner* — Kahsay Habte
(74) *Attorney, Agent, or Firm* — Ice Miller LLP

(57) ABSTRACT

A class of compounds containing a tricyclic heteroaryl group is provided. Specifically, a compound of the structure represented by the following formula (I) (each group is as defined in the specification), a pharmaceutical composition containing the compound of the formula (I), and their isotope derivatives, chiral isomers, allosteries, different salts, prodrugs, preparations, etc, are provided. It can effectively inhibit protein kinases (such as EGFR, FAK, SYK, FLT-3, Axl, CDK, JAK, etc.), thereby treating various tumors, non-alcoholic liver disease (NASH), pulmonary fibrosis (IPF), and related variety of diseases.

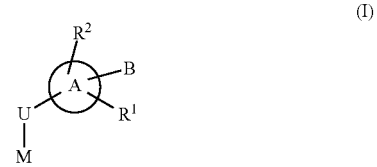

19 Claims, No Drawings

COMPOUND CONTAINING TRICYCLIC HETEROARYL GROUP

CROSS-REFERENCE TO RELATED APPLICATION

This application is a Divisional of co-pending U.S. patent application Ser. No. 16/468,810, filed Jun. 12, 2019, which is a Section 371 of International Application No. PCT/CN2017/115756, filed Dec. 12, 2017, which was published in the Chinese language on Jun. 21, 2018, under International Publication No. WO 2018/108084 A1, which claims priority under 35 U.S.C. § 119(b) to Chinese Patent Application No. 201611141395.2, filed on Dec. 12, 2016, the disclosures of which are incorporated herein by reference in their entireties.

TECHNICAL FIELD

The present invention relates to the field of medicinal chemistry; in particular, the present invention relates to a novel class of derivatives containing a tricyclic heteroaryl group, a method for its synthesis and its use as inhibitor for one or more protein kinases in the preparation of a medicament for the treatment of tumors, non-alcoholic steatohepatitis (NASH), idiopathic pulmonary fibrosis (IPF) and other related diseases.

BACKGROUND

Cancer, also known as malignant tumor, is one of the highest morbidity and mortality in the world. It is characterized by abnormal cell proliferation and metastasis, which spread and metastasize in a short time or relatively short time after onset. Traditional treatment options include resection (if resection conditions are met), radiation therapy, and chemotherapy. The targeted therapy developed in recent years has the advantages of reducing toxicity, negative effects on patients, and improving survival rate. However, the use of targeted drugs will produce resistance for a period of time, and then the growth of cancer cells will spread very rapidly. Common cancers are: blood cancer, lung cancer, liver cancer, bladder cancer, rectal cancer, stomach cancer, and so on.

Idiopathic pulmonary fibrosis (IPF) is a chronic, progressive, fibrotic interstitial lung disease that is confined to the lungs and occurs in the middle-aged and elderly population. Its lung histology and/or High-resolution chest CT (HRCT) is characterized by common interstitial pneumonia (UIP), and the cause is unclear. As a chronic interstitial lung disease, IPF onset is concealed, the condition is gradually worsened, and it can also be manifested as acute exacerbation. The average survival after IPF diagnosis is only 2.8 years, and the mortality rate is higher than most tumors. IPF is called a "tumor-like disease".

Nonalcoholic fatty liver disease (NASH) refers to the clinical pathological syndrome characterized by excessive deposition of intrahepatic fat due to alcohol and other well-defined liver-damaging factors, and acquired metabolic stress liver injury closely related to insulin resistance and genetic susceptibility. With the global trend of obesity and its related metabolic syndrome, nonalcoholic fatty liver disease has become an important cause of chronic liver disease in developed countries such as Europe and the United States and in rich areas of China. The prevalence of NAFLD in ordinary adults is 10% to 30%. Among them, 10% to 20% are NASH, and the latter has a cirrhosis rate of 25% within 10 years. Non-alcoholic fatty liver disease can directly lead to decompensated cirrhosis, hepatocellular carcinoma and transplanted liver recurrence, and can also affect the progression of other chronic liver diseases, and participate in the onset of type 2 diabetes and atherosclerosis. Metabolic syndrome-related malignancies, atherosclerotic cardiovascular and cerebrovascular diseases, and cirrhosis are important factors influencing the quality of life and life expectancy of patients with nonalcoholic fatty liver disease. To this end, nonalcoholic fatty liver disease is a new challenge in the field of contemporary medicine, and the risk of non-alcoholic fatty liver disease to human health will continue to increase in the near future.

With the progress of research on tumor molecular biology, our understanding on the molecular mechanism of tumorigenesis and development, as well as different pathogenic targets, has deepened. In many information transmission and pathways involved in the induction of cancer, protein kinases are a class of biologically active organisms that catalyze the transfer of the gamma phosphate of ATP to the residues of many important proteins, phosphorylate them, and thus transmit signals, thereby participating in a series of Cell activity is closely related to cell growth, differentiation and proliferation. The development of selective protein kinase inhibitors to block or regulate diseases that are abnormal due to these signaling pathways has been recognized as an effective research strategy for anticancer drug development. Several protein kinase inhibitors were validated in clinical trials, and were approved for marketing.

The epidermal growth factor receptor tyrosine kinase (EGFR) is a transmembrane glycoprotein composed of 1186 amino acids and encoding a molecular weight of 170-kDa. EGFR can mediate multiple signaling pathways and transmit extracellular signals into the cell, which plays an important role in regulating the proliferation, differentiation and apoptosis of normal cells and tumor cells (*Cell,* 2000, 100, 113-127). EGFR is a constitutive expression component of many normal epithelial tissues (such as skin and hair follicles), and in most solid tumors, EGFR is overexpressed or highly expressed. For example, in lung cancer, the expression rate of EGFR ranges from 40 to 80%. Therefore, selectively inhibiting EGFR and interfering with its signal transduction pathway can achieve the purpose of treating lung cancer, and opens up a feasible way for targeted treatment of lung cancer. Clinically, combined with traditional radiotherapy and chemotherapy, first-line drugs with EGFR-targeted drugs such as gefitinib (Iressa®) and erlotinib (Tarceva®) have proven to be very effective in the treatment of lung cancer. However, the use of these drugs will lead to acquired resistance within 6-12 months. The resistance of approximately 50% of cases is related to a mutation in one amino acid residue in the EGFR kinase domain (mutation of the 790 threonine residue to methionine, T790M) (*The New England Journal of Medicine,* 2005, 352, 786-792). The T790M mutation results in steric hindrance when the inhibitor binds to EGFR or increases the affinity of EGFR to ATP, making the anticancer effect of such reversible binding competitive inhibitors greatly diminished. The emergence of drug resistance not only reduces the patient's sensitivity to drugs, but also greatly reduces the quality of life of cancer patients. Therefore, studies targeting other targets including inhibitors of other protein kinases are even more important.

The spleen tyrosine kinase (SYK) gene was first cloned from pig spleen cDNA in 1991 and encodes a non-receptor protein tyrosine kinase. The human SYK gene is located in the q22 region of chromosome 9, and the SYK protein contains 635 amino acids. It plays an important role in autoimmune diseases and hematological malignancies. For example, SYK gene can inhibit the proliferation and metastasis of malignant tumor cells such as breast cancer, melanoma and liver cancer. Currently, SYK inhibitors have been used in clinical phase II/III trials of rheumatoid arthritis, chronic lymphocytic leukemia, and the like. Recent studies have shown that the use of SYK inhibitors or interference with the expression of the SYK gene can effectively slow the progression of liver fibrosis/hardening and has a good therapeutic effect (see CN 105664178A).

Focal Adhesion Kinase (FAK) is a non-receptor tyrosine protein kinase that was identified in 1992 as a highly phosphorylated protein associated with the oncogene v-src, located in normal cells enriched with integrin adhesion areas. FAK is a key molecule in the cell's important cytoskeletal proteins and various signaling pathways, and plays an important role in cell survival, proliferation, migration and invasion. A number of scientific studies have shown that FAK inhibitors may be effective anti-tumor drugs. Recent scientific studies have also shown that FAK inhibitors may also be effective in the treatment of pulmonary fibrosis.

AXL is an important tyrosine receptor kinase, with full name in English of AXL receptor tyrosine kinase. AXL is also called UFO/ARK/Tyro, and its ligand is vitamin K-dependent growth promoting factor GAS6. The first discovery of AXL was as a transforming gene for chronic myeloid leukemia (CML). AXL is overexpressed in metastatic colon cancer, thyroid cancer, breast cancer, prostate cancer, and melanoma. Inhibition of AXL activity can inhibit tumor growth, spread and metastasis.

FLT-3 (Fms-related tyrosine kinase 3) belongs to a family member of the type III receptor tyrosine kinase and is a signaling molecule. FLT-3 is expressed in various tissues such as liver, spleen, lymph, brain, placenta and gonads, and is also expressed in normal bone marrow cells and lymphoid cell precursors, and is expressed in many hematopoietic malignancies. Its signal transduction pathway is associated with many tumor conduction pathways. Therefore, FLT-3 has become an ideal anti-tumor drug target.

Cell cycle is mainly influenced by a series of serine/threonine kinases called Cyclin-dependent kinases (CDKs), which promote cell cycle progression, transcription of genetic information, and normal cell division and proliferation via the combination of themselves with subunit cyclins (cydins). CDK4/6 is a key regulator of the cell cycle that triggers a shift in the cell cycle from the growth phase (G1 phase) to the DNA replication phase (SI phase). During cell proliferation, a complex of cyclin D (Cyclin D) and CDK4/6 is capable of phosphorylating retinoblastoma protein (Rb). The tumor suppressor protein Rb phosphorylales to release its transcription factor E2F, which binds lightly in an unphosphorylated state. E2F activation further promotes cell cycle through the restriction point (R point) and progresses from G1 phase to S phase, entered the cycle of cell proliferation. Therefore, inhibition of CDK4/6 prevents the formation of the Cyclin D-CDK4/6 complex, which can block the progression of the cell cycle from the G1 phase to the S phase, thereby achieving the purpose of inhibiting tumor proliferation.

Janus kinase (JAK) is a cytoplasmic tyrosine kinase that transduces cytokine signaling from membrane receptors to STAT transcription factors. Scientific research has shown that inhibition of JAK can be a promising target for anti-cancer drugs.

In summary, the development of novel protein kinase inhibitors is of great significance.

SUMMARY OF THE INVENTION

The purpose of the present invention is to provide a novel protein kinase inhibitor.

In the first aspect of the present invention, a compound of the following formula (I), or the optical isomers, pharmaceutically acceptable salts, prodrugs, deuterated derivatives, hydrates, or solvates thereof is provided:

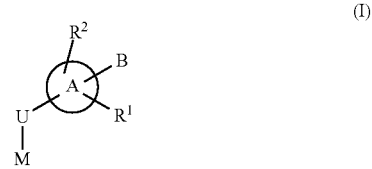

wherein M is a group shown the following formula (II):

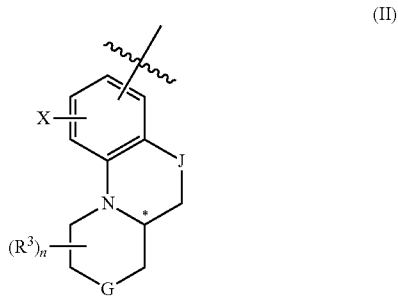

in formula (I) and formula (II):
"$\sim\sim\sim$" the attachment site of formula (II) to U in formula (I);
"*" indicates a chiral center;
A is selected from aryl or heteroaryl;
B is aryl, heteroaryl, $C_{3-8}$ cycloalkyl, 3- to 12-membered heterocyclic, $NR^a R^b$, $OR^b$, $SR^b$, or $SO_2R^b$, wherein the aryl, heteroaryl, cycloalkyl, heterocyclyl can be independently substituted with one or more $R^e$;
U is $NR^d$, O or S;
X is hydrogen, halogen, $C_{1-4}$ alkyl, $C_{1-4}$ haloalkyl, $C_{3-6}$ cycloalkyl. $C_{2-4}$ alkenyl, $C_{2-4}$ alkynyl, 3- to 10-membered heterocyclic, $OR^e$, $SR^e$, $NR^e R^e$, CN, $C(O)R^e$, $C(O)OR^e$, $C(O)NR^e R^e$, $OC(O)R^e$, $NR^e C(O)R^e$, or $S(O)_2 R^e$;
J and G are each independently $NR^f$, O, S, S(O), $S(O)_2$ or $CR^g R^g$;
$R^1$ and $R^2$ are each independently selected from the group consisting of hydrogen, halogen, $C_{1-4}$ alkyl, $C_{3-6}$ cycloalkyl, 3- to 8-membered heterocyclic, or C(O)$NR^e R^e$; wherein the alkyl, cycloalkyl, and heterocyclic can be optionally substituted with one or more $R^e$;
each of the $R^3$ is independently hydrogen or $C_{1-4}$ alkyl; when two $R^3$ are simultaneously attached to the same carbon atom, the two $R^3$ and the carbon atom to which they are attached may optionally form a carbonyl group (C=O);
n is 0, 1, 2, or 3;
$R^a$ is hydrogen, $C_{1-4}$ alkyl, $C_{3-6}$ cycloalkyl, or 3- to 12-membered heterocyclic; wherein the alkyl, cycloalkyl, heterocyclyl may independently be optionally substituted by one or more halogens, $OR^e$, CN, $SO_2NR^e R^e$, as long as the chemical structure formed is stable and meaningful;

$R^b$ is aryl, heteroaryl, $C_{1-4}$ alkyl, $C_{3-8}$ cycloalkyl, 3- to 12-membered heterocyclic, $C(O)R^e$, or $C(O)NR^eR^e$; wherein the aryl, heteroaryl, alkyl, cycloalkyl, heterocyclyl can be optionally substituted by one or more $R^c$;

each $R^c$ is independently halogen, $C_{1-4}$ alkyl, $C_{3-8}$ cycloalkyl, 3- to 8-membered heterocyclic, $C(O)NR^eR^e$, $NR^eC(O)R^e$, $OR^e$, CN, or $SO_2NR^eR^e$;

$R^d$ is hydrogen or $C_{1-4}$ alkyl;

each $R^e$ is independently selected from the group consisting of hydrogen, $C_{1-4}$ alkyl, $C_{1-4}$ haloalkyl, $C_{2-4}$ alkenyl, $C_{2-4}$ alkynyl, $C_{3-8}$ cycloalkyl, 3- to 8-membered heterocyclic, aryl, or heteroaryl; or two $R^e$ together with the nitrogen atom to which they are attached form 3- to 8-membered heterocyclic containing 1 or 2 N atoms, and 0 or 1 hetero atom selected from O and S;

$R^f$ is hydrogen, $C_{1-8}$ alkyl, $C_{1-8}$ haloalkyl, $C_{2-8}$ alkenyl, $C_{2-8}$ alkynyl, $C_{3-8}$ cycloalkyl, 3-to 12-membered heterocyclic, aryl, heteroaryl, $C(O)R^e$, $C(O)OR^e$, $C(O)NR^eR^e$, $S(O)_2R^e$, or $S(O)_2NR^hR^h$;

each $R^g$ is each independently selected from the group consisting of hydrogen, halogen, or $C_{1-4}$ alkyl; or two $R^g$ together with the carbon atom to which they are attached form a carbonyl group (C=O); or two $R^g$ together with the same carbon atom to which they attached form 3- to 8-membered cyclic structure which optionally comprise 0, 1 or 2 heteroatoms selected from N, O, S;

each $R^h$ is independently hydrogen or $C_{1-4}$ alkyl; or two $R^h$ together with the nitrogen atom to which they are attached form 3- to-membered cyclic structure;

wherein each of the above alkyl, alkenyl, alkynyl, cycloalkyl, heterocyclic, cyclic structure, aryl and heteroaryl is optionally and independently substituted by 1 to 3 substituents each independently selected from the group consisting halogen, $C_{1-4}$ alkyl, $C_{1-4}$ haloalkyl, $C_{2-4}$ alkenyl, $C_{2-4}$ alkynyl, $C_{3-8}$ cycloalkyl, 3- to 12-membered heterocyclic, aryl, heteroaryl, CN, $NO_2$, $OR^e$, $SR^e$, $NR^eR^e$, $C(O)R^e$, $C(O)OR^e$, $C(O)NR^eR^e$, $NR^eC(O)R^e$, or $S(O)_2R^e$, provided that the chemical structure formed is stable and meaningful;

unless otherwise specified, the aryl is aromatic groups having 6 to 12 carbon atoms; the heteroaryl is 5- to 15-membered heteroaromatic groups; and the cyclic structure is saturated or unsaturated cyclic groups with or without heteroatoms;

with the proviso that A is not any group selected from group consisting of:

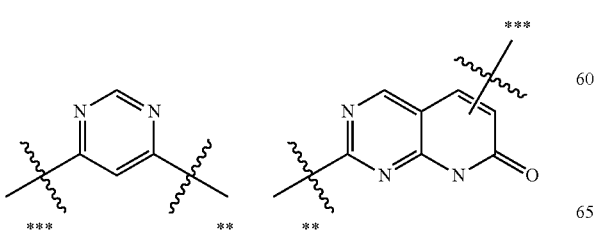

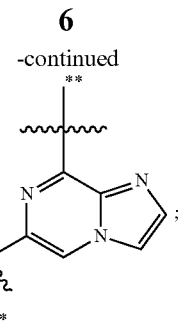

wherein "" means connecting to U; "*" means connecting to B;

and the compound of formula (I) is not

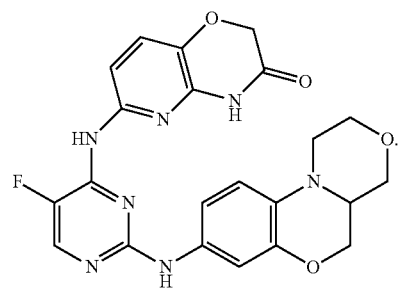 [SMILES: O=C1COc2ccc(Nc3nc(Nc4ccc5c(c4)OCC4COCCN54)ncc3F)nc2N1]

In another preferred embodiment, the M described is a group represented by the following formula (IIa):

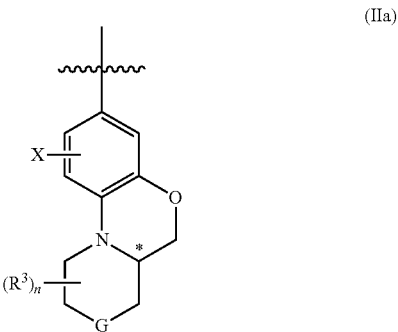

(IIa)

wherein X, $R^3$, G, and n are as defined above.

In another preferred embodiment, the M is selected from the group of formula (IIb), (IIc), or (IId):

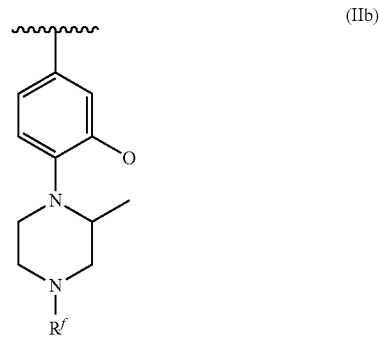

(IIb)

-continued (IIc)

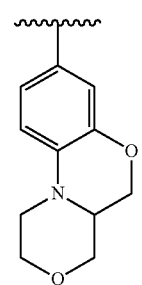

(IId)

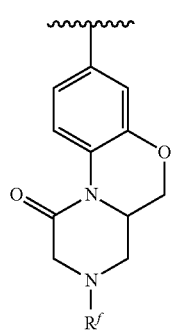

wherein $R^f$ is as defined in claim 1.

In another preferred embodiment, the formula (I), A is independently selected from group consisting of:

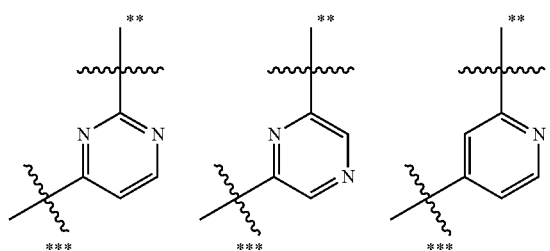 [SMILES: *c1ccnc(*)n1 ; *c1cncc(*)n1 ; *c1ccnc(*)c1]

wherein "" means connecting to U; "*" means connecting to B;
U is $NR^d$.

In another preferred embodiment, the formula (I), B is independently selected from group consisting of:

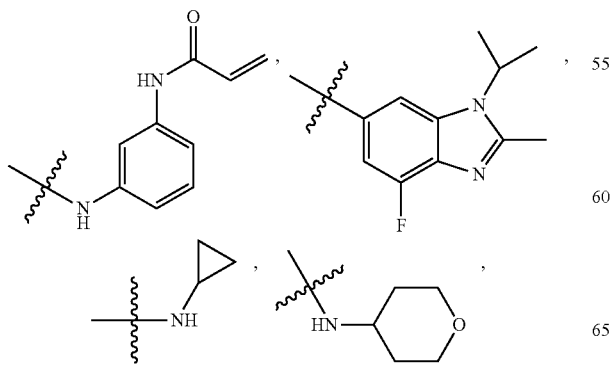

-continued

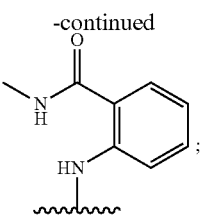

In another preferred embodiment, $R^1$, $R^2$, A, U, M, and B are each respectively the corresponding groups of the compound of formula (I) as prepared in embodiments.

In another preferred embodiment, the formula (I) is:

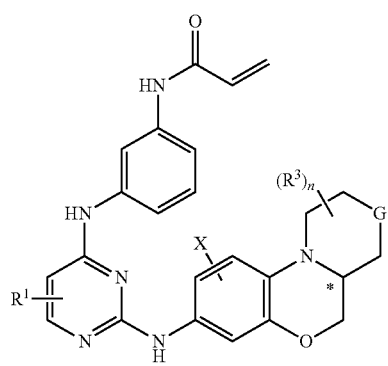

X is H;
G is $NR^f$ or O; wherein $R^f$ is as defined in claim 1;
$R^1$ is selected from hydrogen, halogen, or $C_{1-4}$ alkyl, wherein the alkyl group may be optionally substituted by one or more halogens;
each $R^3$ is independently hydrogen, or two $R^3$ link to the same carbon atom to form a carbonyl group (C=O);
n is 0, 1, or 2.

In another preferred embodiment, the formula (I) is:

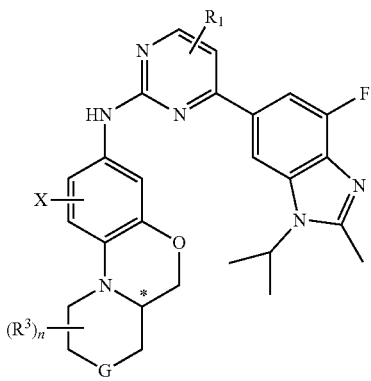

X is H;
G is $NR^f$ or O; wherein $R^f$ is as defined in claim 1;
$R^1$ is selected from the group consisting of hydrogen, halogen, or $C_{1-4}$ alkyl;
each $R^3$ is independently hydrogen, or two $R^3$ link to the same carbon atom to form a carbonyl group (C=O);
n is 0, 1, or 2.

In another preferred embodiment, the formula (I) is:

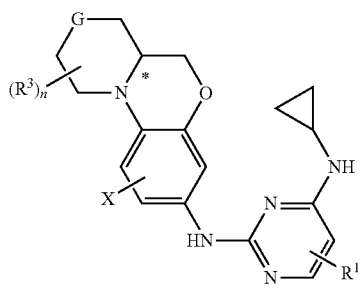

X is H;
G is NR$^f$ or O; wherein R$^f$ is as defined in claim 1;
R$^1$ is selected from the group consisting of hydrogen, halogen, or CONH$_2$;
each R$^3$ is independently hydrogen, or two R$^3$ link to the same carbon atom to form a carbonyl group (C=O);
n is 0, 1, or 2.

In another preferred embodiment, the formula (I) is:

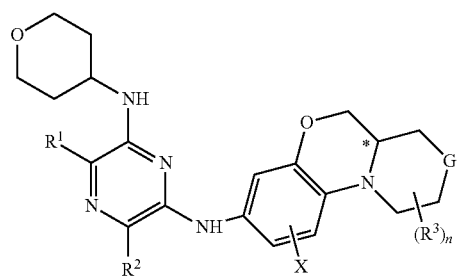

X is H;
G is NR$^f$ or O; wherein R$^f$ is as defined in claim 1;
R$^1$ is selected from hydrogen, or C$_{1-4}$ alkyl; R$^2$ is CONH$_2$;
each R$^3$ is independently hydrogen, or two R$^3$ link to the same carbon atom to form a carbonyl group (C=O);
n is 0, 1, or 2.

In another preferred embodiment, the formula (I) is:

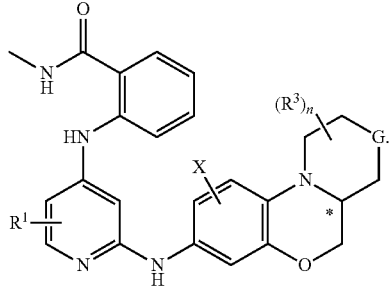

X is H;
G is NR$^f$ or O; wherein R$^f$ is as defined in claim 1;
R$^1$ is selected from hydrogen, halogen, or C$_{1-4}$ alkyl, wherein the alkyl group may be optionally substituted by one or more halogens;
each R$^3$ is independently hydrogen, or two R$^3$ link to the same carbon atom to form a carbonyl group (C=O);
n is 0, 1, or 2.

In another preferred embodiment, the compound is selected from the group consisting of:

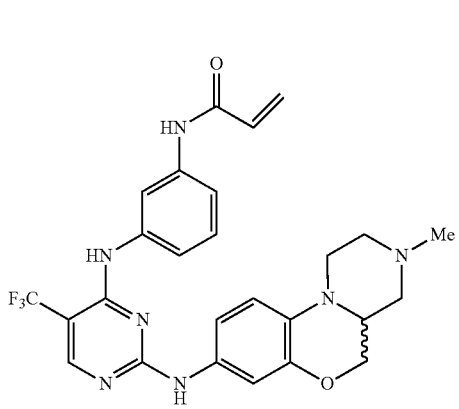

A1

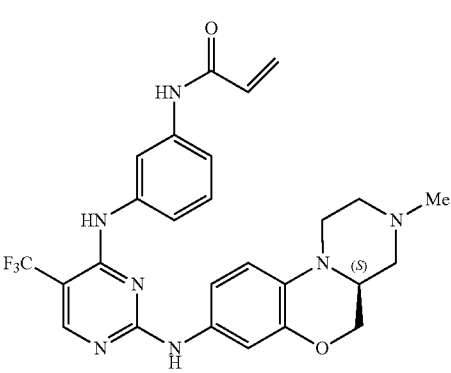

A1S

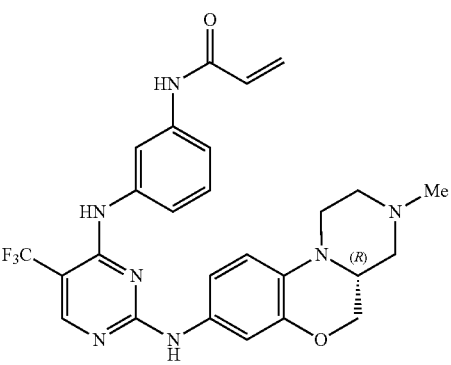

A1R

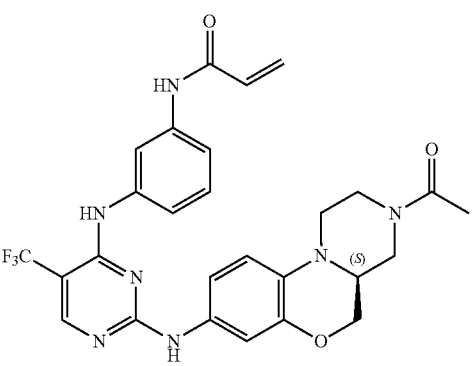

A2S

-continued
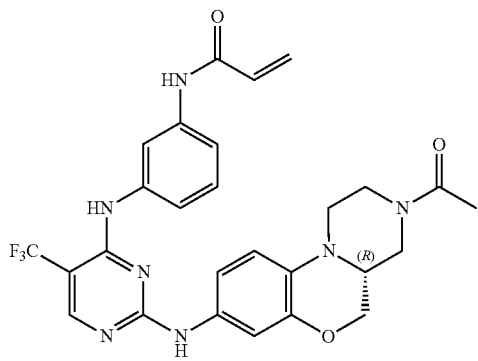
A2R
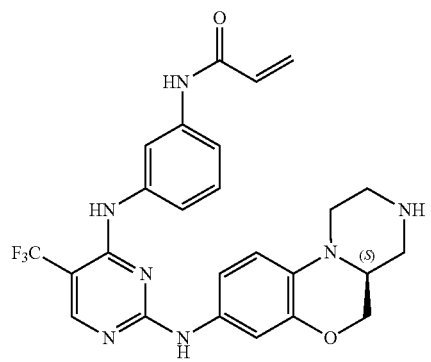
A3S
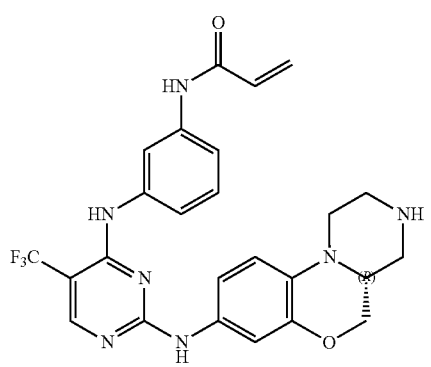
A3R
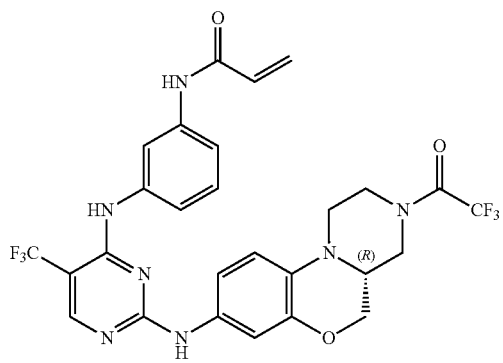
A4R
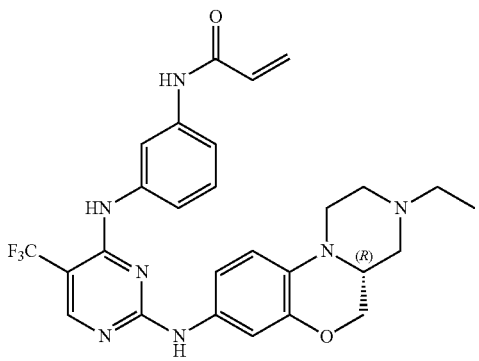
A5R
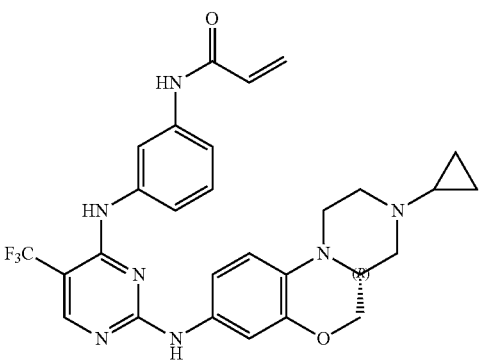
A6R
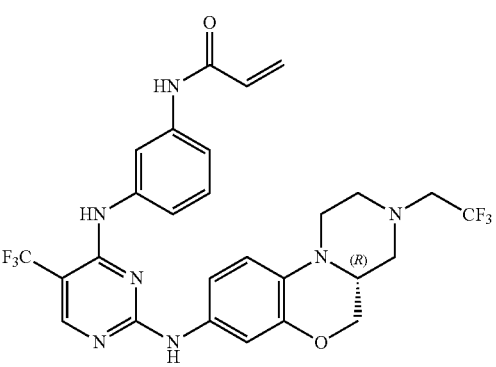
A7R
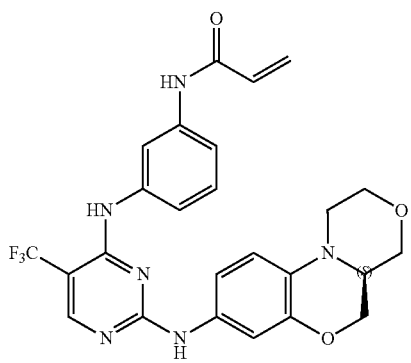
A8S A8R
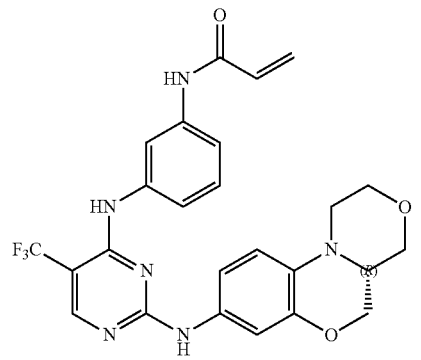
A9S
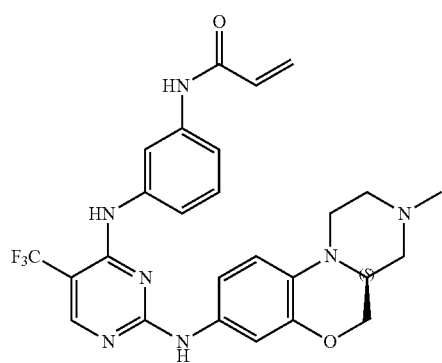
A9R
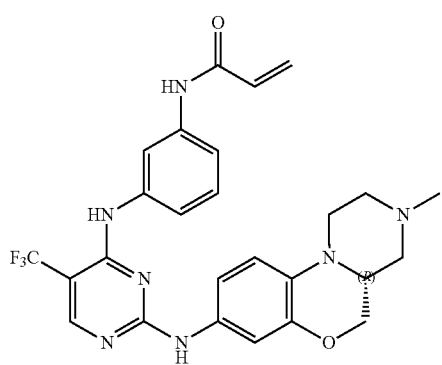
B1S
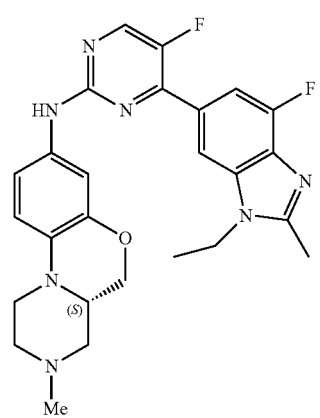
B1R
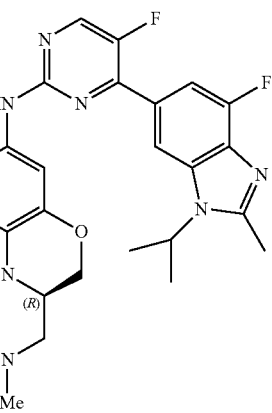
82R
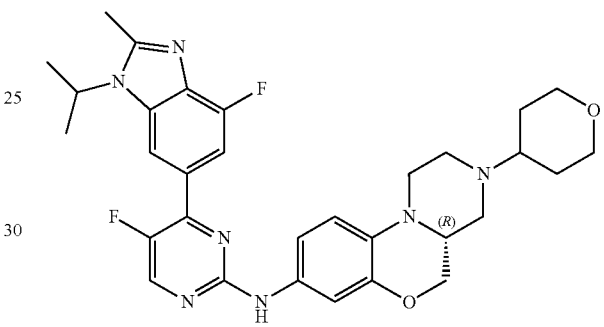
83R
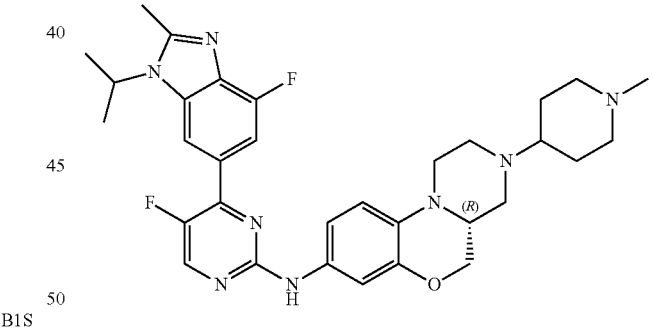
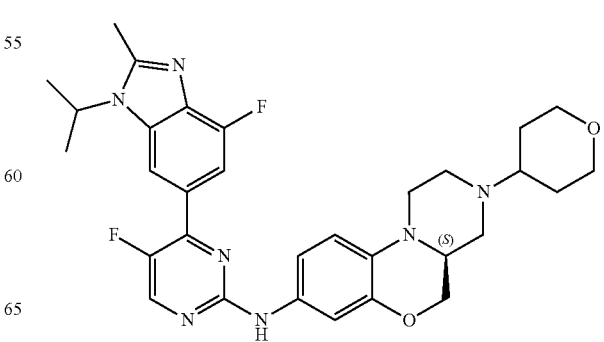

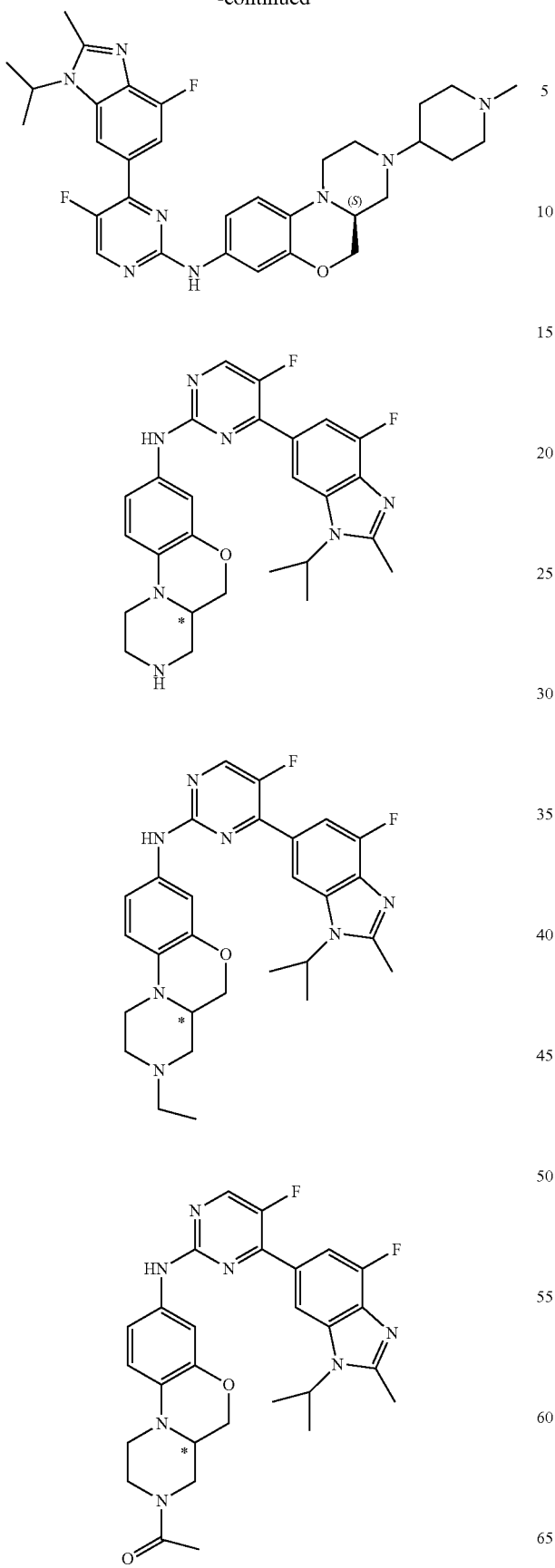
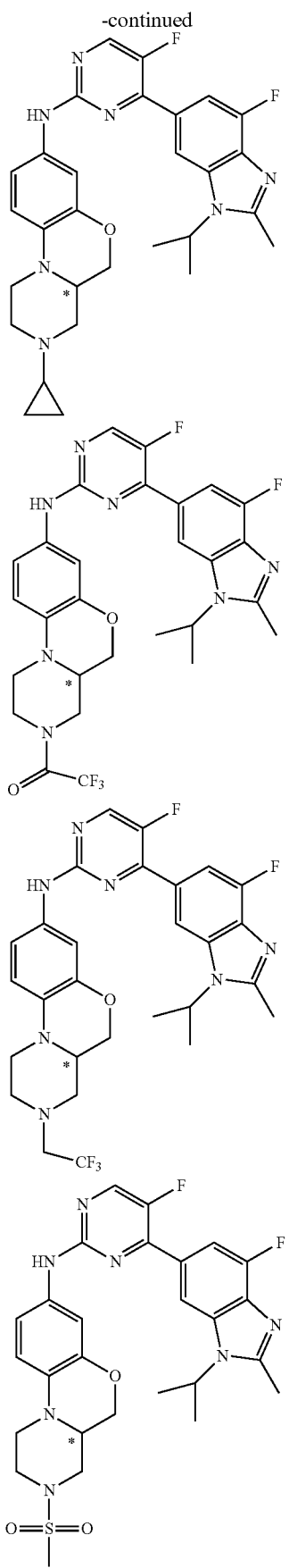

17
-continued
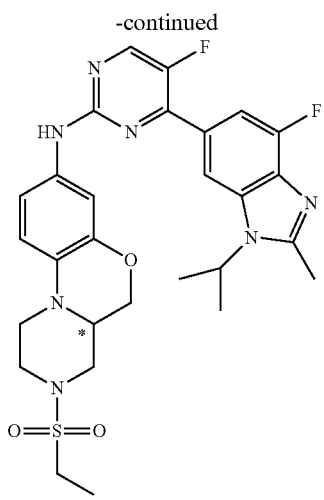
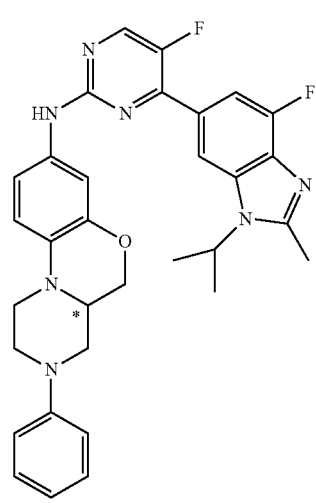
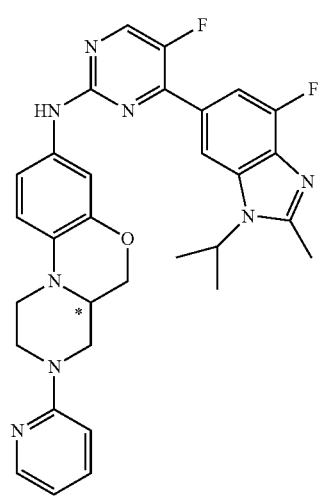
18
-continued
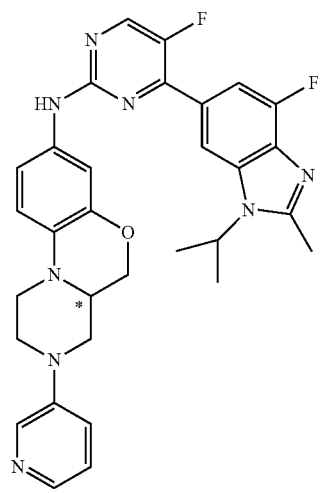
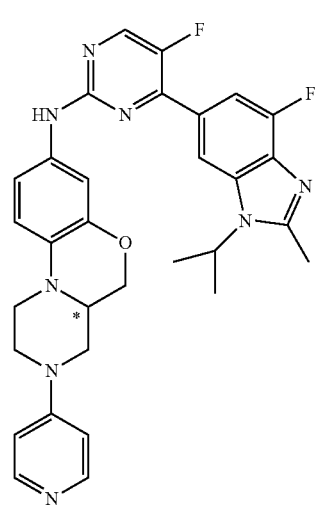
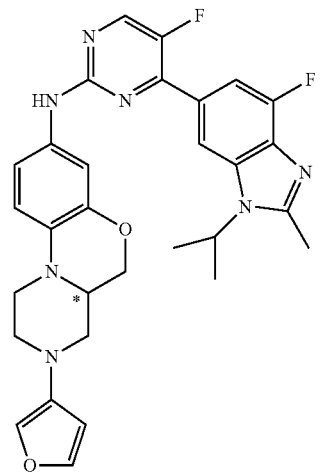

19
-continued
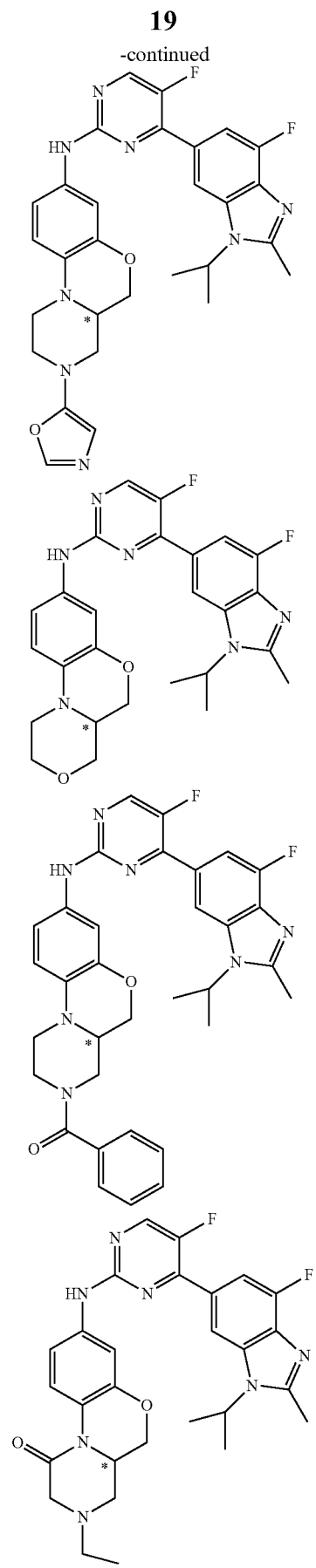
20
-continued
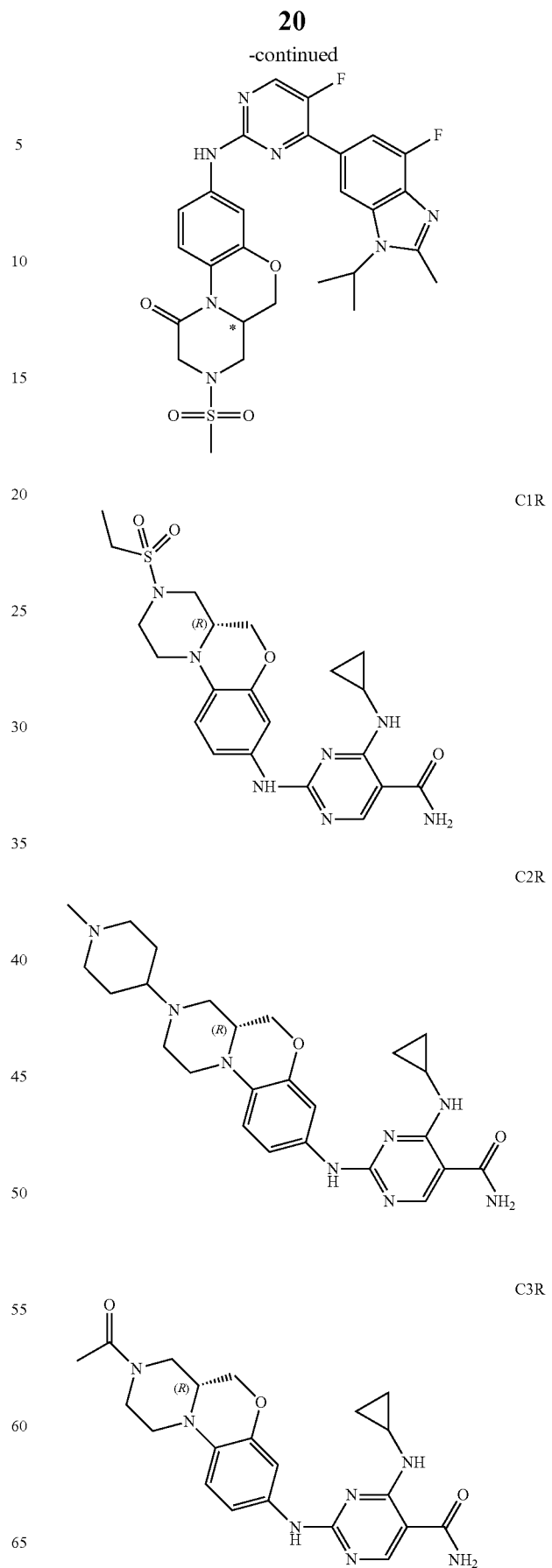
C1R
C2R
C3R

-continued
C4R
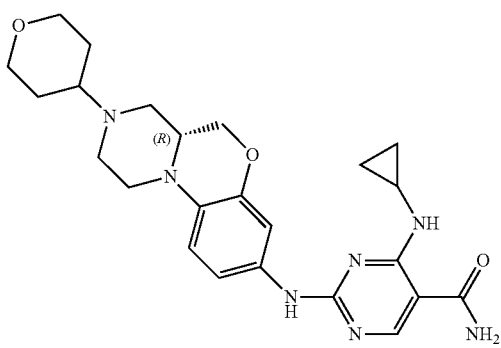
C5R
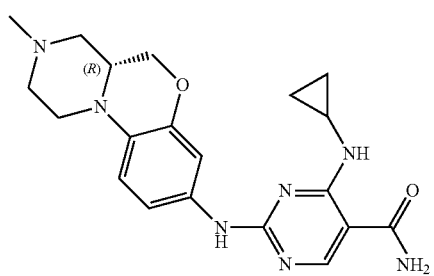
C6R
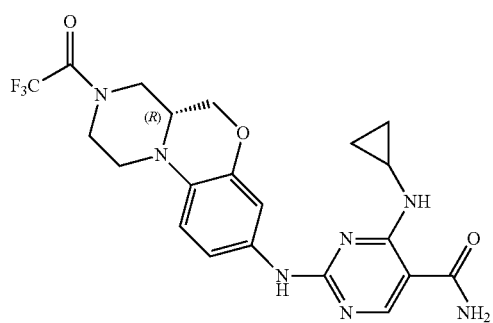
C7R
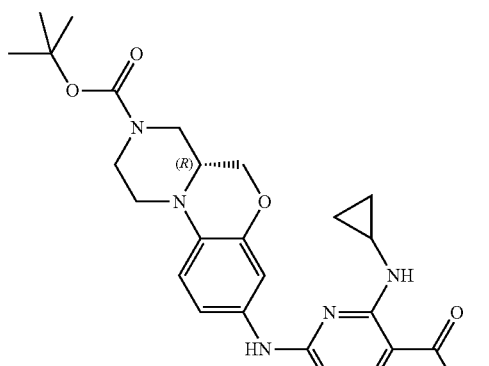
C8R
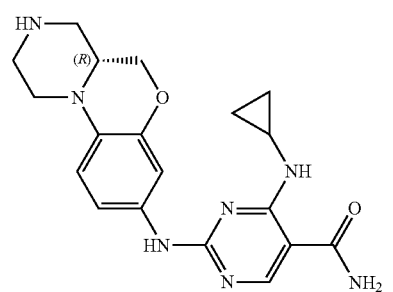
-continued
C9R
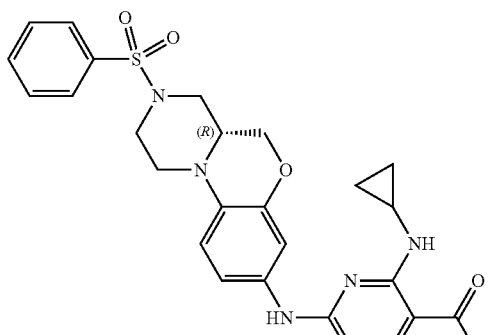
C10R
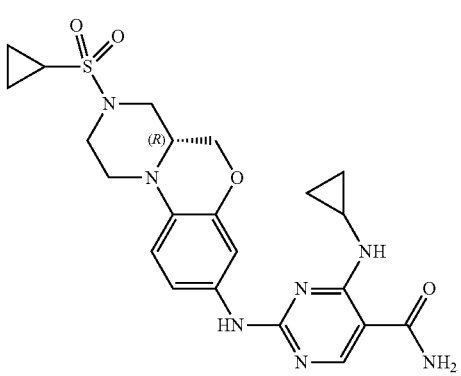
C11R
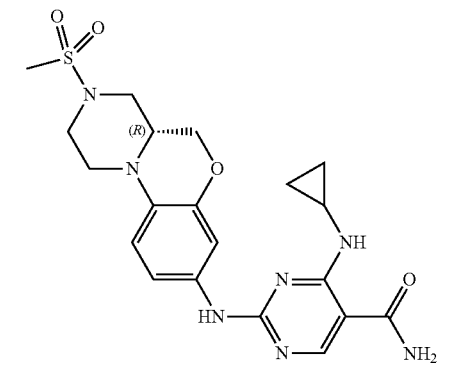
C12R
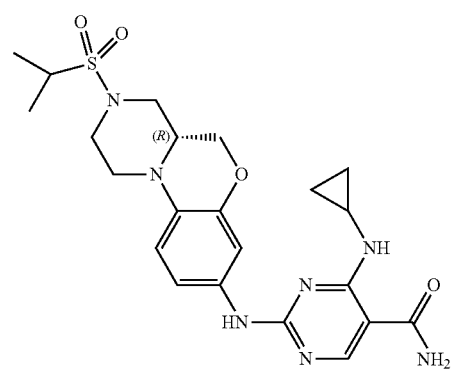

C13R
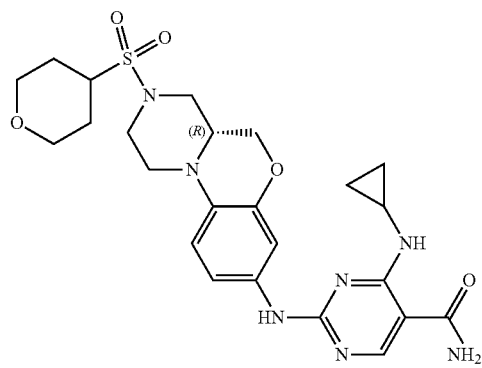
C14R
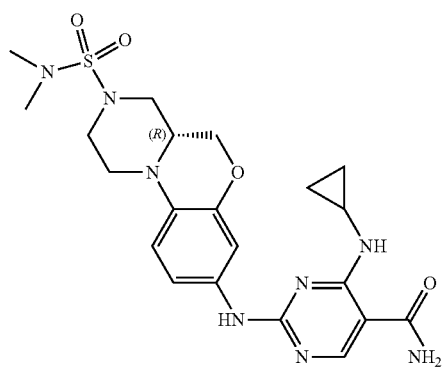
C15R
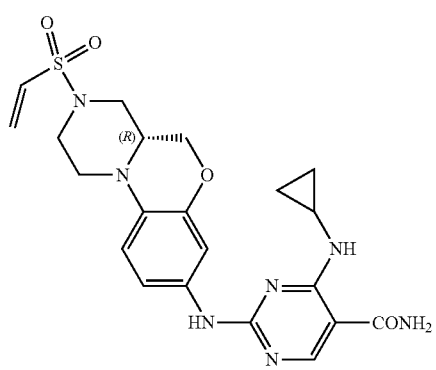
C16R
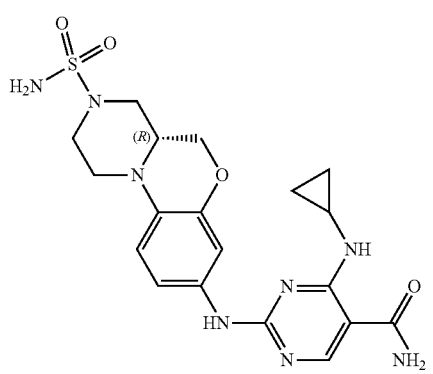
C17
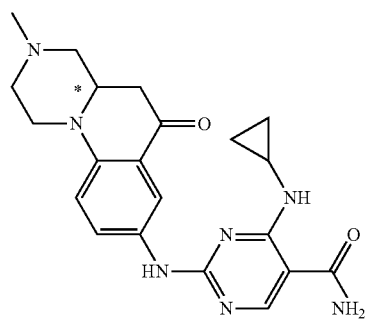
C18
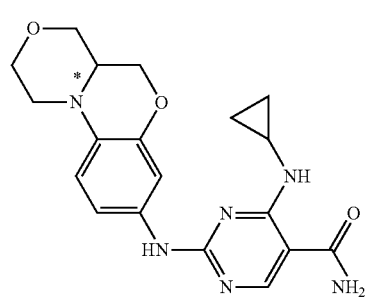
C19R
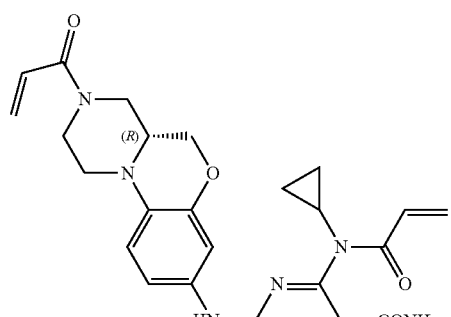
C20R
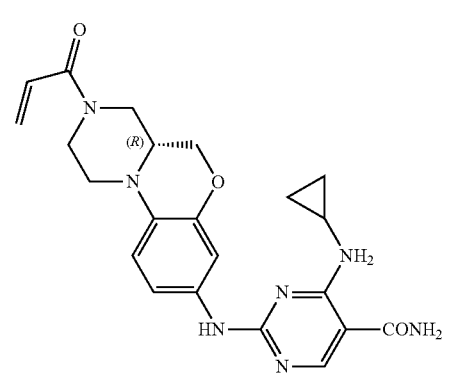

-continued
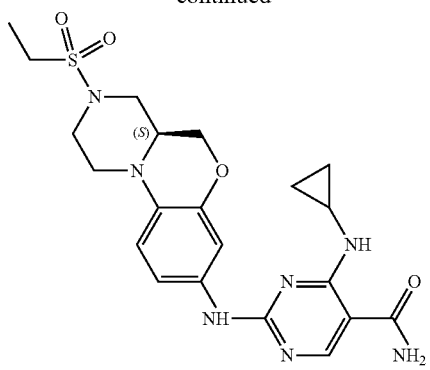
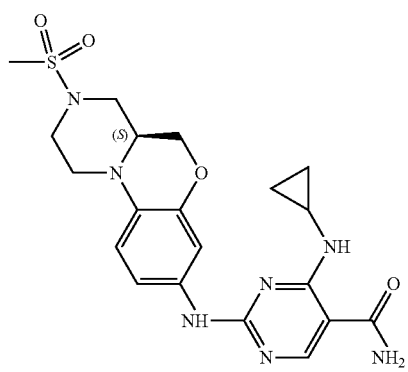
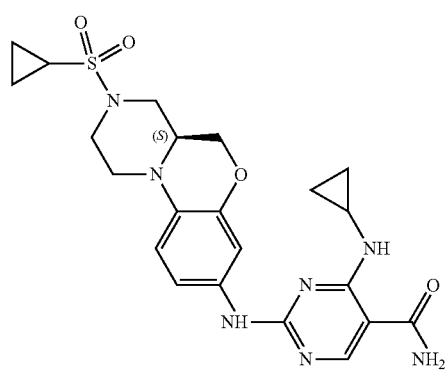
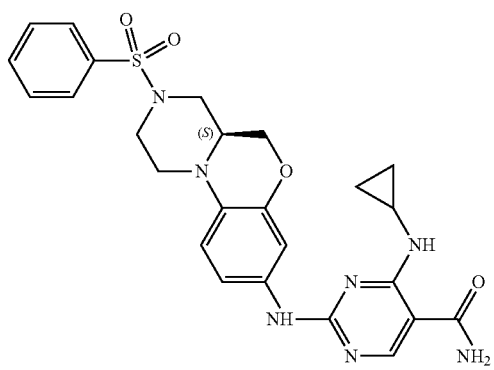
-continued
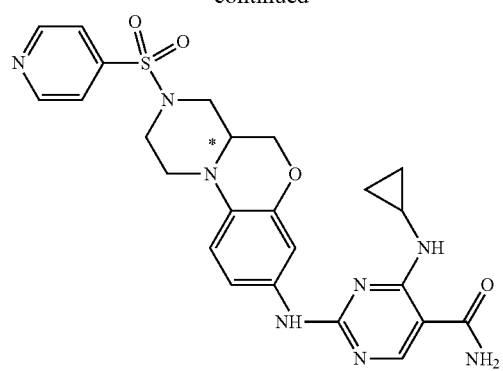
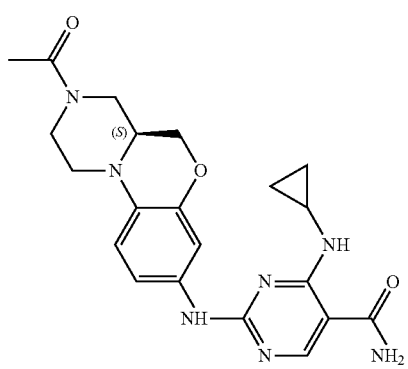
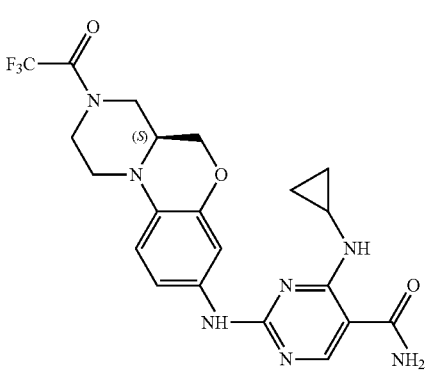
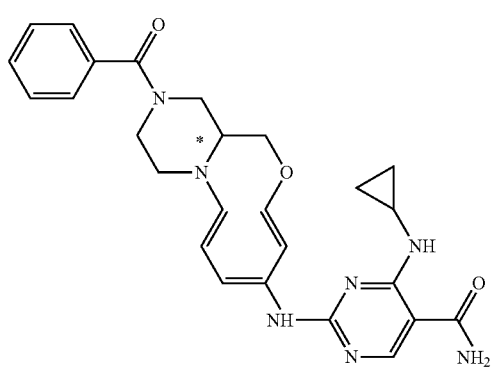

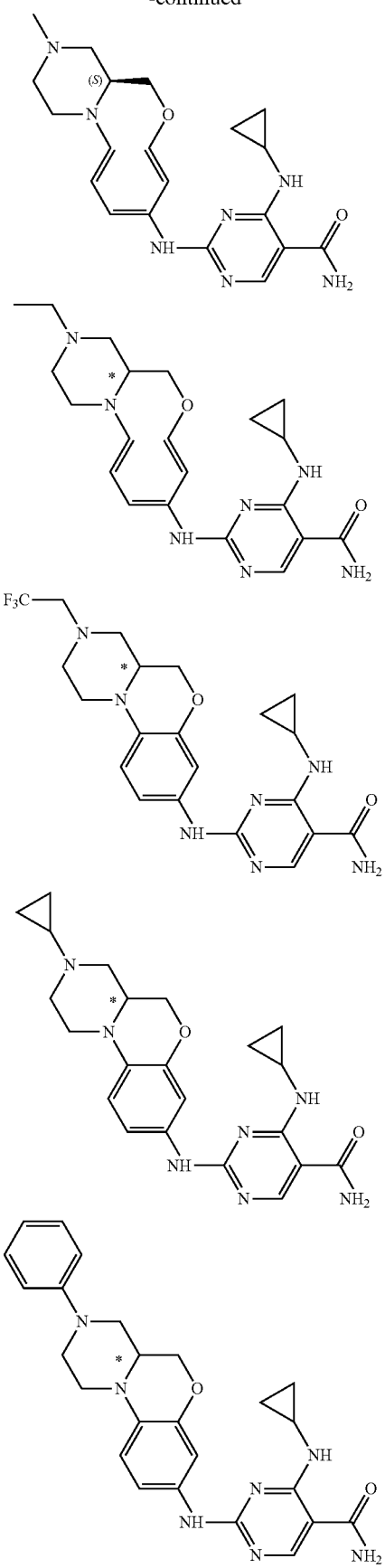
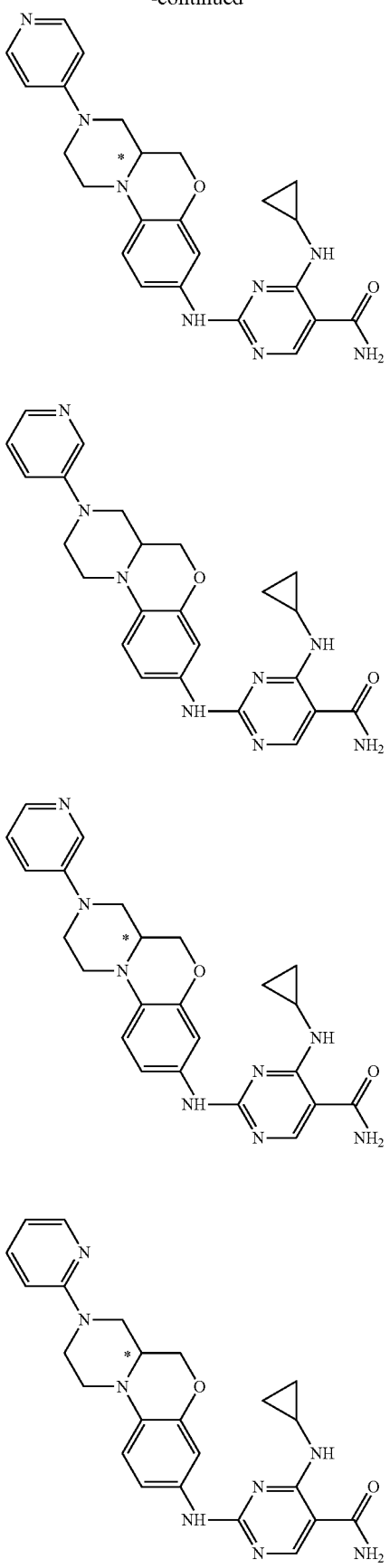

-continued
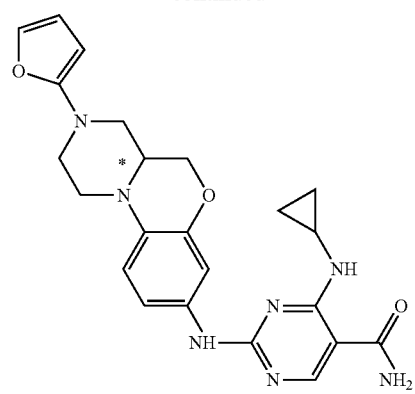
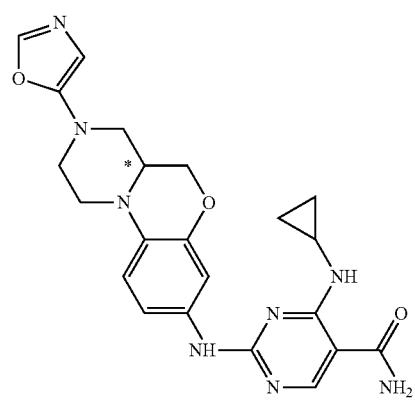
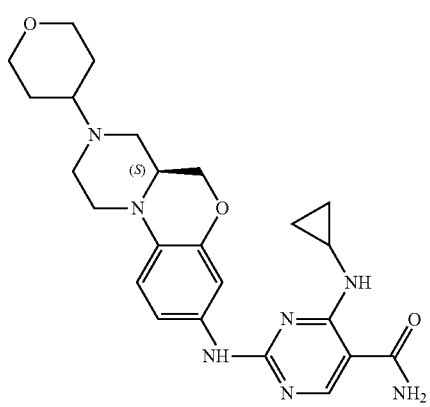
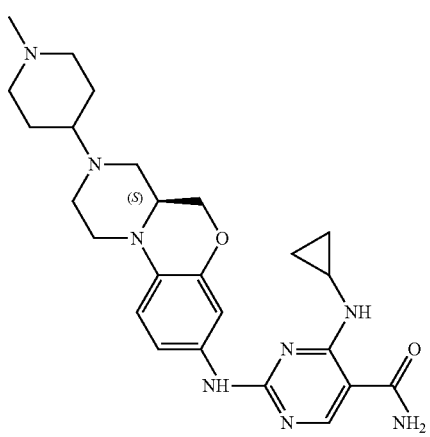
-continued
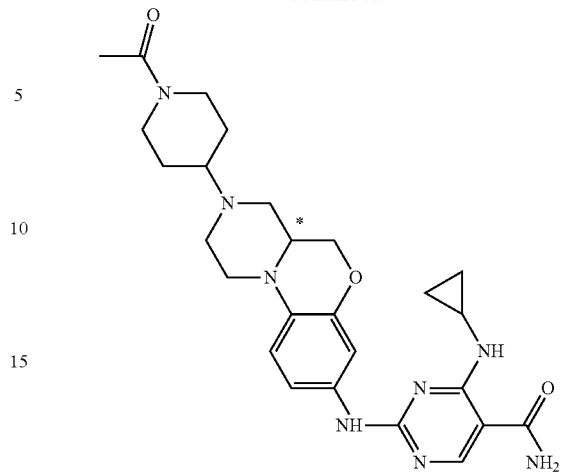
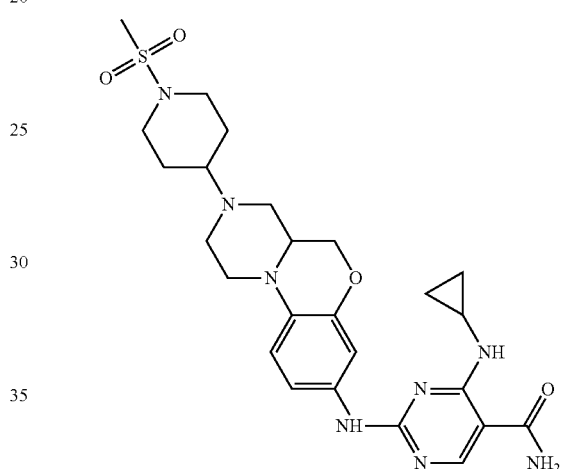
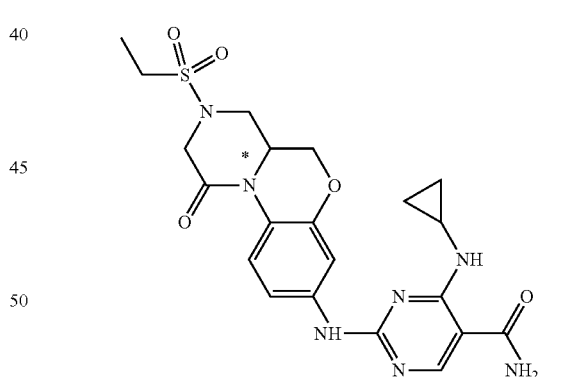
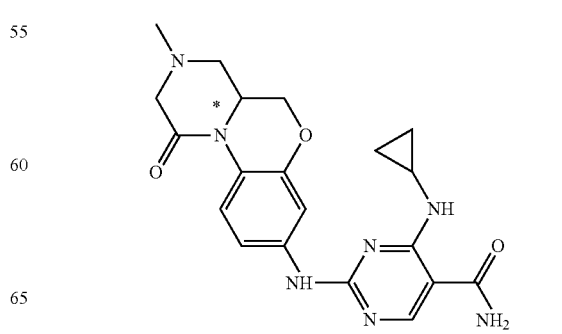

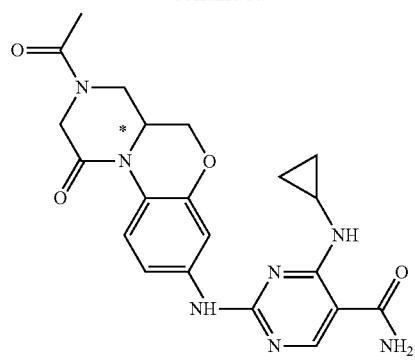
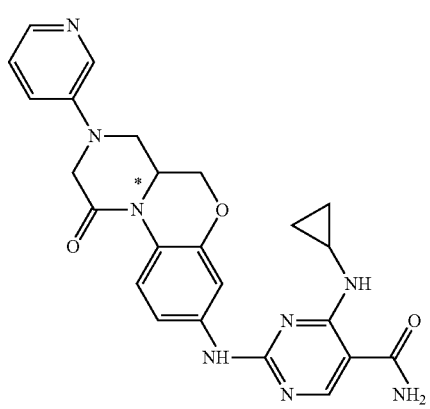
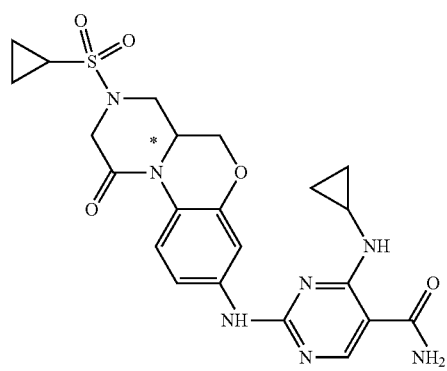
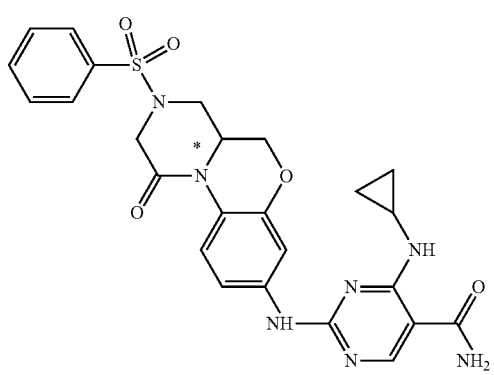
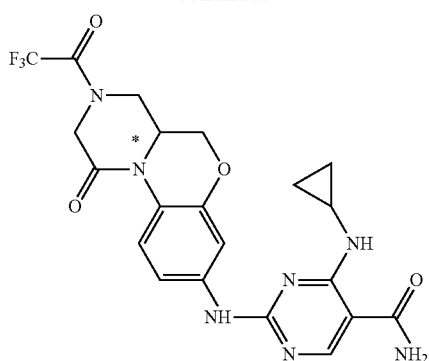
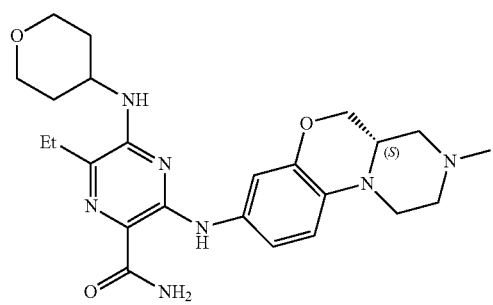
D1S
D1R
D2S
D2R -continued
D3R
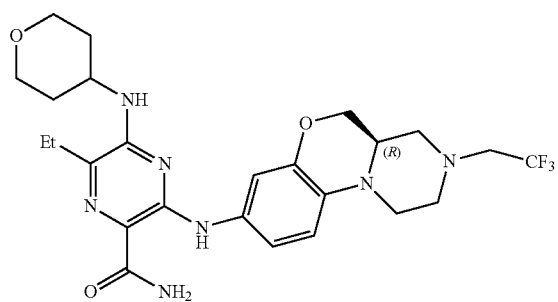
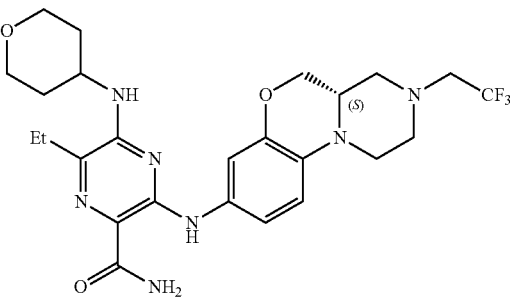
D4R
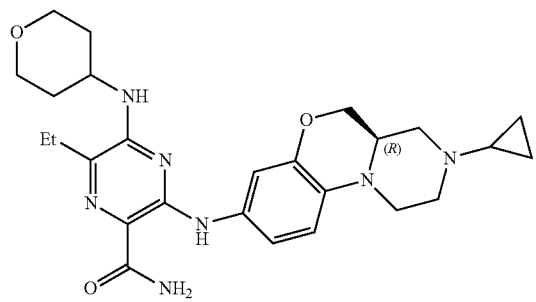
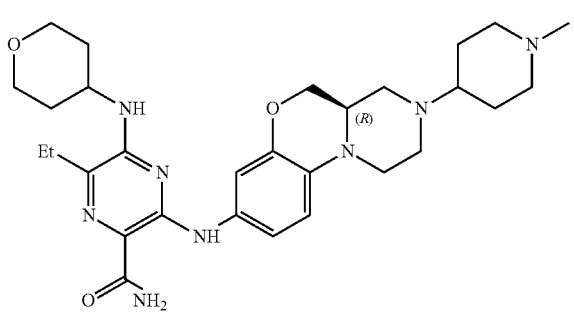
D5S
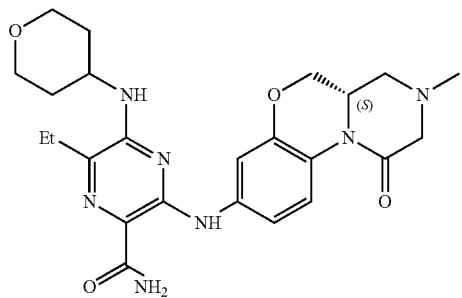
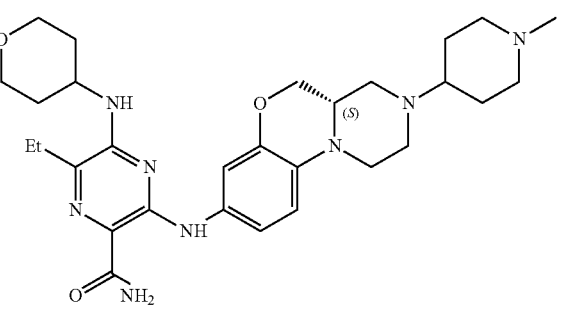
D6R
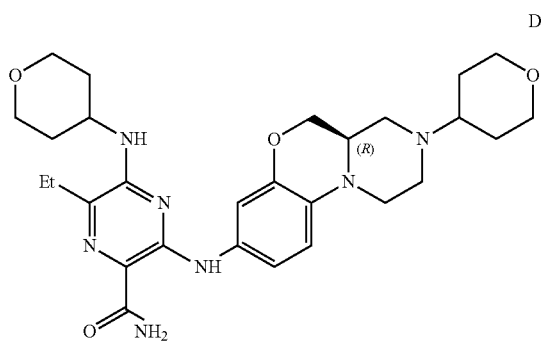
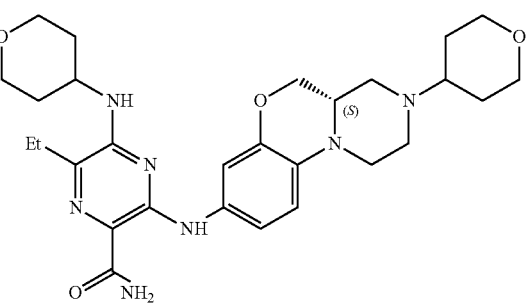
D7R

35
-continued
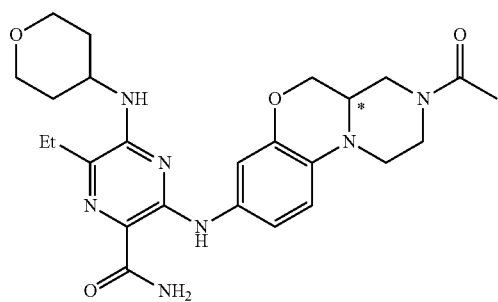
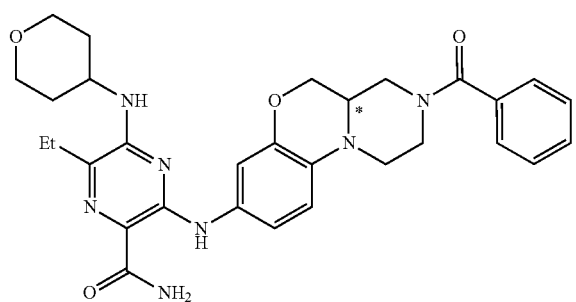
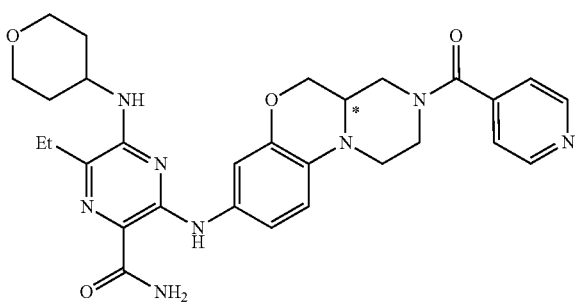
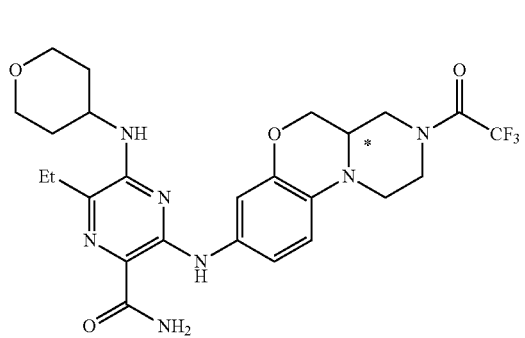
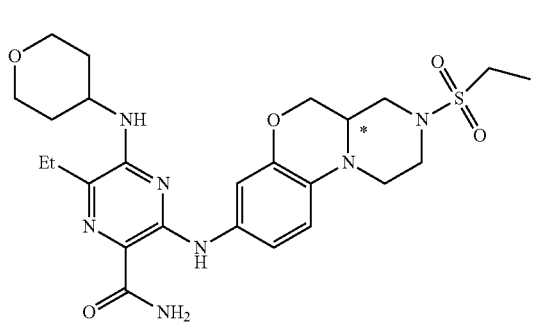
36
-continued
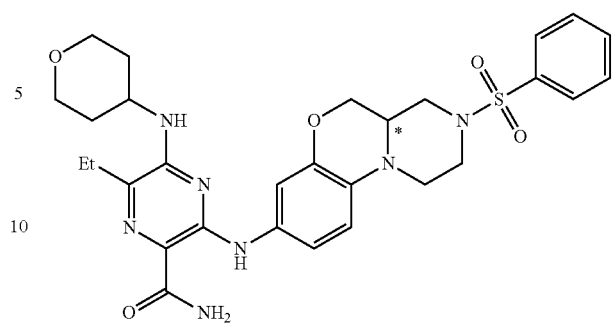
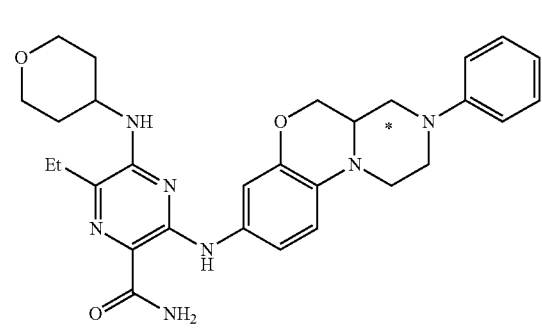
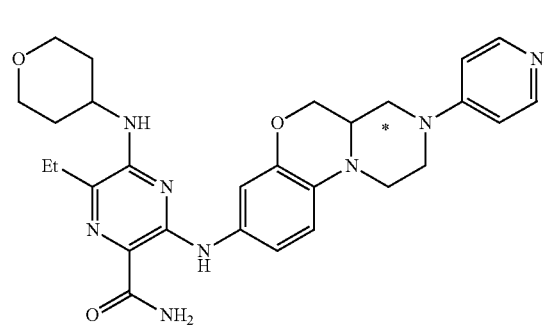
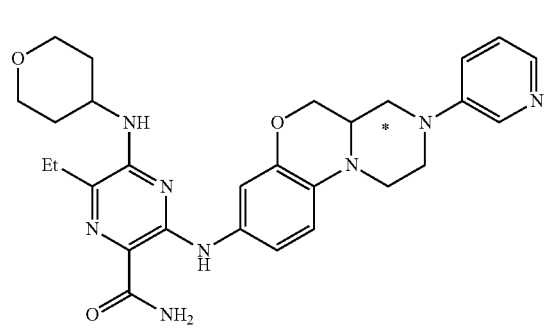
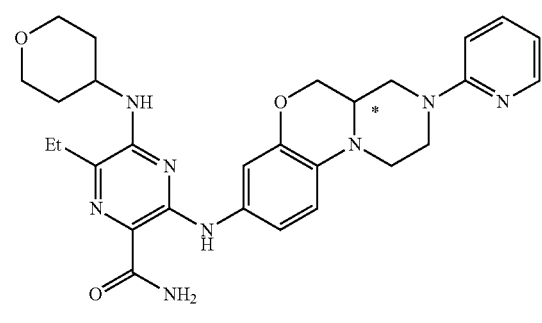

37
-continued
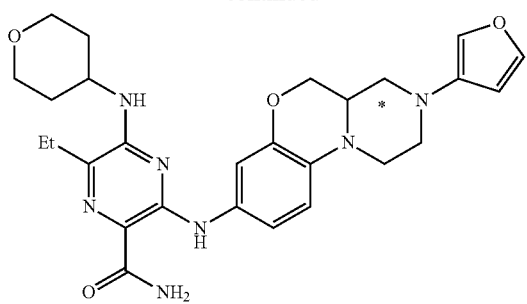
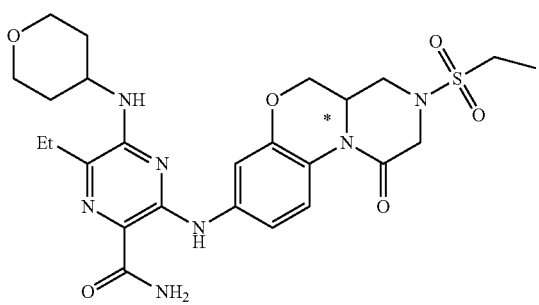
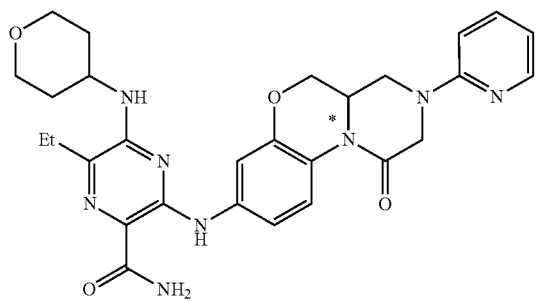
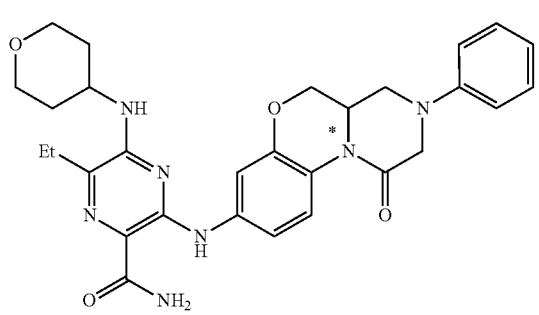
E1
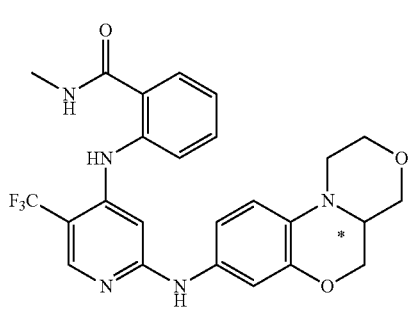
38
-continued
E1S
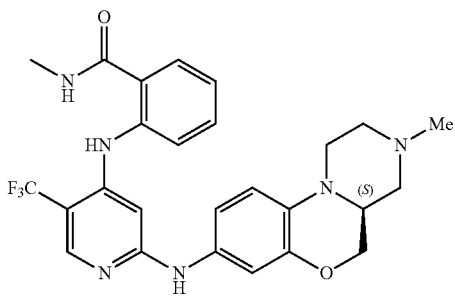
E1R
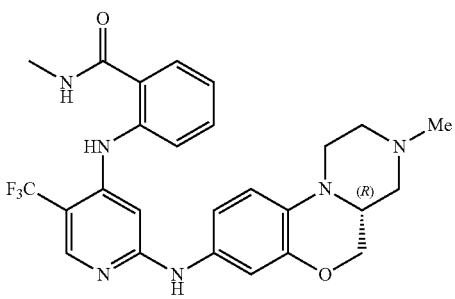
E2R
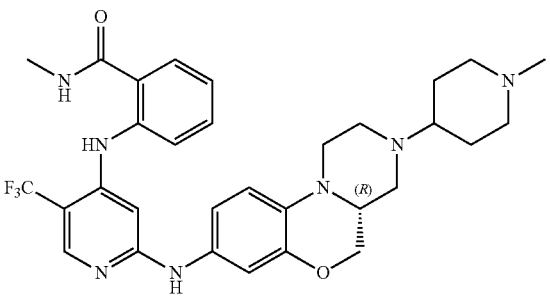
E3R
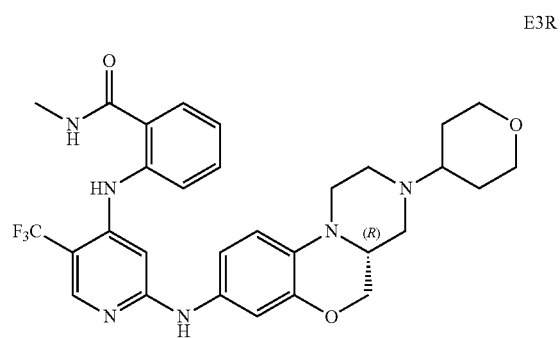
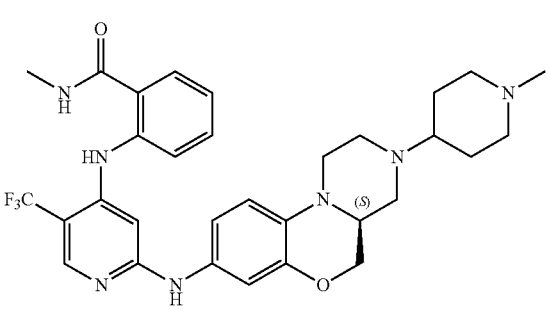

39
-continued
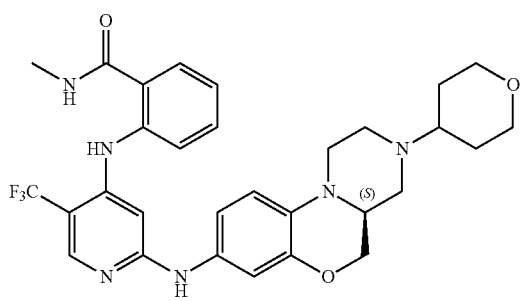
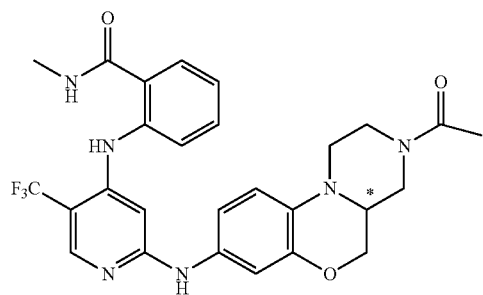
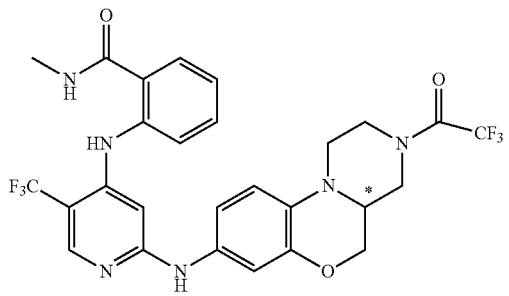
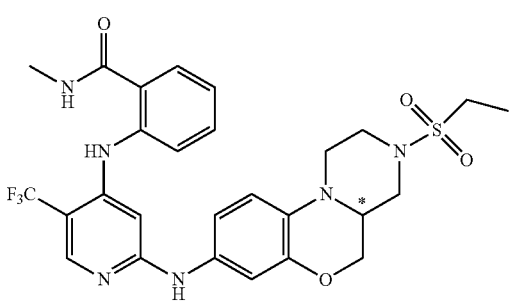
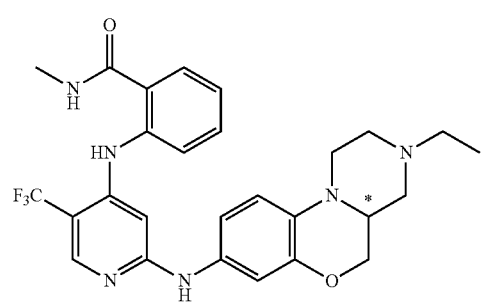
40
-continued
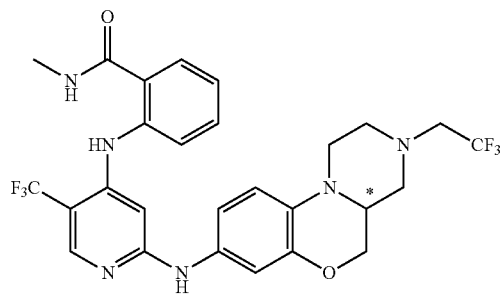
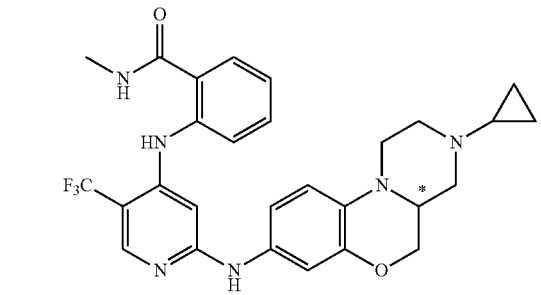
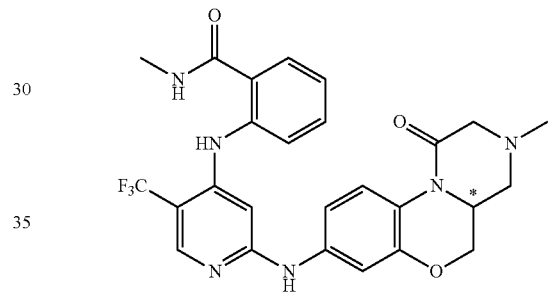
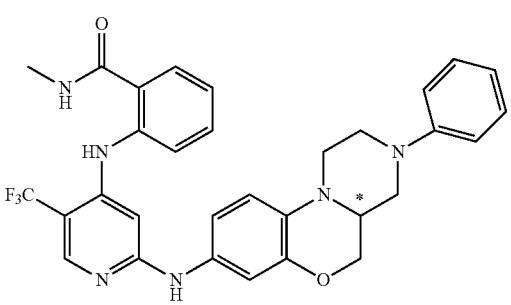
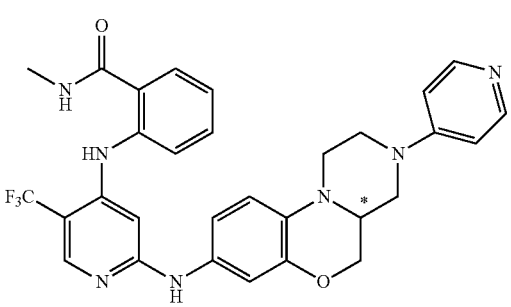

-continued

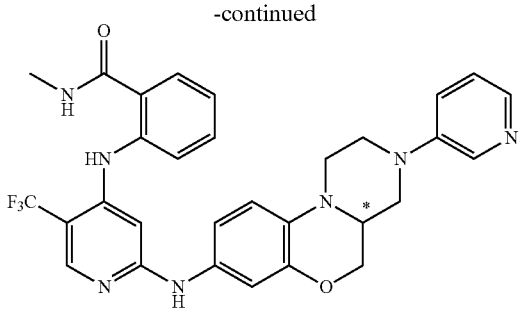

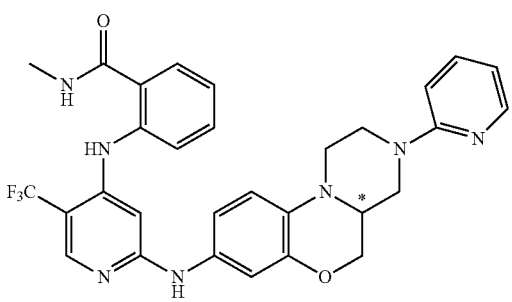

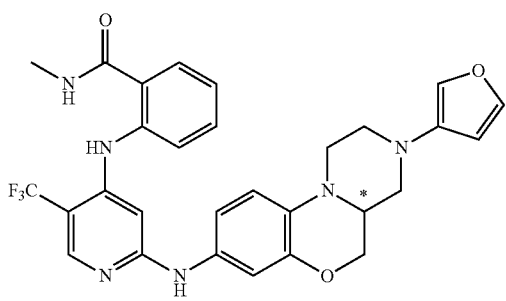

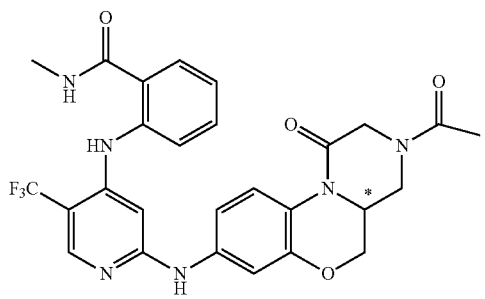

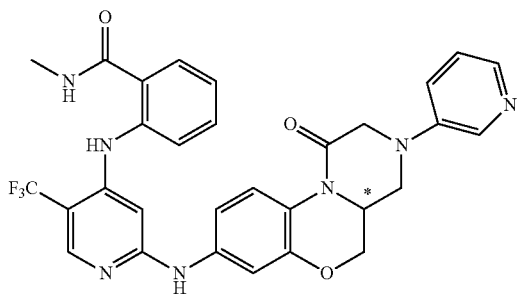

According to a second aspect of the invention, there is provided a compound according to the first aspect of the invention, or an optical isomer thereof, a pharmaceutically acceptable salt, a prodrug, a deuterated derivative, a hydrate, a solvate use for:

(a) Preparation of a drug for the treatment of a disease associated with protein kinase activity or expression;

(b) Preparation of a protein kinase targeting inhibitor, and/or (c) Non-therapeutic inhibition of protein kinase activity in vitro;

Wherein, the protein kinase is selected from the group consisting of: EGFR, CDK, SYK, JAK, Flt-3, Axl, FAK, or a combination thereof.

According to a third aspect of the invention, there is provided a compound according to the first aspect of the invention, or an optical isomer thereof, a pharmaceutically acceptable salt, a prodrug, a deuterated derivative, a hydrate, a solvate, its use as an EGFR inhibitor or for the treatment of diseases associated with high expression of EGFR.

According to a fourth aspect of the invention, there is provided a compound according to the first aspect of the invention, or an optical isomer thereof, a pharmaceutically acceptable salt, a prodrug, a deuterated derivative, a hydrate, a solvate, its use as a CDK inhibitor, or for the treatment of diseases associated with high CDK expression.

According to a fifth aspect of the invention, there is provided a compound according to the first aspect of the invention, or an optical isomer thereof, a pharmaceutically acceptable salt, a prodrug, a deuterated derivative, a hydrate, a solvate, its use as a SYK and JAK inhibitor, or for the treatment of diseases associated with high expression of SYK and JAK.

According to a sixth aspect of the invention, there is provided a compound according to the first aspect of the invention, or an optical isomer thereof, a pharmaceutically acceptable salt, a prodrug, a deuterated derivative, a hydrate, a solvate, its use as a Flt-3 and Axl inhibitor, or for the treatment of diseases associated with high expression of Flt-3 and Axl.

According to a seventh aspect of the invention, there is provided a compound according to the first aspect of the invention, or an optical isomer thereof, a pharmaceutically acceptable salt, a prodrug, a deuterated derivative, a hydrate, a solvate, its use, as a FAK inhibitor, or for the treatment of diseases associated with high expression of FAK.

According to an eighth aspect of the invention, a pharmaceutical composition comprising: (i) an effective amount of a compound of formula I according to the first aspect of the invention, or an optical isomer thereof, pharmacy Acceptable salts, prodrugs, deuterated derivatives, hydrates, solvates; and (ii) pharmaceutically acceptable carriers.

A ninth aspect of the invention provides a method of inhibiting protein kinase activity, the method comprising the steps of: administering to a subject, an inhibitory effective amount of a compound of formula I according to the first aspect of the invention, or optical isomerism thereof Or a pharmaceutically acceptable salt, a prodrug, a deuterated derivative, a hydrate, a solvate, or an inhibitory effective amount of a pharmaceutical composition according to the eighth aspect of the invention; The protein kinase is selected from the group consisting of EGFR, FAK, SYK, FLT-3, Axl, CDK, JAK, or a combination thereof.

According to a tenth aspect of the invention, there is provided a process for the preparation of a compound according to the first aspect of the invention, which comprises the steps:

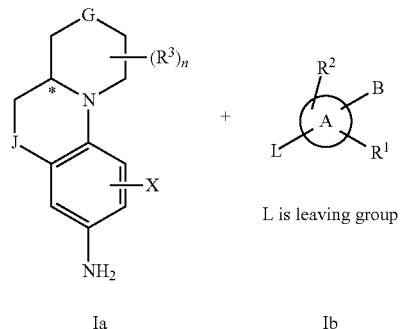
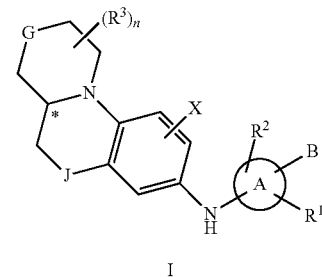

Reaction of compound Ia with Ib in an inert solvent to give a compound of formula I;

Preferably, the compound of formula Ia is prepared by the following method:

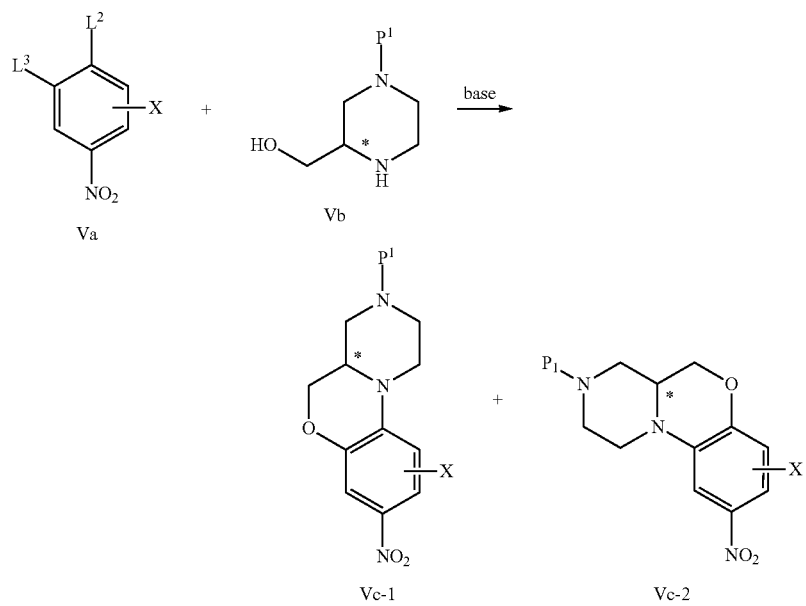

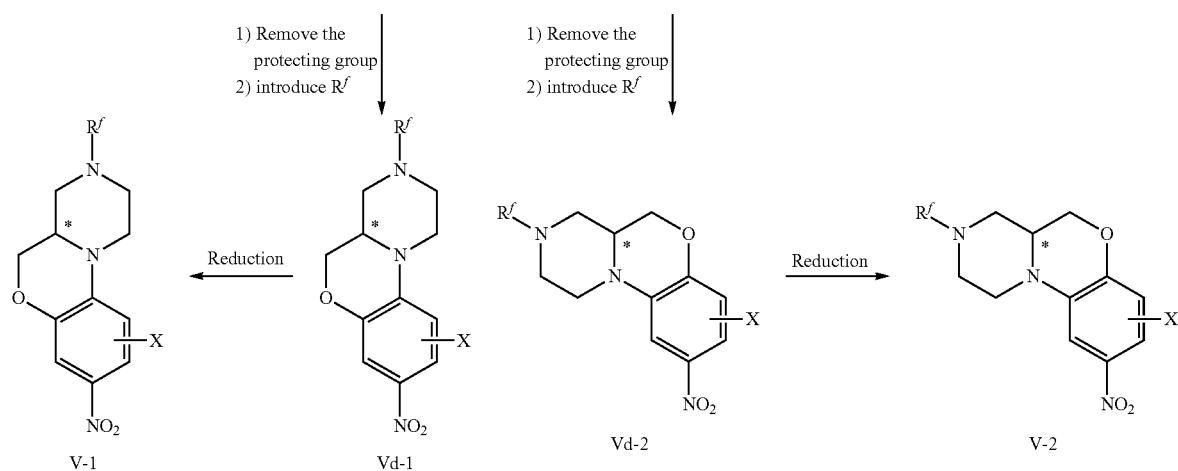

$L^2$ and $L^3$ are same or different leaving group
$P^1$ is protecting group (i) The compound of the formula (Va) is reacted with a compound of the formula (Vb) under basic conditions to give a compound of the formula (Vc-1) and (Vc-2);

Optionally (ii) reacting with a compound of formula (Vc-1) and (Vc-2) under acidic conditions to deprotect the protecting group;

(iii) The deprotected formula (Vc-1) and (Vc-2) were carried on for the reaction individually to afford the formula (Vd-1) and (Vd-2), respectively;

And optionally (iv) reducing the compounds of formula (Vd-1) and (Vd-2), respectively, to give compounds of formula (V-1) and (V-2), respectively.

It is to be understood that within the scope of the present invention, the various technical features of the present invention and the various technical features specifically described hereinafter (as in the embodiments) may be combined with each other to form a new or preferred technical solution. Due to space limitations, we will not repeat them here.

Detail Implementation

After long-term and intensive research, die present inventors have unexpectedly discovered a novel class of tricyclic aryl containing compounds as protein kinase inhibitors, as well as their preparation methods and applications. The protein kinase inhibitor can inhibit various protein kinases including EGFR, FAK, SYK, FLT-3, Axl, CDK, JAK and the like. The compounds of the invention may be applied to the treatment of various diseases associated with the activity of said kinases. Based on the above findings, the inventors completed the present invention.

Terminology

Unless otherwise stated, "or" as used herein has the same meaning as "and/or" (refers to "or" and "and").

Unless otherwise specified, among all compounds of the present invention, each chiral carbon atom (chiral center) may optionally be in the R configuration or the S configuration, or a mixture of the R configuration and the S configuration.

As used herein, the term "alkyl", alone or as part of another substituent, refers to a straight (i.e., unbranched) or branched saturated hydrocarbon group containing only carbon atoms, or a combination of straight and branched chains. When the alkyl group has a carbon number limitation (e.g., $C_{1-10}$), it means that the alkyl group has 1 to 10 carbon atoms. For example, $C_{1-8}$ alkyl refers to an alkyl group containing from 1 to 8 carbon atoms, including methyl, ethyl, propyl, isopropyl, butyl, isobutyl, sec-butyl, tert-butyl, or the like.

As used herein, the term "alkenyl", when used alone or as part of another substituent, refers to a straight or branched, carbon chain group having at least one carbon-carbon double bond. Alkenyl groups can be substituted or unsubstituted. When the alkenyl group has a carbon number limit (e.g., $C_{2-8}$), it means that the alkenyl group has 2-8 carbon atoms. For example, $C_{2-8}$ alkenyl refers to alkenyl groups having 2-8 carbon atoms, including ethenyl, propenyl, 1,2-butenyl, 2,3-butenyl, butadienyl, or the like.

As used herein, the term "alkynyl", when used alone or as part of another substituent, refers to an aliphatic hydrocarbon group having at least one carbon-carbon triple bond. The alkynyl group can be straight or branched, or a combination thereof. When the alkynyl group has a carbon number limitation (e.g., $C_{2-8}$ alkynyl group), it means that the alkynyl group has 2 to 8 carbon atoms. For example, the term "$C_{2-8}$ alkynyl" refers to a straight or branched alkynyl group having 2-8 carbon atoms, including ethynyl, propynyl, isopropynyl, butynyl, isobutynyl, secondary Butynyl, tert-butynyl, or the like.

As used herein, when used alone or as part of another substituent, the term "cycloalkyl" refers to a unit ring having a saturated or partially saturated ring, a bicyclic or polycyclic (fused ring, bridged or spiro) ring system. When a certain cycloalkyl group has a carbon number limitation (e.g., $C_{3-10}$), it means that the cycloalkyl group has 3 to 10 carbon atoms. In some preferred embodiments, the term "C3-8 cycloalkyl" refers to a saturated or partially saturated monocyclic or bicyclic alkyl group having from 3 to 8 carbon atoms, including cyclopropyl, cyclobutyl, cyclopentyl, cycloheptyl, or the like. "Spirocycloalkyl" refers to a bicyclic or polycyclic group that shares a carbon atom (called a spiro atom) between the monocyclic rings. These may contain one or more double bonds, but none of the rings have fully conjugated π electrons. system.

"Fused cycloalkyl" means an all-carbon bicyclic or polycyclic group in which each ring of the system shares an adjacent pair of carbon atoms with other rings in the system, wherein one or more of the rings may contain one or more Key, but none of the rings have a fully conjugated π-electron system. "Bridge cycloalkyl" refers to an all-carbon polycyclic group in which two rings share two carbon atoms that are not directly bonded, which may contain one or more double bonds, but none of the rings have a fully conjugated pi-electron system. The atoms contained in the cycloalkyl group are all carbon atoms. Some examples of cycloalkyl groups are as follows, and the present invention is not limited to the following cycloalkyl groups.

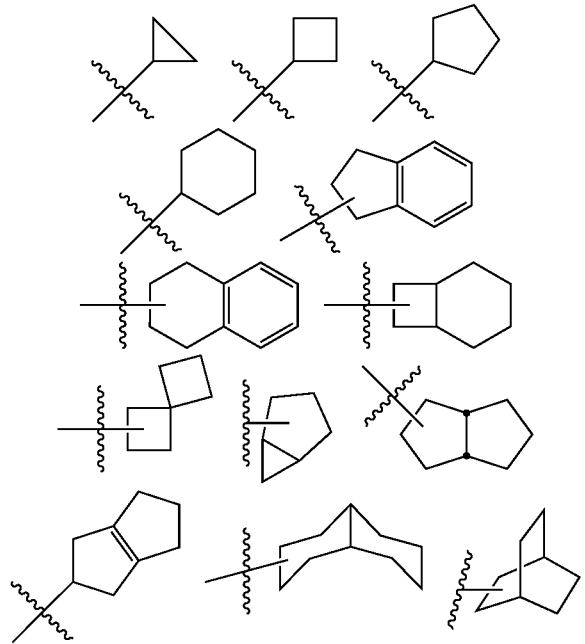

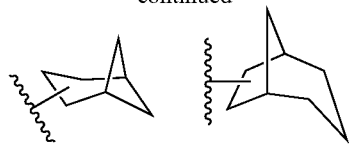

Unless otherwise stated, the following terms used in the specification and claims have the following meanings. "Aryl" means an all-carbon monocyclic or fused polycyclic (i.e., a ring that shares a pair of adjacent carbon atoms) groups having a conjugated n-electron system, such as phenyl and naphthyl. The aryl ring may be fused to other cyclic groups (including saturated and unsaturated rings), but may not contain heteroatoms such as nitrogen, oxygen, or sulfur, while the point of attachment to the parent must be on the carbon atoms of the ring in a conjugated pi-electron system. The aryl group can be substituted or unsubstituted. The following are some examples of aryl groups, and the present invention is not limited to the aryl groups described below.

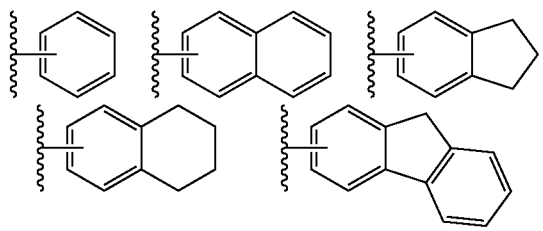

"Heteroaryl" refers to a heteroaromatic group containing one to more heteroatoms. The heteroatoms referred to herein include oxygen, sulfur, and nitrogen. For example, furyl, thienyl, pyridyl, pyrazolyl, pyrrolyl, N-alkylpyrrolyl, pyrimidinyl, pyrazinyl, imidazolyl, tetrazolyl, and the like. The heteroaryl ring may be fused to an aryl, heterocyclic or cycloalkyl ring wherein the ring to which the parent structure is attached is a heteroaryl ring. The heteroaryl group con be optionally substituted or unsubstituted. The following are some examples of heteroaryl groups, and the present invention is not limited to the following heteroaryl groups. Among them, the last three heteroaryl groups are tricyclic heteroaryl groups, which are the focus of the present invention.

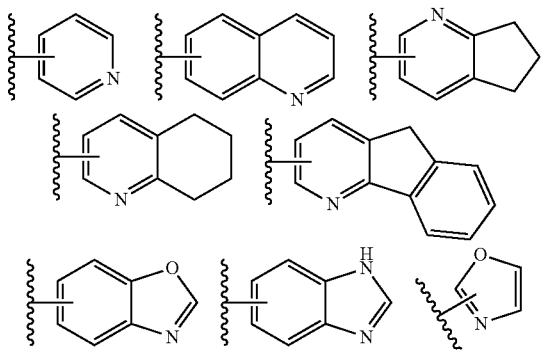

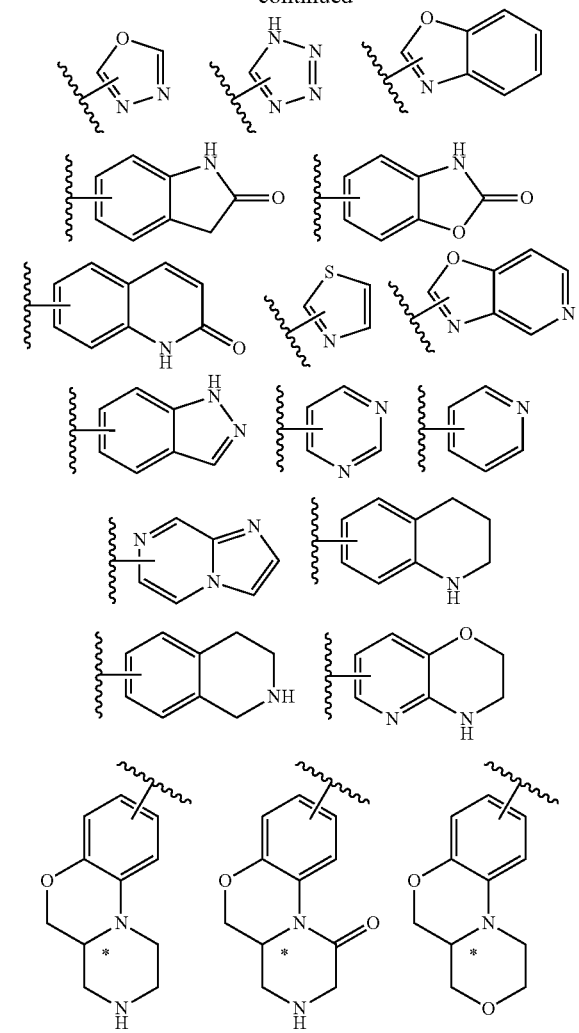

"Heterocyclyl" means a saturated or partially unsaturated monocyclic or polycyclic cyclic hydrocarbon substituent wherein one or more of the ring atoms are selected from nitrogen, oxygen or sulfur and the remaining ring atoms are carbon. Non-limiting examples of monocyclic heterocyclic groups include pyrrolidinyl, piperidinyl, piperazinyl, morpholinyl, thiomorpholinyl, homopiperazinyl. Polycyclic heterocyclic group refers to a heterocyclic group including a spiro ring, a fused ring, and a bridged ring. "Spirocyclic heterocyclyl" refers to a polycyclic heterocyclic group in which each ring of the system shares an atom (referred to as a spiro atom) with other rings in the system, wherein one or more of the ring atoms is selected from the group consisting of nitrogen and oxygen. Or sulfur, the remaining ring atoms are carbon. "Fused ring heterocyclyl" refers to a polycyclic heterocyclic group in which each ring of the system shores on adjacent pair of atoms with other rings in the system, and one or more rings may contain one or more double bonds, but none One ring has a fully conjugated pi-electron system, and wherein one or more ring atoms are selected from nitrogen, oxygen or sulfur, and the remaining ring atoms are carbon. "Bridged heterocyclyl" refers to a polycyclic heterocyclic group in which any two rings share two atoms which are not directly bonded, these may contain one or more double bonds, but none of the rings have a fully conjugated pi-electron system, and wherein one or more of the ring atoms are selected from nitrogen, oxygen or sulfur, and the remaining ring atoms are carbon. If a heterocyclic group has both a saturated ring and an aromatic ring (for example, the saturated ring and the aromatic ring are fused together), the point attached to the parent must be on the saturated ring. Note: When the point attached to the parent is on the aromatic ring, it is called a heteroaryl group and is not called a heterocyclic group. Some examples of the heterocyclic group are as follows, and the present invention is not limited to the following heterocyclic group.

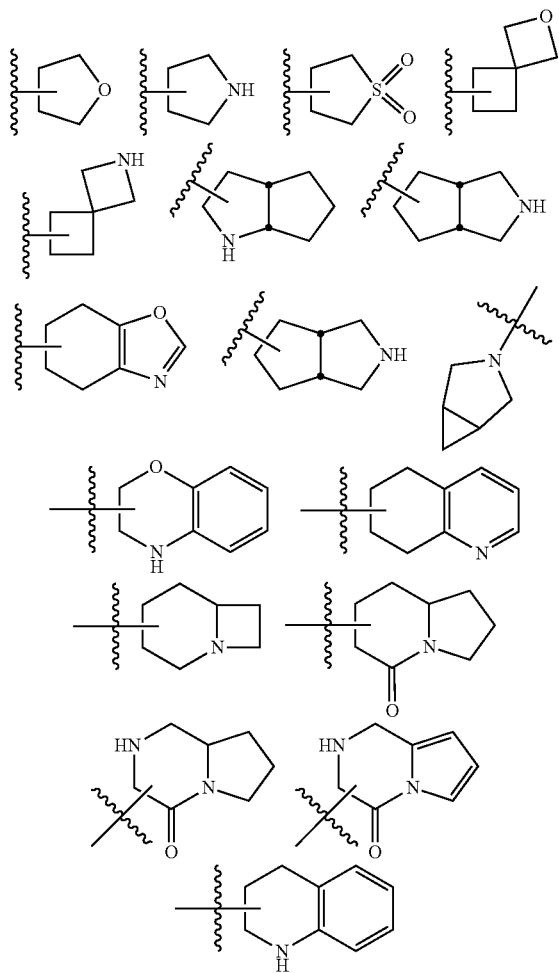

As used herein, the term "halogen", when used alone or as part of another substituent, refers to F, Cl, Br, and I.

As used herein, the term "substituted" (when with or without "optionally") means that one or more hydrogen atoms on a particular group are replaced by a particular substituent. Particular substituents are the substituents described above in the corresponding paragraphs, or the substituents which appear in the examples. Unless otherwise stated, an optionally substituted group may have a substituent selected from a particular group at any substitutable position of the group, and the substituents may be the same or different at each position. A cyclic substituent, such as a heterocyclic group, may be attached to another ring, such as a cycloalkyl group, to form a spirobicyclic ring system, i.e., the two rings have a common carbon atom. Those skilled in the art will appreciate that the combinations of substituents contemplated by the present invention are those that are stable or chemically achievable. The substituents are, for example but not limited to, $C_{1-8}$ alkyl, $C_{2-8}$ alkenyl, $C_{2-8}$ alkynyl, $C_{3-8}$ cycloalkyl, 3- to 12-membered heterocyclic, aryl, Heteroaryl, halogen, hydroxy, carboxy (—COOH), $C_{1-8}$ aldehyde, $C_{2-10}$ acyl, $C_{2-10}$ ester, amino.

For convenience and in accordance with conventional understanding, the term "optionally substituted" or "optionally substituted" applies only to sites which are capable of being substituted by a substituent, and does not include those which are not chemically achievable.

As used herein, unless otherwise specified, the term "pharmaceutically acceptable salt" refers to a salt that is suitable for contact with the tissue of a subject (e.g., a human) without causing unpleasant side effects. In some embodiments, a pharmaceutically acceptable salt of a compound of the invention includes a salt (e.g., a potassium salt, a sodium salt, a magnesium salt, a calcium salt) of a compound of the invention having an acidic group or is basic A salt of a compound of the invention (e.g., a sulfate, a hydrochloride, a phosphate, a nitrate, a carbonate).

Utility:

The present invention provides a compound of the formula (I) or formula (II), or a deuterated derivative thereof, a salt thereof, an isomer (enantiomer or diastereomer, if present In the case of a hydrate, a pharmaceutically acceptable carrier or excipient for inhibiting the use of a protein kinase. The protein kinases referred to herein include EGFR, CDK, SYK, JAK, Flt-3, Axl, and FAK, but are not limited to the above several kinases.

The compounds of the invention are useful as one or more kinase inhibitors, for example, in some embodiments, certain classes of compounds of the invention are useful as EGFR kinase inhibitors; In some embodiments, certain classes of compounds of the invention are useful as CDK kinase inhibitors; in some embodiments, certain classes of compounds of the invention are useful as SYK kinase inhibitors; in some embodiments, one of the inventions Classes of compounds are useful as FAK kinase inhibitors; in some embodiments, certain classes of compounds of the invention are useful as dual inhibitors of SYK kinase and JAK kinase; in other embodiments, certain classes of compounds of the invention are useful It is a dual inhibitor of Flt-3 kinase and Axl kinase.

In cancer patients, the expression or activity of various protein kinases mentioned above is significantly increased. These levels of overexpression and/or abnormal protein kinase activity are directly linked to the development of tumors. The compounds of the invention are single and/or dual inhibitors of these protein kinases. Diseases are prevented, alleviated or cured by modulating these protein kinase activities. The diseases include allergic asthma, myelofibrosis, rheumatoid arthritis, B-cell lymphoma, monocytic leukemia, splenomegaly, eosinophilic syndrome, primary thrombocytopenia, systemic Giant cell disease, liver cancer, rectal cancer, bladder cancer, throat cancer, non-small cell lung cancer, small cell lung cancer, lung adenocarcinoma, lung squamous cell carcinoma, breast cancer, prostate cancer, glioma, ovarian cancer, head and neck Squamous cell carcinoma, cervical cancer, esophageal cancer, kidney cancer, pancreatic cancer, colon cancer, skin cancer, lymphoma, gastric cancer, multiple myeloma and solid tumors, and the like.

In a certain sense, dual protein kinase inhibitors interfere with two different kinases at the same time, and the antitumor effects produced are often superimposed, thus having the potential to treat various cancers more effectively.

The compounds of the present invention are useful as a combination drug with biological agents such as the PD-1 inhibitors Opdivo® and Keytruda® for the treatment of various cancers and related diseases.

The compound of the present invention and its deuterated derivatives, and pharmaceutically acceptable salts or isomers thereof, if present, or hydrates and/or compositions thereof, and pharmaceutically acceptable excipients or The carriers are formulated together and the resulting compositions are administered to mammals, such as men, women and animals, for the treatment of conditions, conditions and diseases. The composition may be: a tablet, a pill, a suspension, a solution, an emulsion, a capsule, an aerosol, a sterile injectable solution, sterile powder, etc. In some embodiments, pharmaceutically acceptable excipients include microcrystalline cellulose, lactose, sodium citrate, calcium carbonate, calcium hydrogen phosphate, mannitol, hydroxypropyl-beta-cyclodextrin, beta-cyclodextrin, (increased), glycine, disintegrants (such as starch, croscarmellose sodium, complex silicates and high molecular weight polyethylene glycols), granulating binders (such as polyvinylpyrrolidone, sucrose, gelatin and Acacia gum) and lubricants (such as magnesium stearate, glycerin and talc). In a preferred embodiment, the pharmaceutical composition is a dosage form suitable for oral administration, including but not limited to tablets, solutions, suspensions, capsules, granules, powders. The amount of the compound or pharmaceutical composition of the invention administered to a patient is not fixed and is usually administered in a pharmaceutically effective amount. At the same time, the amount of the compound actually administered can be determined by the physician based on the actual conditions, including the condition being treated, the route of administration selected, the actual compound administered, the individual condition of the patient, and the like. The dosage of the compound of the invention depends on the particular use of the treatment, the mode of administration, the condition of the patient, and the judgment of the physician. The proportion or concentration of a compound of the invention in a pharmaceutical composition depends on a variety of factors including dosage, physicochemical properties, route of administration, and the like.

It is to be understood that within the scope of the present invention, the various technical features of the present invention and the various technical features specifically described hereinafter (as in the embodiments) may be combined with each other to constitute a new or preferred technical solution.

General Synthetic Method for Compounds

The compound of formula I of the present invention can be prepared by the following method:

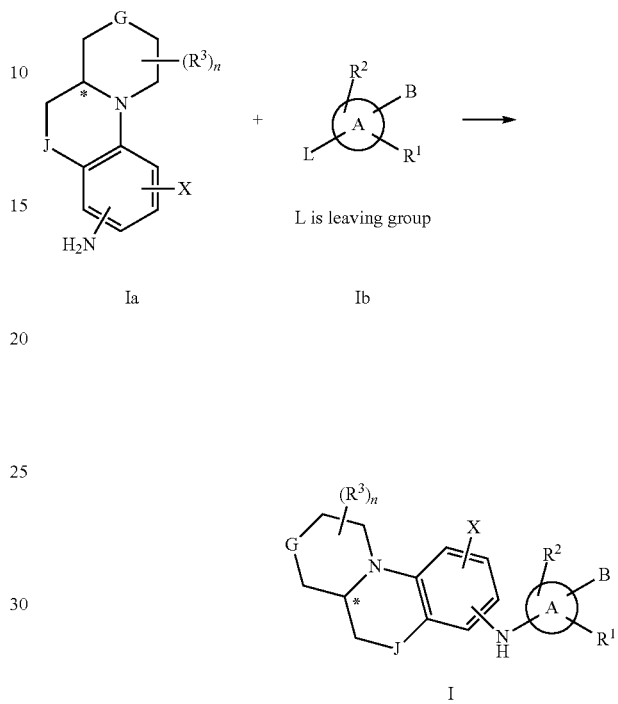

Reaction of (Ia) with (Ib) in an inert solvent to give compound (I);

In the above formulas, the definition of each group is as described above. The reagents and conditions for each step may be selected from the conventional reagents or conditions for carrying out such preparation methods in the art. After the structure of the compound of the present invention is disclosed, the above selection may be carried out by those skilled in the art based on the knowledge in the art.

More specifically, the compound of the formula I of the present invention can be obtained by the following method, however, the conditions of the method, such as the reactant, the solvent, the base, the amount of the compound used, the reaction temperature, the time required for the reaction, and the like are not limited to the following explanation. The compounds of the present invention may also be conveniently prepared by combining various synthetic methods described in the specification or known in the art, and such combinations are readily made by those skilled in the art to which the present invention pertains.

In the production method of the present invention, each reaction is usually carried out in an inert solvent at a reaction temperature of usually −20 to 150° C. (preferably 0 to 120° C.). The reaction time in each step is usually from 0.5 to 48 h, preferably from 2 to 12 h.

Scheme 1 describes a general synthetic method for compounds 1-A7 and 1-A8:
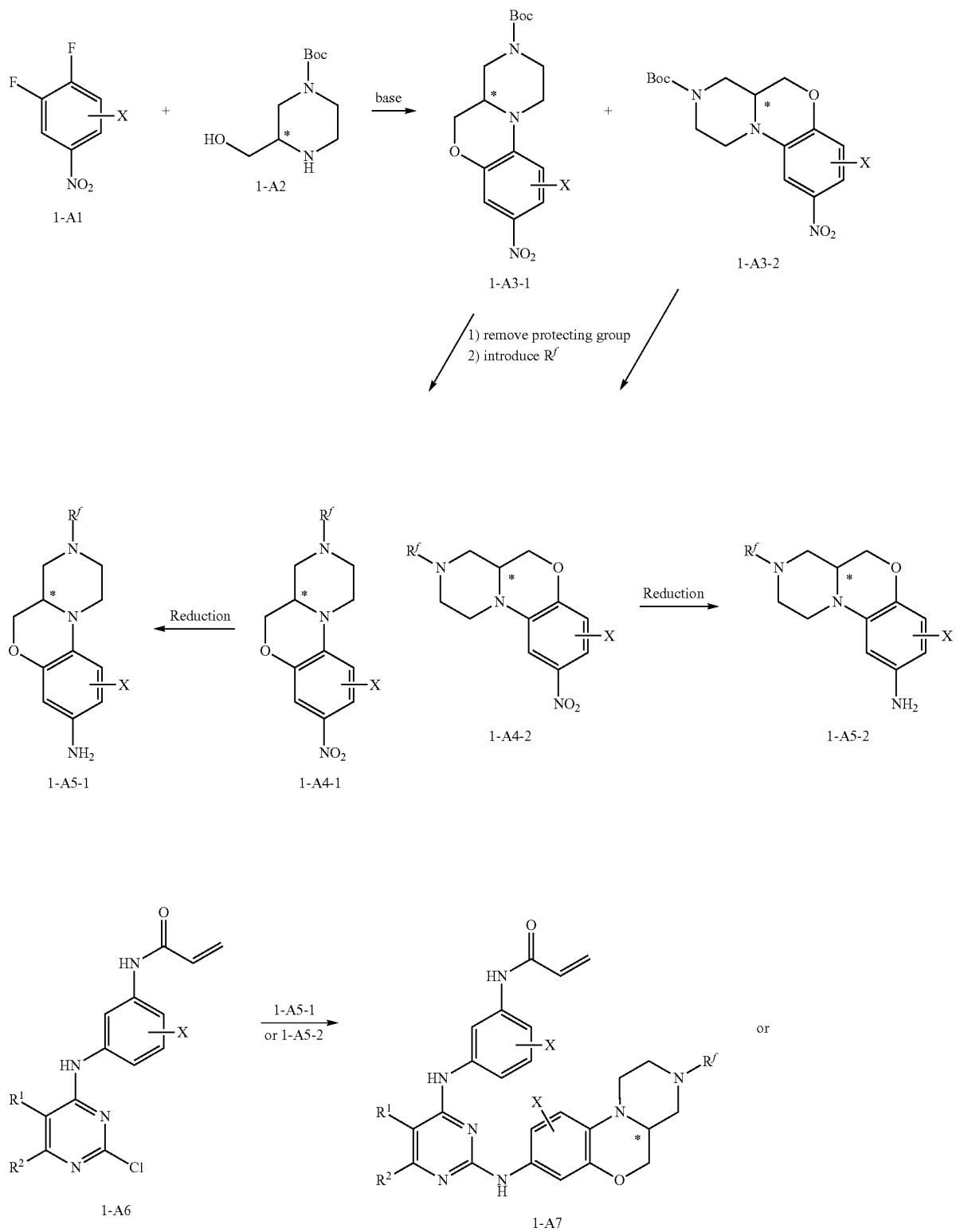

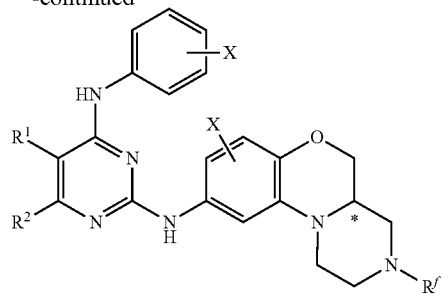
1-A8
Scheme 2 describes a general synthetic method for compounds 2-B4 and 2-B5:
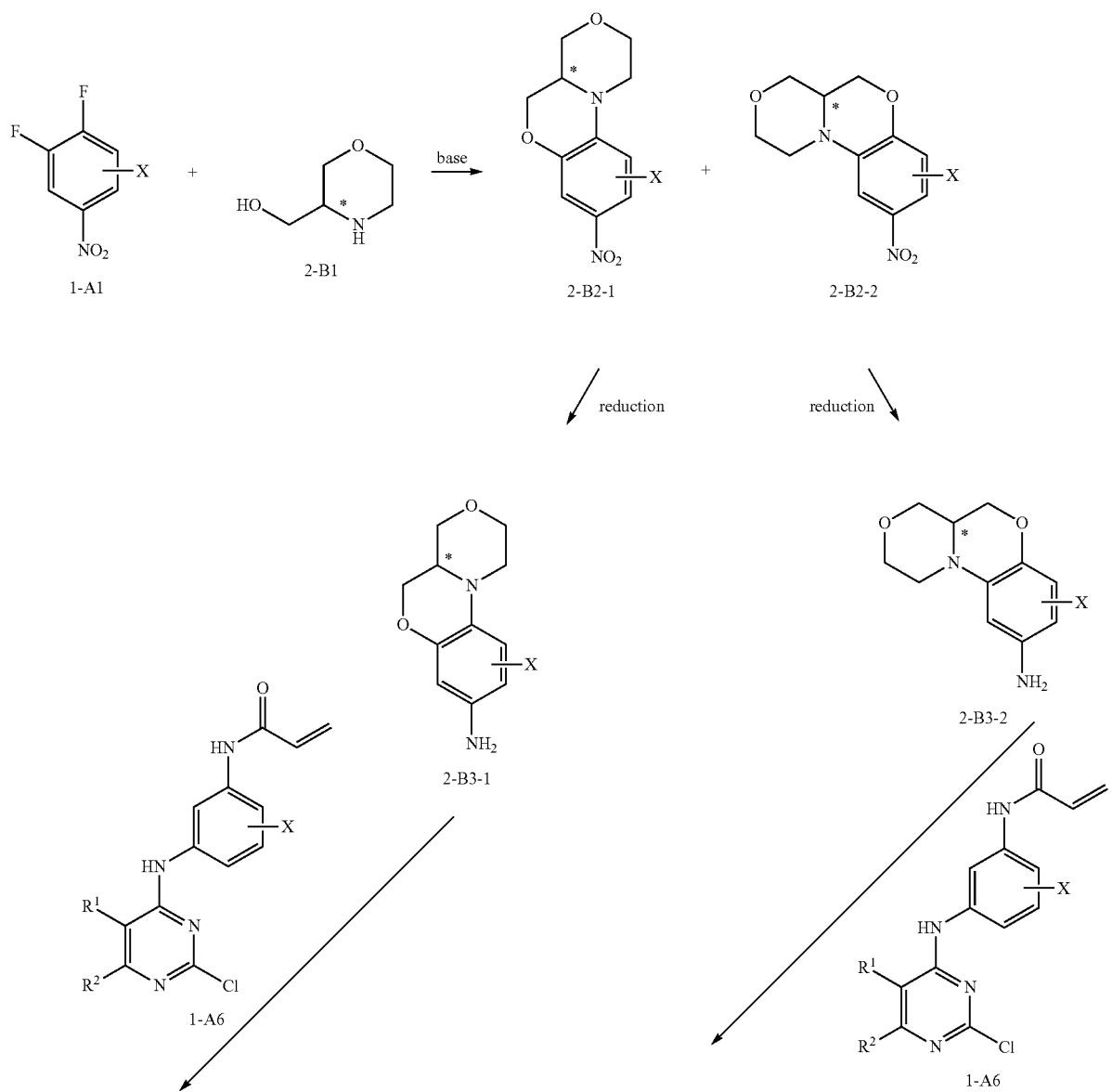

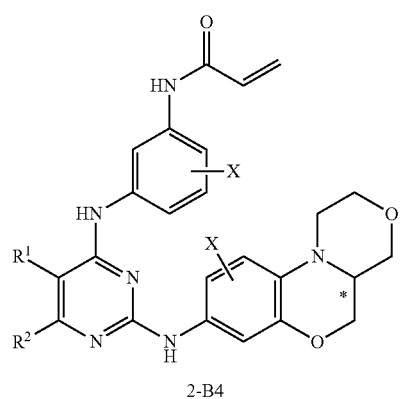
2-B4
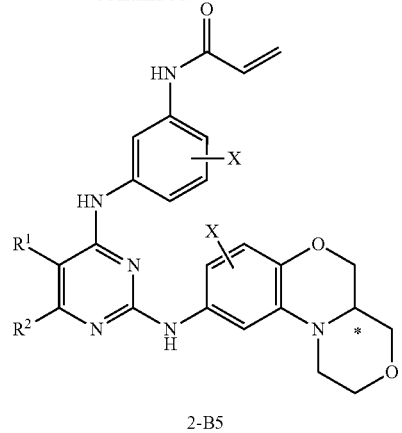
2-B5
Scheme 3 describes a general synthetic method for compound 3-C8:
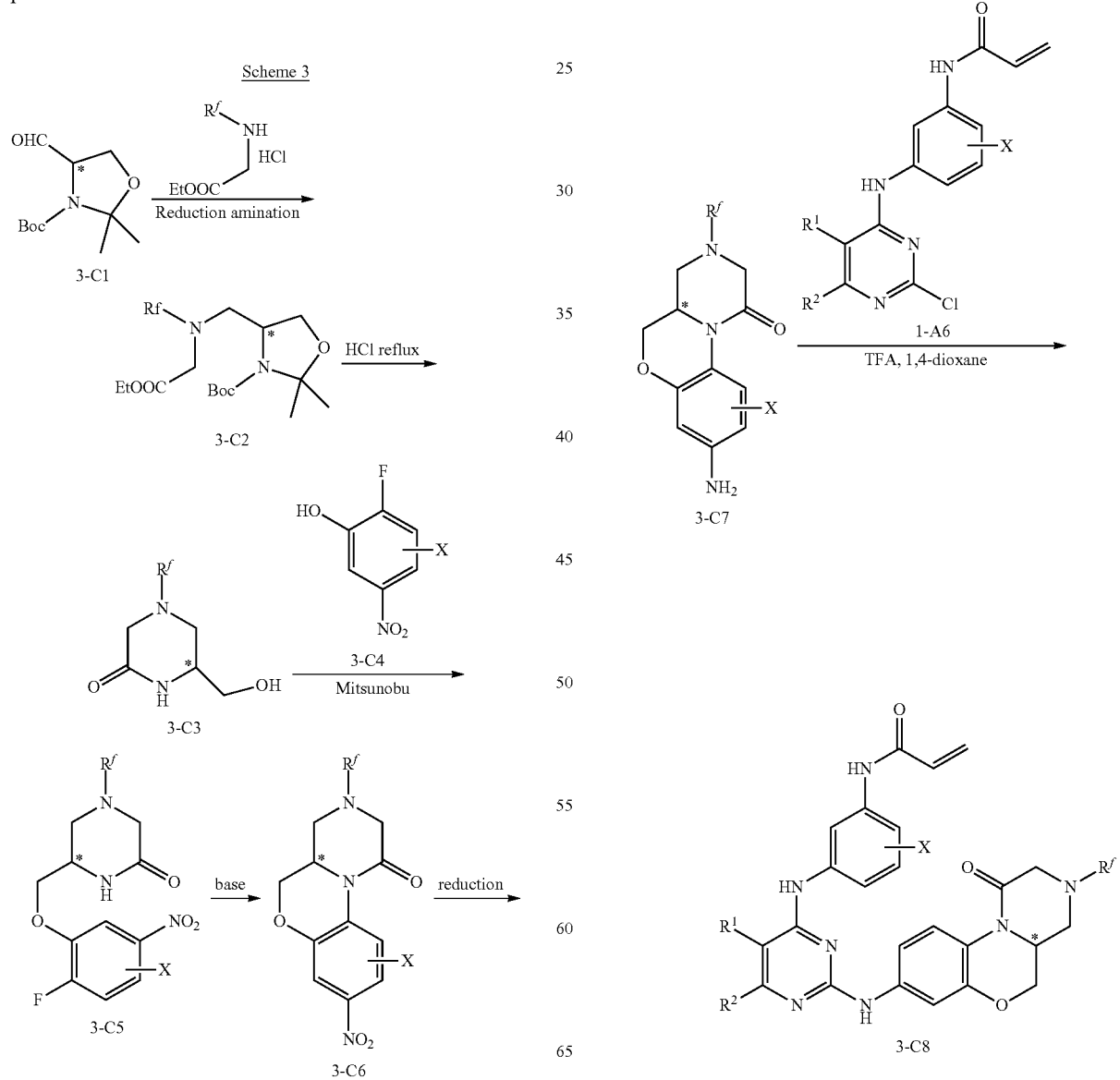

Scheme 4 describes a general synthetic method for compound 4-D2:
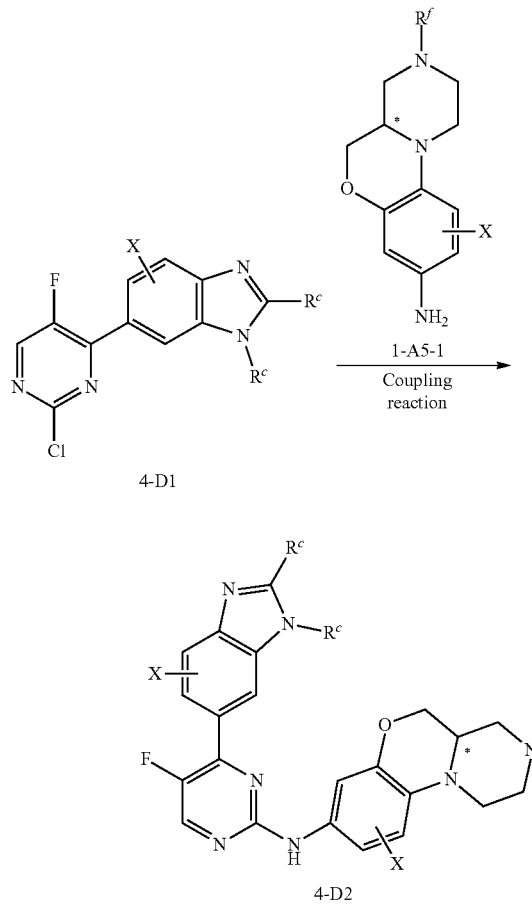
Scheme 5 describes a general synthetic method for compound 5-E2:
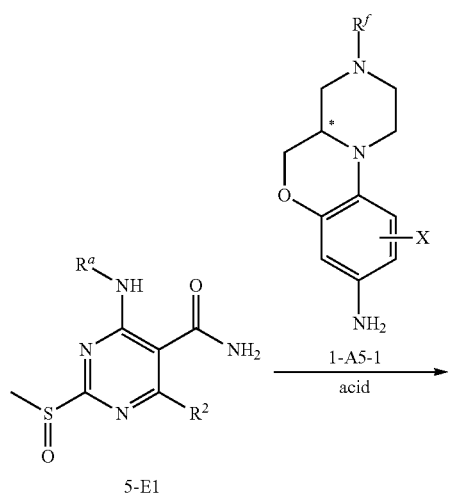
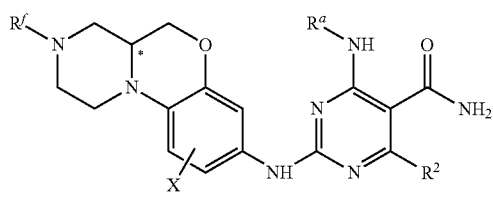
Scheme 6 describes a general synthetic method for compound 6-F4:
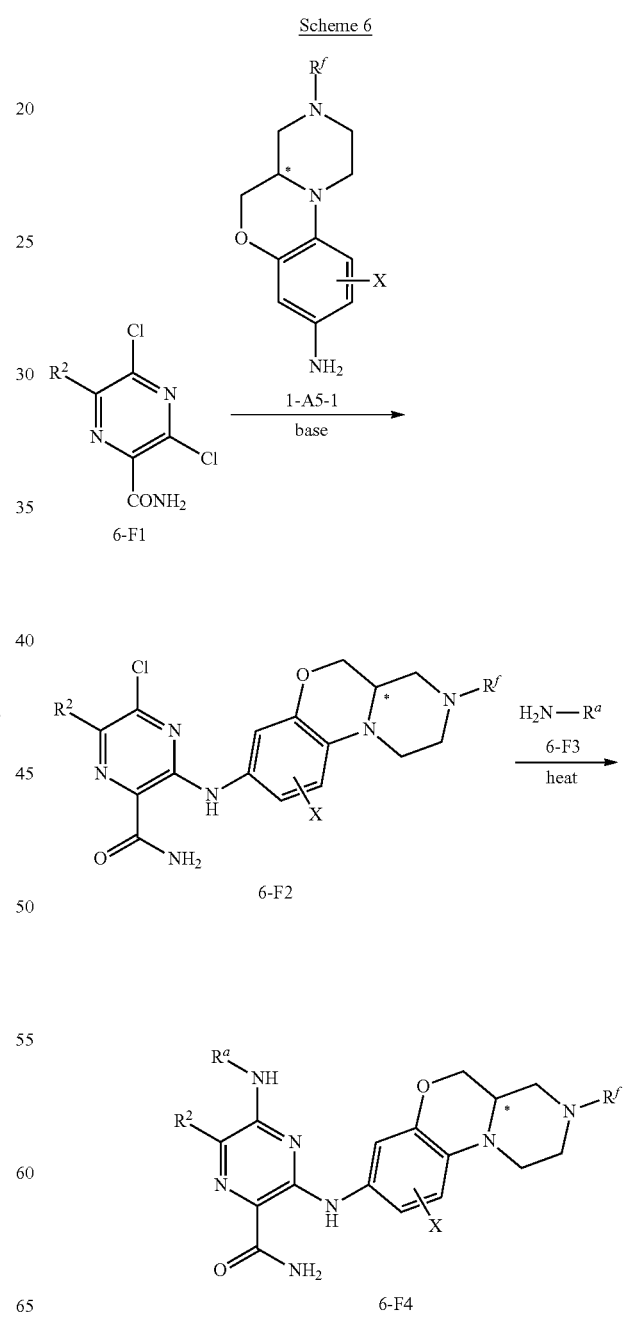

Scheme 7 describes a general synthetic method for compound 7-G3:
Scheme 8 describes a general synthetic method for compound 8-H3:
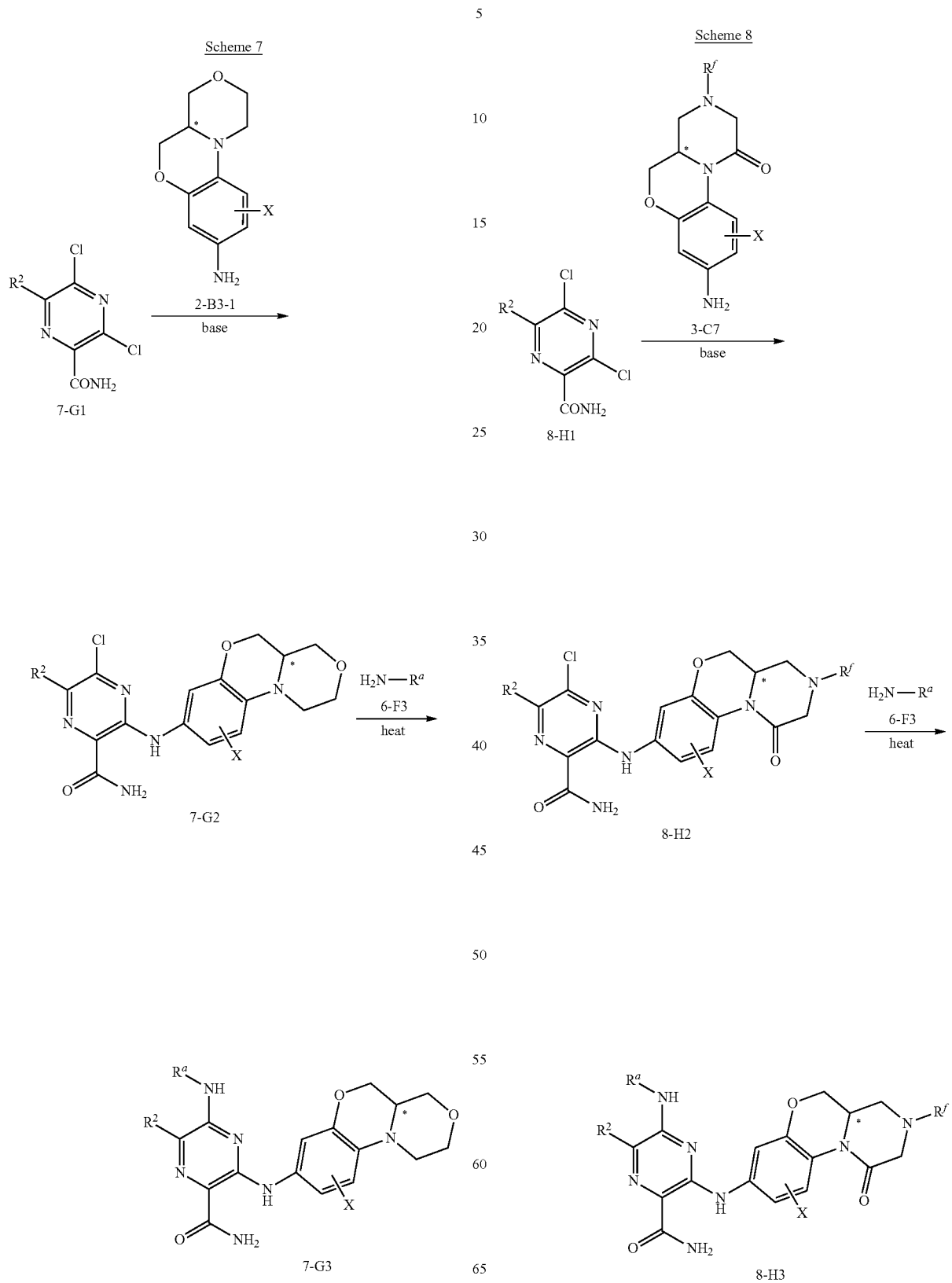

Scheme 9 describes a general synthetic method for compound 9-I2:

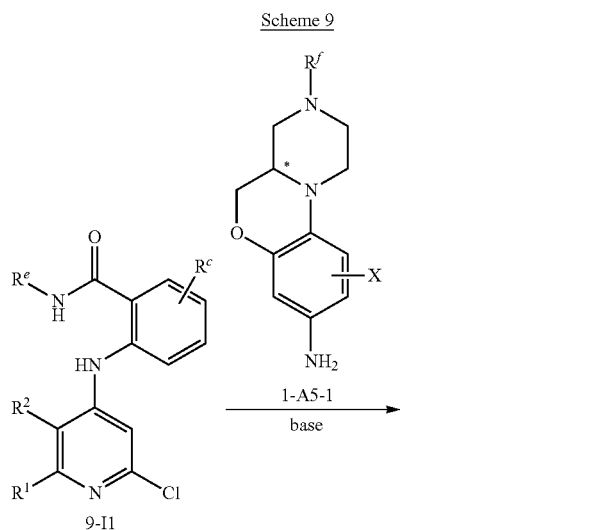

Scheme 10 describes a general synthetic method for compound 10-J2:

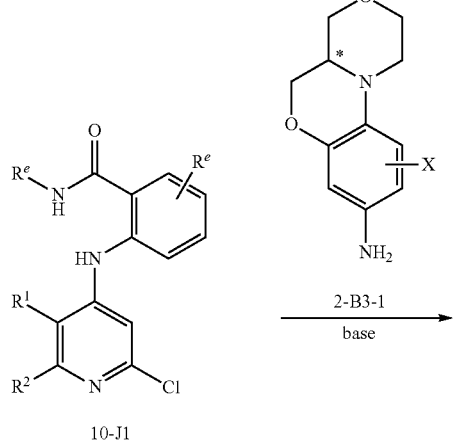

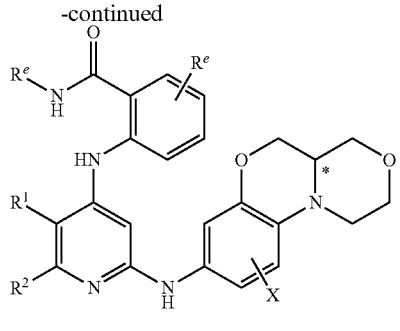

Pharmaceutical Composition and Method of Administration

Since the compound of the present invention has excellent inhibitory activity against a series of protein kinases, the compound of the present invention and various crystal forms thereof, pharmaceutically acceptable inorganic or organic salts, hydrates or solvates, and compounds containing the present invention are The pharmaceutical composition of the main active ingredient can be used to treat, prevent, and alleviate diseases associated with EGFR, FAK, SYK, FLT-3, Axl, CDK, JAK activity or expression levels.

The pharmaceutical compositions of the present invention comprise a safe or effective amount of a compound of the present invention, or a pharmaceutically acceptable salt thereof, and a pharmaceutically acceptable excipient or carrier. By "safe and effective amount" it is meant that the amount of the compound is sufficient to significantly improve the condition without causing serious side effects. In general, the pharmaceutical compositions contain from 1 to 2000 mg of the compound of the invention per agent, more preferably from 5 to 200 mg of the compound of the invention per agent. Preferably, the "one dose" is a capsule or tablet.

"Pharmaceutically acceptable carrier" means: one or more compatible solid or liquid fillers or gel materials which are suitable for human use and which must be of sufficient purity and of sufficiently low toxicity. By "compatibility" it is meant herein that the components of the composition are capable of intermingling with the compounds of the invention and with each other without significantly reducing the efficacy of the compound. Examples of pharmaceutically acceptable carriers are cellulose and its derivatives (such as sodium carboxymethylcellulose, sodium ethylcellulose, cellulose acetate, etc.), gelatin, talc, solid lubricants (such as stearic acid), magnesium stearate), calcium sulfate, vegetable oils (such as soybean oil, sesame oil, peanut oil, olive oil, etc.), polyols (such as propylene glycol, glycerin, mannitol, sorbitol, etc.), emulsifiers (such as Tween®), run Wet agents (such as sodium lauryl sulfate), colorants, flavoring agents, stabilizers, antioxidants, preservatives, pyrogen-free water, and the like.

The mode of administration of the compound or pharmaceutical composition of the present invention is not particularly limited, and representative modes of administration include, but are not limited to, oral, intratumoral, rectal, parenteral (intravenous, intramuscular or subcutaneous), and topical administration.

Solid dosage forms for oral administration include capsules, tablets, pills, powders, and granules. In these solid dosage forms, the active compound is mixed with at least one conventional inert excipient (or carrier), such as sodium citrate or dicalcium phosphate, or mixed with: (a) a filler or compatibilizer, for example, Starch, lactose, sucrose, glucose, mannitol and silicic acid; (b) a binder such as hydroxymethylcellulose, alginate, gelatin, polyvinylpyrrolidone, sucrose, and acacia; (c) a humectant such as glycerin; (d) a disintegrant, for example, Agar, calcium carbonate, potato starch or tapioca starch, alginic acid, certain complex silicates, and sodium carbonate; (e) a slow solvent such as paraffin; (f) an absorption accelerator, for example, a quaternary amine compound; (g) Wetting agents such as cetyl alcohol and glyceryl monostearate; (h) an adsorbent, for example, kaolin; and (i) a lubricant such as talc, calcium stearate, magnesium stearate, solid polyethylene glycol, sodium lauryl sulfate, or a mixture thereof. In capsules, tablets and pills, the dosage form may also contain a buffer.

Solid dosage forms such as tablets, dragees, capsules, pills, and granules can be prepared with coatings and shells such as enteric coatings and other materials known in the art. They may contain opacifying agents and the release of the active compound or compound in such compositions may be released in a portion of the digestive tract in a delayed manner. Examples of embedding components that can be employed are polymeric and waxy materials. If necessary, the active compound may also be in microencapsulated form with one or more of the above-mentioned excipients.

Liquid dosage forms for oral administration include pharmaceutically acceptable emulsions, solutions, suspensions, syrups or elixirs. In addition to the active compound, the liquid dosage form may contain inert diluents conventionally employed in the art, such as water or other solvents, solubilizers and emulsifiers, for example, ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil or a mixture of these substances.

In addition to these inert diluents, the compositions may contain adjuvants such as wetting agents, emulsifying and suspending agents, sweetening agents, flavoring agents and perfumes.

In addition to the active compound, the suspension may contain suspending agents, for example, ethoxylated isostearyl alcohol, polyoxyethylene sorbitol and sorbitan esters, microcrystalline cellulose, aluminum methoxide and agar or mixtures of these and the like.

Compositions for parenteral injection may comprise a physiologically acceptable sterile aqueous or nonaqueous solution, dispersion, suspension or emulsion, and a sterile powder for reconstitution into a sterile injectable solution or dispersion. Suitable aqueous and nonaqueous vehicles, diluents, solvents or vehicles include water, ethanol, polyols, and suitable mixtures thereof.

Dosage forms for the compounds of the invention for topical administration include ointments, powders, patches, propellants and inhalants. The active ingredient is admixed under sterile conditions with a physiologically acceptable carrier and any preservatives, buffers, or, if necessary, propellants.

The compounds of the invention may be administered alone or in combination with other pharmaceutically acceptable compounds.

When a pharmaceutical composition is used, a safe and effective amount of a compound of the invention is administered to a mammal (e.g., a human) in need of treatment wherein the dosage is a pharmaceutically effective dosage, for a 60 kg body weight, The dose to be administered is usually from 1 to 2000 mg, preferably from 5 to 500 mg. Of course, specific doses should also consider factors such as the route of administration, the health of the patient, etc., which are within the skill of the skilled physician.

The main advantages of the invention include:
1. A compound of formula I is provided.
2. Provided is a novel inhibitor of activity of protein kinases such as EGFR, FAK, SYK, FLT-3, Axl, CDK, JAK, etc., and preparation and application thereof, wherein the inhibitor can inhibit the above at a very low concentration Protein kinase activity.
3. A class of pharmaceutical compositions for treating diseases associated with protein kinase activity such as EGFR, FAK, SYK, FLT-3, Axl, CDK, JAK, etc. are provided.

The invention is further illustrated below in conjunction with specific embodiments. It is to be understood that the examples are not intended to limit the scope of the invention. The experimental methods in the following examples which do not specify the specific conditions are usually in accordance with conventional conditions or according to the conditions recommended by the manufacturer. Percentages and parts are by weight unless otherwise stated.

EXAMPLE 1. PREPARATION OF COMPOUND A1

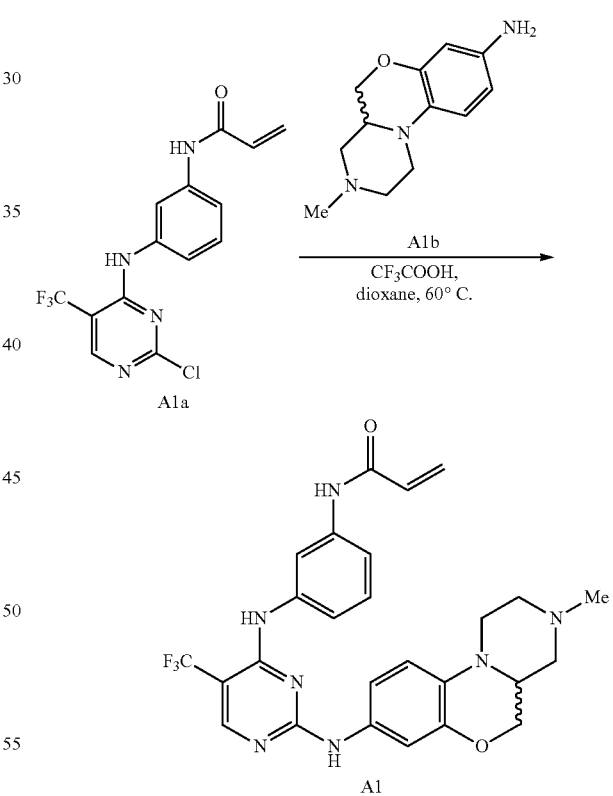

Compound A1a (34.2 mg, 0.10 mmol) and A1b (21.9 mg, 0.10 mmol) were dissolved in 2 mL of 1,4-dioxane, and 100 mg of trifluoroacetic acid was added. The reaction mixture were heated to 60° C. and reacted for 6 h. LCMS to monitor the reaction. Upon completion, the reaction was cooled to room temperature, and was concentrated under reduced pressure, the residue was purified via preparative HPLC to afford a yellow solid A1 (5.4 mg, yield 10%). $^1$H NMR (400 MHz, CD$_3$OD) δ 8.21 (s, 1H), 7.83-7.60 (m, 2H), 7.33 (dd, J=8.4 Hz, 8.0 Hz, 1H), 7.20 (d, J=7.6 Hz, 1H), 7.00-6.89 (m, 2H), 6.70-6.55 (br s, 1H), 6.47-6.30 (m, 2H), 5.77 (d, J=9.6 Hz, 2.4 Hz, 1H), 4.15 (dd, J=10.4 Hz, 2.4 Hz, 1H), 3.94-3.84 (m, 1H), 3.71-3.60 (m, 1H), 3.05-2.90 (m, 2H), 2.87-2.80 (m, 1H), 2.70-2.58 (m, 1H), 2.33 (s, 3H), 2.29-2.20 (m, 1H), 1.83 (t, J=10.8 Hz, 1H); MS m/z 526.2 [M+H]$^+$.

EXAMPLE 2. PREPARATION OF COMPOUND A1S

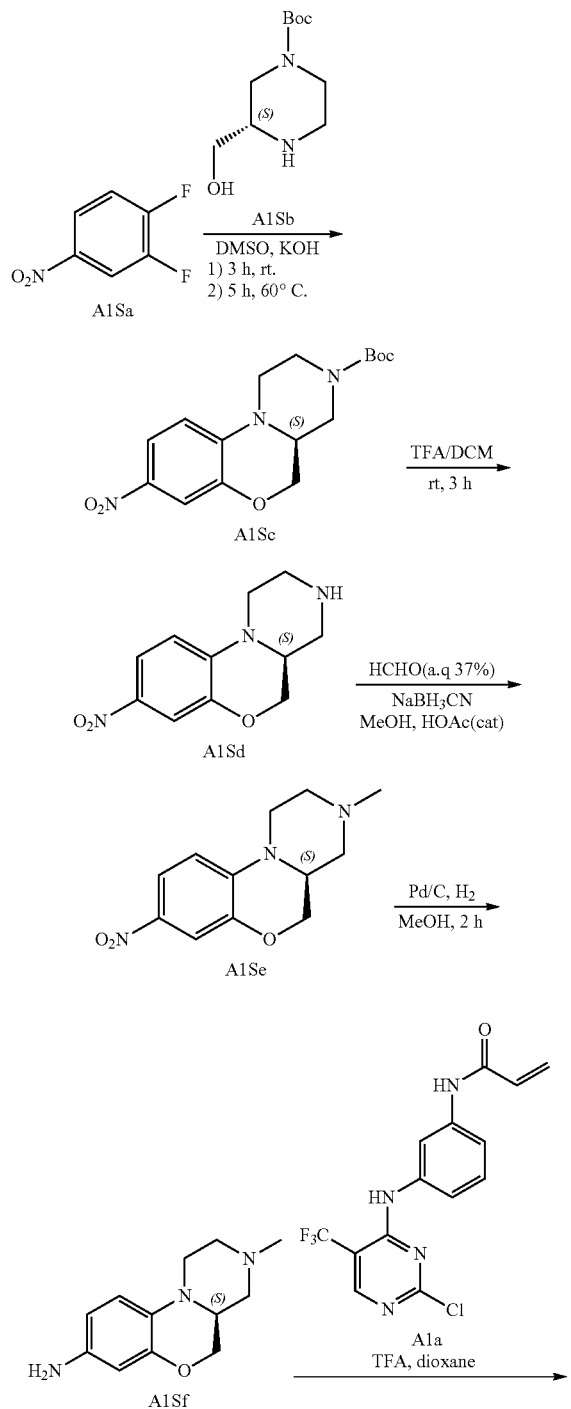

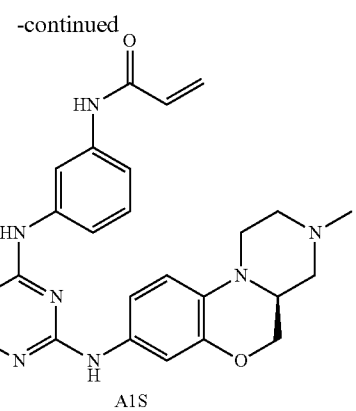

30 mL DMSO was stirred in room temperature and was added A1Sa (3.0 g, 18.8 mmol), compound A1Sb (3.0 g, 13.8 mmol, 100% ee) and KOH (2.4 g, 42.8 mmol) in turn. The reaction mixture was heated to 30° C. and stirred for 3 hours. The reaction was cooled to room temperature when it was finished, and was added 300 mL water, then the solid was precipitated from the solution, the mixture was stirred overnight at room temperature, and was filtrated. The filtrate were added to mixed solution (petroleum ether/EAOAc=5:1, 25 mL), and stirred for half hour at room temperature, and filtrated to afford yellow solid compound A1Sc (3.0 g, yield 64%). MS 336.2 [M+H]$^+$.

Compound A1Sc (2.0 g, 6.0 mmol) was dissolved in CH$_2$Cl$_2$ (20 mL), and was added trifluoroacetic acid (5 mL) under stirring at room temperature. After stirring 1 hour at room temperature, TLC results showed the reaction was finished. The reaction solution was concentrated in vacuo to remove trifluoroacetic acid, the residue was dissolved in CH$_2$Cl$_2$ (30 mL), and The pH value of the solution was adjusted to 9~10 by using saturated aq. Na$_2$CO$_3$, and separated. The water phase was exacted with CH$_2$Cl$_2$ twice. The combined organic phase was washed by brine (30 mL) once, dried over Na$_2$SO$_4$ and filtered. The filtrate was concentrated in vacuo to afford yellow solid A1Sd (1.2 g, yield 86%). MS m/z 236.1 [M+H]$^+$.

Compound A1Sd (1.2 g, 5.1 mmol) was dissolved in 20 mL MeOH, and was added formaldehyde (37% water solution, 6 mL), then was added 2 drops acetic acid. After stirring 30 minutes at room temperature, the reaction was added sodium cyanoborohydride (0.8 g, 12.7 mmol), then was stirred for 3 hours at room temperature. TLC results showed the reaction was finished. The reaction was concentrated in vacuo to afford crude product, which was purified via column chromatography (DCM/MeOH=60:1) to afford yellow solid A1Se (1.0 g. yield 79%). MS m/z 250.2 [M+H]$^+$.

To 3 mL of MeOH was added compound A1Se (145 mg, 0.58 mmol) and 15 mg Pd/C catalyst, the mixture was hydrogenated for 1 hour at room temperature and atmosphere pressure, TLC results showed the reaction was finished. The reaction mixture was filtrated through a celite pad. The filtrate was concentrated to afford brown solid compound A1Sf (100 mg, yield 79%), which was used for next step directly. MS m/z 220.2 [M+H]$^+$.

Compound A1a (100 mg, 0.29 mmol) and A1Sf (64 mg, 0.29 mmol) were dissolved in 1.5 mL 1,4-dioxane, and were added 100 mL trifluoroacetic acid (100 mL) dropwise. The reaction mixture were heated to 60° C. and reacted for 6 hours. When the reaction was finished, aq. Na$_2$HCO$_3$ was added to adjust the pH value of the solution to 8-9, then CH$_2$Cl$_2$ (10 mL×3) was added for extraction 3 times, the combined organic phase was dried over Na$_2$SO$_4$ and filtered. The filtrate was concentrated in vacuo, the residue was purified by preparative TLC, then by preparative HPLC to afford white solid compound A1S (29.3 mg, 100% ee). $^1$H NMR (CD$_3$OD, 400 Hz): δ 8.21 (s, 1H), 7.74 (br, 1H), 7.65 (br, 1H), 7.33 (dd, J=8.0 Hz, 8.00 Hz, 1H), 7.21-7.19 (m, 1H), 6.97-6.94 (m, 2H), 6.62 (br, 1H), 6.47-6.33 (m, 2H), 5.77 (dd, J=9.6 Hz, 2.4 Hz, 1H), 4.15 (dd, J=10.8 Hz, 2.0 Hz, 1H), 3.88 (t, J=9.6 Hz, 1H), 3.66 (d, J=11.6 Hz, 1H), 3.05-2.96 (m, 2H), 2.86 (d, J=10.8 Hz, 1H), 2.66 (td, J=12.0 Hz, 2.4 Hz, 1H), 2.37 (s, 3H), 2.28 (td, J=12.0 Hz, 3.2 Hz, 1H), 1.88 (t, J=10.8 Hz, 1H); MS m/z 526.2 [M+H]$^+$.

EXAMPLE 3. PREPARATION OF COMPOUND A1R

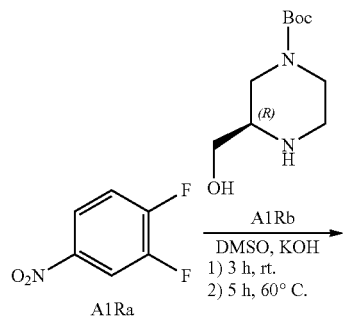

According to the preparation of intermediate A1Sf in the Example 4, the intermediate A1Rf was prepared by using A1Rb (100% ee) as starting materials. Compound Aa1a (80 mg, 0.23 mmol) and A1Rf (51 mg, 0.23 mmol) were dissolved in 1.5 mL 1,4-dioxane, then was added trifluoroacetic acid (100 mL) dropwise. The reaction mixture was heated to 60° C. and reacted for 6 hours. When the reaction was finished, aq. NaHCO$_3$ was added to adjust the pH value of the solution to 8~9, then CH$_2$Cl$_2$ (10 mL×3) was added for extraction 3 times, the combined organic phase was dried over Na$_2$SO$_4$ and filtered. The filtrate was concentrated in vacuo, the residue was purified by preparative TLC, then by preparative HPLC to afford white solid compound A1R (12.5 mg, 99.9% ee). $^1$H NMR (CD$_3$OD, 400 Hz): δ 8.21 (s, 1H), 7.74 (br, 1H), 7.64 (br, 1H), 7.33 (t, J=8.0 Hz, 1H), 7.21-7.19 (m, 1H), 6.96-6.94 (m, 2H), 6.62 (br, 1H), 6.47-6.33 (m, 2H), 5.77 (dd, J=9.6 Hz, 2.4 Hz, 1H), 4.15 (dd, J=10.4 Hz, 2.4 Hz, 1H), 3.88 (t, J=9.6 Hz, 1H), 3.65 (d, J=12.4 Hz, 1H), 3.00-2.94 (m, 2H), 2.84 (d, J=10.8 Hz, 1H), 2.65 (td, J=12.0 Hz, 2.4 Hz, 1H), 2.34 (s, 3H), 2.25 (td, J=11.6 Hz, 3.2 Hz, 1H), 1.84 (t, J=10.8 Hz, 1H); MS m/z 526.2 [M+H]$^+$.

EXAMPLE 4. PREPARATION OF COMPOUND A2S

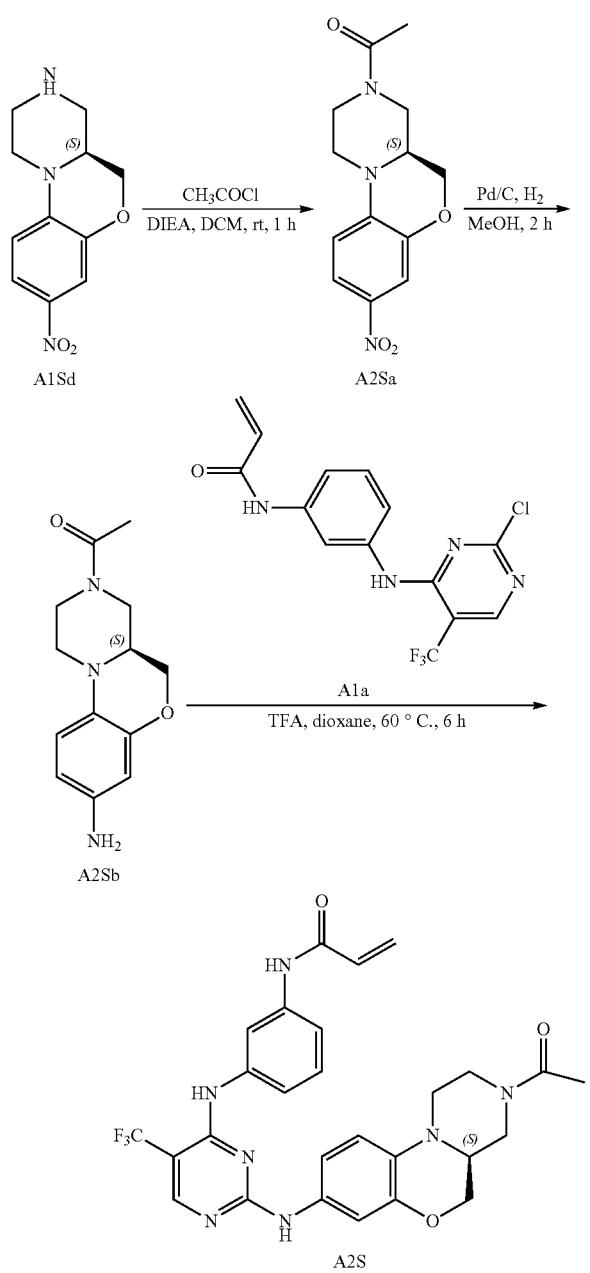

At room temperature compound A1Sd (180 mg, 0.77 mmol) was dissolved in 4 mL CH$_2$Cl$_2$, and was added DIPEA (200 mg, 1.54 mmol), then added acetyl chloride (90 mg, 1.16 mmol). The reaction was stirred for 1 hour at room temperature, TLC results showed the reaction was finished. The reaction was diluted by CH$_2$Cl$_2$ (50 mL). The organic phase was washed by brine (10 mL×2), dried over Na$_2$SO$_4$ and filtered. The filtrate was concentrated in vacuo to afford yellow solid compound A2Sa (150 mg).

At room temperature compound A2Sa (150 mg, 0.54 mmol) was dissolved in 3 mL MeOH, and was added 15 mg Pd/C catalyst, the mixture was hydrogenated for 1 hour at room temperature and atmosphere pressure, TLC results showed the reaction was finished. The reaction mixture was filtrated through a celite pad. The filtrate was concentrated to afford brown solid compound A2Sb (100 mg).

Compound A1a (40 mg, 0.11 mmol) and compound A2Sb (30 mg, 0.12 mmol) were dissolved in 1 mL dioxane, then was added 100 mg trifluoroacetic acid dropwise. The reaction mixture was heated to 60° C. and reacted for 6 hours. When the reaction was finished, aq. NaHCO$_3$ was added to adjust the pH value of the solution to 8~9, then CH$_2$Cl$_2$ (10 mL×3) was added for extraction 3 times, the combined organic phase was dried over Na$_2$SO$_4$ and filtered. The filtrate was concentrated in vacuo to afford crude product, the crude product was purified via column chromatography (EtOAC/petroleum ether=1:1) to afford white solid compound A2S (22 mg, yield 34%). $^1$H NMR (CDCl$_3$, 400 MHz): δ 8.29 (s, 1H), 7.32 (t, J=8.0 Hz, 2H), 7.26-7.03 (m, 3H), 7.00-6.89 (m, 1H), 6.86 (br s, 1H), 6.75-6.65 (m, 1H), 6.46 (d, J=16.8 Hz, 1H), 6.31-6.20 (m, 1H), 5.79 (d, J=10.4 Hz, 1H), 4.72-4.59 (m, 1H), 4.30-4.20 (m, 1H), 4.10-3.83 (m, 1.5H), 3.78-3.63 (m, 1.5H), 3.43-3.35 (m, 0.5H), 3.14-2.58 (m, 3H), 2.45-2.36 (m, 0.5H), 2.20-2.10 (m, 3H); MS m/z 554.2 (M+H)$^+$.

EXAMPLE 5. PREPARATION OF COMPOUND A2R

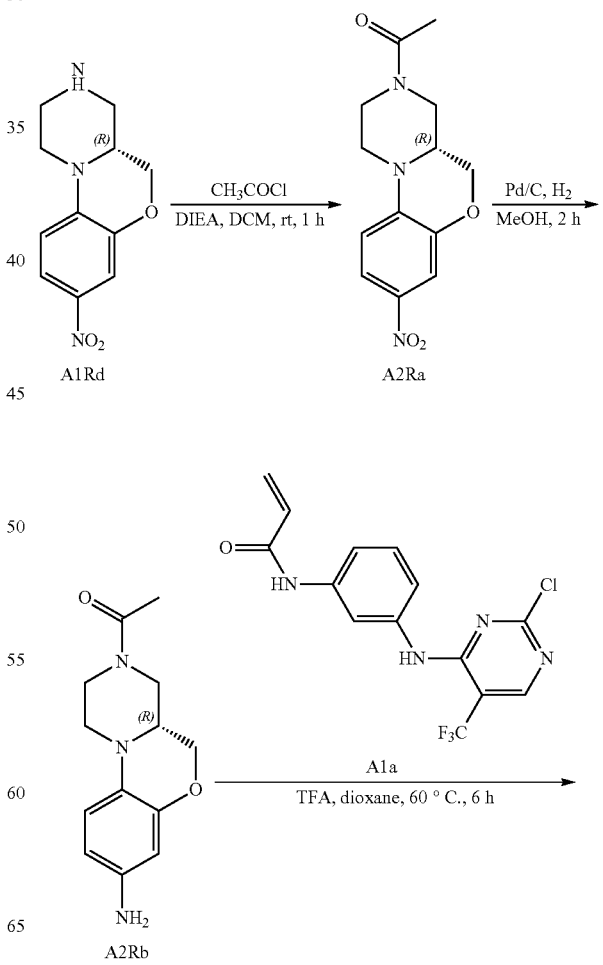

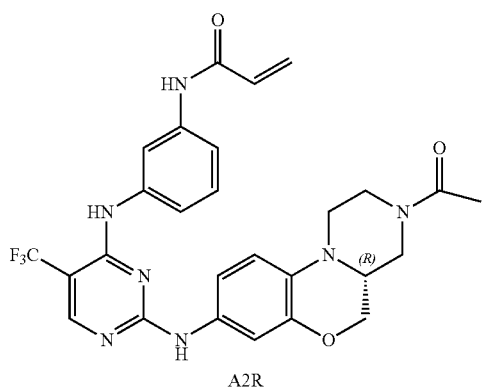

A2R

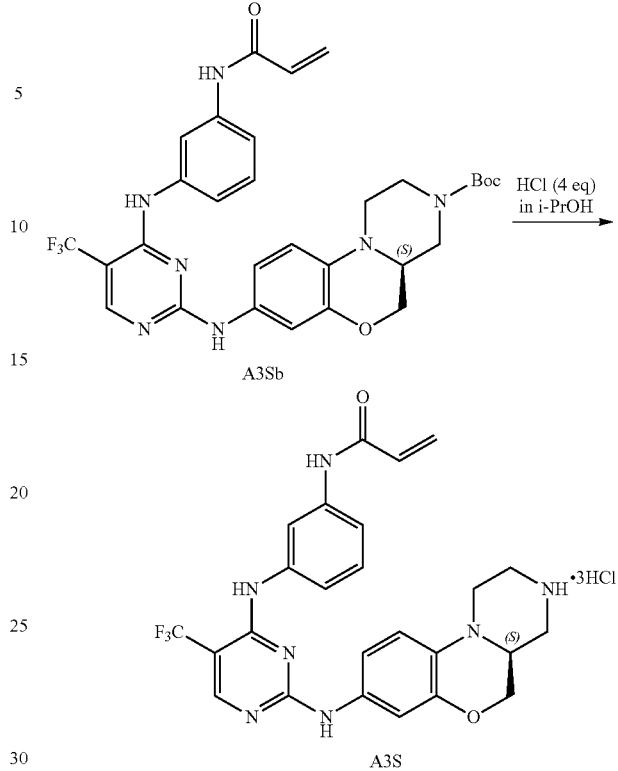

A3Sb

A3S

According to the preparation method in the Example 4, the intermediate A2Rb was prepared by using A1Rd as starting materials. Compound A1a (40 mg, 0.11 mmol) and A2Rb (30 mg, 0.12 mmol) were dissolved in 1 mL 1,4-dioxane, then was added trifluoroacetic acid (100 mg) dropwise. The reaction mixture was heated to 60° C. and reacted for 6 hours. When the reaction was finished, aq. NaHCO$_3$ was added to adjust the pH value of the solution to 8~9, then CH$_2$Cl$_2$ (10 mL×3) was added for extraction 3 times, the combined organic phase was dried over Na$_2$SO$_4$ and filtered. The filtrate was concentrated in vacuo, the crude product was purified via column chromatography (petroleum ether/EtOAC=1/1) to afford white solid compound A2R (22 mg, yield 34%). $^1$H NMR (CDCl$_3$, 400 Hz): δ 8.29 (s, 1H), 7.32 (t, J=8.0 Hz, 2H), 7.26-7.03 (m, 3H), 7.00-6.89 (m, 1H), 6.86 (br s, 1H), 6.75-6.65 (m, 1H), 6.46 (d, J=16.8 Hz, 1H), 6.31-6.20 (m, 1H), 5.79 (d, J=10.4 Hz, 1H), 4.72-4.59 (m, 1H), 4.30-4.20 (m, 1H), 4.10-3.83 (m, 1.5H), 3.78-3.63 (m, 1.5H), 3.43-3.35 (m, 0.5H), 3.14-2.58 (m, 3H), 2.45-2.36 (m, 0.5H), 2.20-2.10 (m, 3H); MS m/z 554.2 (M+H)$^+$.

EXAMPLE 6. PREPARATION OF COMPOUND A3S

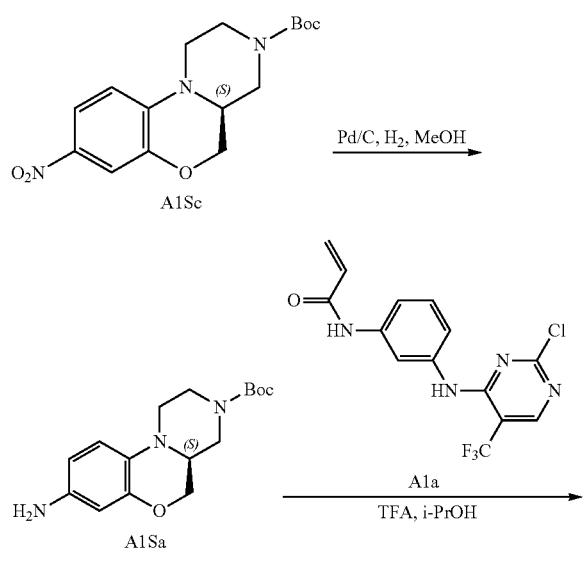

Compound A1Sc (300 mg, 0.896 mmol) was put in 50 mL flask, and was dissolved by using MeOH (10 mL), then was added Pd/C (10%, 50 mg), the flask air was exchanged by H$_2$, The reaction mixture was stirred for 1 hour at room temperature and H$_2$ atmosphere. TLC results indicated the reaction was complete. The reaction mixture was filtrated and concentrated in vacuo to afford brown solid compound A3Sa (280 mg, yield 99%). MS m/z 306.2 (M+H)$^+$.

Compound A1a (120 mg, 0.351 mmol) and A3Sa (107 mg, 0.351 mmol) were dissolved in isopropyl alcohol (3 mL), then was added trifluoroacetic acid (40 mg, 0.351 mmol) dropwise. The reaction mixture was heated to 40° C. and reacted for 16 hours. When the reaction was finished, the reaction mixture was poured into aq. NaHCO$_3$, extracted with EtOAc 3 times (10 mL×3), the combined organic phase was washed by brine (10 mL), dried over Na$_2$SO$_4$ and filtered. The filtrate was concentrated in vacuo, the crude product was purified via preparative TLC (CH$_2$Cl$_2$/MeOH=30/1) to afford pale yellow solid compound A3Sb (180 mg, yield 84%). MS m/z 612.2 (M+H)$^+$.

Compound A3Sb (5 mg, 0.008 mmol) was dissolved in isopropyl alcohol (1 mL), and was added HCl (1% isopropyl alcohol solution, 109 mg, 0.033 mmol). The reaction mixture was heated to 70° C. and reacted for 16 hours. TLC results indicated the reaction was complete. The reaction solvent were remove in vacuo, and the residue were mashed by using dry Et$_2$O to afford yellow solid A3S HCl salt (4 mg, yield 80%). $^1$H NMR (DMSO-d$_6$, 400 MHz) δ 10.30 (s, 1H), 9.74-9.58 (br, 1H), 9.25-9.10 (m, 2H), 9.10-8.78 (br, 1H), 8.34 (s, 1H), 7.85-7.60 (m, 2H), 7.32 (dd, J=8.4 Hz, 8.0 Hz, 1H), 7.22-6.80 (m, 3H), 6.77-6.49 (m, 1H), 6.48 (dd, J=17.2 Hz, 10.0 Hz, 1H), 6.25 (dd, J=17.2 Hz, 2.0 Hz, 1H), 5.75 (dd, J=10.4 Hz, 2.0 Hz, 1H), 4.25-4.18 (m, 1H), 3.98-3.70 (m, 4H), 3.42-3.20 (m, 3H), 3.10-2.97 (m, 1H), 2.85-2.63 (m, 2H); MS m/z 512.3 [M+H]$^+$.

EXAMPLE 7. PREPARATION OF COMPOUND A3R

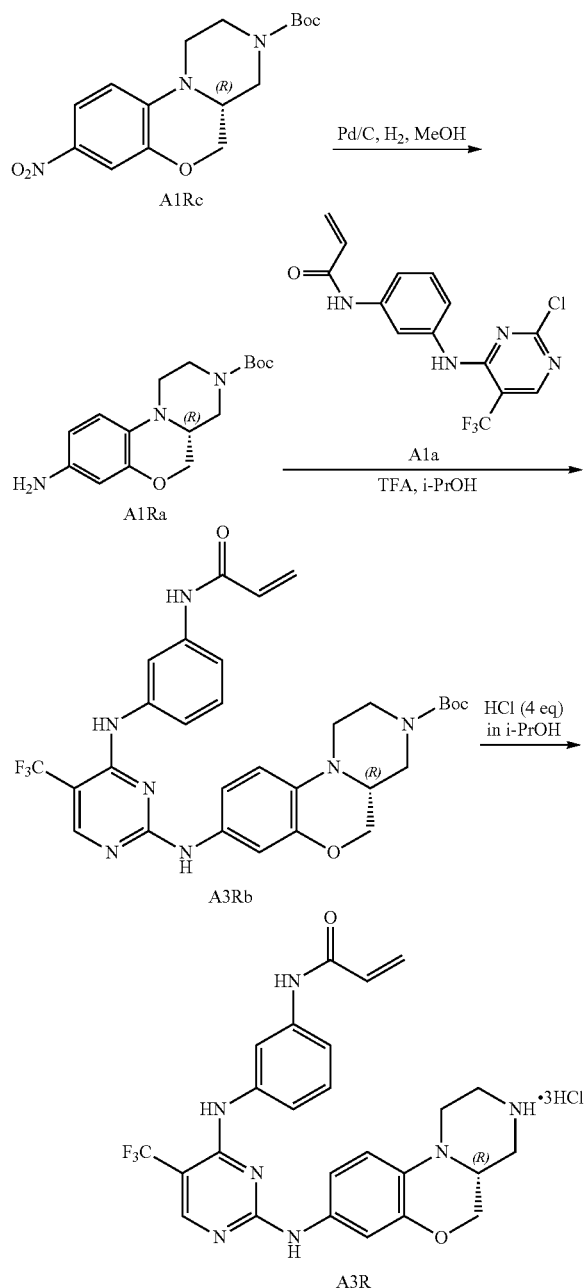

According to the preparation method in the Example 6, Compound A3Rb was made by using A1Rc as starting material. Compound A3Rb (45 mg, 0.074 mmol) was dissolved in isopropyl alcohol (3 mL), and was added HCl (1% isopropyl alcohol solution, 986 mg, 0.296 mmol). The reaction mixture was heated to 70° C. and reacted for 16 hours. TLC results indicated the reaction was complete. The reaction solvent were remove in vacuo, and the residue were mashed by using $Et_2O$ to afford yellow solid A3R HCl salt (33.20 mg, yield 74%). $^1$H NMR (DMSO-$d_6$, 400 MHz) δ 10.37 (s, 1H), 9.93-9.70 (br, 1H), 9.40-9.20 (m, 2H), 9.20-8.97 (br, 1H), 8.36 (s, 1H), 7.83-7.60 (m, 2H), 7.32 (dd, J=8.0 Hz, 8.0 Hz, 1H), 7.22-6.80 (m, 3H), 6.73-6.44 (m, 2H), 6.25 (dd, J=17.2 Hz, 2.0 Hz, 1H), 5.75 (dd, J=10.4 Hz, 2.0 Hz, 1H), 4.25-4.18 (m, 1H), 4.10-3.80 (m, 4H), 3.42-3.22 (m, 3H), 3.10-2.94 (m, 1H), 2.90-2.63 (m, 2H); MS m/z 512.3 $[M+H]^+$.

EXAMPLE 8. PREPARATION OF COMPOUND A4R

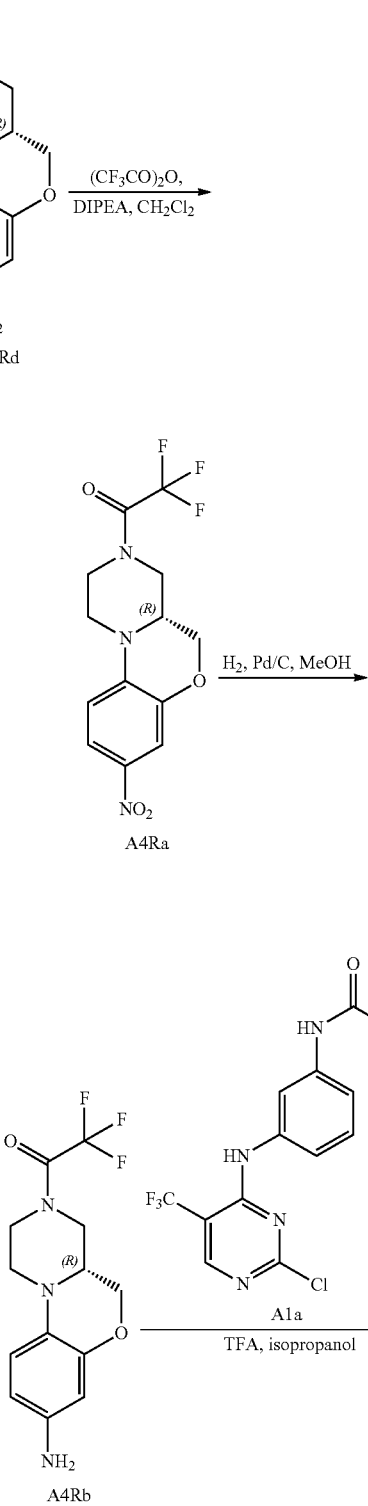

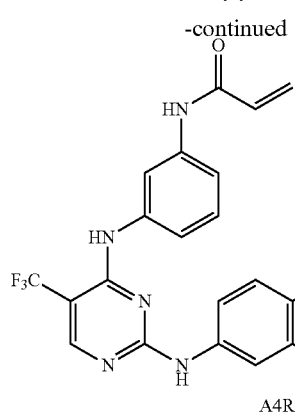

A4R

Compound A1Rd trifluoroacetate salt (500 mg, 1.43 mmol) and DIPEA (554 mg, 4.29 mmol) were added into CH$_2$Cl$_2$ (20 mL), then the mixture was added trifluoroacetic anhydride (601 mg, 2.86 mmol), the reaction mixture was stirred for 2 hours at room temperature. The LCMS indicated the reaction was complete, the reaction mixture was poured into H$_2$O (50 mL), extracted with CH$_2$Cl$_2$ (20 mL×4), the combined organic phase was washed by brine (10 mL×2), dried over Na$_2$SO$_4$ and filtered. The filtrate was concentrated in vacuo, the residue was purified via preparative TLC (petroleum ether/EtOAC=2:1) to afford compound yellow solid A4Ra (320 mg, yield 68%). $^1$H NMR (CDCl$_3$, 400 MHz) δ 7.86-7.80 (m, 1H), 7.70 (d, J=2.4 Hz, 1H), 6.82 and 6.78 (two d, J=9.2 Hz, 8.8 Hz, 1H), 4.71-4.65 and 4.60-4.55 (two m, 1H), 4.39-4.33 (m, 1H), 4.19-3.90 (m, 3H), 3.52-3.36 (m, 2H), 3.19-3.00 (m, 2H), 2; MS m/z 332.2 [M+H]$^+$.

Compound A4Ra (200 mg, 0.60 mmol) was dissolved in MeOH (6 mL), then was added Pd/C (10%, 100 mg) carefully, the reaction system was exchange with H$_2$ three times. The reaction mixture was stirred for 2 hours at room temperature. The LCMS indicated the reaction was complete; the reaction mixture was filtrated through a celite pad. The celite pad was washed by MeOH three times, the combined organic phase was concentrated in vacuo to afford brown solid A4Rb (170 mg, yield 93%). MS m/z 302.3 [M+H]$^+$.

Compound A4Rb (17 mg, 0.06 mmol) and compound A1a (21 mg, 0.06 mmol) were dissolved in isopropyl alcohol (2 mL), then was added trifluoroacetic acid (10 mg, 0.09 mmol). The reaction mixture was heated to 40° C. and reacted for 16 hours under stirring. The reaction mixture was cooled to room temperature, then was poured into saturated aq. NaHCO$_3$, extracted with EtOAc (10 mL×3), the combined organic phase was washed by brine (10 mL), dried over Na$_2$SO$_4$ and filtered. The filtrate was concentrated in vacuo, the residue was purified via preparative TLC (CH$_2$Cl$_2$/MeOH=35/1) to afford pale yellow solid compound A4R (15 mg, yield 44%). $^1$H NMR (DMSO-d$_6$, 400 MHz) δ 10.15 (s, 1H), 9.58-9.37 (br, 1H), 8.78-8.61 (br, 1H), 8.31 (s, 1H), 7.74 (s, 1H), 7.64-7.56 (m, 1H), 7.32 (dd, J=8.4 Hz, 8.0 Hz, 1H), 7.20-7.10 (m, 1H), 7.07-7.01 (m, 1H), 7.00-6.83 (m, 1H), 6.66-6.45 (m, 1H), 6.44-6.38 (m, 1H), 6.28-6.20 (m, 1H), 5.79-5.68 (m, 1H), 4.39-4.24 (m, 2H), 3.96-3.72 (m, 3H), 3.50-3.40 (m, 0.5H), 3.19-2.95 (m, 2H), 2.79-2.71 (m, 0.5H), 2.67-2.53 (m, 1H); MS m/z 608.1 (M+H)$^+$.

EXAMPLE 9. PREPARATION OF COMPOUND A5R

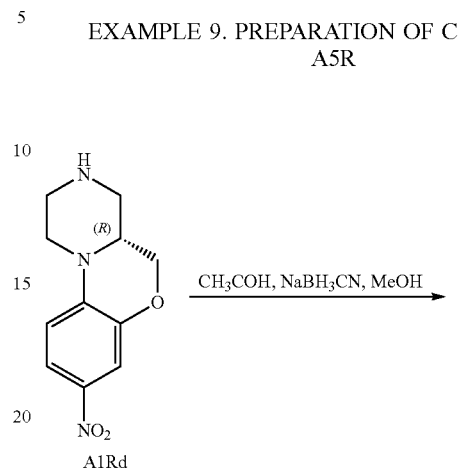

A1Rd

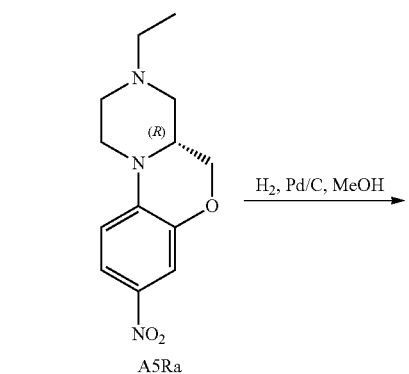

A5Ra

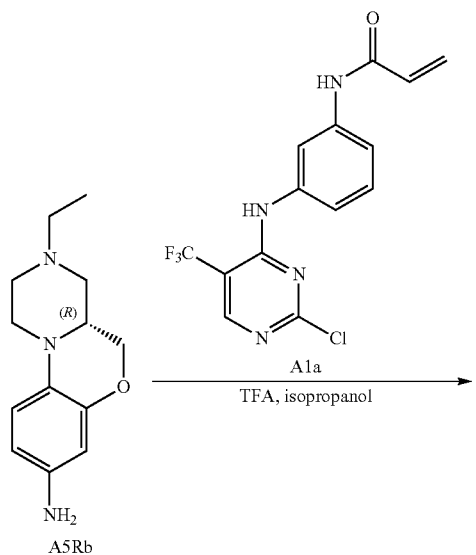

A5Rb

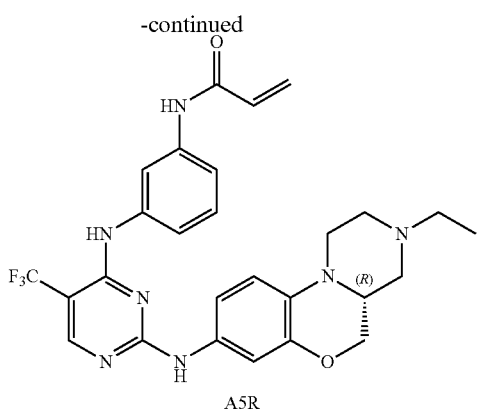

A5R

Compound A1Rd trifluoroacetate salt (590 mg, 1.69 mmol) and acetaldehyde (1.30 g, 29.45 mmol) were dissolved in MeOH (30 mL), then the mixture was added sodium cyanoborohydride (678 mg, 10.79 mmol) in batches to maintain the reaction temperature lower than 10° C., the reaction mixture was stirred for 2 hours at room temperature, the reaction system was stirred for 1 hour at room temperature. TLC results showed the reaction was finished. The reaction solvent were remove in vacuo, and the residue were dispersed in saturated aq. NaHCO$_3$, extracted with EtOAc three time (25 mL×3), the combined organic phase was washed by brine, dried over Na$_2$SO$_4$ and filtered. The filtrate was concentrated in vacuo, the residue was purified via column chromatography (CH$_2$Cl$_2$/MeOH=50/1) to afford yellow solid compound A5Ra (430 mg, yield 97%). $^1$H NMR (CDCl$_3$, 400 MHz) δ 7.80 (dd, J=9.2 Hz, 2.8 Hz, 1H), 7.65 (d, J=2.8 Hz, 1H), 6.74 (d, J=9.2 Hz, 1H), 4.26 (dd, J=10.8 Hz, 2.8 Hz, 1H), 4.00 (dd, J=10.8 Hz, 8.4 Hz, 1H), 3.80-3.74 (m, 1H), 3.43-3.36 (m, 1H), 3.08-2.90 (m, 3H), 2.50-2.46 (m, 2H), 2.21-2.14 (m, 1H), 1.81 (dd, J=7.6 Hz, 7.2 Hz, 1H), 1.13 (t, J=7.2 Hz, 3H); MS m/z 264.2 [M+H]$^+$.

Compound A5Ra (408 mg, 1.55 mmol) was put in 50 mL flask, and was dissolved by using MeOH (3 mL), then was added Pd/C (10%, 4 mg), the reaction system was exchanged with H$_2$. The reaction mixture was stirred for 1 hour at room temperature H$_2$ atmosphere. TLC results indicated the reaction was complete; the reaction mixture was filtrated and concentrated in vacuo to afford brown solid compound A5Rb (361 mg, yield 99%), which was used for next step directly without further purification.

Compound A5Rb (361 mg, 1.55 mmol) and Compound A1a (583 mg, 1.70 mmol) were dissolved in dry isopropyl alcohol (8 mL), then was added trifluoroacetic acid (194 mg, 1.70 mmol). The reaction mixture was heated to 40° C. and reacted for 16 hours under stirring. The reaction mixture was cooled to room temperature, then was poured into saturated aq. NaHCO$_3$ (10 mL), extracted with EtOAc (20 mL×3), the combined organic phase was washed by brine (20 mL), dried over Na$_2$SO$_4$ and filtered. The filtrate was concentrated in vacuo, the residue was purified via column chromatography (DCM/MeOH=50:1) to afford pale yellow solid compound A5R (416 mg, yield 50%). $^1$H NMR (DMSO-d$_6$, 400 MHz) δ 10.17 (s, 1H), 9.49-9.39 (br, 1H), 8.80-8.60 (br, 1H), 8.30 (s, 1H), 7.70 (s, 1H), 7.65-7.57 (m, 1H), 7.32 (dd, J=8.0 Hz, 8.0 Hz, 1H), 7.18-7.08 (m, 1H), 7.04 (dd, J=8.8 Hz, 2.0 Hz, 1H), 6.89-6.79 (br, 1H), 6.53-6.38 (m, 2H), 6.25 (dd, y=16.8 Hz, 1.6 Hz, 1H), 5.75 (dd, J=10.0 Hz, 1.6 Hz, 1H), 4.19-4.11 (m, 1H), 3.85-3.75 (m, 1H), 3.60-3.50 (m, 1H), 2.96-2.80 (m, 3H), 2.50-2.43 (m, 1H), 2.41-2.29 (m, 2H), 2.09-1.99 (m, 1H), 1.62 (dd, J=10.8 Hz, 10.8 Hz, 1H), 1.02 (t, J=7.2 Hz, 3H); MS m/z 540.2 (M+H)$^+$.

EXAMPLE 10. PREPARATION OF COMPOUND A6R

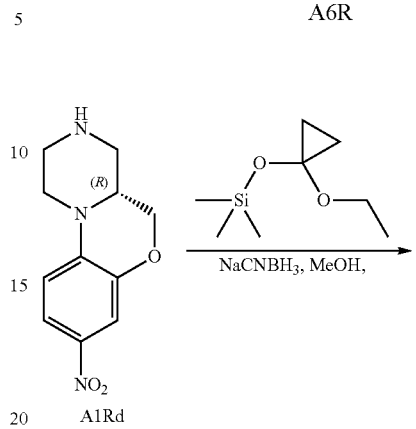

A1Rd

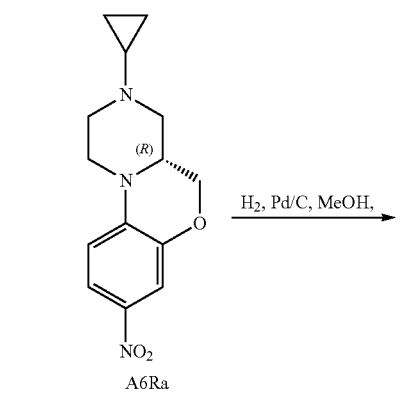

A6Ra

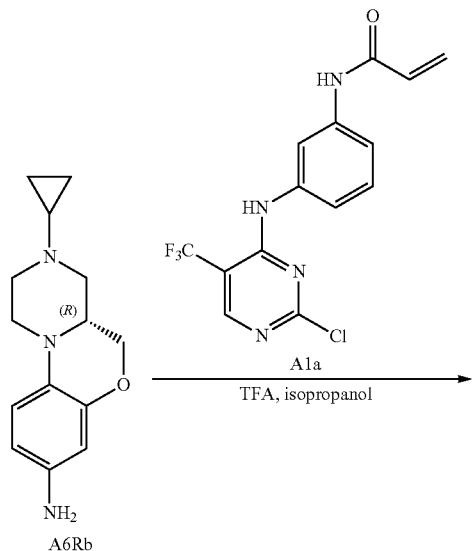

A6Rb

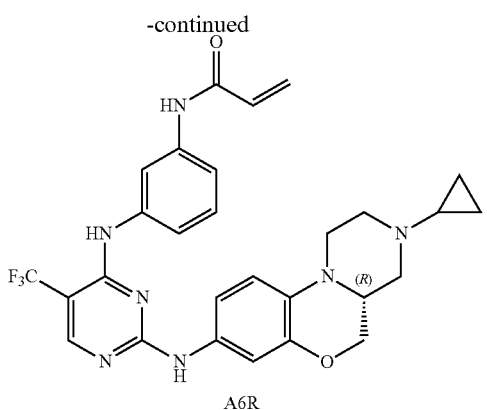

A6R

Compound A1Rd trifluoroacetate salt (150 mg, 0.43 mmol) and (1-ethoxycyclopropoxy) trimethylsilane (234 mg, 1.34 mmol) were dissolved in MeOH (6 mL), and the mixture was added sodium cyanoborohydride (84 mg, 1.34 mmol) under stirring. The reaction mixture was heated to 65° C. and reacted for 16 hours under stirring. TLC results indicated the reaction was complete; The reaction mixture was cooled to room temperature, then was poured into saturated aq. $Na_2CO_3$ (10 mL), extracted with EtOAc (15 mL×3), the combined organic phase was washed by brine (15 mL), dried over $Na_2SO_4$ and filtered. The filtrate was concentrated in vacuo, the residue was purified via column chromatography (DCM/MeOH=60:1) to afford yellow solid compound A6Ra (95 mg, yield 80%). $^1$H NMR (CDCl$_3$, 400 MHz) δ 7.79 (dd, J=9.2 Hz, 2.4 Hz, 1H), 7.65 (d, J=2.8 Hz, 1H), 6.73 (d, J=9.2 Hz, 1H), 4.26 (dd, J=10.8 Hz, 3.2 Hz, 1H), 3.99 (dd, J=10.8 Hz, 8.4 Hz, 1H), 3.79-3.71 (m, 1H), 3.34-3.27 (m, 1H), 3.15-3.08 (m, 1H), 3.04-2.88 (m, 2H), 2.47-2.41 (m, 1H), 2.09 (dd, J=10.4 Hz, 10.0 Hz, 1H), 1.71-1.65 (m, 1H), 0.55-0.42 (m, 4H); MS m/z 276.2 $[M+H]^+$.

Compound A6Ra (30 mg, 0.11 mmol) was put in 50 mL flask, and was dissolved by using MeOH (3 mL), then was added Pd/C (10%, 4 mg), the air in reaction system was exchanged with $H_2$. The reaction mixture was stirred for 1 hour at room temperature $H_2$ atmosphere. TLC results indicated the reaction was complete; the reaction mixture was filtrated and concentrated in vacuo to afford brown solid compound A6Rb (25 mg, yield 94%), which was used for next step without further purification.

Compound A6Rb (25 mg, 0.10 mmol) and Compound A1a (29 mg, 0.08 mmol) were dissolved in dry isopropyl alcohol (2 mL), then was added trifluoroacetic acid (11 mg, 0.10 mmol). The reaction mixture was heated to 40° C. and reacted for 16 hours under stirring. TLC results indicated the reaction was complete; The reaction mixture was cooled to room temperature, then was poured into saturated aq. $Na_2CO_3$ (10 mL), extracted with EtOAc (10 mL×3), the combined organic phase was washed by brine (10 mL), dried over $Na_2SO_4$ and filtered. The filtrate was concentrated in vacuo, the residue was purified via column chromatography (DCM/MeOH=20:1) to afford A6R (30 mg, yield 64%). $^1$H NMR (DMSO-d$_6$, 400 MHz) δ 10.16 (s, 1H), 9.50-9.35 (br, 1H), 8.78-8.60 (m, 1H), 8.30 (s, 1H), 7.69 (s, 1H), 7.65-7.57 (m, 1H), 7.31 (dd, J=8.0 Hz, 8.0 Hz, 1H), 7.18-7.08 (m, 1H), 7.03 (dd, J=8.8 Hz, 2.4 Hz, 1H), 6.94-6.78 (m, 1H), 6.60-6.38 (m, 2H), 6.24 (dd, J=16.8 Hz, 2.0 Hz, 1H), 5.75 (dd, J=10.4 Hz, 2.0 Hz, 1H), 4.20-4.12 (m, 1H), 3.84-3.77 (m, 1H), 3.59-3.51 (m, 1H), 3.00-2.74 (m, 3H), 2.51-2.32 (m, 2H), 1.94 (dd, J=10.4 Hz, 10.4 Hz, 1H), 1.67-1.61 (m, 1H), 0.47-0.30 (m, 4H); MS m/z 552.3 $[M+H]^+$.

EXAMPLE 11. PREPARATION OF COMPOUND A7R

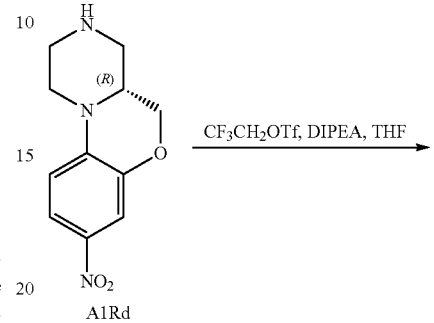

A1Rd

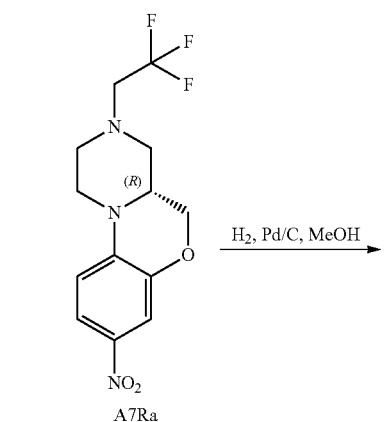

A7Ra

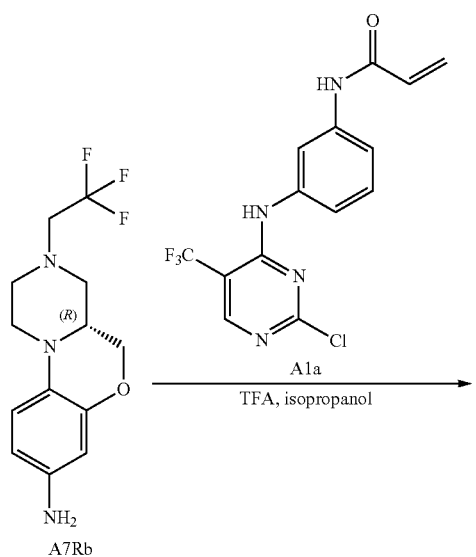

A7Rb

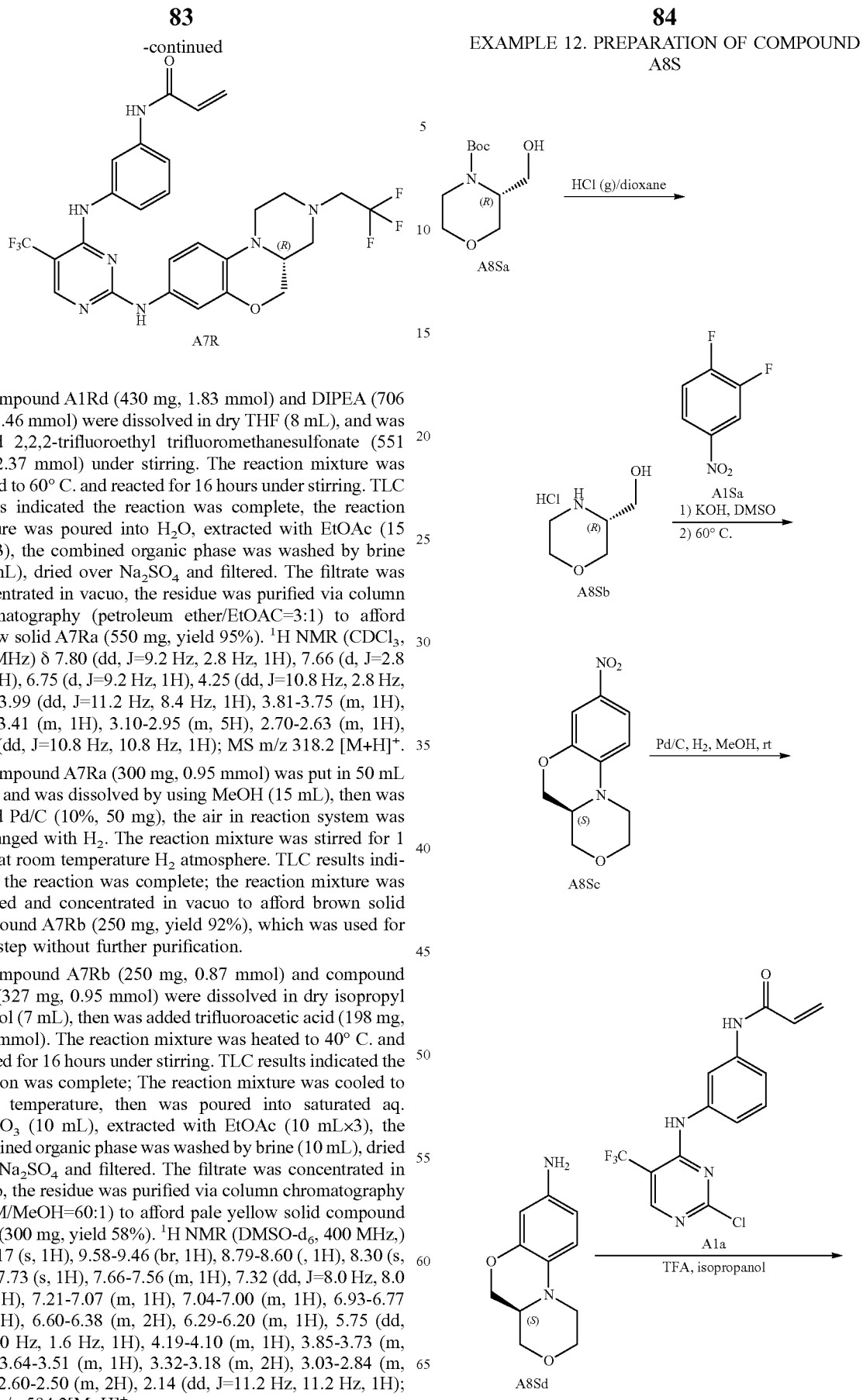

EXAMPLE 12. PREPARATION OF COMPOUND A8S

Compound A1Rd (430 mg, 1.83 mmol) and DIPEA (706 mg, 5.46 mmol) were dissolved in dry THF (8 mL), and was added 2,2,2-trifluoroethyl trifluoromethanesulfonate (551 mg, 2.37 mmol) under stirring. The reaction mixture was heated to 60° C. and reacted for 16 hours under stirring. TLC results indicated the reaction was complete, the reaction mixture was poured into H₂O, extracted with EtOAc (15 mL×3), the combined organic phase was washed by brine (15 mL), dried over Na₂SO₄ and filtered. The filtrate was concentrated in vacuo, the residue was purified via column chromatography (petroleum ether/EtOAC=3:1) to afford yellow solid A7Ra (550 mg, yield 95%). ¹H NMR (CDCl₃, 400 MHz) δ 7.80 (dd, J=9.2 Hz, 2.8 Hz, 1H), 7.66 (d, J=2.8 Hz, 1H), 6.75 (d, J=9.2 Hz, 1H), 4.25 (dd, J=10.8 Hz, 2.8 Hz, 1H), 3.99 (dd, J=11.2 Hz, 8.4 Hz, 1H), 3.81-3.75 (m, 1H), 3.48-3.41 (m, 1H), 3.10-2.95 (m, 5H), 2.70-2.63 (m, 1H), 2.31 (dd, J=10.8 Hz, 10.8 Hz, 1H); MS m/z 318.2 [M+H]⁺.

Compound A7Ra (300 mg, 0.95 mmol) was put in 50 mL flask, and was dissolved by using MeOH (15 mL), then was added Pd/C (10%, 50 mg), the air in reaction system was exchanged with H₂. The reaction mixture was stirred for 1 hour at room temperature H₂ atmosphere. TLC results indicated the reaction was complete; the reaction mixture was filtrated and concentrated in vacuo to afford brown solid compound A7Rb (250 mg, yield 92%), which was used for next step without further purification.

Compound A7Rb (250 mg, 0.87 mmol) and compound A1a (327 mg, 0.95 mmol) were dissolved in dry isopropyl alcohol (7 mL), then was added trifluoroacetic acid (198 mg, 1.74 mmol). The reaction mixture was heated to 40° C. and reacted for 16 hours under stirring. TLC results indicated the reaction was complete; The reaction mixture was cooled to room temperature, then was poured into saturated aq. Na₂CO₃ (10 mL), extracted with EtOAc (10 mL×3), the combined organic phase was washed by brine (10 mL), dried over Na₂SO₄ and filtered. The filtrate was concentrated in vacuo, the residue was purified via column chromatography (DCM/MeOH=60:1) to afford pale yellow solid compound A7R (300 mg, yield 58%). ¹H NMR (DMSO-d₆, 400 MHz,) δ 10.17 (s, 1H), 9.58-9.46 (br, 1H), 8.79-8.60 (, 1H), 8.30 (s, 1H), 7.73 (s, 1H), 7.66-7.56 (m, 1H), 7.32 (dd, J=8.0 Hz, 8.0 Hz, 1H), 7.21-7.07 (m, 1H), 7.04-7.00 (m, 1H), 6.93-6.77 (m, 1H), 6.60-6.38 (m, 2H), 6.29-6.20 (m, 1H), 5.75 (dd, J=10.0 Hz, 1.6 Hz, 1H), 4.19-4.10 (m, 1H), 3.85-3.73 (m, 1H), 3.64-3.51 (m, 1H), 3.32-3.18 (m, 2H), 3.03-2.84 (m, 3H), 2.60-2.50 (m, 2H), 2.14 (dd, J=11.2 Hz, 11.2 Hz, 1H); MS m/z 594.2[M+H]⁺.

1H), 3.49-3.40 (m, 1H), 3.13 (dd, J=10.8 Hz, 10.4 Hz, 1H), 2.99-2.87 (m, 1H), 2.60-2.50 (m, 1H); MS m/z 513.2 (M+H)$^+$.

EXAMPLE 13. PREPARATION OF COMPOUND A8R

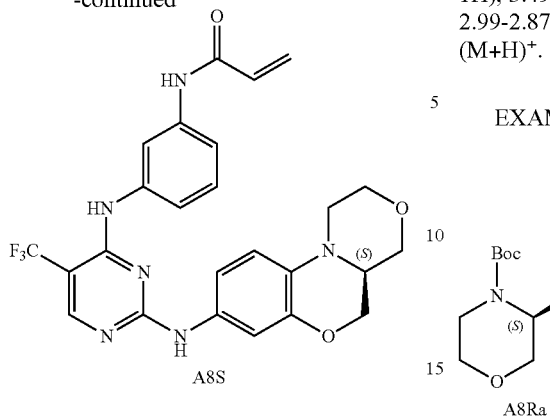

A8S

Tert-butyl (R)-3-(hydroxymethyl)morpholine-4-carboxylate (2.0 g, 9.21 mmol) was dissolved in dry 1,4-dioxane (10 mL), and was added HCl (4M 1,4-dioxane solution, 5 mL) under stirring. The reaction mixture were stirred for 3 hours at room temperature, and then removed the solvent at 35° C. in vacuo, the residue was added chloroform and solubilized by ultrasound, then was concentrated to afford crude white solid A8Sb, which was used for next step directly. The obtained crude A8Sb and compound (1.5 g, 9.43 mmol) were dissolved in DMSO (6 mL), and was added KOH power (2.1 g, 37.49 mmol). The mixture were stirred for 3 hours at room temperature, then was heated to 60° C. and reacted for 16 hours under stirring. TLC results indicated the reaction was complete; the reaction mixture was cooled to room temperature, then was poured into water, extracted with EtOAc (15 mL×3), the combined organic phase was washed by brine (15 mL), dried over Na$_2$SO$_4$ and filtered. The filtrate was concentrated in vacuo, the residue was purified via column chromatography (petroleum ether/EtOAC=1:1) to afford yellow solid A8Sc (400 mg, two steps yield 18%).

Compound A8Sc (140 mg, 0.59 mmol) was put in 50 mL flask, and was dissolved by using MeOH (5 mL), then was added Pd/C (10%, 20 mg), the air in reaction system was exchanged with H$_2$. The reaction mixture was stirred for 1 hour at room temperature H$_2$ atmosphere. TLC results indicated the reaction was complete; the reaction mixture was filtrated and concentrated in vacuo to afford brown solid compound A8Sd (110 mg, yield 90%). MS m/z 207.2 [M+H]$^+$.

Compound A1a (25 mg, 0.073 mmol) and A8Sd (15 mg, 0.073 mmol) were dissolved in dry isopropyl alcohol (2 mL), then was added trifluoroacetic acid (8 mg, 0.073 mmol). The reaction mixture was heated to 40° C. and reacted for 16 hours under stirring. TLC results indicated the reaction was complete; The reaction mixture was cooled to room temperature, then was poured into saturated aq. NaHCO$_3$ (10 mL), extracted with EtOAc (10 mL×3), the combined organic phase was washed by brine (10 mL), dried over Na$_2$SO$_4$ and filtered. The filtrate was concentrated in vacuo, the residue was purified via Preparative TLC (DCM/MeOH=25:1) to afford off-white solid compound A8S (7.64 mg, yield 20%, 99% ee). $^1$H NMR (DMSO-d$_6$, 400 MHz) δ 10.17 (s, 1H), 9.55-9.35 (br, 1H), 8.78-8.60 (br, 1H), 8.31 (s, 1H), 7.70 (s, 1H), 7.64-7.56 (m, 1H), 7.31 (dd, J=8.4 Hz, 8.0 Hz, 1H), 7.20-7.07 (m, 1H), 7.04 (dd, J=8.8 Hz, 2.0 Hz, 1H), 6.93-6.79 (br, 1H), 6.58-6.38 (m, 2H), 6.24 (dd, J=16.8 Hz, 2.0 Hz, 1H), 5.75 (dd, J=10.0 Hz, 2.0 Hz, 1H), 4.17-4.07 (m, 1H), 3.96-3.90 (m, 1H), 3.85-3.71 (m, 2H), 3.61-3.52 (m,

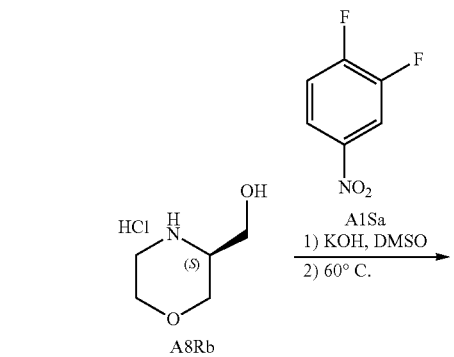

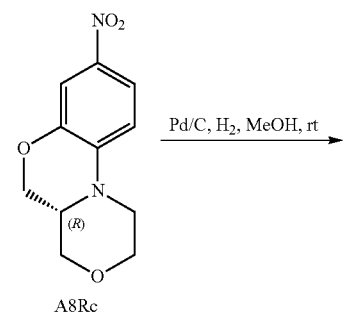

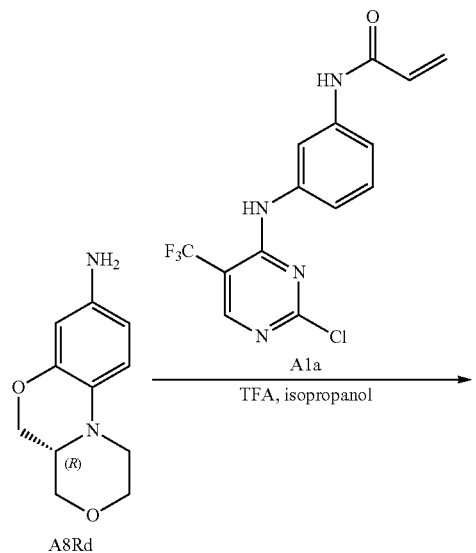

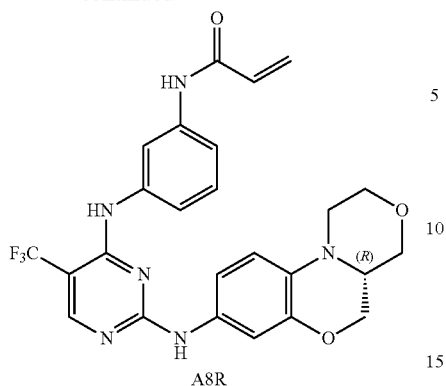

A8R

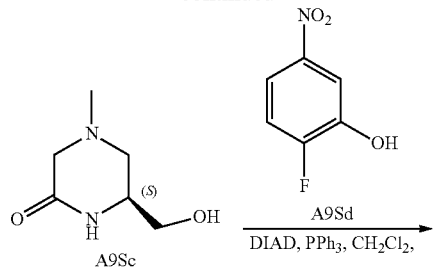

According to the preparation method of intermediate A8Sd in the Example 12, intermediate A8Rd was made by using A8Ra (>99% ee) as starting material. Compound A1a (45 mg, 0.131 mmol) and A8Rd (30 mg, 0.146 mmol) were dissolved in dry isopropyl alcohol (2 mL), then was added trifluoroacetic acid (17 mg, 0.146 mmol). The reaction mixture was heated to 40° C. and reacted for 16 hours under stirring. The reaction mixture was cooled to room temperature, then was poured into saturated aq. NaHCO$_3$ (10 mL), extracted with EtOAc (10 mL×3), the combined organic phase was washed by brine (10 mL), dried over Na$_2$SO$_4$ and filtered. The filtrate was concentrated in vacuo, the residue was purified via Preparative TLC (DCM/MeOH=25:1) to afford gray solid compound A8R (19.4 mg, yield 29%, >99% ee). $^1$H NMR (DMSO-d$_6$, 400 MHz) δ 10.16 (s, 1H), 9.55-9.33 (br, 1H), 8.78-8.60 (br, 1H), 8.31 (s, 1H), 7.70 (s, 1H), 7.64-7.56 (m, 1H), 7.31 (dd, J=8.4 Hz, 8.0 Hz, 1H), 7.21-7.08 (m, 1H), 7.04 (dd, J=8.8 Hz, 2.0 Hz, 1H), 6.94-6.80 (br, 1H), 6.58-6.38 (m, 2H), 6.24 (dd, J=16.8 Hz, 2.0 Hz, 1H), 5.75 (dd, J=10.0 Hz, 2.0 Hz, 1H), 4.17-4.07 (m, 1H), 3.96-3.90 (m, 1H), 3.85-3.71 (m, 2H), 3.61-3.52 (m, 1H), 3.50-3.40 (m, 1H), 3.13 (dd, J=10.8 Hz, 10.8 Hz, 1H), 2.99-2.88 (m, 1H), 2.60-2.50 (m, 1H); MS m/z 513.2 (M+H)$^+$.

EXAMPLE 14. PREPARATION OF COMPOUND A9S

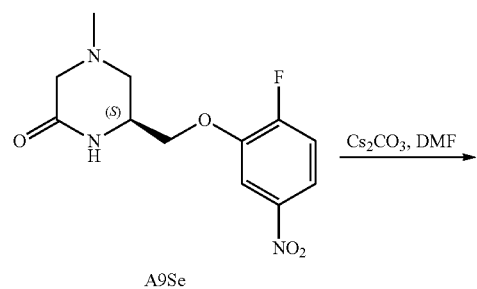

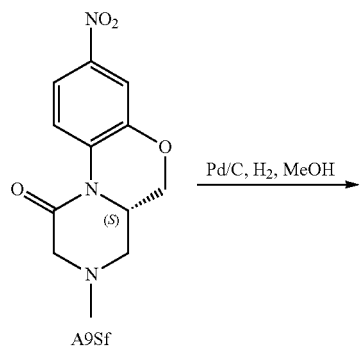

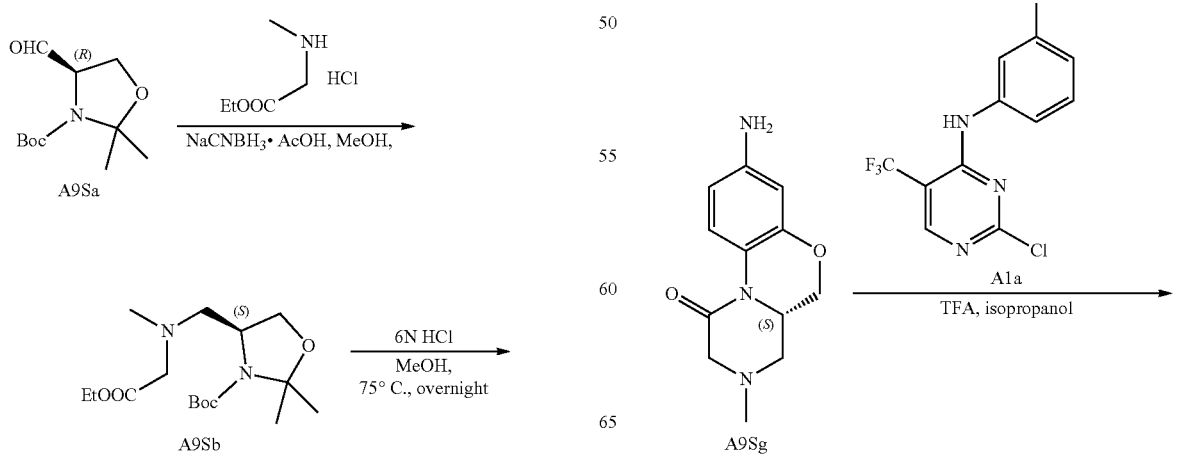

-continued

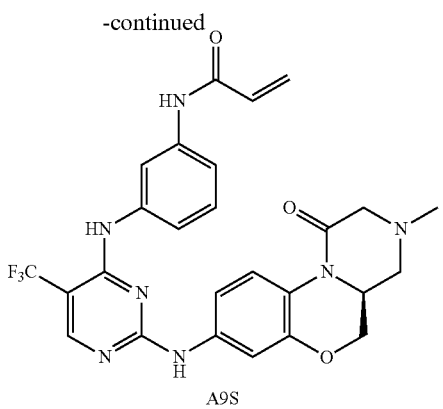

A9S

Compound A9Sa (1.3 g, 5.67 mmol) and Sarcosine ethyl ester hydrochloride (1.7 g, 11.07 mmol) was dissolved in dry MeOH (15 mL). the mixture was stirred for 2 hours at room temperature, and was added acetic acid (664 mg, 11.06 mmol); then the reaction bottom was placed in ice-water bath, and was added sodium cyanoborohydride (692 mg, 11.01 mmol), and keep its temperature lower than 5° C. After the addition, the reaction was stirred for 3 hours at room temperature, then was poured into saturated aq. NaHCO$_3$ (10 mL), extracted with EtOAc (15 mL×3), the combined organic phase was washed by brine (15 mL), dried over Na$_2$SO$_4$ and filtered. The filtrate was concentrated in vacuo, the residue was purified via column chromatography (petroleum ether/EtOAC=4:1) to afford colorless oil compound A9Sb (800 mg, yield 43%). MS m/z 331.2[M+H]$^+$.

Compound A9Sb (800 mg, 2.42 mmol) was dissolved in MeOH (8 mL), then was added HCl (6N solution, 0.8 mL), the reaction was heated to 75° C. and reacted for 16 hours under stirring. The reaction mixture was cooled to room temperature, then was poured into saturated aq. NaHCO$_3$ (10 mL), extracted with EtOAc (10 mL×2), the water phase was concentrated in vacuo. The obtained solid was dispersed in CH$_2$Cl$_2$/MeOH/ammonium hydroxide (100/10/1), filtrated, the filtrate was concentrated to afford yellow solid compound A9Sc (320 mg, yield 92%). $^1$H NMR (CDCl$_3$, 400 MHz) δ 6.79 (s, 1H), 3.74-3.66 (m, 2H), 3.63-3.55 (m, 1H), 3.14 (d, J=16.4 Hz, 1H), 3.03 (d, J=16.8 Hz, 1H), 2.72 (dd, J=12.0 Hz, 4.4 Hz, 1H), 2.58 (dd, J=12.0 Hz, 5.2 Hz, 1H), 2.34 (s, 3H); MS m/z 145.1[M+H]$^+$.

Compound A9Sc (100 mg, 0.69 mmol), compound A9Sd (174 mg, 1.11 mmol) and triphenyl phosphine (365 mg, 1.39 mmol) was dissolved in dry CH$_2$Cl$_2$, the reaction mixture was added diisopropyl azodiformate (283 mg, 1.40 mmol) at room temperature, then was stirred for 16 hours at room temperature. The reaction was concentrated in vacuo to afford crude product, which was purified via preparative TLC (EtOAc) to afford yellow solid A9Se (85 mg, yield 43%). $^1$H NMR (CDCl$_3$, 400 MHz) δ 7.96-7.83 (m, 2H), 7.23 (dd, J=9.2 Hz, 0.8 Hz, 1H), 6.32 (s, 1H), 4.25-4.16 (m, 1H), 4.14 (dd, J=8.8 Hz, 8.0 Hz, 1H), 4.01-3.92 (m, 1H), 3.20 (d, J=16.4 Hz, 1H), 3.05 (d, J=16.8 Hz, 1H), 2.77 (dd, J=15.8 Hz, 3.6 Hz, 1H), 2.58 (dd, J=16.4 Hz, 5.2 Hz, 1H), 2.37 (s, 3H).

Compound A9Se (50 mg, 0.177 mmol) was suspended in dry DMF (3 mL), and was added Cs$_2$CO$_3$ (115 mg, 0.353 mmol), the mixture was heated to 45° C. and reacted for 3 hours under stirring. The reaction mixture was cooled to room temperature, then was poured into ice water, extracted with EtOAc (10 mL×3), the combined organic phase was washed by brine, dried over Na$_2$SO$_4$ and filtered. The filtrate was concentrated in vacuo, the residue was purified via preparative TLC (DCM/MeOH=60:1) to afford yellow solid compound A9Sf (28 mg, yield 60%). $^1$H NMR (CDCl$_3$, 400 MHz) δ 8.45 (d, J=9.2 Hz, 1H), 7.82-7.76 (m, 2H), 4.40 (dd, J=10.4 Hz, 2.4 Hz, 1H), 4.11 (dd, J=10.4 Hz, 10.4 Hz, 1H), 4.04-3.96 (m, 1H), 3.52 (dd, J=16.8 Hz, 2.0 Hz, 1H), 3.13-3.02 (m, 2H), 2.40-2.36 (m, 4H); MS m/z 264.2 [M+H]$^+$.

Compound A9Sf (26 mg, 0.099 mmol) was put in 25 mL flask, and was dissolved by using MeOH (3 mL), then was added Pd/C (10%, 5 mg), the air in reaction system was exchanged with H$_2$. The reaction mixture was stirred for 40 minutes at room temperature H$_2$ atmosphere. TLC results indicated the reaction was complete; the reaction mixture was filtrated and concentrated in vacuo to afford gray solid compound A9Sg (23 mg, yield 99%). $^1$H NMR (CDCl$_3$, 400 MHz) δ 8.00 (d, J=8.4 Hz, 1H), 6.27 (dd, J=8.8 Hz, 2.4 Hz, 1H), 6.20 (d, J=2.8 Hz, 1H), 4.25 (dd, J=10.4 Hz, 2.4 Hz, 1H), 4.03 (dd, J=10.4 Hz, 10.0 Hz, 1H), 4.00-3.90 (m, 1H), 3.80-3.45 (br s, 2H), 3.44 (dd, J=16.4 Hz, 2.0 Hz, 1H), 3.04-2.95 (m, 2H), 2.36-2.27 (m, 4H).

Compound A9Sg (8 mg, 0.034 mmol) and compound A1a (12 mg, 0.035 mmol) were dissolved in dry isopropyl alcohol (1 mL), then was added trifluoroacetic acid (4 mg, 0.035 mmol). The reaction mixture was heated to 40° C. and reacted for 16 hours under stirring. TLC results indicated the reaction was complete; The reaction mixture was cooled to room temperature, then was poured into saturated aq. NaHCO$_3$ (10 mL), extracted with EtOAc (10 mL×3), the combined organic phase was washed by brine (10 mL), dried over Na$_2$SO$_4$ and filtered. The filtrate was concentrated in vacuo, the residue was purified via Preparative TLC (DCM/MeOH=25:1) to afford pale yellow solid compound A9S (5 mg, yield 27%). $^1$H NMR (DMSO-d$_6$, 400 MHz) δ 10.14 (s, 1H), 9.70-9.57 (br, 1H), 8.77 (br s, 1H), 8.36 (s, 1H), 7.90-7.80 (m, 1H), 7.76 (s, 1H), 7.57 (d, J=8.0 Hz, 1H), 7.32 (dd, J=8.4 Hz, 8.0 Hz, 1H), 7.24-7.10 (m, 2H), 7.04 (d, J=8.8 Hz, 1H), 6.43 (dd, J=16.8 Hz, 10 Hz, 1H), 6.24 (dd, J=17.2 Hz, 2.0 Hz, 1H), 5.74 (dd, J=10.0 Hz, 2.0 Hz, 1H), 4.33-4.26 (m, 1H), 3.92-3.75 (m, 2H), 3.31-3.25 (m, 1H), 3.00-2.85 (m, 2H), 2.35-2.25 (m, 1H), 2.20 (s, 3H); MS m/z 540.2 (M+H)$^+$.

EXAMPLE 15. PREPARATION OF COMPOUND A9R

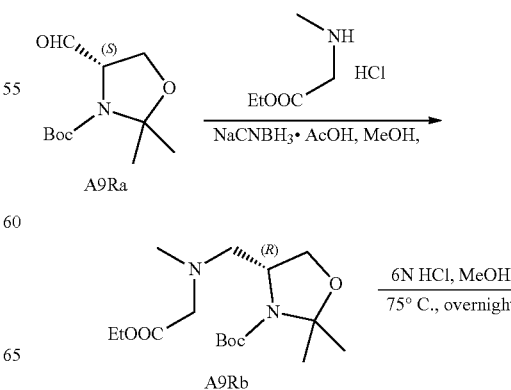

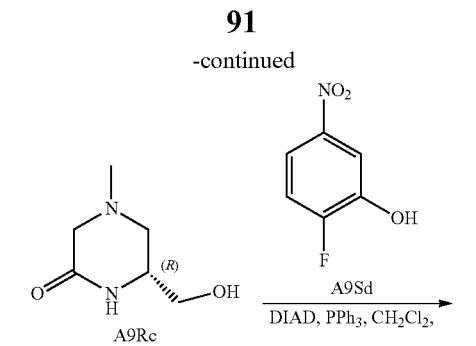

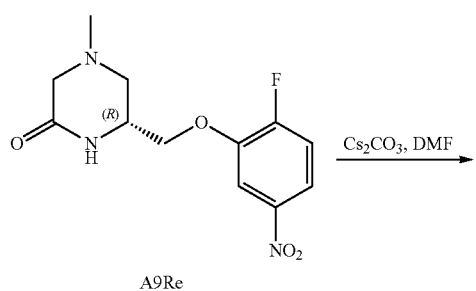

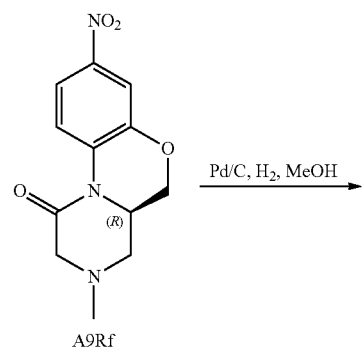

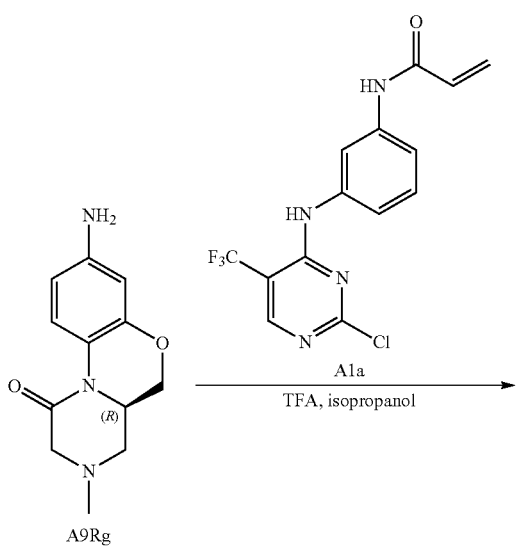

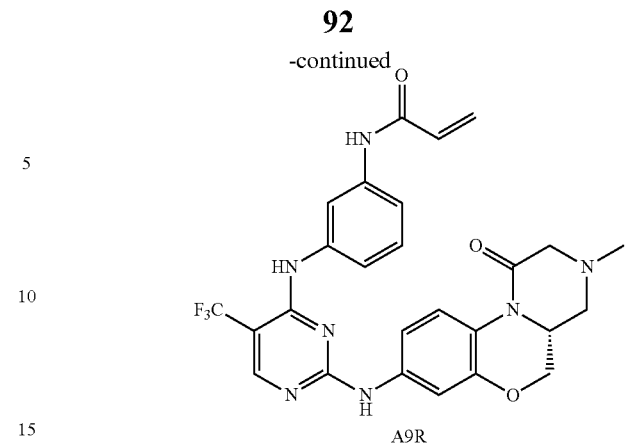

According to the preparation method of intermediate A9Sg in the Example 14, intermediate A8Rg was made by using A9Ra (>99% ee) as starting material. Compound A9Rg (8 mg, 0.034 mmol) and compound A1a (12 mg, 0.035 mmol) were dissolved in dry isopropyl alcohol (1 mL), then was added trifluoroacetic acid (4 mg, 0.035 mmol). The reaction mixture was heated to 40° C. and reacted for 16 hours under stirring. The reaction mixture was cooled to room temperature, then was poured into saturated aq. NaHCO$_3$ (10 mL), extracted with EtOAc (10 mL×3), the combined organic phase was washed by brine (10 mL), dried over Na$_2$SO$_4$ and filtered. The filtrate was concentrated in vacuo, the residue was purified via preparative TLC (DCM/MeOH=25:1) to afford pale yellow solid compound A9R (5 mg, yield 27%). $^1$H NMR (DMSO-d$_6$, 400 MHz) δ 10.14 (s, 1H), 9.70-9.56 (br, 1H), 8.76 (br s, 1H), 8.36 (s, 1H), 7.90-7.80 (m, 1H), 7.75 (s, 1H), 7.57 (d, J=7.2 Hz, 1H), 7.32 (dd, J=8.0 Hz, 8.0 Hz, 1H), 7.23-7.10 (m, 2H), 7.04 (d, J=8.8 Hz, 1H), 6.43 (dd, J=17.2 Hz, 10 Hz, 1H), 6.24 (dd, J=17.2 Hz, 2.0 Hz, 1H), 5.74 (dd, J=10.0 Hz, 2.0 Hz, 1H), 4.33-4.26 (m, 1H), 3.92-3.75 (m, 2H), 3.31-3.25 (m, 1H), 3.00-2.85 (m, 2H), 2.35-2.25 (m, 1H), 2.24 (s, 3H); MS m/z 540.2 (M+H)$^+$.

EXAMPLE 16. PREPARATION OF COMPOUND B1S

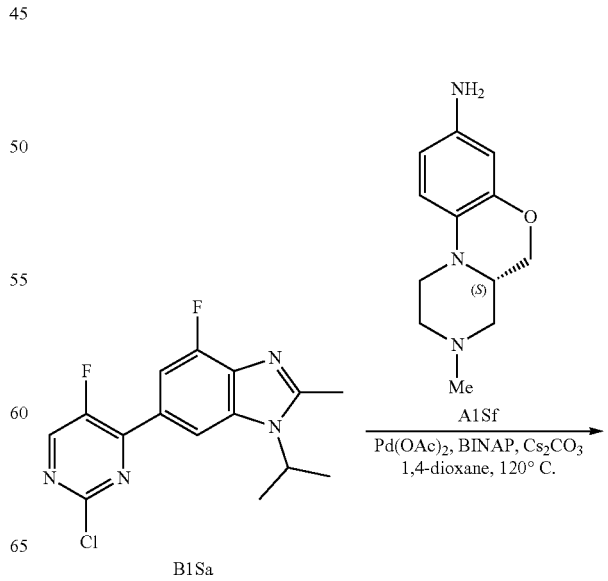

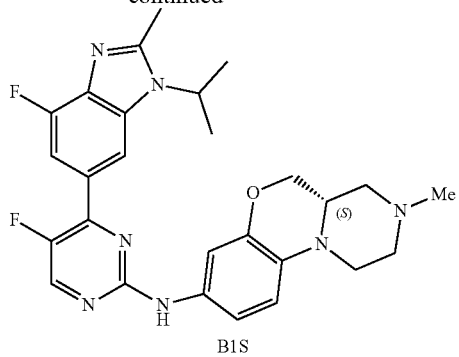

B1S

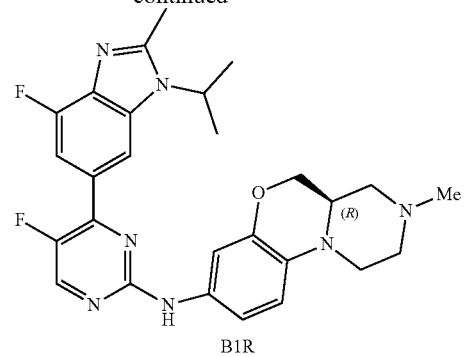

B1R

Compound A1Sf (66 mg, 0.301 mmol), B1Sa (80 mg, 0.248 mmol), Pd(OAc)$_2$ (20 mg), BINAP (20 mg) and Cs$_2$CO$_3$ (294 mg, 0.903 mmol) were added to 1,4-dioxane (3 mL), the air in reaction system was exchanged with N$_2$, then the mixture was heat to 120° C. and reacted for 2 hours in seal, the LCMS indicated the reaction was complete, the reaction mixture was filtered, the filtrate was concentrated in vacuo, the residue was purified via column chromatography (DCM/MeOH=30:1~25:1) to afford yellow solid compound B1S (32 mg, yield 25%, >99% ee). $^1$H NMR (CD$_3$OD, 400 MHz) δ 8.39-8.36 (m, 2H), 7.78 (dd, J=12.0 Hz, 0.8 Hz, 1H), 7.35 (d, J=2.4 Hz, 1H), 7.07 (dd, J=8.8 Hz, 2.8 Hz, 1H), 6.83 (d, J=9.2 Hz, 1H), 4.94-4.89 (m, 1H), 4.24 (dd, J=10.4 Hz, 2.8 Hz, 1H), 3.99 (dd, J=10.8 Hz, 9.2 Hz, 1H), 3.77-3.72 (m, 1H), 3.13-3.07 (m, 1H), 3.00 (d, J=11.2 Hz, 1H), 2.93-2.87 (m, 1H), 2.78-2.70 (m, 1H), 2.69 (s, 3H), 2.38 (s, 3H), 2.37-2.27 (m, 1H), 1.91 (dd, J=11.2 Hz, 10.8 Hz, 1H), 1.72 (d, J=6.8 Hz, 6H); MS m/z 506.3 [M+H]$^+$.

EXAMPLE 17. PREPARATION OF COMPOUND B1R

A1Rf (50 mg, 0.228 mmol), B1S (73 mg, 0.228 mmol), Pd(OAc)$_2$ (20 mg), BINAP (20 mg) Cs$_2$CO$_3$ (223 mg, 0.684 mmol) were added to 1,4-dioxane (3 mL), the air in reaction system was exchanged with N$_2$, then the mixture was heat to 120° C. and reacted for 2 hours in seal. The LCMS indicated the reaction was complete, the reaction mixture was filtered, the filtrate was concentrated in vacuo, the residue was purified via column chromatography (DCM/MeOH=30:1~25:1) to afford yellow solid compound B1R (45 mg, yield 39%, >99% ee). $^1$H NMR (CD$_3$OD, 400 MHz) δ 8.39-8.36 (m, 2H), 7.78 (d, J=12.0 Hz, 1H), 7.35 (d, J=2.8 Hz, 1H), 7.07 (dd, J=8.8 Hz, 2.8 Hz, 1H), 6.84 (d, J=8.8 Hz, 1H), 4.91-4.85 (m, 1H), 4.25 (dd, J=10.4 Hz, 2.4 Hz, 1H), 3.99 (dd, J=10.4 Hz, 8.8 Hz, 1H), 3.79-3.73 (m, 1H), 3.15-3.07 (m, 1H), 3.06-2.99 (m, 1H), 2.95-2.89 (m, 1H), 2.79-2.69 (m, 1H), 2.68 (s, 3H), 2.40 (s, 3H), 2.39-2.30 (m, 1H), 1.94 (dd, J=11.2 Hz, 10.8 Hz, 1H), 1.72 (d, J=7.2 Hz, 6H); MS m/z 506.3 [M+H]$^+$.

EXAMPLE 18. PREPARATION OF COMPOUND B2R

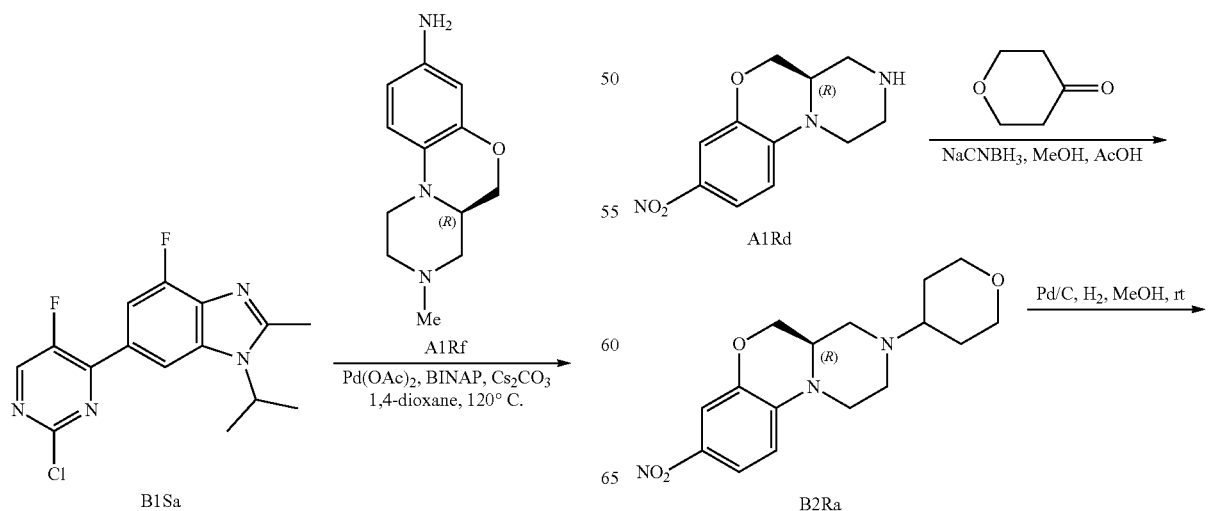

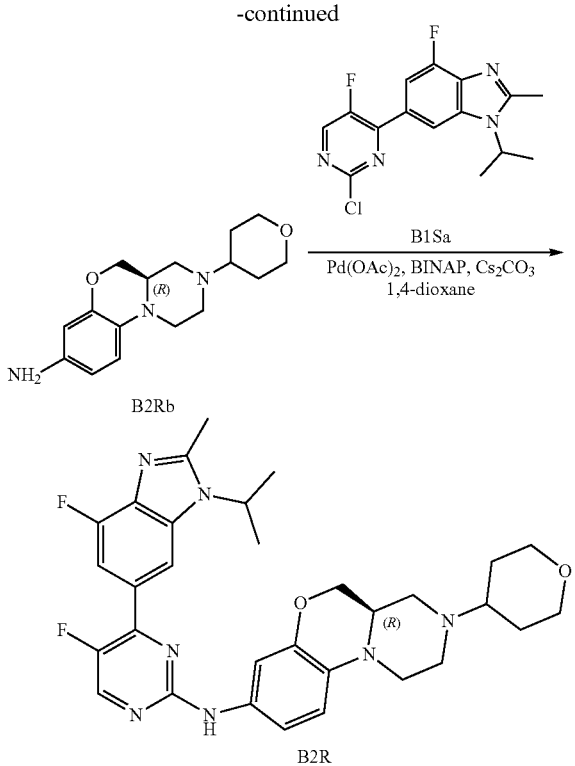

Compound A1Rd (600 mg, 2.55 mmol) and tetrahydro-4H-pyran-4-one (511 mg, 5.10 mmol) were dissolved in MeOH (25 mL), the mixture was added acetic acid (153 mg, 2.55 mmol); then the reaction was added sodium cyanoborohydride (481 mg, 7.65 mmol) in batches, and keep its temperature lower than 10° C. The reaction was stirred overnight at room temperature, TLC results indicated the reaction was complete; the reaction was concentrated in vacuo, the obtained residue was dispersed in saturated aq. $Na_2CO_3$, extracted with EtOAc (20 mL×3), the combined organic phase was washed by brine (20 mL), dried over $Na_2SO_4$ and filtered. The filtrate was concentrated in vacuo, the residue was purified via column chromatography (DCM/MeOH=30:1) to afford yellow solid compound B2Ra (800 mg, yield 98%). MS m/z 320.2 $[M+H]^+$.

Compound B2Ra (200 mg, 0.63 mmol) was put in 50 mL flask, and was dissolved by using MeOH (5 mL), then was added Pd/C (10%, 30 mg), the air in reaction system was exchanged with $H_2$. The reaction mixture was stirred for 1 hour at room temperature and $H_2$ atmosphere. TLC results indicated the reaction was complete; the reaction mixture was filtrated and concentrated in vacuo and the residue was purified via column chromatography (DCM/MeOH=30:1) to afford brown solid compound B2Rb (80 mg, yield 44%). MS m/z 290.2 $[M+H]^+$.

Compound B2Rb (30 mg, 0.10 mmol), B1Sa (50 mg, 0.16 mmol), $Pd(OAc)_2$ (2.3 mg, 0.01 mmol), BINAP (12.5 mg, 0.02 mmol), $Cs_2CO_3$ (65 mg, 0.20 mmol) and 1,4-dioxane (2.0 mL) were added to seal sequencely, and the reaction was exchanged with $N_2$, then the reaction mixture was heat to 120° C. and reacted for 2 hours in seal. The reaction was cooled to room temperature, then was poured into water, extracted with EtOAc (5 mL×3), the combined organic phase was washed by brine, dried over $Na_2SO_4$ and filtered. The filtrate was concentrated in vacuo, the residue was purified via column chromatography (DCM/MeOH=15:1) to afford crude product, which was further purified via preparative HPLC to afford yellow solid compound B2R (22 mg, yield 37%). $^1$H NMR (DMSO-$d_6$, 400 MHz) δ 9.48 (s, 1H), 8.58 (d, J=3.6 Hz, 1H), 8.22 (s, 1H), 7.64 (d, J=12.4 Hz, 1H), 7.30 (d, J=2.4 Hz, 1H), 7.13 (dd, J=8.8 Hz, 2.0 Hz, 1H), 6.79 (d, J=8.8 Hz, 1H), 4.87-4.78 (m, 1H), 4.26-4.20 (m, 1H), 3.94-3.86 (m, 3H), 3.68 (d, J=11.6 Hz, 1H), 3.34-3.24 (m, 2H), 3.03-2.87 (m, 3H), 2.64 (s, 3H), 2.52-2.37 (m, 2H), 2.35-2.25 (m, 1H), 1.88 (dd, J=10.8 Hz, 10.0 Hz, 1H), 1.78-1.68 (m, 2H), 1.62 (d, J=6.8 Hz, 6H), 1.47-1.35 (m, 2H); MS m/z 576.3 $(M+H)^+$.

EXAMPLE 19. PREPARATION OF COMPOUND B3R

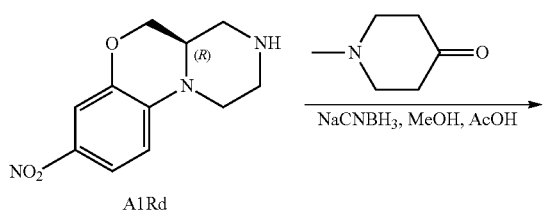

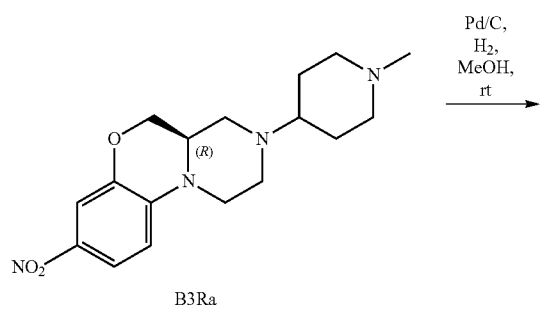

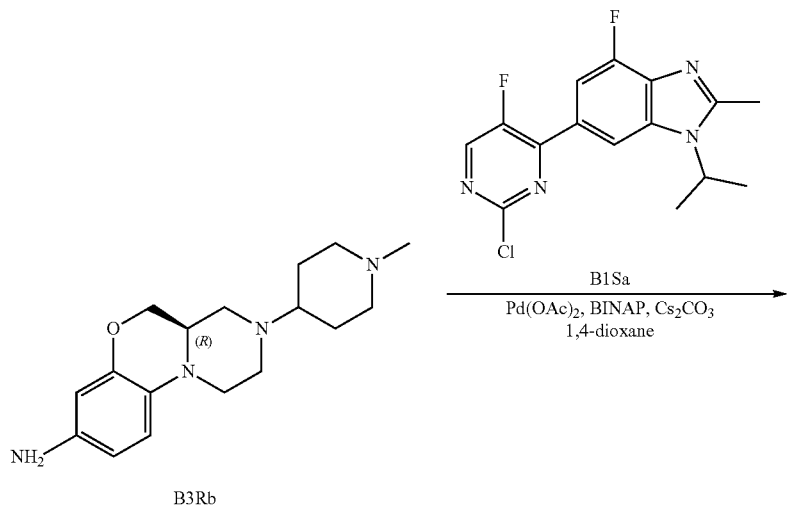

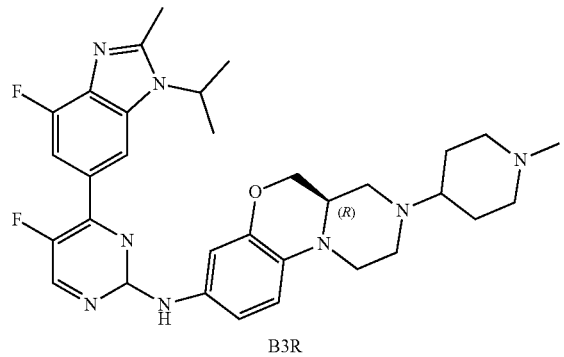

Compound A1Rd (970 mg, 4.12 mmol) and 1-methyl-4-piperidone (933 mg, 8.24 mmol) were dissolved in MeOH (35 mL), the mixture was added acetic acid (247 mg, 4.12 mmol) under stirring; then the reaction was added sodium cyanoborohydride (776 mg, 12.35 mmol) in batches, and keep its temperature lower than 10° C. The reaction was stirred for 16 hours at room temperature, TLC results indicated the reaction was complete; the reaction was concentrated in vacuo, the obtained residue was dispersed in saturated aq. $Na_2CO_3$ (20 mL), extracted with EtOAc (25 mL×3), the combined organic phase was washed by brine (20 mL), dried over $Na_2SO_4$ and filtered. The filtrate was concentrated in vacuo, the residue was purified via column chromatography (DCM/MeOH=20:1) to afford yellow solid compound (860 mg, yield 63%). MS m/z 333.2 $[M+H]^+$.

Compound B3Ra (373 mg, 1.12 mmol) was put in 50 mL flask, and was dissolved by using MeOH (7 mL), then was added Pd/C (10%, 40 mg), the air in reaction system was exchanged with $H_2$. The reaction mixture was stirred for 2 hours at room temperature and $H_2$ atmosphere. TLC results indicated the reaction was complete; the reaction mixture was filtrated and concentrated in vacuo and the residue was purified via column chromatography (DCM/MeOH/ $NH_3 \cdot H_2O$=10/1/0.25) to afford brown solid compound B3Rb (150 mg, yield 44%). MS m/z 303.3 $[M+H]^+$.

Compound B3Rb (30 mg, 0.099 mmol), B1Sa (48 mg, 0.15 mmol), $Pd(OAc)_2$ (2.3 mg, 0.01 mmol), BINAP (12.5 mg, 0.02 mmol), $Cs_2CO_3$ (65 mg, 0.20 mmol) and 1,4-dioxane (2.0 mL) was added into seal, and the reaction was exchanged with $N_2$, then the reaction mixture was heat to 120° C. and reacted for 2 hours in seal. The reaction was cooled to room temperature, then was poured into water, extracted with EtOAc (5 mL×3), the combined organic phase was washed by brine, dried over $MgSO_4$ and filtered. The filtrate was concentrated in vacuo, the residue was purified via column chromatography (DCM/MeOH/ $NH_3 \cdot H_2O$=10/1/0.05) to afford crude product, which was further purified via preparative HPLC to afford yellow solid compound B3R (12 mg, yield 21%). $^1H$ NMR (DMSO-$d_6$, 400 MHz) δ 9.46 (s, 1H), 8.57 (d, J=4.0 Hz, 1H), 8.21 (s, 1H), 7.64 (d, J=12.4 Hz, 1H), 7.30 (d, J=2.0 Hz, 1H), 7.13 (dd, J=8.4 Hz, 2.4 Hz, 1H), 6.78 (d, J=8.8 Hz, 1H), 4.87-4.78 (m, 1H), 4.25-4.19 (m, 1H), 3.89 (dd, J=9.6 Hz, 9.6 Hz, 1H), 3.66 (d, J=11.6 Hz, 1H), 3.01-2.85 (m, 4H), 2.85-2.74 (m, 2H), 2.64 (s, 3H), 2.35-2.25 (m, 1H), 2.16 (s, 3H), 1.93-1.78 (m, 4H), 1.77-1.68 (m, 2H), 1.62 (d, J=6.8 Hz, 6H), 1.48-1.35 (m, 2H); MS m/z 589.4 $(M+H)^+$.

EXAMPLE 20. PREPARATION OF COMPOUND C1R

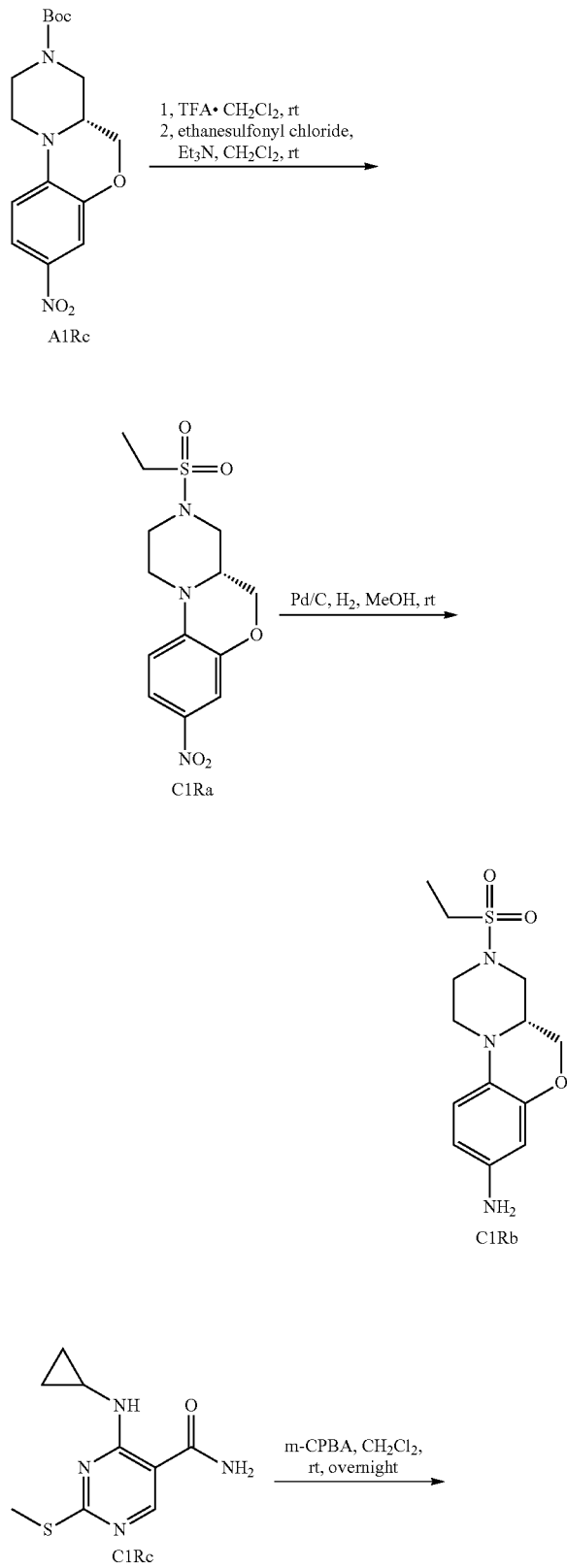

Compound A1Rc (200 mg, 0.60 mmol) was dissolved in CH$_2$Cl$_2$ (10 mL), the reaction mixture was added trifluoroacetic acid (1.5 mL). The reaction mixture was stirred for 2 hours at room temperature. Then trifluoroacetic acid was removed in vacuo, the resulted residue was dissolved in CH$_2$Cl$_2$ (10 mL), and was added ethanesulfonyl chloride (116 mg, 0.90 mmol) and Et$_3$N (121 mg, 1.20 mmol), then was stirred for 16 hours at room temperature. The reaction mixture was washed by water (10 mL×2), the organic phase was dried over MgSO$_4$ and filtered. The filtrate was concentrated in vacuo, the residue was purified via column chromatography (DCM/EtOAc=1/1) to afford yellow solid C1Ra (150 mg, yield 77%). MS m/z 328.0 [M+H]$^+$.

Compound C1Ra (150 mg, 0.46 mmol) was dissolved in MeOH (10 mL), then was added Pd/C (10%, 25 mg), The reaction mixture was stirred for 2 hours at room temperature. The reaction mixture was filtrated and the residue was washed by DCM/MeOH (10:1) until the product was washed out. The combined filtrate was concentrated in vacuo to afford gray solid compound C1Rb (100 mg, yield 73%). $^1$H NMR (DMSO-d$_6$, 400 MHz) δ 6.61 (d, J=8.4 Hz, 1H), 6.09 (dd, J=8.4 Hz, 2.0 Hz, 1H), 6.03 (d, J=2.4 Hz, 1H), 4.56 (br s, 2H), 4.22 (dd, J=10.4 Hz, 2.4 Hz, 1H), 3.82 (dd, J=10.4 Hz, 9.2 Hz, 1H), 3.70 (d, J=12.4 Hz, 1H), 3.59 (dd, J=10.0H, 10 Hz, 2H), 3.10 (q, J=12 Hz, 2H), 3.01-2.95 (m, 1H), 2.91-2.82 (m, 1H), 2.70-2.55 (m, 2H), 1.22 (t, J=7.2 Hz, 3H); MS m/z 298.0 [M+H]$^+$.

Compound C1Rc (120 mg, 0.54 mmol) were dissolved in CH$_2$Cl$_2$ (10 mL), and was added mCPBA (186 mg, 1.08 mmol), the reaction mixture was stirred for 16 hours at room temperature, then the mixture was concentrated in vacuo, the resulted residue was purified via column chromatography (CH$_2$Cl$_2$/MeOH=30:1) to afford colorless solid compound C1Rd (70 mg, yield 54%). MS m/z 241.0 [M+H]$^+$.

Compound C1Rd (70 mg, 0.29 mmol) and C1Rb (70 mg, 0.20 mmol) were dissolved in NMP (2 mL), then was added TsOH—H₂O (57 mg, 0.30 mmol), the reaction mixture was stirred for 16 hours at 100° C. The reaction was cooled to room temperature, then was poured into water (4 mL), extracted with CH₂Cl₂ (5 mL×3), the combined organic phase was washed by brine (5 mL), dried over MgSO₄ and filtered. The filtrate was concentrated in vacuo, the residue was purified via column chromatography (DCM/MeOH=15/1) to afford crude product, then was were mashed by using CH₃CN to afford gray solid compound C1R (30 mg, yield 32%). ¹H NMR (DMSO-d₆, 400 MHz) δ 9.34 (br s, 1H), 9.10 (s, 1H), 8.48 (s, 1H), 7.90-7.60 (br, 1H), 7.60 (s, 1H), 7.29 (d, J=8.8 Hz, 1H), 7.20-6.98 (br s, 1H), 6.84 (d, J=8.8 Hz, 1H), 4.30 (dd, J=10.4 Hz, 2.4 Hz, 1H), 3.93-3.82 (m, 2H), 3.70-3.60 (m, 2H), 3.11 (q, J=7.2 Hz, 2H), 3.07-2.96 (m, 2H), 2.75-2.65 (m, 1H), 2.70-2.54 (m, 2H), 1.22 (t, J=7.2 Hz, 3H), 0.89-0.80 (m, 2H), 0.57-0.50 (m, 2H); MS m/z 474.2 [M+H]⁺.

EXAMPLE 21. PREPARATION OF COMPOUND C2R

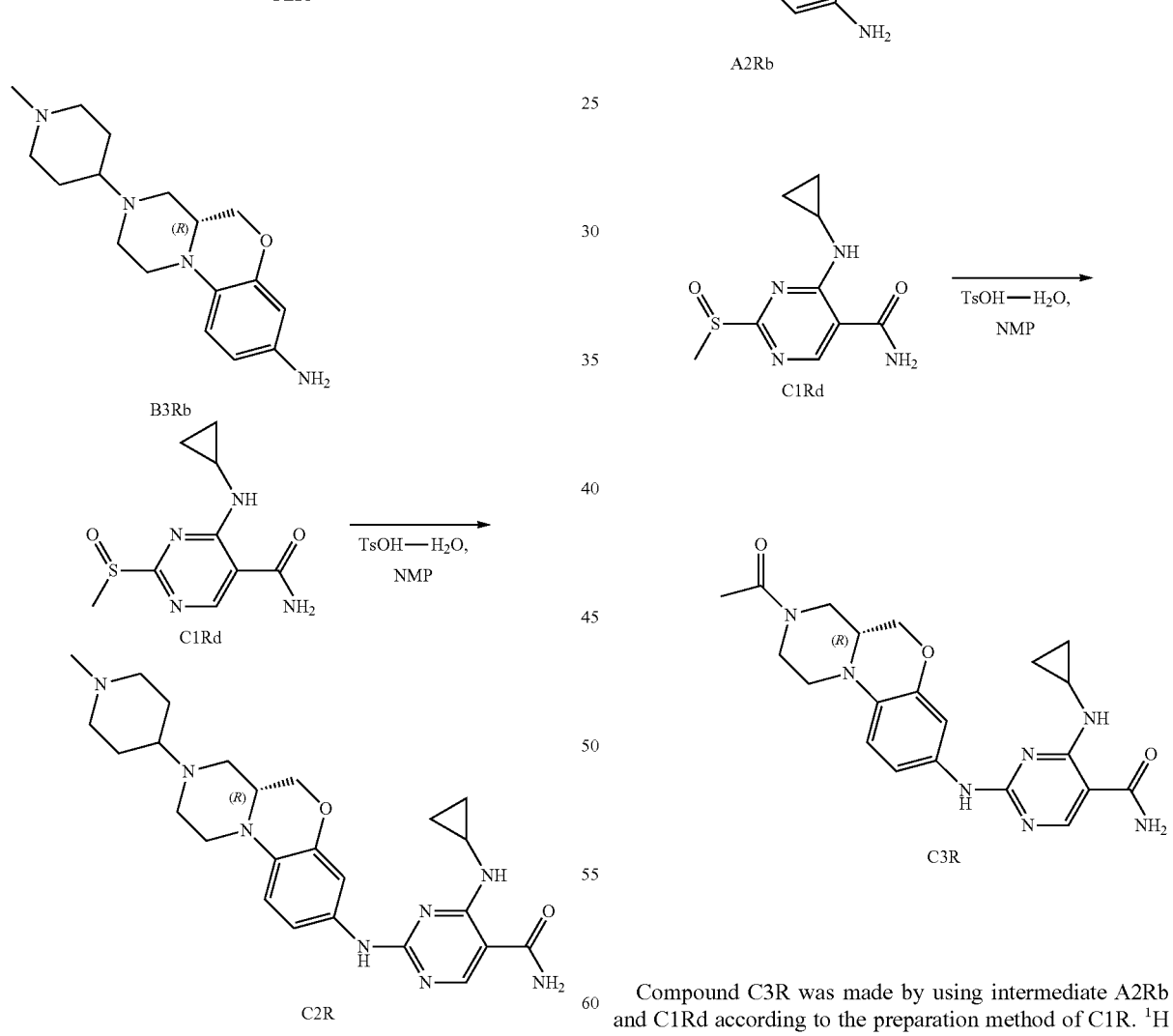

Compound C2R was made by using intermediate B3Rb and C1Rd according to the preparation method of C1R. ¹H NMR (500 MHz, CD₃OD) δ 8.35 (s, 1H), 7.57 (s, 1H), 7.06 (dd, J=8.7, 2.2 Hz, 1H), 6.77 (d, J=8.9 Hz, 1H), 4.57 (s, 1H), 4.20 (dd, J=10.5, 2.5 Hz, 1H), 4.01-3.86 (m, 1H), 3.71 (d, J=11.7 Hz, 1H), 3.10-2.59 (m, 7H), 2.43 (m, 1H), 2.35 (s, 3H), 2.20 (t, J=12.0 Hz, 2H), 2.03-1.92 (m, 3H), 1.65-1.60 (m, 2H), 0.89-0.87 (m, 2H), 0.57-0.55 (m, 2H). LCMS m/z 479.2 [M+H]⁺.

EXAMPLE 22. PREPARATION OF COMPOUND C3R

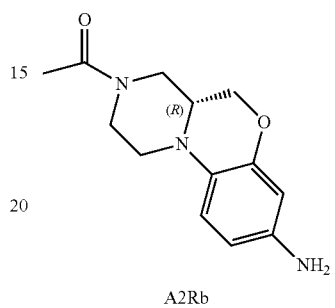

A2Rb

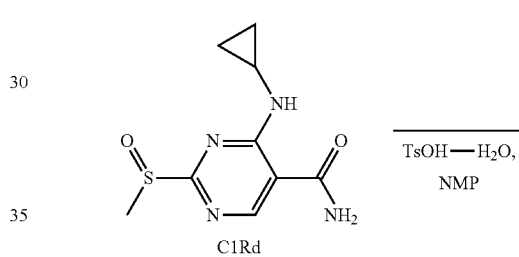

C1Rd

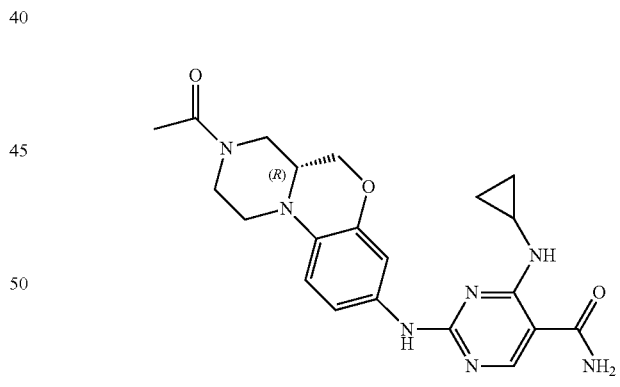

C3R

Compound C3R was made by using intermediate A2Rb and C1Rd according to the preparation method of C1R. ¹H NMR (500 MHz, CDCl₃) δ 8.78 (s, 1H), 8.20 (s, 1H), 7.57 (s, 1H), 7.22 (s, 1H), 7.05 (t, J=9.3 Hz, 1H), 6.74 (dd, J=15.5, 8.9 Hz, 1H), 5.59 (s, 2H), 4.65 (dd, J=52.1, 12.8 Hz, 1H), 4.35-3.95 (m, 2H), 3.72 (d, J=10.2 Hz, 1H), 3.49 (s, 1H), 3.03-2.45 (m, 5H), 2.15 (d, J=4.7 Hz, 3H), 0.91-0.88 (m, 2H), 0.63 (t, J=7.7 Hz, 2H).

EXAMPLE 23. PREPARATION OF COMPOUND C4R

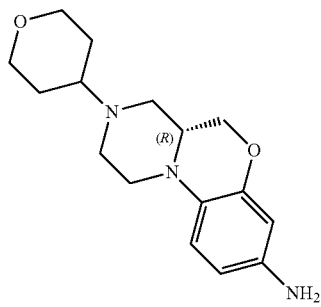

B2Rb

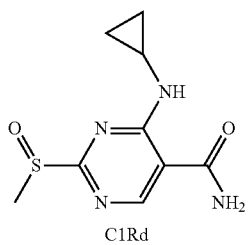

C1Rd

TsOH—H₂O, NMP →

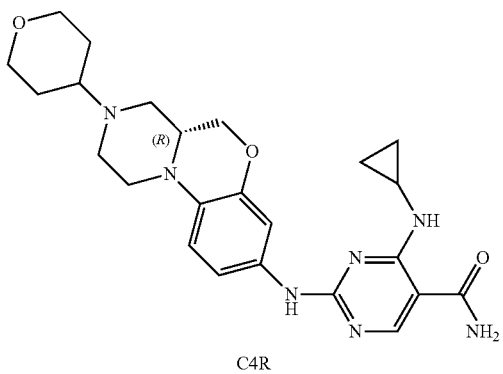

C4R

Compound C4R was made by using intermediate B2Rb and C1Rd according to the preparation method of C1R. ¹H NMR (500 MHz, CDCl₃) δ 8.78 (s, 1H), 8.20 (s, 1H), 7.48 (d, J=42.2 Hz, 2H), 7.05 (d, J=8.0 Hz, 1H), 6.72 (d, J=8.9 Hz, 1H), 5.65 (s, 2H), 4.18 (dd, J=10.4, 2.5 Hz, 1H), 4.05-3.99 (m, 3H), 3.65 (d, J=11.4 Hz, 1H), 3.39 (t, J=11.2 Hz, 2H), 3.11-2.76 (m, 5H), 2.48-2.43 (m, 2H), 2.01 (t, J=10.6 Hz, 1H), 1.78 (d J=12.3 Hz, 2H), 1.60 (dd, J=8.3, 3.7 Hz, 2H), 0.88 (t, J=13.9 Hz, 2H), 0.64-0.61 (m, 2H). LCMS m/z 466.3 [M+H]⁺.

EXAMPLE 24. PREPARATION OF COMPOUND C5R

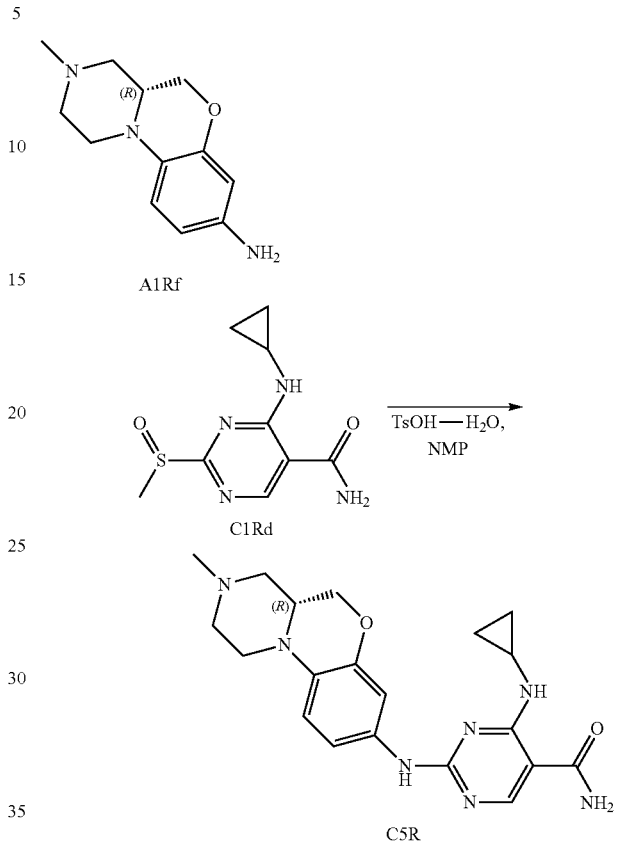

Compound C5R was made by using intermediate A1Rf and C1Rd according to the preparation method of C1R. ¹H NMR (500 MHz, CDCl₃) δ 8.77 (s, 1H), 8.18 (s, 1H), 7.54 (s, 1H), 7.34 (d, J=4.6 Hz, 1H), 7.05 (d, J=7.0 Hz, 1H), 6.72 (d, J=8.8 Hz, 1H), 5.51 (s, 2H), 4.17 (dd, J=10.5, 2.6 Hz, 1H), 4.02-3.98 (m, 1H), 3.63 (d, J=11.5 Hz, 1H), 3.49 (s, 1H), 3.23-3.11 (m, 1H), 3.02-2.78 (m, 4H), 2.35 (s, 3H), 2.28-2.23 (m, 1H), 0.88 (dd, J=13.7, 6.8 Hz, 2H), 0.64-0.61 (m, 2H). LCMS m/z 396.2 [M+H]⁺.

EXAMPLE 25. PREPARATION OF COMPOUND C6R

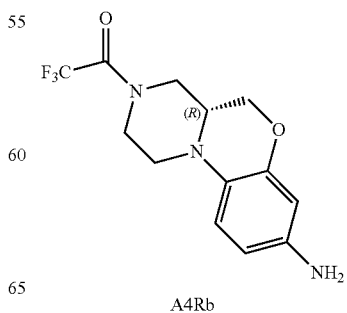

A4Rb

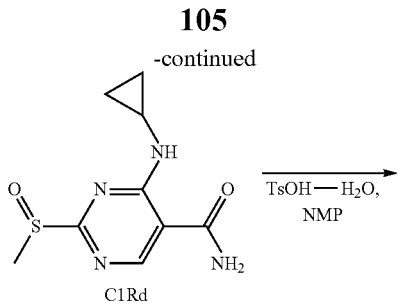

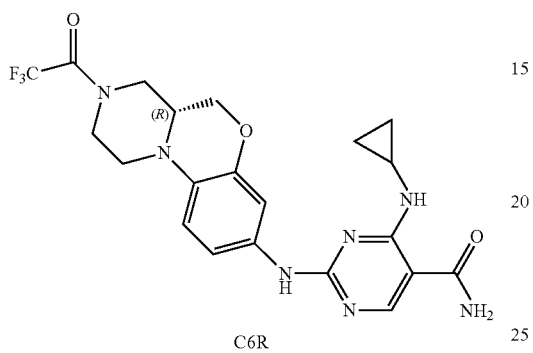

Compound C6R was made by using intermediate A4Rb and C1Rd according to the preparation method of C1R. $^1$H NMR (500 MHz, CDCl$_3$) δ 8.80 (s, 1H), 8.19 (s, 1H), 7.63 (s, 1H), 7.23 (s, 1H), 7.04 (d, J=4.1 Hz, 1H), 6.74 (dd, J=15.9, 8.8 Hz, 1H), 5.49 (s, 2H), 4.56 (dd, J=59.4, 12.8 Hz, 1H), 4.29-4.25 (m, 1H), 4.07-4.03 (m, 1H), 3.80-3.77 (m, 1H), 3.49-2.85 (m, 4H), 2.38-2.35 (m, 1H), 2.03 (dd, J=13.4, 5.8 Hz, 1H), 0.83-0.81 (m, 2H), 0.63 (m, 2H). LCMS m/z 478.3 [M+H]$^+$.

EXAMPLE 26 AND 27. PREPARATION OF COMPOUND C7R AND C8R

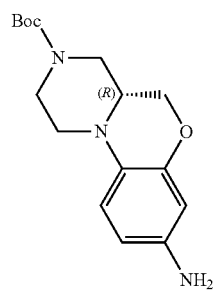

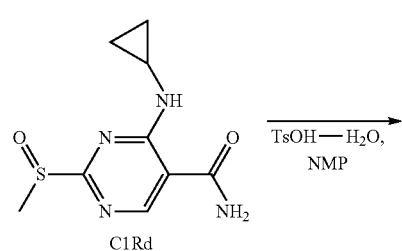

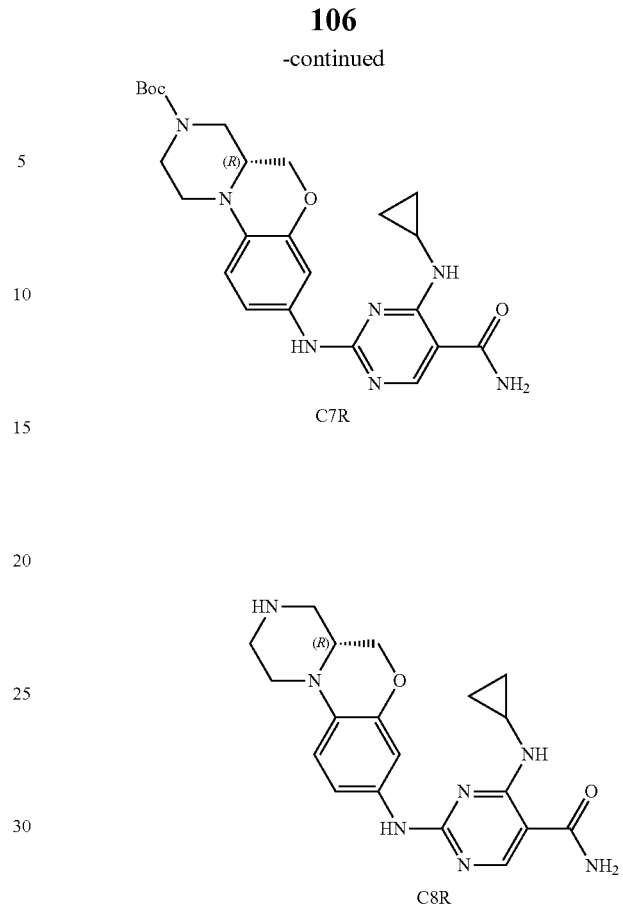

Compound C1Rd (278 mg, 1.15 mmol) and A3Ra (530 mg, 1.73 mmol) were dissolved in N-methyl pyrrolidone (5 mL), then was added TsOH-H$_2$O (556 mg, 2.92 mmol). The reaction mixture was stirred overnight at 100° C. The reaction was cooled to room temperature, then was eluted through column chromatography (petroleum ether/ EtOAC=1:1, then DCM/MeOH=10/1) to afford yellow solid C8R (100 mg, yield 23%), and crude C7R (200 mg, purity 50%). Compound C8R $^1$H NMR (500 MHz, MeOD) δ 8.36 (s, 1H), 7.58 (s, 1H), 7.06 (d, J=8.6 Hz, 1H), 6.79 (d, J=8.9 Hz, 1H), 4.18 (dd, J=10.6, 2.5 Hz, 1H), 3.95-3.91 (m, 1H), 3.68 (d, J=11.8 Hz, 1H), 3.10 (d, J=12.5 Hz, 1H), 2.99-2.84 (m, 4H), 2.63-2.58 (m, 1H), 2.48-2.43 (m, 1H), 0.91-0.88 (m, 2H), 0.58-0.55 (m, 2H). LCMS m/z 382.4 [M+H]$^+$.

-continued

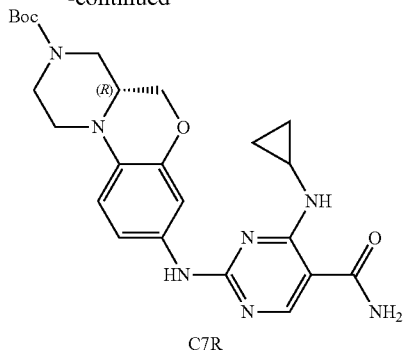

C7R

Compound C8R (20 mg, 0.05 mmol) was dissolved in CH$_2$Cl$_2$ (2 mL), and was added di-tert-butyl dicarbonate (23 mg, 0.1 mmol), then was added Et$_3$N (16 mg, 0.16 mmol), the reaction was stirred for 30 minutes at room temperature. The reaction was added 5 mL CH$_2$Cl$_2$, washed by brine, the organic phase was dried over Na$_2$SO$_4$ and filtered. The filtrate was concentrated in vacuo, the residue was purified via column chromatography (EtOAC/petroleum ether=0~80%) to afford yellow solid compound C7R (11.5 mg, yield 45%). $^1$H NMR (500 MHz, CD$_3$OD) δ 8.36 (s, 1H), 7.60 (s, 1H), 7.08 (dd, J=8.8, 2.3 Hz, 1H), 6.82 (d, J=8.9 Hz, 1H), 4.25 (dd, J=10.7, 2.7 Hz, 1H), 4.13 (d, J=12.9 Hz, 1H), 4.03 (d, J=11.9 Hz, 1H), 3.94-3.98 (m, 1H), 3.75 (d, J=12.0 Hz, 1H), 3.04-2.93 (m, 2H), 2.88-2.85 (m, 1H), 2.65-2.56 (m 2H), 1.48 (s, 9H), 0.91-0.88 (m, 2H), 0.59-0.55 (m, 2H). LCMS m/z 482.4 [M+H]$^+$.

EXAMPLE 28. PREPARATION OF COMPOUND C9R

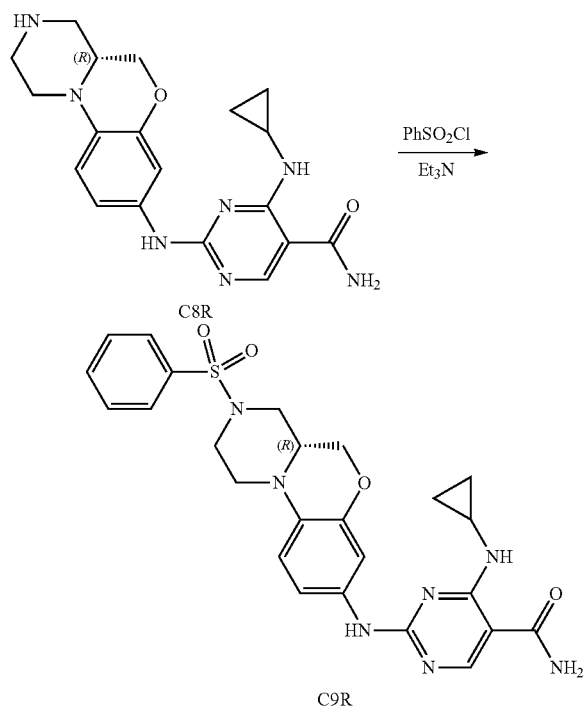

Compound C8R (30 mg, 0.075 mmol) was dissolved in CH$_2$Cl$_2$ (2 mL), and was added benzenesulfonyl chloride (26 mg, 0.15 mmol), then was added Et$_3$N (24 mg, 0.24 mmol), the reaction was stirred for 10 minutes at room temperature. The reaction was added 5 mL CH$_2$Cl$_2$, washed by brine, the organic phase was dried over Na$_2$SO$_4$ and filtered. The filtrate was concentrated in vacuo, the residue was purified via column chromatography (EtOAC/petroleum ether=0~100%) to afford yellow solid compound (17 mg, yield 41%). $^1$H NMR (500 MHz, CD$_3$OD) δ 8.35 (s, 1H), 7.82-7.80 (m, 2H), 7.70-7.68 (m, 1H), 7.64-7.61 (m, 2H), 7.58 (s, 1H), 7.05 (d, J=8.6 Hz, 1H), 6.77 (d, J=8.7 Hz, 1H), 4.24 (dd, J=10.7, 2.6 Hz, 1H), 3.90-3.86 (m, 1H), 3.84-3.80 (m, 2H), 3.77-3.74 (m, 1H), 3.13 (s, 1H), 2.86-2.82 (m, 1H), 2.78-2.73 (m, 1H), 2.50-2.45 (m, 1H), 2.12 (t, J=10.9 Hz, 1H), 0.91-0.86 (m, 3H), 0.57-0.54 (m, 2H). LCMS m/z 522.3 [M+H]$^+$.

EXAMPLE 29. PREPARATION OF COMPOUND C10R

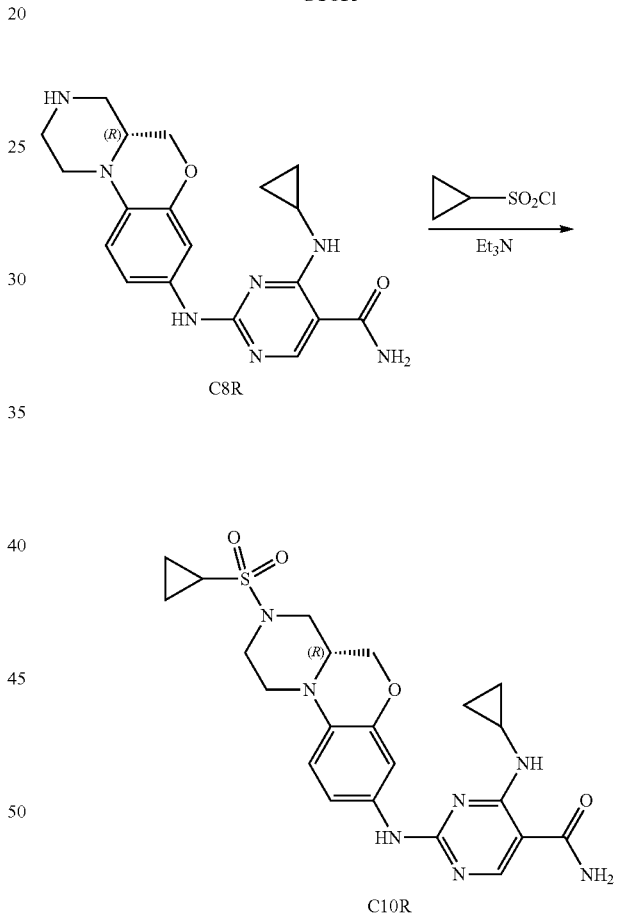

Compound C10R was made by using intermediate C8R and Cyclopropanesulfonyl chloride according to the preparation method of C9R. $^1$H NMR (500 MHz, CD$_3$OD) δ 8.36 (s, 1H), 7.63 (s, 1H), 7.10 (d, J=8.2 Hz, 1H), 6.84 (d, J=8.8 Hz, 1H), 4.27 (dd, J=10.7, 2.5 Hz, 1H), 4.00 (dd, J=10.6, 8.5 Hz, 1H), 3.88 (d, J=12.3 Hz, 1H), 3.78 (d, J=10.9 Hz, 1H), 3.71 (d, J=11.3 Hz, 1H), 3.14-3.09 (m, 2H), 2.89-2.85 (m, 1H), 2.76 (t, J=11.1 Hz, 2H), 2.52-2.49 (m, 1H), 1.10-1.01 (m, 4H), 0.92-0.88 (m, 2H), 0.59-0.56 (m, 2H). LCMS m/z 486.3 [M+H]$^+$.

EXAMPLE 30. PREPARATION OF COMPOUND C11R

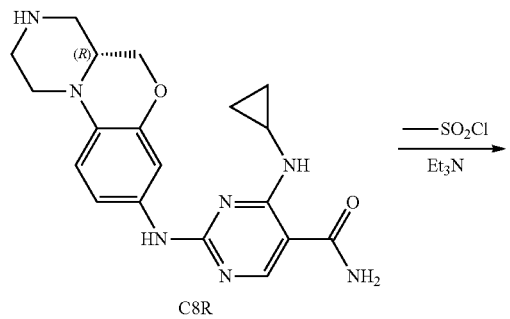

Compound C11R was made by using intermediate C8R and methanesulfonyl chloride according to the preparation method of C9R. $^1$H NMR (500 MHz, DMSO-d$_6$) δ 9.81 (s, 1H), 9.48 (s, 1H), 8.44 (s, 1H), 7.96 (s, 1H), 7.46-7.37 (m, 2H), 7.21 (s, 1H), 6.92-6.90 (m, 1H), 4.34 (d, J=9.8 Hz, 1H), 3.94-3.90 (m, 2H), 3.60 (d, J=10.4 Hz, 2H), 3.12-3.08 (m, 1H), 2.93 (s, 3H), 2.85 (s, 1H), 2.71-2.67 (m, 1H), 2.59-2.55 (m, 1H), 2.33-2.32 (m, 1H), 0.86 (d, J=6.0 Hz, 2H), 0.61-0.57 (m, 2H). LCMS m/z 460.2 [M+H]$^+$.

EXAMPLE 31. PREPARATION OF COMPOUND C12R

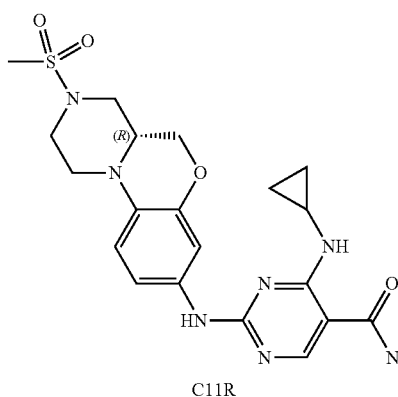

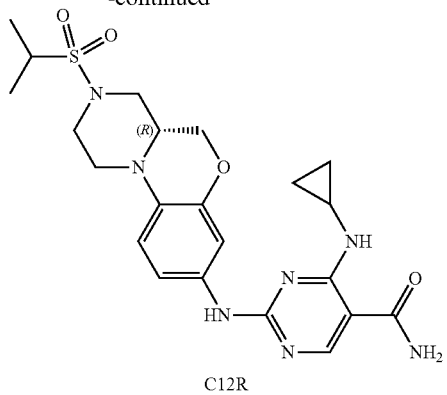

Compound C12R was made by using intermediate C8R and isopropanesulfonyl chloride according to the preparation method of C9R. $^1$H NMR (500 MHz, MeOD) δ 8.39 (s, 1H), 7.64 (s, 1H), 7.12 (d, J=8.8 Hz, 1H), 6.86 (d, J=9.0 Hz, 1H), 4.28 (d, J=11.0 Hz, 1H), 4.01-3.98 (m, 1H), 3.86 (d, J=11.1 Hz, 1H), 3.77 (d, J=11.9 Hz, 1H), 3.70-3.66 (m, 1H), 3.22-3.17 (m, 1H), 3.11-3.07 (m, 1H), 2.91-2.81 (m, 2H), 2.75-2.71 (m, 1H), 1.36 (d, J=6.79 Hz, 6H), 0.92 (d, J=6.3 Hz, 2H), 0.61-0.58 (m, 2H). LCMS m/z 488.28 [M+H]$^+$.

EXAMPLE 32. PREPARATION OF COMPOUND C13R

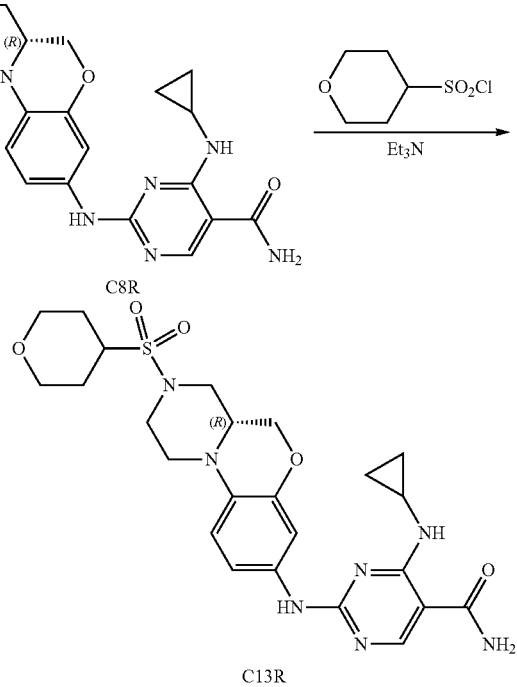

Compound C13R was made by using intermediate C8R and tetrahydro-2H-pyran-4-sulfonyl chloride according to the preparation method of C9R. $^1$H NMR (500 MHz, CDCl$_3$) δ 8.80 (s, 1H), 8.20 (s, 1H), 7.60 (s, 1H), 7.23 (s, 1H), 7.05 (d, J=10.0 Hz, 1H), 6.73 (dd, J=8.9 Hz, 3.2 Hz, 1H), 5.50 (s, 2H), 4.22 (d, J=10.8 Hz, 1H), 4.09 (d, J=11.5 Hz, 2H), 4.01-3.98 (m, 1H), 3.85 (d, J=12.1 Hz, 1H), 3.74

(d. J=10.3 Hz, 2H), 3.37 (t, J=11.9 Hz, 2H), 3.22-3.17 (m, 3H), 2.88-2.85 (m, 2H), 1.99-1.86 (m, 5H), 0.90 (d, J=5.3 Hz, 2H), 0.65-0.60 (m, 2H). LCMS m/z 530.24 [M+H]$^+$.

EXAMPLE 33. PREPARATION OF COMPOUND C14R

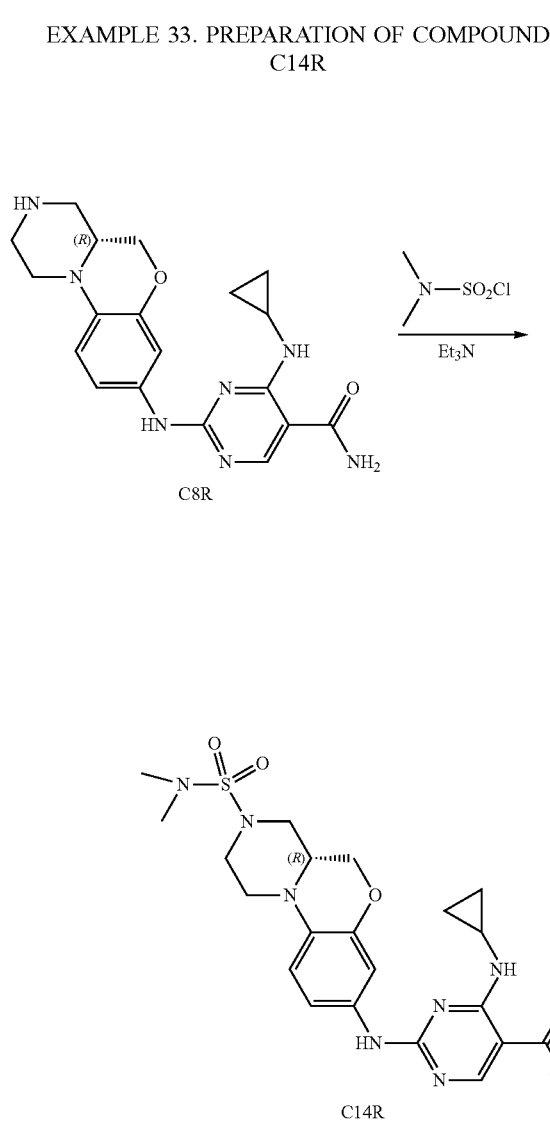

Compound C8R (5 mg, 0.013 mmol) was dissolved in CH$_2$Cl$_2$ (1 mL), and was added dimethylsulfamoyl chloride (2.5 mg, 0.013 mmol), then was added Et$_3$N (4 mg, 0.039 mmol), the reaction was stirred for 3 hours at 80° C. The reaction was added 5 mL CH$_2$Cl$_2$, washed by brine, the organic phase was dried over Na$_2$SO$_4$ and filtered. The filtrate was concentrated in vacuo, the residue was purified via column chromatography (MeOH/DCM=0~10%) to afford yellow solid compound C14R (2.0 mg, yield 31%). $^1$HNMR (500 MHz, CDCl$_3$) δ 8.78 (s, 1H), 8.20 (s, 1H), 7.57 (s, 1H), 7.14 (s, 1H), 7.06-7.04 (m, 1H), 6.74-6.73 (m, 1H), 5.52 (s, 2H), 4.23-4.20 (m, 1H), 4.03-3.99 (m, 1H), 3.75-3.70 (m, 2H), 3.61-3.58 (m, 1H), 3.21-3.17 (m, 1H), 3.12-3.06 (m, 1H), 2.90-2.80 (m, 7H), 2.74-2.69 (m, 1H), 0.90-0.88 (m, 2H), 0.65-0.62 (m, 2H). LCMS m/z 489.24 [M+H]$^+$.

EXAMPLE 34. PREPARATION OF COMPOUND C15R

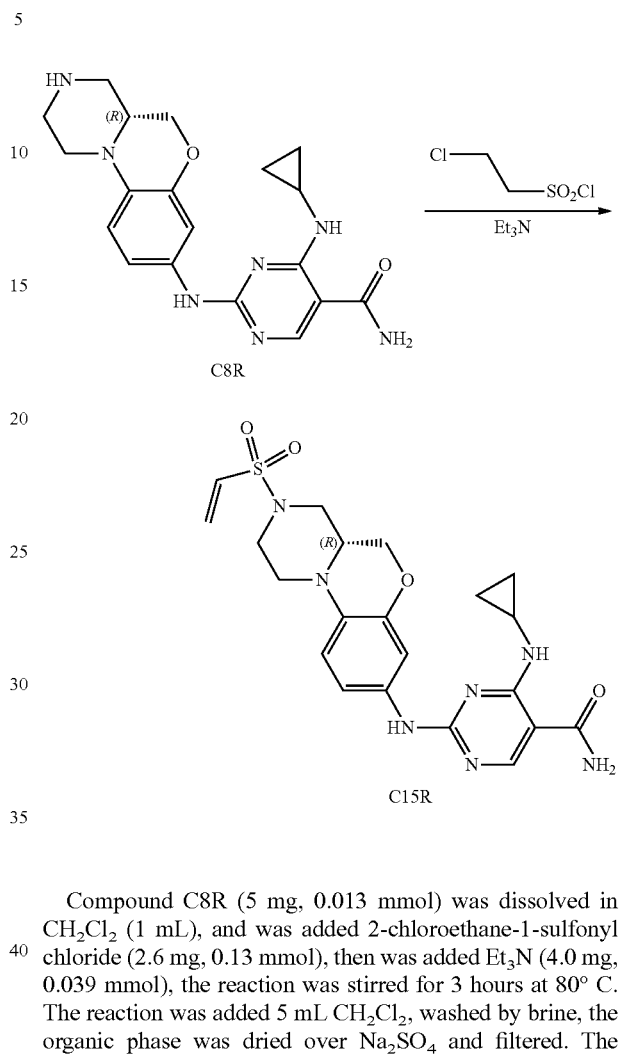

Compound C8R (5 mg, 0.013 mmol) was dissolved in CH$_2$Cl$_2$ (1 mL), and was added 2-chloroethane-1-sulfonyl chloride (2.6 mg, 0.13 mmol), then was added Et$_3$N (4.0 mg, 0.039 mmol), the reaction was stirred for 3 hours at 80° C. The reaction was added 5 mL CH$_2$Cl$_2$, washed by brine, the organic phase was dried over Na$_2$SO$_4$ and filtered. The filtrate was concentrated in vacuo, the residue was purified via column chromatography (MeOH/DCM=0~10%) to afford yellow solid compound C15R (0.41 mg, yield 7%). LCMS m/z 472.19 [M+H]$^+$.

EXAMPLE 35. PREPARATION OF COMPOUND C16R

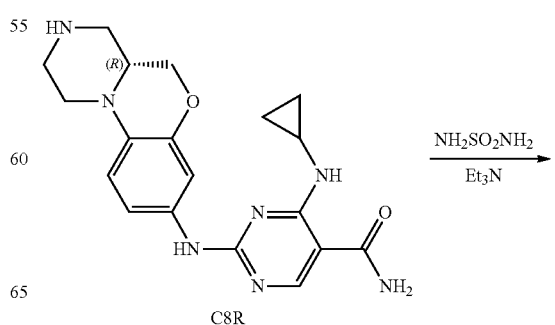

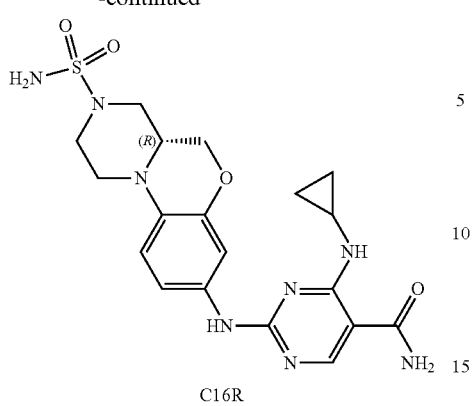

C16R

Compound C8R (5 mg, 0.013 mmol) was dissolved in dioxane (1 mL), and was added sulfuric diamide (3 mg, 0.026 mmol), then was added Et₃N (4 mg, 0.039 mmol), the mixture was reacted for 5 hours at 100° C. TLC results indicated the reaction was complete; the reaction was added saturated aq. NH₄Cl, exacted with EtOAc, washed by brine, the organic phase was dried over Na₂SO₄ and filtered. The filtrate was concentrated in vacuo, the residue was purified via preparative TLC (MeOH/DCM=0~10%) to afford pale yellow solid compound C16R (1.47 mg, yield 25%). $^1$H NMR (500 MHz, CD₃OD) δ 8.36 (s, 1H), 7.61 (s, 1H), 7.09 (d, J=8.9 Hz, 1H), 6.84 (d, J=8.9 Hz, 1H), 4.27 (dd, J=10.7, 2.6 Hz, 1H), 4.00 (dd, J=10.7, 8.5 Hz, 1H), 3.87 (d, J=11.5 Hz, 1H), 3.69-3.55 (m, 3H), 3.18-3.11 (m, 2H), 2.89-2.82 (m, 2H), 2.78 (dd, J=12.9, 10.3 Hz, 1H), 2.48 (t, 7-11.0 Hz, 1H), 2.03 (s, 1H), 0.89 (dd, J=6.2, 3.4 Hz, 5H), 0.59-0.54 (m, 2H). LCMS m/z 461.26 [M+H]⁺.

EXAMPLE 36. PREPARATION OF COMPOUND C17

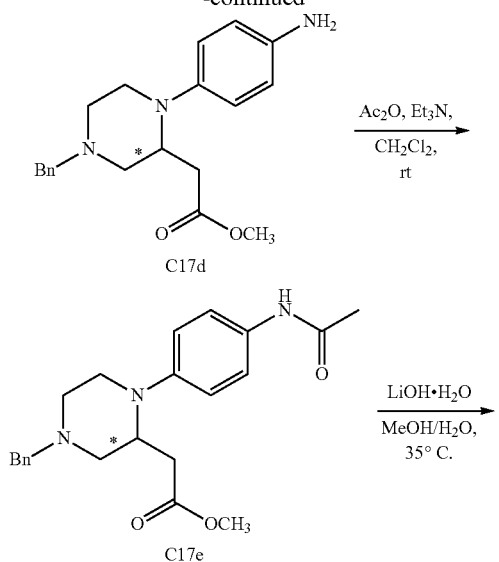

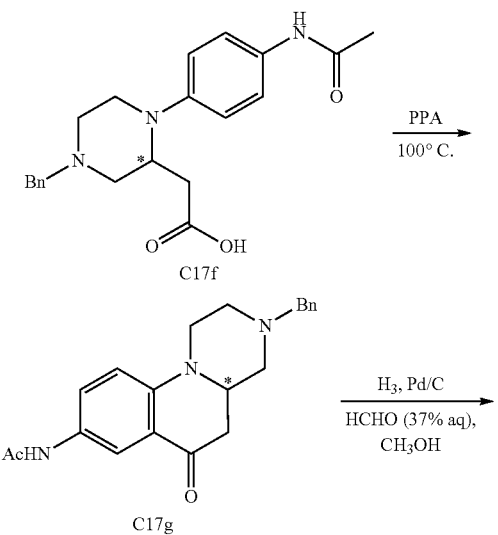

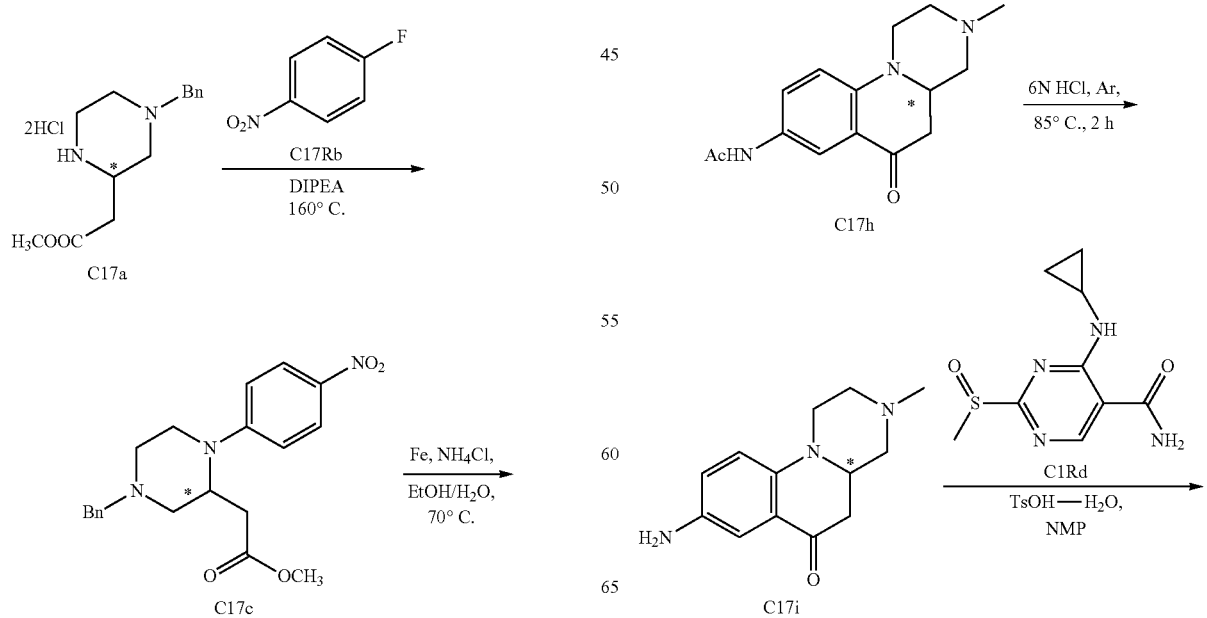

-continued

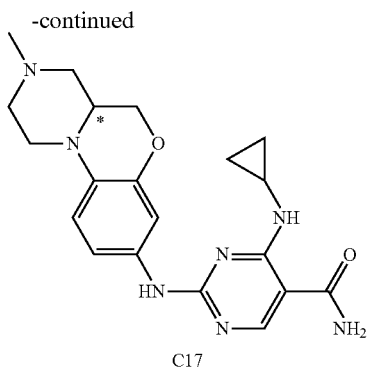

C17

Compound C17a (1.1 g, 3.43 mmol), 1-fluoro-4-nitrobenzene C17b (1.4 g, 9.93 mmol) DIPEA (2.6 g, 20.16 mmol) was dissolved in dry NMP (9 mL), the mixture was heated to 160° C. by microwave and reacted for 5 hours (totally 8 batches 1.1 g C17a reaction scale), the reaction mixture was cooled to room temperature, then poured into ice water, exacted with EtOAc 3 times, the combined organic phase was washed by brine, dried over $Na_2SO_4$ and filtered. The filtrate was concentrated in vacuo, the residue was purified via column chromatography (petroleum ether/EAOAc=6:1) to afford yellow solid compound C17c (1.8 g, yield 18%). $^1$H NMR (400 MHz, $CDCl_3$) δ 8.12 (d, J=6.5 Hz, 2H), 7.33 (m, 5H), 6.84 (d, J=6.3 Hz, 2H), 4.47 (s, 1H), 3.65-3.57 (m, 2H), 3.54 (s, 3H), 3.48 (m, 1H), 3.21 (td, J=12.3, 3.7 Hz, 1H), 3.08 (dd, J=15.5, 9.3 Hz, 1H), 2.97 (d, J=11.3 Hz, 1H), 2.85 (d, J=11.8 Hz, 1H), 2.48 (dd, J=15.6, 3.7 Hz, 1H), 2.33 (dd, J=11.7, 2.6 Hz, 1H), 2.26 (td, J=11.6, 3.6 Hz, 1H). LCMS m/z 370.2 $[M+H]^+$.

Compound C17c (1.8 g, 4.87 mmol), $NH_4Cl$ (1.1 g, 20.56 mmol) and Fe powder (1.1 g, 19.70 mmol) were dissolved in $EtOH/H_2O$ (50 mL/10 mL), the reaction mixture was heated to 70° C. and reacted for 3 hours. The reaction was cooled to room temperature, filtrated, the filtrate was concentrated in vacuo, the crude product was purified via column chromatography (DCM/MeOH=20:1) to afford yellow solid compound C17d (1.6 g, yield 97%). $^1$H NMR (400 MHz,) δ 7.32 (m, 7.9 Hz, 5H), 6.80 (d, J=8.6 Hz, 2H), 6.64 (d, J=8.8 Hz, 2H), 4.02 (d, J=9.7 Hz, 1H), 3.59 (d, J=13.8 Hz, 2H), 3.49 (s, 3H), 3.49 (s, 2H), 3.04 (d, J=12.5 Hz, 2H), 2.83 (d, J=23.6 Hz, 2H), 2.68 (d, J=8.8 Hz, 1H), 2.52 (d, J=10.0 Hz, 1H), 2.34 (m, 2H). LCMS m/z 340.2 $[M+H]^+$.

Compound C17d (1.6 g, 4.71 mmol) and $Et_3N$ (1.4 g, 13.86 mmol) was dissolved in dry $CH_2Cl_2$ (25 mL), then was added a cede anhydride (964 mg, 9.44 mmol), the mixture was reacted for 3 hours at room temperature under stirring, then poured into ice-water, exacted with EtOAc 3 times, the combined organic phase was washed by brine, dried over $Na_2SO_4$ and filtered. The filtrate was concentrated in vacuo, the crude product was purified via column chromatography (DCM/MeOH=50:1) to afford a yellow solid compound C17e (1.7 g, yield 95%). $^1$H NMR (400 MHz, $CDCl_3$) δ 7.39-7.28 (m, 7H), 7.03 (s, 1H), 6.86 (d, J=8.9 Hz, 2H), 4.23 (d, J=7.5 Hz, 1H), 3.59 (d, J=13.2 Hz, 1H), 3.51 (s, 3H), 3.47 (m, 3H), 3.24 (d, J=11.8 Hz, 1H), 3.02 (ddd, J=25.4, 13.4, 9.1 Hz, 2H), 2.89 (d, J=11.2 Hz, 1H), 2.79 (d, J=11.4 Hz, 1H), 2.47-2.24 (m, 3H), 2.12 (s, 3H). LCMS m/z 382.2 $[M+H]^+$. Compound C17e (1.7 g, 4.46 mmol) was dissolved in $MeOH/H_2O$ (25 mL/5 mL), then was added Lithium hydroxide monohydrate (750 mg, 17.86 mmol), the mixture was heated to 35° C. and stirred overnight. The reaction was concentrated to remove the MeOH, added water (20 mL), exacted with EtOAc one time, the water phase was naturalized with dilute HCl to adjust its pH value to 6, the aqueous phase was concentrated, the residue was dispersed in DCM/MeOH (10/1), and stirred, filtrated, the solid was washed by DCM/MeOH (10/1) several times. The combined filtrate was concentrated, the obtained residue was purified via column chromatography (DCM/MeOH=10:1) to afford a gray solid compound C17f (1.6 g, yield 98%). LCMS m/z 368.2 $[M+H]^+$.

Compound C17f (1.6 g, 4.35 mmol) and 10 mL polyphosphoric acid were putted in 50 mL flask, The mixture was heated to 100° C. and reacted for 7 hours, the reaction mixture was cooled to room temperature, then poured into ice water, and was neutralized with NaOH solution to adjust its pH value to 8. The obtained mixture was concentrated in vacuo, the obtained solid was dispersed in DCM/MeOH (10/1), and stirred, filtrated, the solid was washed by DCM/MeOH (10/1) several times. The combined filtrate was concentrated, the obtained residue was purified via column chromatography (DCM/MeOH=20:1) to afford gray solid compound C17g (890 mg, yield 58%). LCMS m/z 350.2 [M+H].

Compound C17g (640 mg, 1.83 mmol) and formaldehyde aqueous solution (37%, 3.0 g, 37.0 mmol) was put in 250 mL flask, and were dissolved by using MeOH (100 mL), then was added Pd/C (10%, 100 mg), the flask air was exchanged by $H_2$, The reaction mixture was stirred overnight at room temperature and $H_2$ atmosphere. TLC results indicated few starting material remained. The reaction mixture was filtrated and concentrated in vacuo, the crude product was purified via column chromatography (DCM/MeOH=50:1~25/1) to afford a yellow solid compound C17h (160 mg, yield 32%). LCMS m/z 274.2 $[M+H]^+$.

Compound C17h (8 mg, 0.029 mmol) was dissolved in dilute HCl solution (6 N, 0.5 mL), the flask air was exchanged by Argon. The reaction mixture was heated to 85° C. and stirred for 2 hours. The reaction solution was neutralized with NaOH solution to adjust its pH value to 8, and was extracted with EtOAc 3 times, the combined organic phase was washed by brine, dried over $Na_2SO_4$ and filtered. The filtrate was concentrated in vacuo to afford yellow solid compound C17i (3 mg, yield 74%). NMR (400 MHz, DMSO-$d_6$) δ 7.00 (d, J=2.2 Hz, 1H), 6.84 (t, J=6.7 Hz, 2H), 4.76 (s, 2H), 3.70 (d, J=11.5 Hz, 1H), 3.21-3.01 (m, 1H), 2.85 (dd, J=27.1, 11.4 Hz, 2H), 2.63-2.53 (m, 2H), 2.43 (d, J=8.6 Hz, 2H), 2.19 (s, 3H), 1.91 (m, 1H). LCMS m/z 232.2 $[M+H]^+$.

Compound C17 was prepared by using intermediate C17i and C1Rd according the preparation method of compound C1R. $^1$H NMR (500 MHz, $CD_3OD$) δ 8.87 (s, 1H), 8.48 (s, 1H), 8.28 (s, 1H), 8.16 (s, 1H), 7.27 (d, J=9.3 Hz, 2H), 6.91 (d, J=9.3 Hz, 1H), 5.85 (s, 1H), 3.77 (d, J=11.5 Hz, 1H), 3.45 (t, J=8.0 Hz, 1H), 2.98-2.88 (m, 4H), 2.58 (d, J=8.5 Hz, 2H), 2.36 (s, 3H), 2.33-2.31 (m, 1H), 2.10 (t, J=10.8 Hz, 1H), 0.92 (d, J=5.5 Hz, 2H), 0.64 (d, J=1.7 Hz, 2H). LCMS m/z 408.4 $[M+H]^+$.

EXAMPLE 37. PREPARATION OF COMPOUND C18R

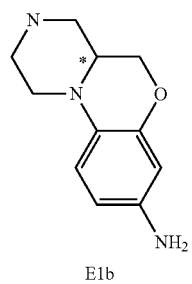

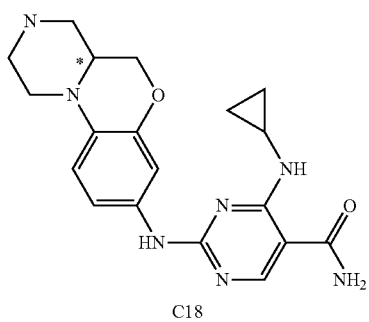

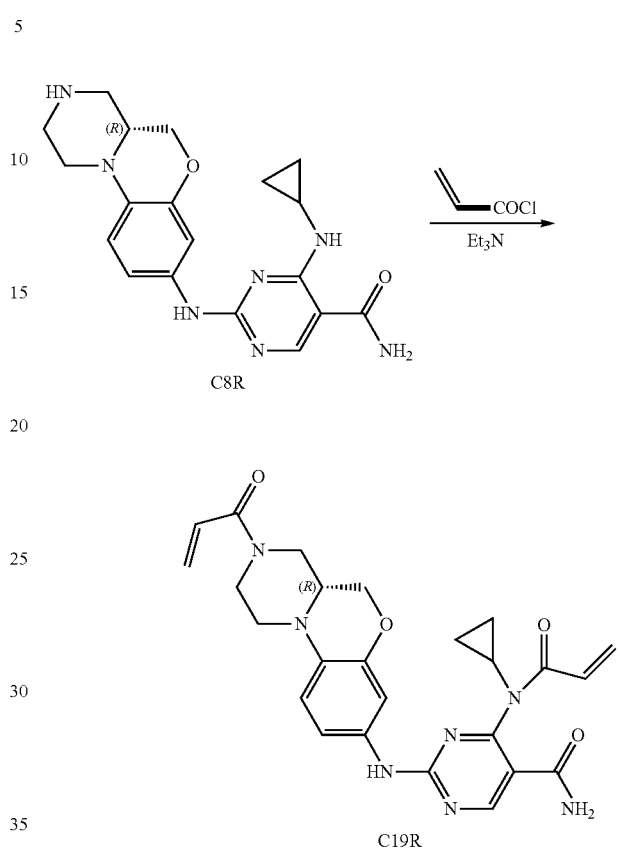

Intermediate E1b is racemate of A8Rd and A8Sd, which was synthesized according to the preparation method of A8Rd and A8Sd.

Compound C18R was prepared from intermediate E1b and C1Rd according to the preparation method of compound C1R. $^1$H NMR (500 MHz, CD$_3$OD) δ 8.78 (s, 1H), 8.20 (s, 1H), 7.54 (s, 1H), 7.24 (s, 1H), 7.05 (dd, J=8.6, 2.1 Hz, 1H), 6.69 (d, J=8.8 Hz, 1H), 5.60 (s, 2H), 4.14 (dd, J=10.6, 2.6 Hz, 1H), 4.04 (dd, J=11.4, 3.3 Hz, 1H), 3.97 (dd, J=10.4, 9.2 Hz, 1H), 3.86 (dd, J=10.9, 2.9 Hz, 1H), 3.77-3.73 (m, 1H), 3.47 (d, J=11.3 Hz, 1H), 3.29 (t, J=10.7 Hz, 1H), 3.21-3.16 (m, 1H), 2.90-2.90 (m, 2H), 0.92-0.89 (m, 2H), 0.64-0.62 (m, 2H). LCMS m/z 383.3 [M+H]$^+$.

EXAMPLE 38. PREPARATION OF COMPOUND C19R

Compound C19R was prepared from the reaction of compound C8R with acryloyl chloride in DCM and Et$_3$N. $^1$H NMR (500 MHz, CDOD$_3$) δ 8.50 (s, 1H), 6.96-6.93 (m, 1H), 6.87-6.81 (m, 1H), 6.74 (dd, J=8.7 Hz, 2.4 Hz, 1H), 6.68-6.60 (m, 2H), 6.37 (dd, J=16.8 Hz, 1.8 Hz, 1H), 6.28 (dd, J=16.8 Hz, 1.8 Hz, 1H), 5.80 (dd, J=10.6 Hz, 1.8 Hz, 1H), 5.73 (dd, J=10.6 Hz, 1.8 Hz, 1H), 4.60-4.58 (m, 1H), 4.33 (dd, J=10.8 Hz, 2.6 Hz, 1H), 4.03-4.00 (m, 1H), 3.94-3.87 (m, 2H), 3.16-3.10 (m, 1H), 3.05-2.98 (m, 1H), 2.82-2.63 (m, 3H), 0.77-0.73 (m, 2H), 0.53-0.50 (m, 2H). LCMS m/z 490.28 [M+H]$^+$.

EXAMPLE 39. PREPARATION OF COMPOUND C20R

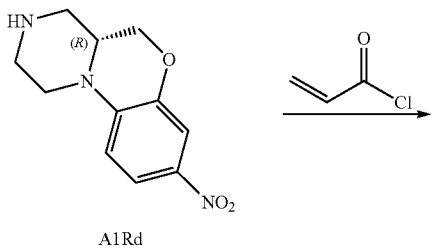

-continued

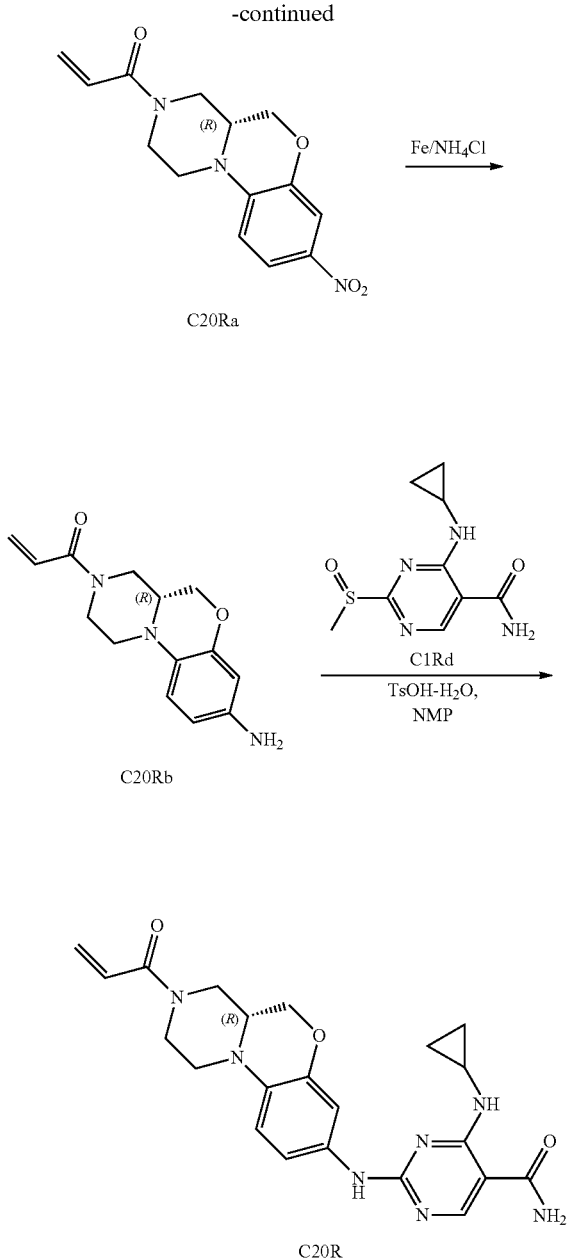

EXAMPLE 40. PREPARATION OF COMPOUND D1S

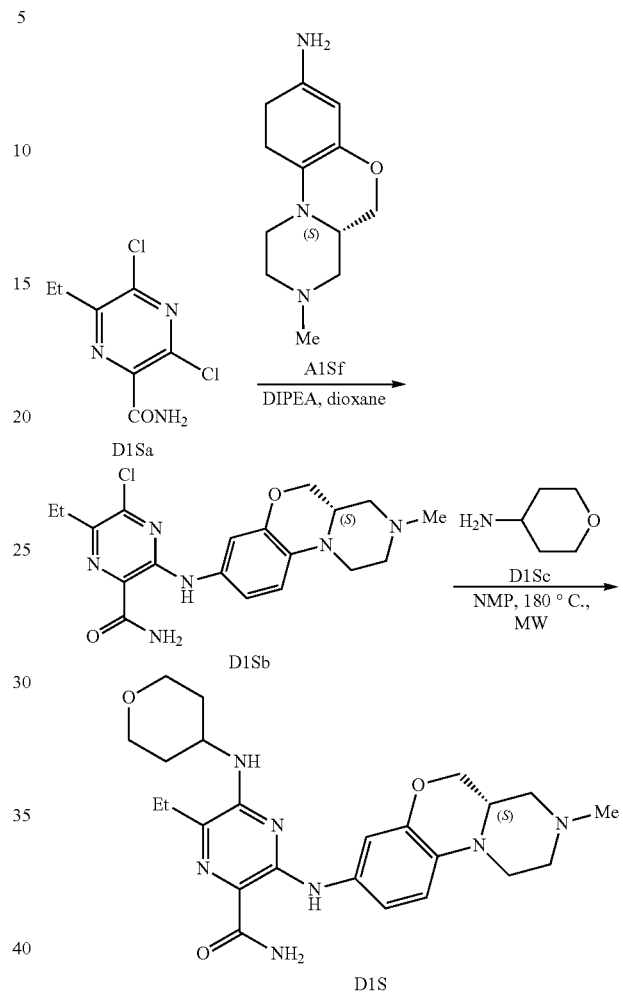

Compound C20Ra was prepared from the reaction of A1Rd with acryloyl chloride in DCM and Et₃N. Compound C20Rb was prepared from the reduction of C20Ra by Fe powder and NH₄Cl (refer to the preparation of C17Rd). Compound C20R was prepared from the reaction of compound C20Rb and compound C1Rd (refer to the preparation method of A8Rd and A8Sd). $^1$H NMR (500 MHz, CDCl₃) δ 8.82 (s, 1H), 8.24 (s, 1H), 7.57 (s, 1H), 7.34 (s, 1H), 7.05 (s, 1H), 6.73 (s, 1H), 6.62-6.57 (m, 1H), 6.33 (d, J=16.8 Hz, 1H), 5.75 (dd, J=10.5 Hz, 1.5 Hz, 1H), 5.64 (s, 2H), 4.73-4.63 (m, 1H), 4.26-4.23 (m, 1H), 4.02 (dd, J=10.5 Hz, 8.9 Hz, 1H), 3.72 (d, J=11.8 Hz, 1H), 3.42-3.38 (m, 1H), 3.07-2.96 (m, 2H), 2.90-2.86 (m, 1H), 2.74-2.69 (m, 1H), 2.58-2.53 (m, 1H), 0.90-0.88 (m, 2H), 0.63-0.61 (m, 2H). LCMS m/z 436.24 [M+H]⁺.

Compound D1Sa (100 mg, 0.455 mmol), A1Sf (109 mg, 0.499 mmol) and DIPEA (117 mg, 0.909 mmol) were dissolved in 1,4-dioxane (3 mL) in a sealed tube, the reaction mixture was healed to 130° C. and stirred for 16 hours. The LCMS indicated the reaction was complete, the reaction mixture was concentrated in vacuo, the residue was purified via column chromatography (DCM/MeOH=30:1) to afford a pale yellow solid compound D1Sb (160 mg, yield 88%). $^1$H NMR (DMSO-d₆, 400 MHz) δ 10.93 (s, 1H), 8.21 (s, 1H), 7.98 (s, 1H), 7.14 (d, J=2.0 Hz, 1H), 6.93-6.82 (m, 2H), 4.23 (dd, J=10.8 Hz, 2.8 Hz, 1H), 3.90 (dd, J=10.4 Hz, 9.2 Hz, 1H), 3.66 (d, J=11.6 Hz, 1H), 3.05-2.95 (m, 1H), 2.89-2.74 (m, 4H), 2.65-2.55 (m, 1H), 2.22 (s, 3H), 2.13-2.03 (m, 1H), 1.68 (dd, J=10.8 Hz, 10.8 Hz, 1H), 1.24 (t, J=7.4 Hz, 3H). MS m/z 403.2 [M+H]⁺, 405.2 [M+H]⁺.

Compound D1Sb (200 mg, 0.498 mmol) and D1Sc (251 mg, 2.488 mmol) were dissolved in NMP (5 mL), the reaction mixture was heated to 180° C. and stirred for 1 hour in a microwave reactor. The LCMS indicated the reaction was complete, the reaction mixture was poured into EtOAc (10 mL), washed by brine (10 mL×2), the combined organic phase was dried over Na₂SO₄, filtrated, and concentrated in vacuo, the residue was purified via column chromatography (DCM/MeOH=30:1) to afford compound D1S (113 mg, yield 49%, >99% ee) as a yellow solid. $^1$H NMR (DMSO-$d_6$, 400 MHz) δ 10.91 (s, 1H), 7.51 (s, 1H), 7.35 (d, J=2.0 Hz, 1H), 7.21 (s, 1H), 6.85-6.75 (m, 3H), 4.22 (dd, J=10.4 Hz, 2.4 Hz, 1H), 4.14-4.00 (m, 1H), 3.97-3.85 (m, 3H), 3.64 (d, J=11.6 Hz, 1H), 3.43 (dd, J=12.0 Hz, 12.0 Hz, 2H), 3.01-2.93 (m, 1H), 2.89-2.75 (m, 2H), 2.61-2.51 (m, 3H), 2.22 (s, 3H), 2.14-2.04 (m, 1H), 1.90-1.82 (m, 2H), 1.72-1.53 (m, 3H), 1.18 (t, J=7.2 Hz, 3H). MS m/z 468.4 [M+H]$^+$.

EXAMPLE 41. PREPARATION OF COMPOUND D1R

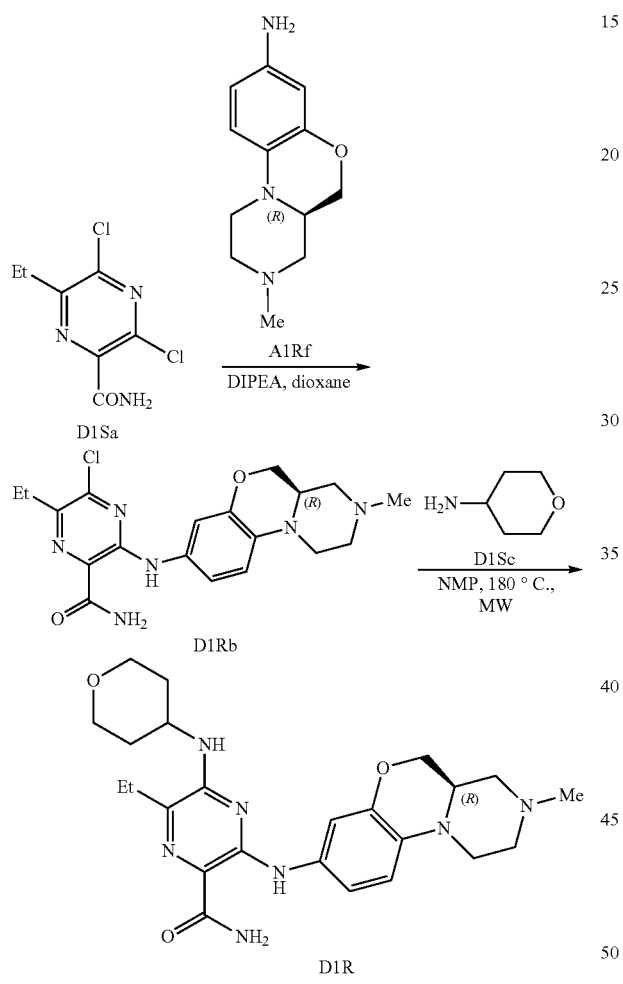

Compound D1Ra (100 mg, 0.455 mmol), A1Rf (109 mg, 0.499 mmol) and DIPEA (117 mg, 0.909 mmol) were dissolved in 1,4-dioxane (3 mL) in a sealed tube, the reaction mixture was heated to 130° C. and stirred for 16 hours. The LCMS indicated the reaction was complete, the reaction mixture was concentrated in vacuo, the residue was purified via column chromatography (DCM/MeOH=30:1) to afford D1Rb (150 mg, yield 82%) as light yellow solid. $^1$H NMR (DMSO-$d_6$, 400 MHz) δ 10.93 (s, 1H), 8.21 (s, 1H), 7.98 (s, 1H), 7.14 (d, J=2.0 Hz, 1H), 6.93-6.82 (m, 2H), 4.23 (dd, J=10.8 Hz, 2.8 Hz, 1H), 3.90 (dd, J=10.4 Hz, 9.2 Hz, 1H), 3.66 (d, J=11.2 Hz, 1H), 3.05-2.95 (m, 1H), 2.89-2.74 (m, 4H), 2.65-2.55 (m, 1H), 2.22 (s, 3H), 2.13-2.03 (m, 1H), 1.68 (dd, J=10.4 Hz, 10.0 Hz, 1H), 1.24 (t, J=7.4 Hz, 3H). MS m/z 403.2 [M+H]$^+$, 405.2 [M+H]$^+$.

Compound D1Rb (200 mg, 0.498 mmol) and (251 mg, 2.488 mmol) were dissolved in NMP (5 mL), the reaction mixture was heated to 180, 3 in microwave and stirred for 1 hour in seal. The LCMS indicated the reaction was complete, the reaction mixture was poured into EtOAc (10 mL), washed by brine (10 mL ch, the ethyl acetate layer was dried over Na$_2$SO$_4$, filtrated, and concentrated in vacuo, the residue was purified via column chromatography (DCM/MeOH=30:1) to afford H1-7R (123 mg, yield 53%) as a yellow solid.

Compound D1Rb (200 mg, 0.498 mmol) and D1Rc (251 mg, 2.488 mmol) were dissolved in NMP (5 mL), the reaction mixture was heated to 180° C. in microwave and stirred for 1 hour in seal. The LCMS indicated the reaction was complete, the reaction mixture was poured into EtOAc (10 mL), washed by brine (10 mL×2), the organic phase was dried over Na$_2$SO$_4$, filtrated, and concentrated in vacuo, the residue was purified via column chromatography (DCM/MeOH=30:1) to afford D1R (123 mg, yield 53%, >99% ee) as a yellow solid. $^1$H NMR (DMSO-$d_6$, 400 MHz) δ 10.91 (s, 1H), 7.51 (s, 1H), 7.35 (d, J=1.6 Hz, 1H), 7.21 (s, 1H), 6.85-6.75 (m, 3H), 4.22 (dd, J=10.4 Hz, 2.4 Hz, 1H), 4.14-4.00 (m, 1H), 3.97-3.85 (m, 3H), 3.64 (d, J=11.6 Hz, 1H), 3.43 (dd, J=12.4 Hz, 11.6 Hz, 2H), 3.01-2.93 (m, 1H), 2.88-2.75 (m, 2H), 2.61-2.51 (m, 3H), 2.22 (s, 3H), 2.14-2.04 (m, 1H), 1.90-1.82 (m, 2H), 1.72-1.53 (m, 3H), 1.18 (t, J=7.2 Hz, 3H). MS m/z 468.4 [M+H]$^+$.

EXAMPLE 42. PREPARATION OF COMPOUND D2S

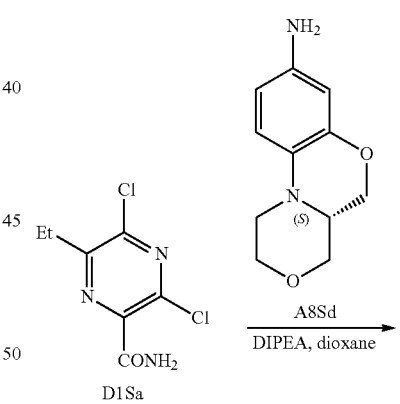

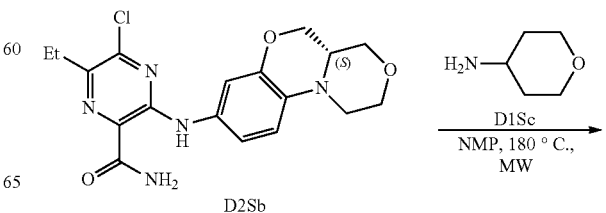

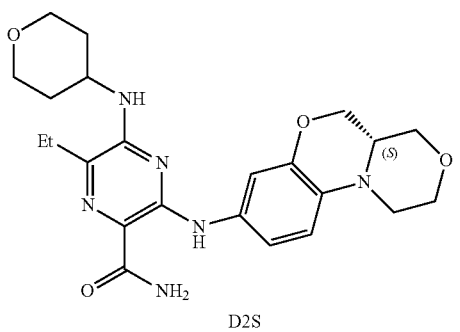

D2S

Compound D1Sa (25 mg, 0.114 mmol), A8Sd (26 mg, 0.126 mmol) and DIPEA (29 mg, 0.228 mmol) were dissolved in 1,4-dioxane (2 mL), the reaction solution was heated to 130° C. and stirred for 16 hours in seal. The LCMS indicated the reaction was complete, the reaction mixture was concentrated in vacuo, the residue was purified via column chromatography (DCM/MeOH=50:1) to afford compound D2Sb (43 mg, yield 97%) as a pale yellow solid. MS m/z 390.2 [M+H]$^+$, 392.2 [M+H]$^+$.

Compound D2Sb (43 mg, 0.111 mmol) and D1Sc (56 mg, 0.553 mmol) were dissolved in NMP (1 mL), the reaction mixture was heated to 180° C. by microwave and stirred for 1 hour in seal. The LCMS indicated the reaction was complete, the reaction mixture was poured into EtOAc (5 mL), washed by brine (2 mL×2), the organic phase was dried over Na$_2$SO$_4$, filtrated, and concentrated in vacuo, the residue was purified via column chromatography (DCM/MeOH=50:1) to afford yellow solid compound D2S (22 mg, yield 44%). $^1$H NMR (DMSO-d$_6$, 400 MHz) δ 10.91 (s, 1H), 7.50 (s, 1H), 7.36 (d, J=2.4 Hz, 1H), 7.20 (s, 1H), 6.85-6.75 (m, 3H), 4.21 (dd, J=10.8 Hz, 2.8 Hz, 1H), 4.12-4.01 (m, 1H), 3.97-3.80 (m, 5H), 3.64-3.52 (m, 2H), 3.48-3.37 (m, 2H), 3.16 (dd, J=10.8 Hz, 10.8 Hz, 1H), 3.07-2.97 (m, 1H), 2.70-2.53 (m, 3H), 1.92-1.85 (m, 2H), 1.69-1.55 (m, 2H), 1.18 (t, J=7.2 Hz, 3H). MS m/z 455.2 [M+H]$^+$.

EXAMPLE 43. PREPARATION OF COMPOUND D2R

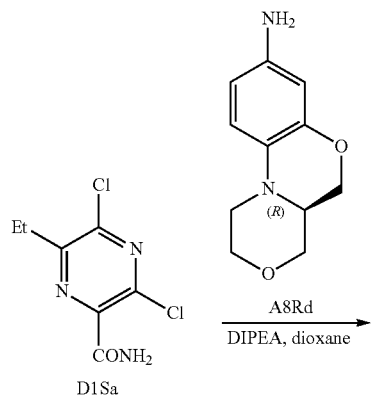

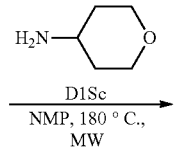

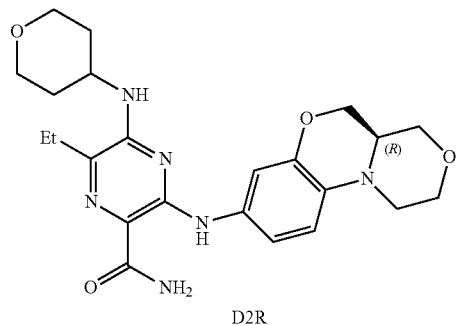

D2R

Compound D1Sa (26 mg, 0.119 mmol), A8Rd (27 mg, 0.131 mmol) and DIPEA (31 mg, 0.237 mmol) were dissolved in 1,4-dioxane (2 mL), the reaction solution was heated to 130° C. and stirred for 16 hours in seal. The LCMS indicated the reaction was complete, the reaction mixture was concentrated in vacuo, the residue was purified via column chromatography (DCM/MeOH=50:1) to afford pale yellow solid compound D2Rb (44 mg, yield 96%). MS m/z 3902 [M+H]$^+$, 392.2 [M+H]$^+$.

Compound D2Rb (44 mg, 0.113 mmol)) and D1Sc (57 mg, 0.566 mmol)) were dissolved in NMP (1 mL). The reaction mixture was heated to 180° C. by microwave and stirred for 1 hour in seal. The LCMS indicated the reaction was complete, the reaction mixture was poured into EtOAc (5 mL), washed by brine (2 mL×2), the organic phase was dried over Na$_2$SO$_4$, filtrated, and concentrated in vacuo, the residue was purified via preparative TLC (DCM/MeOH=50:1) to afford yellow solid compound D2R (20 mg, yield 39%). $^1$H NMR (DMSO-d$_6$, 400 MHz) δ 10.91 (s, 1H), 7.50 (s, 1H), 7.36 (d, J=2.4 Hz, 1H), 7.20 (s, 1H), 6.85-6.75 (m, 3H), 4.21 (dd, J=10.8 Hz, 2.8 Hz, 1H), 4.13-4.01 (m, 1H), 3.97-3.82 (m, 5H), 3.64-3.52 (m, 2H), 3.47-3.38 (m, 2H), 3.16 (dd, J=10.8 Hz, 10.8 Hz, 1H), 3.07-2.97 (m, 1H), 2.70-2.53 (m, 3H), 1.92-1.85 (m, 2H), 1.69-1.55 (m, 2H), 1.18 (t, J=7.2 Hz, 3H). MS m/z 455.2 [M+H]$^+$.

EXAMPLE 44. PREPARATION OF COMPOUND D3R

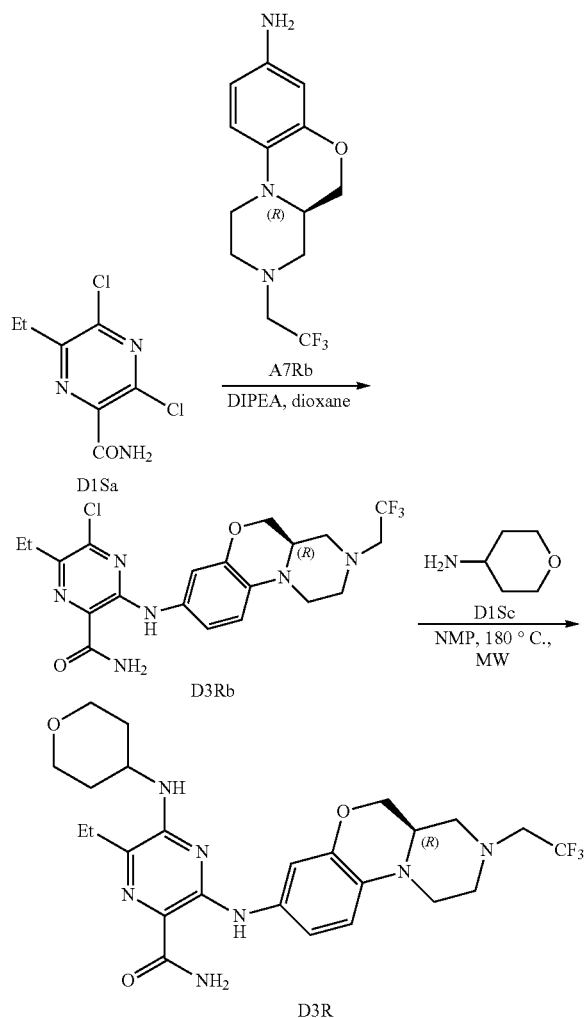

Compound D1Sa (23 mg, 0.105 mmol), A7Rb (30 mg, 0.104 mmol) and DIPEA (40 mg, 0.310 mmol) were dissolved in 1,4-dioxane (2 mL), the reaction solution was heated to 130° C. and stirred for 16 hours in seal. The LCMS indicated the reaction was complete, the reaction mixture was concentrated in vacuo, the residue was purified via column chromatography (DCM/MeOH=100:1) to afford pale yellow solid compound D3Rb (47 mg, yield 95%). MS m/z 471.2 [M+H]$^+$, 473.2 [M+H]$^+$.

Compound D3Rb (47 mg, 0.100 mmol) and D1Sc (60 mg, 0.593 mmol) were dissolved in NMP (1 mL). The reaction mixture was heated to 180° C. by microwave and stirred for 1 hour in seal. The LCMS indicated the reaction was complete, the reaction mixture was poured into EtOAc (5 mL), washed by brine (3 mL×2), the organic phase was dried over Na$_2$SO$_4$, filtrated, and concentrated in vacuo, the residue was purified via preparative TLC (DCM/MeOH=40:1) to afford compound D3R (25 mg, yield 47%) as a yellow solid. $^1$H NMR (DMSO-d$_6$, 400 MHz) δ 10.90 (s, 1H), 7.50 (d, s, 1H), 7.34 (d, J=2.0 Hz, 1H), 7.20 (s, 1H), 6.85-6.75 (m, 3H), 4.24 (dd, J=10.8 Hz, 2.8 Hz, 1H), 4.15-4.01 (m, 1H), 3.96-3.85 (m, 3H), 3.71-3.65 (m, 1H), 3.48-3.39 (m, 2H), 3.33-3.20 (m, 2H), 3.04-2.90 (m, 3H), 2.62-2.51 (m, 4H), 2.18 (dd, J=11.2 Hz, 10.4 Hz, 1H), 1.93-1.82 (m, 2H), 1.67-1.56 (m, 2H), 1.18 (t, J=7.2 Hz, 3H). MS m/z 536.2 [M+H]$^+$.

EXAMPLE 45. PREPARATION OF COMPOUND D4R

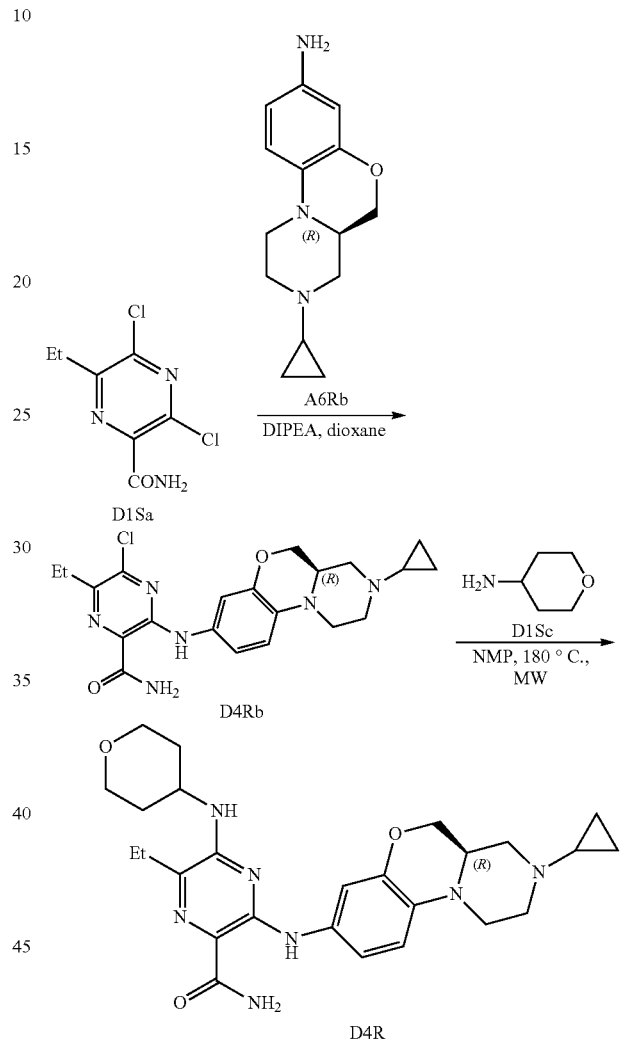

Compound D1Sa (26 mg, 0.118 mmol), A6Rb (29 mg, 0.118 mmol) and DIPEA (46 mg, 0.357 mmol) were dissolved in 1,4-dioxane (2 mL), the reaction solution was heated to 130° C. and stirred for 16 hours in seal. The LCMS indicated the reaction was complete, the reaction mixture was concentrated in vacuo, the residue was purified via column chromatography (DCM/MeOH=100:1) to afford compound D4Rb (47 mg, yield 92%) as a pale yellow solid. MS m/z 429.2 [M+H]$^+$, 430.2 [M+H]$^+$.

Compound D4Rb (47 mg, 0.110 mmol) and D1Sc (67 mg, 0.662 mmol) were dissolved in NMP (1 mL). The reaction mixture was heated to 180° C. by microwave and stirred for 1 hour in seal. The LCMS indicated the reaction was complete, the reaction mixture was poured into EtOAc (5 mL), washed by brine (3 mL×2), the organic phase was dried over Na$_2$SO$_4$, filtrated, and concentrated in vacuo, the residue was purified via preparative TLC (DCM/MeOH=35:1)

to afford compound D4R (25 mg, yield 46%) as a yellow solid. $^1$H NMR (DMSO-d$_6$, 400 MHz) δ 10.89 (s, 1H), 7.50 (s, 1H), 7.34 (d, J=2.0 Hz, 1H), 7.19 (s, 1H), 6.85-6.75 (m, 3H), 4.24 (dd, J=10.8 Hz, 2.8 Hz, 1H), 4.13-4.00 (m, 1H), 3.96-3.87 (m, 3H), 3.70-3.63 (m, 1H), 3.47-3.38 (m, 2H), 3.04-2.83 (m, 3H), 2.56 (q, J=7.6 Hz, 2H), 2.45-2.32 (m, 1H), 1.98 (dd, J=10.8 Hz, 10.8 Hz, 1H), 1.92-1.82 (m, 2H), 1.70-1.55 (m, 3H), 1.18 (t, J=7.6 Hz, 3H), 0.89-0.81 (m, 1H), 0.48-0.40 (m, 2H), 0.38-0.31 (m, 2H). MS m/z 494.2 [M+H]$^+$.

EXAMPLE 46. PREPARATION OF COMPOUND D5S

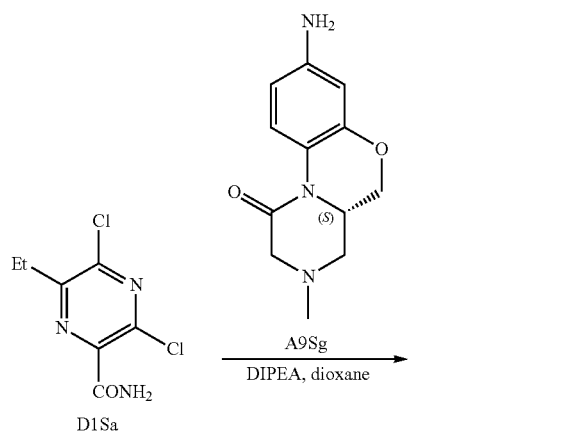

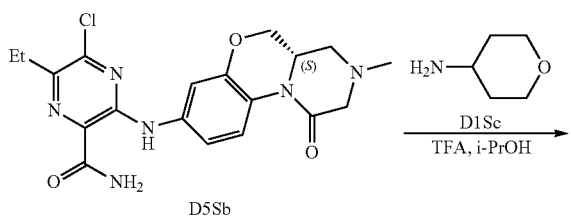

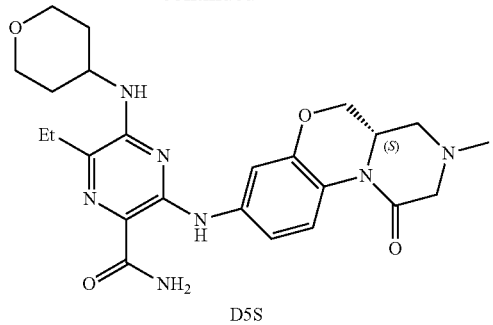

Compound D1Sa (27 mg, 0.123 mmol), A9Sg (29 mg, 0.124 mmol) and DIPEA (48 mg, 0.372 mmol) were dissolved in 1,4-dioxane (1 mL), the reaction solution was heated to 150° C. and stirred for 16 hours in seal. The LCMS indicated the reaction was complete, the reaction mixture was concentrated in vacuo, the residue was purified via column chromatography (DCM/MeOH=25:1) to afford compound D5Sb (9 mg, yield 18%) as a pale yellow solid. MS m/z 417.2 [M+H]$^+$, 419.2 [M+H]$^+$.

Compound D5Sb (7 mg, 0.017 mmol) and D1Sc (10 mg, 0.099 mmol) were dissolved in isopropyl alcohol (0.5 mL), then was added trifluoroacetic acid (3 mg, 0.026 mmol). The reaction solution was healed to 100° C. and stirred for 16 hours in seal. The reaction was cooled to room temperature, then poured into saturated aq. NaHCO$_3$ (5 mL), exacted with EtOAc (5 mL×3), the combined organic phase was washed by brine (5 mL), dried over Na$_2$SO$_4$, filtrated, and concentrated in vacuo, the residue was purified via preparative TLC (DCM/MeOH=20:1) to afford compound D5S (4 mg, yield 49%) as a yellow solid. $^1$H NMR (DMSO-d$_6$, 400 MHz) δ 11.20 (s, 1H), 8.08 (d, J=8.8 Hz, 1H), 7.64 (d, J=2.8 Hz, 1H), 7.57 (s, 1H), 7.30 (s, 1H), 6.91 (d, J=7.2 Hz, 1H), 7.57 (dd, J=9.2 Hz, J=2.4 Hz, 1H), 4.42-4.36 (m, 1H), 4.14-4.05 (m, 1H), 4.02-3.88 (m, 4H), 3.48-3.38 (m, 2H), 3.05-2.85 (m, 3H), 2.59 (q, J=7.2 Hz, 2H), 2.35-2.30 (m, 1H), 2.25 (s, 3H), 1.93-1.85 (m, 2H), 1.70-1.59 (m, 2H), 1.19 (t, J=7.2 Hz, 3H). MS m/z 482.2 [M+H]$^+$.

EXAMPLE 47. PREPARATION OF COMPOUND D6R

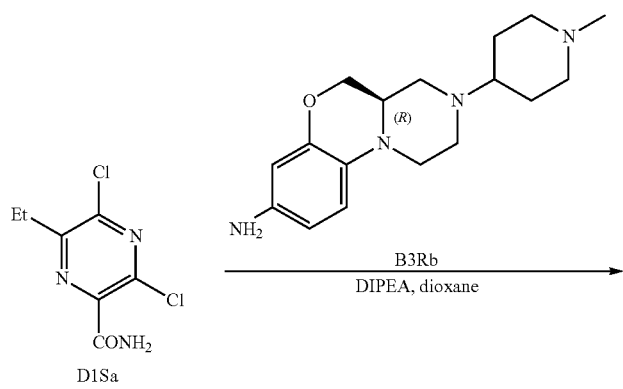

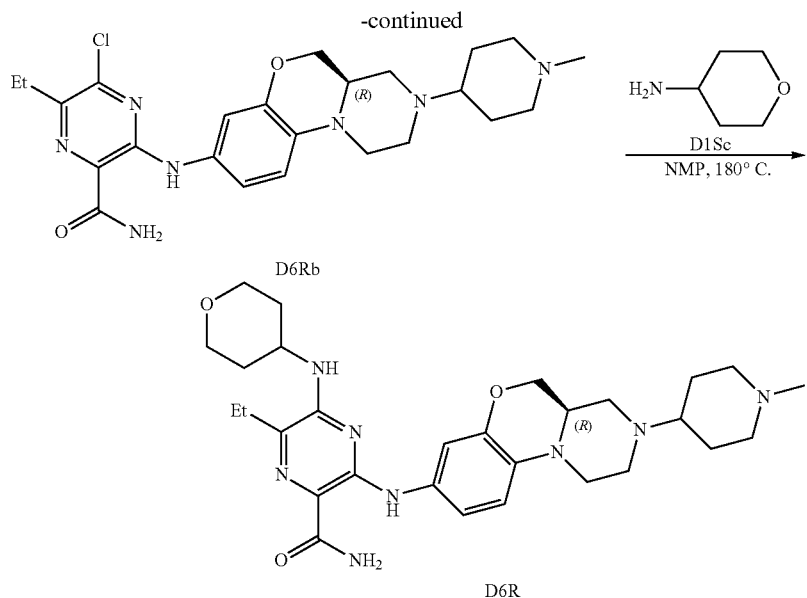

Compound D1Sa (30 mg, 0.137 mmol), B3Rb (41 mg, 0.137 mmol) and DIPEA (35 mg, 0.274 mmol) were dissolved in 1,4-dioxane (2 mL), the reaction solution was heated to 130° C. and stirred for 16 hours in seal. The LCMS indicated the reaction was complete, the reaction mixture was concentrated in vacuo, the residue was purified via preparative TLC (DCM/MeOH=15:1) to afford compound D6Rb (30 mg, yield 45%) as a pale yellow solid. MS m/z 486.2 [M+H], 488.2 [M+H]⁺.

Compound D6Rb (30 mg, 0.062 mmol) and D1Sc (31 mg, 0.309 mmol) were added to NMP (1 mL). The reaction mixture was heated to 180° C. by microwave and stirred for 1 hour in seal. The LCMS indicated the reaction was complete, the reaction mixture was poured into EtOAc (5 mL), washed by brine (3 mL×2), the organic phase was dried over Na$_2$SO$_4$, filtrated, and concentrated in vacuo, the residue was purified via preparative TLC (DCM/MeOH=5:1) to afford compound D6R (3 mg, yield 9%) as a yellow solid. $^1$H NMR (DMSO-d$_6$, 400 MHz) δ 10.88 (s, 1H), 7.50 (s, 1H), 7.33 (d, J=2.0 Hz, 1H), 7.18 (s, 1H), 6.83-6.74 (m, 3H), 4.27-4.20 (m, 1H), 4.13-4.00 (m, 1H), 3.95-3.85 (m, 3H), 3.66 (d, J=11.2 Hz, 1H), 3.48-3.38 (m, 2H), 3.01-2.75 (m, 6H), 2.56 (q, J=7.2 Hz, 2H), 2.37-2.24 (m, 2H), 2.24-2.09 (m, 3H), 1.92-1.80 (m, 5H), 1.80-1.70 (m, 2H), 1.67-1.55 (m, 2H), 1.50-1.36 (m, 2H), 1.18 (t, J=7.2 Hz, 3H). MS m/z 551.3[M+H]⁺.

EXAMPLE 48. PREPARATION OF COMPOUND D7R

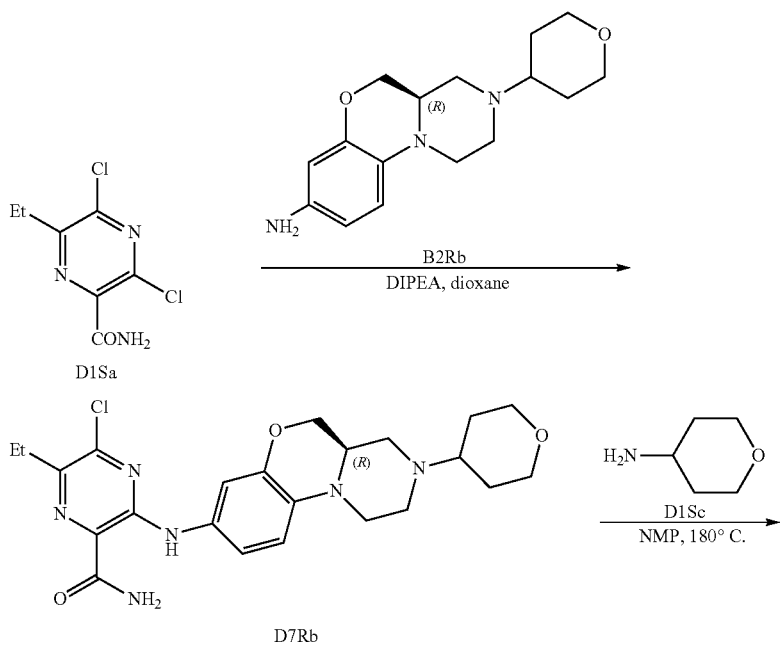

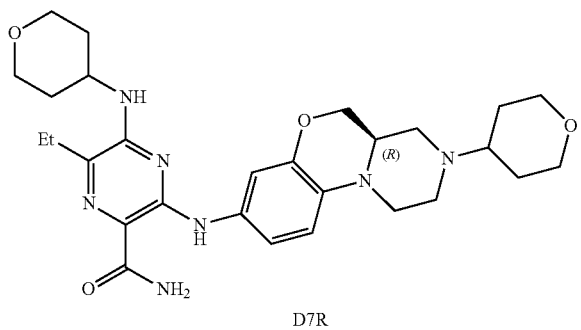

D7R

Compound D1Sa (46 mg, 0.21 mmol), B2Rb (40 mg, 0.14 mmol) and DIPEA (36 mg, 0.28 mmol) were dissolved in 1,4-dioxane (2 mL), the reaction solution was heated to 130° C. and stirred for 16 hours in seal. The LCMS indicated the reaction was complete, the reaction mixture was concentrated in vacuo; the residue was poured into water, filtrated. The residue was washed by DCM to afford yellow solid D7Rb (36 mg, yield 55%). MS m/z 473.2 [M+H]$^+$, 475.2 [M+H]$^+$.

Compound D7Rb (35 mg, 0.074 mmol) and D1Sc (37 mg, 0.37 mmol) were added to NMP (1 mL). The reaction mixture was heated to 180° C. by microwave and stirred for 1 hour in seal. The reaction mixture was poured into water, exacted with DCM (5 mL×3), the combined organic phase was washed by brine, dried over MgSO$_4$, filtrated, and concentrated in vacuo at the temperature lower than 35° C., the crude product was purified via column chromatography (DCM/MeOH=30:1) to afford compound D7R (14 mg, yield 35%) as a yellow solid. $^1$H NMR (DMSO-d$_6$, 400 MHz) δ 10.89 (s, 1H), 7.50 (s, 1H), 7.34 (d, J=2.0 Hz, 1H), 7.21 (s, 1H), 6.85-6.75 (m, 3H), 4.24 (dd, J=10.4 Hz, 2.0 Hz, 1H), 4.13-4.01 (m, 1H), 3.97-3.85 (m, 5H), 3.67 (d, J=11.2 Hz, 1H), 3.53-3.36 (m, 3H), 3.35-3.23 (m, 2H), 3.03-2.87 (m, 3H), 2.56 (q, J=7.2 Hz, 2H), 2.47-2.37 (m, 1H), 2.35-2.25 (m, 1H), 1.93-1.83 (m, 3H), 1.76-1.55 (m, 4H), 1.48-1.32 (m, 2H), 1.18 (t, J=7.2 Hz, 3H). MS m/z 538.4[M+H]$^+$.

EXAMPLE 49. PREPARATION OF COMPOUND E1

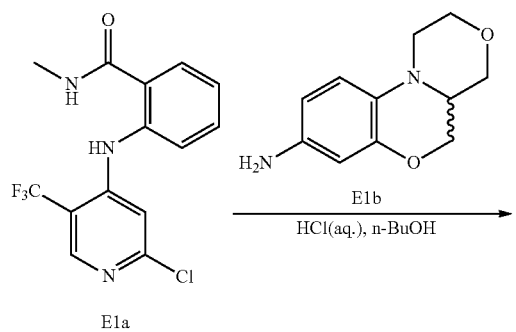

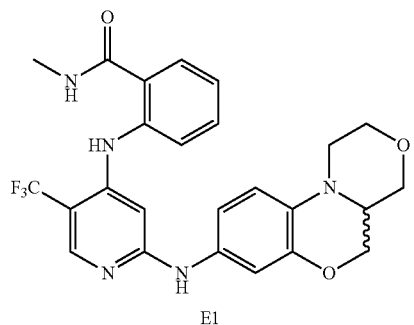

E1

Compound E1a (50 mg, 0.152 mmol), E1b (34 mg, 0.167 mmol) and concentrated HCl solution (0.1 mL) were added into n-butyl alcohol (2 mL) sequencely, the reaction solution was heated to 110° C. and stirred for 16 hours in seal. The LCMS indicated the reaction was complete; the pH value of reaction mixture was adjusted to 7 by using saturated aq. NaHCO$_3$, extracted with EtOAc (5 mL×2), the combined organic phase was washed by brine (5 mL), dried over Na$_2$SO$_4$, filtrated, and concentrated in vacuo, the crude product was purified via preparative TLC (PE/EtOAc=1:1) to afford compound E1 (37 mg, yield 49%) as a gray solid. $^1$H NMR (DMSO-d$_6$, 400 MHz) δ 10.16 (s, 1H), 8.98 (s, 1H), 8.71-8.64 (m, 1H), 8.23 (s, 1H), 7.70 (d, J=8.0 Hz, 1H), 7.56 (d, J=8.4 Hz, 1H), 7.49 (dd, J=7.6 Hz, 7.2 Hz, 1H), 7.13-7.05 (m, 2H), 6.93 (dd, J=8.8 Hz, 2.0 Hz, 1H), 6.76 (d, J=8.8 Hz, 1H), 6.67 (s, 1H), 4.19 (dd, J=10.4 Hz, 2.0 Hz, 1H), 3.94 (dd, J=11.6 Hz, 2.8 Hz, 1H), 3.88-3.80 (m, 2H), 3.62-3.50 (m, 2H), 3.16 (dd, J=10.8 Hz, 10.4 Hz, 1H), 3.04-2.98 (m, 1H), 2.76 (d, J=4.0 Hz, 3H), 2.64-2.55 (m, 1H). MS m/z 500.2 [M+H]$^+$.

EXAMPLE 50. PREPARATION OF COMPOUND E1S

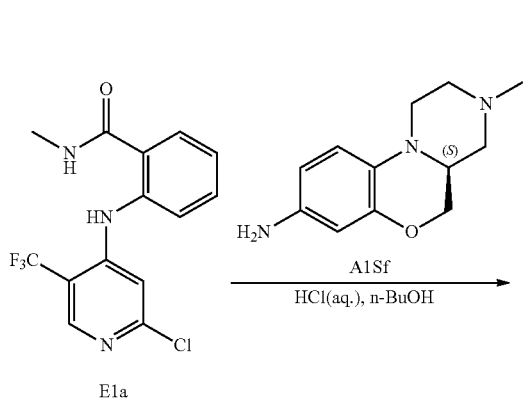

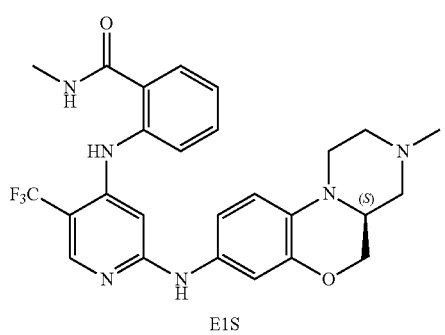

Compound E1a (55 mg, 0.167 mmol), A1Sf (37 mg, 0.167 mmol) and concentrated HCl solution (0.1 mL) were added into n-butyl alcohol (2 mL) sequencely, the reaction solution was heated to 110° C. and stirred for 16 hours in seal. The LCMS indicated the reaction was complete, the reaction mixture was adjusted to pH=7 by using saturated aq. NaHCO$_3$, then was exacted with EtOAc (5 mL×2), the combined organic phase was washed by brine (5 mL), dried over Na$_2$SO$_4$, filtrated, and concentrated in vacuo, the crude product was purified via preparative TLC (DCM/MeOH=15:1) to afford compound E1S (16 mg, yield 19%) as a gray solid. $^1$H NMR (CD$_3$OD, 400 MHz) δ 8.12 (s, 1H), 7.62 (dd, J=8.0 Hz, 1.2 Hz, 1H), 7.52 (d, J=6.8 Hz, 1H), 7.48-7.43 (m, 1H), 7.13-7.08 (m, 1H), 6.83-6.78 (m, 3H), 6.57 (s, 1H), 4.23 (dd, J=10.8 Hz, 2.8 Hz, 1H), 3.95 (dd, J=10.4 Hz, 8.8 Hz, 1H), 3.72 (d, J=12.4 Hz, 1H), 3.10-3.02 (m, 1H), 2.98 (d, J=11.6 Hz, 1H), 2.90-2.84 (m, 4H), 2.76-2.65 (m, 1H), 2.36 (s, 3H), 2.32-2.23 (m, 1H), 1.88 (dd, J=11.2 Hz, 10.8 Hz, 1H). MS m/z 513.2 [M+H]$^+$.

EXAMPLE 51. PREPARATION OF COMPOUND E1R

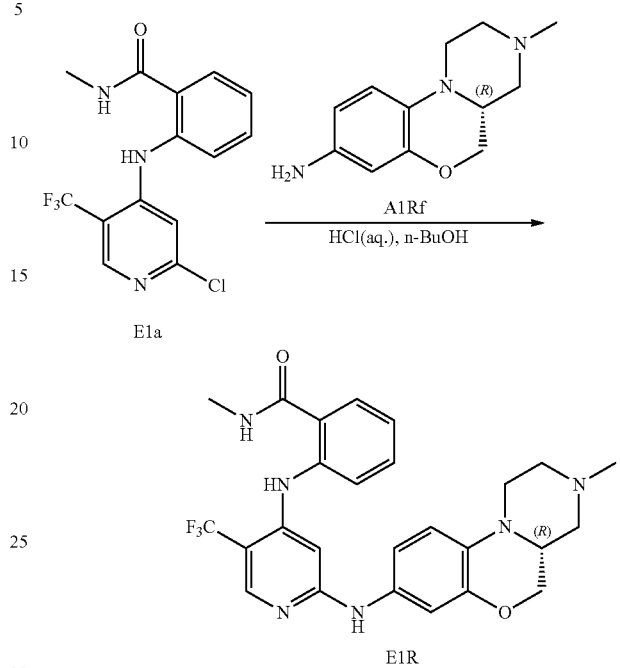

Compound E1a (50 mg, 0.152 mmol), A1Rf (33 mg, 0.152 mmol) and concentrated HCl solution (0.1 mL) were added into n-butyl alcohol (2 mL) sequencely, the reaction solution was heated to 110° C. and stirred for 16 hours in seal. The LCMS indicated the reaction was complete, the reaction mixture was adjusted to pH=7 by using saturated aq. NaHCO$_3$, then was exacted with EtOAc (5 mL×2), the combined organic phase was washed by brine (5 mL), dried over Na$_2$SO$_4$, filtrated, and concentrated in vacuo, the crude product was purified via preparative TLC (DCM/MeOH=15:1) to afford compound E1R (30 mg, yield 39%) as a gray solid. $^1$H NMR (CD$_3$OD, 400 MHz) δ 8.11 (s, 1H), 7.61 (dd, J=7.6 Hz, 1.2 Hz, 1H), 7.50 (d, J=7.6 Hz, 1H), 7.48-7.42 (m, 1H), 7.12-7.07 (m, 1H), 6.82-6.78 (m, 3H), 6.56 (s, 1H), 4.21 (dd, J=10.4 Hz, 2.4 Hz, 1H), 3.94 (dd, J=10.4 Hz, 8.8 Hz, 1H), 3.71 (d, J=12.0 Hz, 1H), 3.09-3.02 (m, 1H), 2.96 (d, J=11.6 Hz, 1H), 2.90-2.84 (m, 4H), 2.74-2.65 (m, 1H), 2.34 (s, 3H), 2.32-2.23 (m, 1H), 1.86 (dd, J=11.2 Hz, 10.8 Hz, 1H). MS m/z 513.2[M+H]$^+$.

EXAMPLE 52. PREPARATION OF COMPOUND E2R

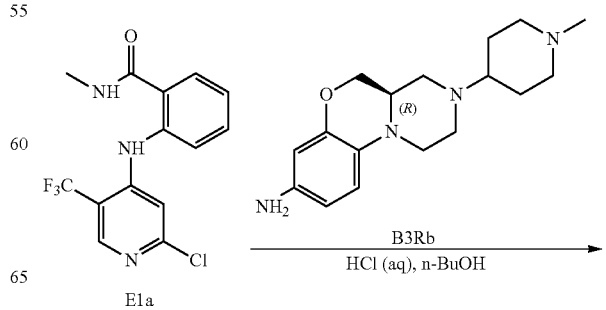

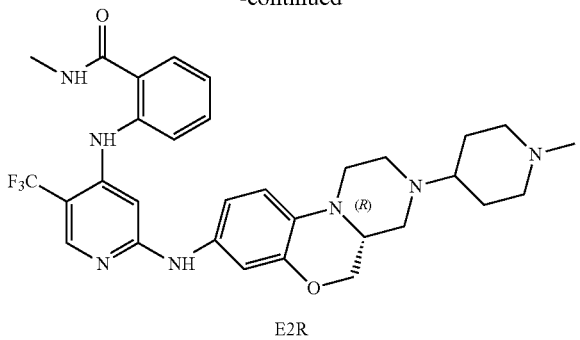

E2R

Compound E1a (30 mg, 0.091 mmol), B3Rb (41 mg, 0.14 mmol) and concentrated HCl solution (0.1 mL) were added into n-butyl alcohol (2 mL) sequencely, the reaction solution was heated to 160° C. and stirred for 8 hours in seal. The LCMS indicated the reaction was complete, the reaction mixture was adjusted to pH=7 by using saturated aq. NaHCO$_3$, then was exacted with DCM (5 mL×3), the combined organic phase was washed by brine (5 mL), dried over Na$_2$SO$_4$, filtrated, and concentrated in vacuo, the residue was purified via preparative TLC (DCM/MeOH=5:1) to afford compound E2R (4.0 mg, yield 7%) as a pale yellow solid. $^1$H NMR (DMSO-d$_6$, 400 MHz) δ 10.16 (s, 1H), 8.96 (s, 1H), 8.72-8.65 (br, 1H), 8.22 (s, 1H), 7.70 (d, J=8.0 Hz, 1H), 7.60-7.44 (m, 2H), 7.10 (dd, J=7.6 Hz, 7.2 Hz, 1H), 7.03 (s, 1H), 6.90 (d, J=7.6 Hz, 1H), 6.75 (d, J=8.8 Hz, 1H), 6.66 (s, 1H), 4.21 (d, J=10.0 Hz, 1H), 3.87 (dd, J=9.6 Hz, 1H), 3.64 (d, J=11.2 Hz, 1H), 3.01-2.70 (m, 9H), 2.35-2.22 (m, 1H), 2.21-2.09 (m, 4H), 1.92-1.80 (m, 3H), 1.77-1.68 (m, 2H), 1.50-1.35 (m, 2H). MS m/z 596.3 [M+H]$^+$.

EXAMPLE 53. PREPARATION OF COMPOUND E3R

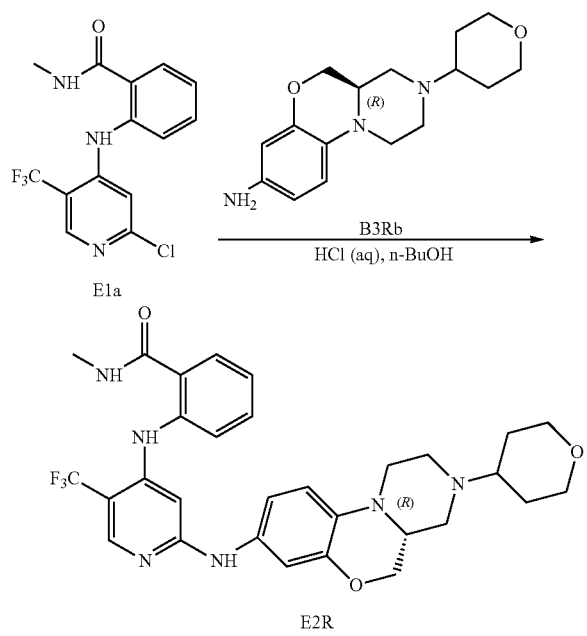

Compound E1a (30 mg, 0.10 mmol), B2Rb (50 mg, 0.16 mmol) and concentrated HCl solution (0.1 mL) were added into n-butyl alcohol (2.0 mL) sequencely, the reaction solution was heated to 150° C. and stirred for 6 hours in seal. The LCMS indicated the reaction was complete, the reaction mixture was adjusted to pH=7 by using saturated aq. NaHCO$_3$, then was exacted with DCM (5 mL×3), the combined organic phase was washed by brine (5 mL), dried over Na$_2$SO$_4$, filtrated, and concentrated in vacuo, the residue was purified via preparative TLC (DCM/MeOH=10:1) to afford compound E3R (10 mg, yield 19%) as a pale yellow solid. $^1$H NMR (DMSO-d$_6$, 400 MHz) δ 10.20-10.13 (br, 1H), 9.00-8.90 (br, 1H), 8.71-8.62 (br, 1H), 8.23 (d, J=8.4 Hz, 1H), 7.74-7.67 (m, 1H), 7.60-7.42 (m, 2H), 7.14-6.99 (m, 2H), 6.95-6.87 (m, 1H), 6.76 (dd, J=8.8 Hz, 8.8 Hz, 1H), 6.67 (d, J=8.4 Hz, 1H), 4.27-4.18 (m, 1H), 3.95-3.82 (m, 3H), 3.70-3.60 (m, 1H), 3.28-3.22 (m, 2H), 3.03-2.85 (m, 4H), 2.81-2.72 (m, 3H), 2.48-2.23 (m, 2H), 1.91-1.81 (m, 1H), 1.78-1.68 (m, 2H), 1.50-1.35 (m, 2H). MS m/z 583.3 [M+H]$^+$.

EXAMPLE 54. DETERMINATION OF INHIBITION OF PROTEIN KINASE ACTIVITY

EGFR and EGFR (T790M/L858R) Kinase Activity Inhibition Experiments

EGFR and EGFR (T790M/L858R) protein kinase activities were determined using the Caliper mobility shift assay. The compound was dissolved in DMSO and diluted with kinase buffer (EGFR (T790M/L85RR): 50 mM HEPES at pH 7.5, 0.0015% Brij-35, 10 mM MgCl$_2$, 2 mM DTT; EGFR: pH 7.5 50 mM HEPES, 0.0015% Brij-35, 10 mM MgCl$_2$, 10 mM MnCl$_2$, 2 mM DTT), 5 L of 5 times the final concentration of the compound (10% DMSO) was added to a 384-well plate. Add 10 μL of 2.5-fold enzyme (using EGFR and EGFR (T790M/L858R), respectively) and incubate for 10 minutes at room temperature, then add 10 μL of 2.5-fold substrate (Peptide FAM-P22 and ATP) solution. After incubation at 28° C. for 60 minutes, the reaction was stopped by adding 25 μL of stop solution (100 mM HEPES, 0.015% Brij-35, 0.2% Coating Reagent #3, 50 mM EDTA, pH 7.5). Conversion rate data was read on a Caliper EZ Reader II (Caliper Life Sciences). The conversion rate was converted into inhibition rate data (% inhibition rate=(max-conversion rate)/(max-min)*100). Where max is the conversion of the DMSO control and min is the conversion of the enzyme-free control. Curves were plotted with compound concentration and inhibition rate on the horizontal and vertical coordinates, and the curve was fitted using XLFit excel add-in version 4.3.1 software and IC$_{50}$ was calculated. The activities of some representative compounds are shown in Table 1.

TABLE 1

Inhibition of EGFR and EGFR (T790M/L858R) kinase activity (IC$_{50}$, nM)

| Compound | EGFR | EGFR(T790M/L858R) |
|---|---|---|
| A1 | <100 | <10 |
| A1S | <100 | <1 |
| A1R | <100 | <1 |
| A2S | <100 | <10 |
| A2R | <100 | <10 |
| A3S | | <1 |
| A3R | <50 | <1 |
| A4R | <100 | <10 |
| A5R | <100 | <1 |
| A6R | <100 | <10 |
| A7R | <500 | <50 |

TABLE 1-continued

Inhibition of EGFR and EGFR (T790M/L858R) kinase activity (IC$_{50}$, nM)

| Compound | EGFR | EGFR(T790M/L858R) |
|---|---|---|
| A8S | <100 | <10 |
| A8R | <100 | <10 |
| A9S | <100 | <10 |
| A9R | <100 | <10 |

CDK2, CDK4 and CDK6 Kinase Activity Inhibition Experiments

CDK2/CycA2, CDK4/CycD3 and CDK6/cycD3 protein kinase activities were determined using the Caliper mobility shift assay. The compound was dissolved in DMSO and diluted with kinase buffer (CDK2/CycA2 and CDK6/cycD3 with 50 mM HEPES (pH 7.5), 10 mM MgCl$_2$, 0.0015% Brij-35, and 2 mM dithiothreitol; CDK4/CycD3 with 20 mM HEPES (pH 7.5), 10 mM MgCl$_2$, 0.01% Triton X-100, and 2 mM dithiothreitol), 5 μl of a 5-fold final concentration of the compound (10% DMSO) was added to a 384-well plate. Add 10 μL of 2.5-fold Axl enzyme solution and incubate for 10 minutes at room temperature, then add 10 μL of 2.5-fold substrate solution (corresponding enzyme and substrate concentration CDK2/CycA2 12 nM, ATP Km 39 μM; CDK4/CycD3 10 nM, ATP Km 221 μM; CDK6/cycD3 15 nM, ATP Km 800 μM). Incubate at 28° C. (60 min CDK2, 180 min CDK4, 60 min CDK6) followed by 25 μl stop solution (100 mM HEPES (pH 7.5), 0.015% Brij-35, 0.2% Coating Reagent #3, 50 mM EDTA) Stop the reaction. Conversion rate data was read on a Caliper EZ Reader II (Caliper Life Sciences). The conversion rate was converted into inhibition rate data (% inhibition rate=(max-conversion rate)/(max-min)*100). Where max is the conversion of the DMSO control and min is the conversion of the enzyme-free control. Curves were plotted with compound concentration and inhibition rate on the horizontal and vertical coordinates, and the curve was fitted using XLFit excel add-in version 4.3.1 software and IC$_{50}$ was calculated. The activity of some representative compounds is shown in Table 2.

TABLE 2

Inhibition of CDK2, CDK4 and CDK6 kinase activity (IC$_{50}$, nM)

| CompoundComp | CDK2 | CDK4 | CDK6 |
|---|---|---|---|
| B1S | <10 | <10 | <50 |
| B1R | <10 | <10 | <50 |
| B2R | <10 | <10 | <50 |
| B3R | <10 | <10 | <10 |

FLT3 Kinase Activity Inhibition Experiment

FLT3 protein kinase activity was measured using the Caliper mobility shift assay. The compound was dissolved in DMSO and diluted with a kinase buffer (50 mM HEPES, pH 7.5, 0.0015% Brij-35, 2 mM DTT), and 5 μL of a 5-fold final concentration of the compound (10% DMSO) was added to a 384-well plate. After adding 10 μL of 2.5-fold FLT3 enzyme solution, incubate for 10 minutes at room temperature, and then add 10 μL of a 2.5-fold substrate (FAM-labeled polypeptide and ATP) solution. After incubation at 28° C. for 60 minutes, the reaction was stopped by adding 25 μL of stop solution (100 mM HEPES, 0.015% Brij-35, 0.2% Coating Reagent #3, 50 mM EDTA, pH 7.5). Conversion rate data was read on a Caliper EZ Reader II (Caliper Life Sciences). The conversion rate was converted into inhibition rate data (% inhibition rate=(max-conversion rate)/(max-min)*100). Where max is the conversion of the DMSO control and min is the conversion of the enzyme-free control. Curves were plotted with compound concentration and inhibition rate on the horizontal and vertical coordinates, and the curve was fitted using XLFit excel add-in version 4.3.1 software and IC50 was calculated. The activity of some representative compounds is shown in Table 3.

Axl Kinase Activity Inhibition Experiment

Axl protein kinase activity was determined using the Caliper mobility shift assay. The compound was dissolved in DMSO and diluted with kinase buffer (50 mM HEPES, pH 7.5, 0.0015% Brij-35, 2 mM DTT), and 5 μL of 5 times the final concentration of the compound (10%) was added to the 384-well plate. DMSO). After adding 10 μL of a 2.5-fold Axl enzyme solution, incubate for 10 minutes at room temperature, and then add 10 μL of a 2.5-fold substrate (FAM-labeled polypeptide and ATP) solution. After incubation at 28° C. for 60 minutes, the reaction was stopped by the addition of 25 L stop solution (100 mM HEPES, 0.015% Brij-35, 0.2% Coating Reagent #3, 50 mM EDTA, pH 7.5). Conversion rate was read on a Caliper EZ Reader II (Caliper Life Sciences). The conversion rate was converted into inhibition rate (% inhibition rate=(max-conversion rate)/(max-min)*100). Where max is the conversion of the DMSO control and min is the conversion of the enzyme-free control. Curves were plotted with compound concentration and inhibition rate on the horizontal and vertical coordinates, and the curve was fitted using XLFit excel add-in version 4.3.1 software and IC$_{50}$ was calculated. The activity of some representative compounds is shown in Table 3.

TABLE 3

FLT3 and AXL kinase activity inhibition (IC$_{50}$, nM)

| Compound | FLT3 | AXL |
|---|---|---|
| D1S | <1 | <10 |
| D1R | <1 | <10 |
| D2S | <10 | |
| D2R | <10 | |
| D3R | <10 | |
| D4R | <1 | |
| D5S | <10 | |
| D6R | <1 | <10 |

FAK Kinase Activity Inhibition Experiment

FAK protein kinase activity was determined by Latha screen analysis. The compound was dissolved in DMSO and diluted with kinase buffer (25 mM HEPES, pH 7.5, 0.01 mM Triton, 10 mM MgCl$_2$, 0.5 mM EGTA, 0.01% BRIJ-35, 2 mM DTT), 2.5 μL was added to the 384-well plate. 4 times the final concentration of the compound (4% DMSO). After adding 5 μL of 2-fold FAK enzyme solution, incubate for 10 minutes at room temperature, and then add 2.5 μL of 4 times substrate (Fluorescein-polyGT and ATP) solution. After incubating for 30 minutes at 25° C. 10 μL of the detection solution (antibody of phosphorylation site 2 nM and EDTA 10 mM) was added to terminate the reaction. The data emitted at 340 nm and emitted at 520 nm was read from Envision, and the luminescence reading data was copied from the Envision program, and the value of the luminescence reading was converted to the percent inhibition by a formula. The conversion rate was converted into inhibition rate data (% inhibition rate=(max-conversion rate)/(max-min)*100). "min" is the control fluorescence reading for the reaction without enzyme; "max" is the fluorescence reading of the sample with DMSO added as a control. Curves were plotted with compound concentration and inhibition rate on the horizontal and vertical coordinates, and the curve was fitted using XLFit excel add-in version 4.3.1 software and $IC_{50}$ was calculated. The activity of some representative compounds is shown in Table 4.

TABLE 4

FAK kinase activity inhibition ($IC_{50}$, nM)

| Compound | FAK |
|---|---|
| E1 | <1 |
| E1S | <1 |
| E1R | <1 |

Syk Kinase Activity Inhibition Assay

SYK protein kinase activity was determined using the Caliper mobility shift assay. The compound was dissolved in DMSO and diluted with kinase buffer (20 mM HEPES, 0.01% Triton X-100, 5 mM $MgCl_2$, 1 mM $MnCl_2$, 2 mM DTT), and 5 μL of 5 times final concentration was added to the 384-well plate. Compound (10% DMSO). After adding 10 μL of 2.5-fold enzyme (with SYK) solution, incubate for 10 minutes at room temperature, and then add 10 μL of 2.5-fold substrate (Peptide FAM-P22 and ATP) solution. Incubate at 28° C. for 30 minutes, then stop the reaction by adding 25 μL of stop solution (100 mM HEPES, 0.015% Brij-35, 0.2% Coating Reagent #3, 50 mM EDTA, pH 7.5). Conversion rate data was read on a Caliper EZ Reader II (Caliper Life Sciences). The conversion rate was converted into inhibition rate data (% inhibition rate=(max-conversion rate)/(max-min)*100). Where max is the conversion of the DMSO control and min is the conversion of the enzyme-free control. Curves were plotted with compound concentration and inhibition rate on the horizontal and vertical coordinates, and the curve was fitted using XLFit excel add-in version 4.3.1 software and $IC_{50}$ was calculated. The activity of some representative compounds is shown in Table 5.

TABLE 5

Syk kinase activity inhibition ($IC_{50}$, nM)

| Compound | Syk |
|---|---|
| C1R | <10 |
| C2R | <50 |
| C3R | <50 |
| C4R | <50 |
| C5R | <50 |
| C6R | <50 |
| C7R | <50 |
| C8R | <50 |
| C9R | <10 |
| C10R | <10 |
| C11R | <10 |
| C12R | <10 |
| C13R | <10 |
| C14R | <10 |
| C15R | <50 |
| C16R | <50 |
| C17R | <50 |
| C18R | <50 |

Jak1 and Jak2 Kinase Activity Inhibition Experiments

Kinase JAk1 and Jak2 enzyme inhibition $IC_{50}$ evaluation experiments: The buffer was configured with the following components: 50 mM HEPES, pH 7.5, 0.00015% Brij-35. Compounds were placed in a concentration gradient in 100% DMSO and diluted to 10% DMSO with buffer and added to 384 well plates. For example, when the initial concentration of the compound is 250 nM, it is made into 12.5 μM with 100% DMSO, and diluted by 5 or 6 concentrations, and then diluted 10-fold with buffer to prepare an intermediate dilution of the compound containing 10% DMSO. Transfer 5 μL to 384-well plate. The Jak1 and Jak2 enzymes were diluted to the optimal concentration with the following buffer: 50 mM HEPES, pH 7.5, 0.00015% Brij-35, 2 mM DTT. Transfer 10 μL to a 384-well plate and incubate with the compound for 10-15 minutes. The substrate was diluted to the optimal concentration with the following buffer: 50 mM HEPES, pH 7.5, 0.00015% Brij-35, 10 mM $MgCl_2$, adenosine triphosphate at Km. The reaction was initiated by adding 10 μL to a 384-well plate and reacted at 28° C. for 1 hour. The conversion rate was then read using a Caliper Reader and the inhibition rate was calculated. The formula is as follows: Percent inhibition=(max-conversion)/(max-min)*100. Where max is the conversion of the DMSO control and min is the conversion of the enzyme-free control. Fit the IC50 value with XLFit excel add-in version 5.4.0.8. Fitting formula: Y=Bottom+(Top-Bottom)/(1+($IC_{50}$/X)^HillSlope).

TABLE 6 inhibition of Jak1 and Jak2 kinase activity ($IC_{50}$, nM)

| Compound | Jak1 | Jak2 |
|---|---|---|
| C1R | <100 | <10 |
| C2R | <500 | <20 |
| C3R | <100 | <10 |
| C4R | <500 | <20 |
| C5R | <100 | <10 |
| C6R | <500 | <50 |
| C7R |  | <50 |
| C8R |  | <10 |
| C9R |  | <50 |
| C10R |  | <10 |
| C11R |  | <10 |
| C12R |  | <10 |
| C13R |  | <10 |
| C14R |  | <10 |
| C15R |  | <50 |
| C16R |  | <50 |
| C17 |  | <50 |
| C18R |  | <50 |

EXAMPLE 55 PHARMACOKINETIC STUDY IN MICE

Instrument: API4000+ LC/MS instrument manufactured by AB Sciex. All measurement data was collected and processed by Analyst 1.6.3 software, and data was calculated and processed by Microsoft Excel. Using the DAS 3.2.8 software, the statistical moment method was used to calculate the pharmacokinetic parameters. t mainly includes kinetic parameters Tmax, T1/2, Cmax, AUC(0-t) and the like. Column: ACQUITY UPLC BEH C18 (2.1 mm×50 mm, 1.7 μm); column temperature 40° C.; mobile phase A is water (0.1% formic acid+5 mM ammonium acetate), mobile phase B is acetonitrile (0.1% acetic acid), The flow rate was 0.30 ml/min and the isocratic elution of 90% B was maintained for 1.5 minutes. Injection volume: 5 μL.

Animals: 12 male ICR mice, weighing 22-26 g, were used after 2 days of feeding in the laboratory of the experimental animal center. They were fasted 12 hours before the administration and 4 hours after the administration, and were free to drink during the test. Mice were randomly divided into four groups of 3 animals each. After intragastric administration, blood samples were taken at two different time points in each group.

Solvent: 0.5% Methylcellulose (aqueous solution containing 0.4% Tween 80). Formulation of intragastric administration solution: The compound is accurately weighed, added to the solvent, and sonicated at room temperature for 5 minutes to completely dissolve the drug to prepare a drug solution of 0.33 mg/ml.

Drug sample: A representative compound of the structure represented by the patent formula (I) of the present invention generally adopts a plurality of samples having similar structures (molecular weight difference of more than 2 units), accurately weighed, and administered together (cassette PK). This allows multiple compounds to be screened simultaneously and their oral absorption rates compared. Single drug administration was also used to study the pharmacokinetics of drug samples in mice.

Blood was taken from the eyelids at 0.25, 0.5, 1, 2, 4, 8, 12, and 24 hours after intragastric administration. In the heparin-treated tube, the supernatant was centrifuged for LC-MS/MS analysis.

Accurately weigh the compounds to different concentrations, perform quantitative analysis on the mass spectrometer to establish a standard curve, and then test the concentration of the compound in the above plasma to obtain the concentration of the compound at different time points. All the measured data were collected and processed by the relevant software, and the statistical moment method was used to calculate the pharmacokinetic parameters (mainly including the kinetic parameters $T_{max}$, $T_{1/2}$, $C_{max}$, $AUC_{(0-t)}$, etc.).

By the above method, the representative compound of the structure represented by the patent formula (I) of the present invention has good oral absorption, and the oral absorption results of the compounds C10R and B2R are shown in the following table:

| Compound Code | PO dose | $T_{max}$ (hour) | $T_{1/2}$ (hour) | $C_{max}$ (ng/mL) | $AUC_{(0-24)}$ (ng/mL * hour) |
|---|---|---|---|---|---|
| C10R | 5 mg/kg | 0.5 | 2.41 | 451.36 | 1243.51 |
| B2R | 5 mg/kg | 1.0 | 5.72 | 494.64 | 2199.55 |

All documents mentioned in the present application are hereby incorporated by reference in their entirety in their entireties in the the the the the the the the In addition, it should be understood that various modifications and changes may be made by those skilled in the art in the form of the appended claims.

The invention claimed is:

1. A compound of the following formula (I), or the optical isomers, pharmaceutically acceptable salts, prodrugs, deuterated forms, hydrates, or solvates thereof:

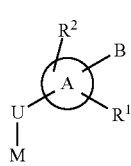

(I)

wherein M is a group having the following formula (II):

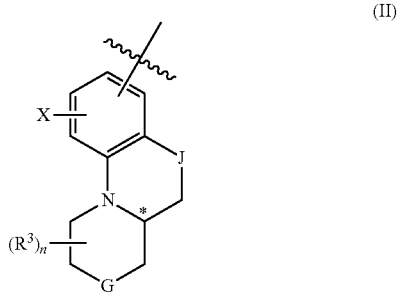

(II)

wherein in formula (I) and formula (II):
"∿∿" represents the attachment site of formula (II) to U in formula (I);
"*" indicates a chiral center;
A is selected from aryl or heteroaryl;
B is

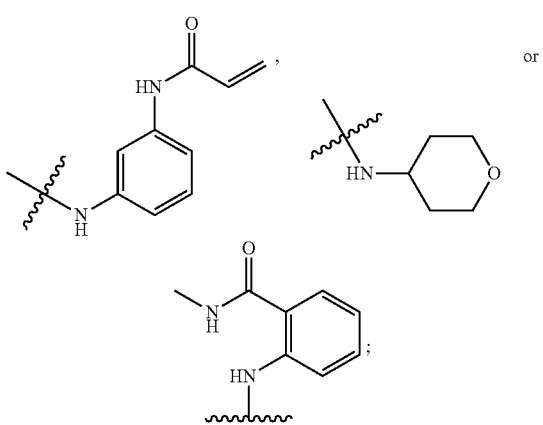

U is $NR^d$, O or S;
X is hydrogen, halogen, $C_{1-4}$ alkyl, $C_{1-4}$ haloalkyl, $C_{3-6}$ cycloalkyl, $C_{2-4}$ alkenyl, $C_{2-4}$ alkynyl, 3- to 10-membered heterocyclic, $OR^e$, $SR^e$, $NR^eR^e$, CN, $C(O)R^e$, $C(O)OR^e$, $C(O)NR^eR^e$, $OC(O)R^e$, $NR^eC(O)R^e$, or $S(O)_2R^e$;
J and G are each independently $NR^f$, O, S, S(O), $S(O)_2$ or $CR^gR^g$;
$R^1$ and $R^2$ are each independently selected from the group consisting of hydrogen, halogen, $C_{1-4}$ alkyl, $C_{3-6}$ cycloalkyl, 3- to 8-membered heterocyclic, or C(O)$NR^eR^e$; wherein the alkyl, cycloalkyl, and heterocyclic can be optionally substituted with one or more $R^c$;
each of the $R^3$ is independently hydrogen or $C_{1-4}$ alkyl; when two $R^3$ are simultaneously attached to the same carbon atom, the two $R^3$ and the carbon atom to which they are attached may optionally form a carbonyl group (C=O);
n is 0, 1, 2, or 3;
$R^a$ is hydrogen, $C_{1-4}$ alkyl, $C_{3-6}$ cycloalkyl, or 3- to 12-membered heterocyclic; wherein the alkyl, cycloalkyl, heterocyclyl may independently be optionally substituted by one or more halogens, $OR^e$, CN, $SO_2NR^eR^e$, as long as the chemical structure formed is stable and meaningful;

$R^b$ is aryl, heteroaryl, $C_{1-4}$ alkyl, $C_{3-8}$ cycloalkyl, 3- to 12-membered heterocyclic, $C(O)R^e$, or $C(O)NR^eR^e$; wherein the aryl, heteroaryl, alkyl, cycloalkyl, heterocyclyl can be optionally substituted by one or more $R^c$;

each $R^c$ is independently halogen, $C_{1-4}$ alkyl, $C_{3-8}$ cycloalkyl, 3- to 8-membered heterocyclic, $C(O)NR^eR^e$, $NR^eC(O)R^e$, $OR^e$, CN, or $SO_2NR^eR^e$;

$R^d$ is hydrogen or $C_{1-4}$ alkyl;

each $R^e$ is independently selected from the group consisting of hydrogen, $C_{1-4}$ alkyl, $C_{1-4}$ haloalkyl, $C_{2-4}$ alkenyl, $C_{2-4}$ alkynyl, $C_{3-8}$ cycloalkyl, 3- to 8-membered heterocyclic, aryl, or heteroaryl; or two $R^e$ together with the nitrogen atom to which they are attached form 3- to 8-membered heterocyclic containing 1 or 2 N atoms, and 0 or 1 hetero atom selected from O and S;

$R^f$ is hydrogen, $C_{1-8}$ alkyl, $C_{1-8}$ haloalkyl, $C_{2-8}$ alkenyl, $C_{2-8}$ alkynyl, $C_{3-8}$ cycloalkyl, 3- to 12-membered heterocyclic, aryl, heteroaryl, $C(O)R^e$, $C(O)OR^e$, $C(O)NR^eR^e$, $S(O)_2R^e$, or $S(O)_2NR^hR^h$;

each $R^g$ is each independently selected from the group consisting of hydrogen, halogen, or $C_{1-4}$ alkyl; or two $R^g$ together with the carbon atom to which they are attached form a carbonyl group (C=O); or two $R^g$ together with the same carbon atom to which they attached form 3- to 8-membered cyclic structure which optionally comprise 0, 1 or 2 heteroatoms selected from N, O, S;

each $R^h$ is independently hydrogen or $C_{1-4}$ alkyl; or two $R^h$ together with the nitrogen atom to which they are attached form 3- to-membered cyclic structure;

wherein each of the above alkyl, alkenyl, alkynyl, cycloalkyl, heterocyclic, cyclic structure, aryl and heteroaryl is optionally and independently substituted by 1 to 3 substituents each independently selected from the group consisting halogen, $C_{1-4}$ alkyl, $C_{1-4}$ haloalkyl, $C_{2-4}$ alkenyl, $C_{2-4}$ alkynyl, $C_{3-8}$ cycloalkyl, 3- to 12-membered heterocyclic, aryl, heteroaryl, CN, $NO_2$, $OR^e$, $SR^e$, $NR^eR^e$, $C(O)R^e$, $C(O)OR^e$, $C(O)NR^eR^e$, $NR^eC(O)R^e$, or $S(O)_2R^e$, provided that the chemical structure formed is stable and meaningful;

unless otherwise specified, the aryl is aromatic groups having 6 to 12 carbon atoms; the heteroaryl is 5- to 15-membered heteroaromatic groups; and the cyclic structure is saturated or unsaturated cyclic groups with or without heteroatoms;

with the proviso that A is not any group selected from group consisting of:

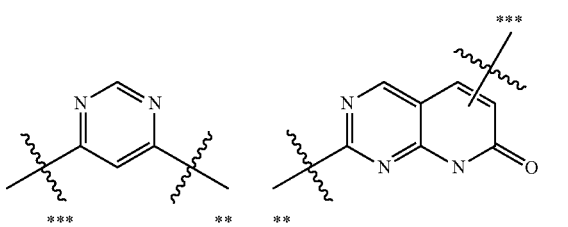

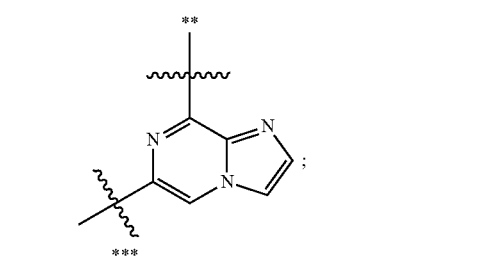

wherein "" means connecting to U; "*" means connecting to B.

2. The compound of claim 1, or the optical isomers, pharmaceutically acceptable salts, prodrugs, deuterated forms, hydrates, or solvates thereof, wherein M is a group represented by the following formula (IIa):

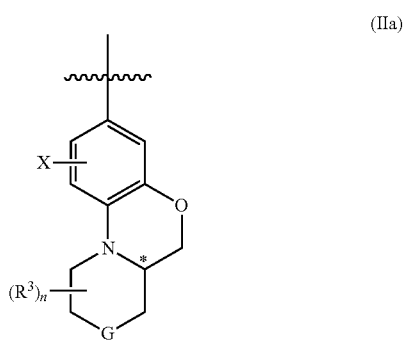

(IIa)

wherein X, $R^3$, G, and n are as defined in claim 1.

3. The compound of claim 1, or the optical isomers, pharmaceutically acceptable salts, prodrugs, deuterated forms, hydrates or solvates thereof, wherein M is selected from the group consisting of formula (IIb), formula (IIc), and formula (IId):

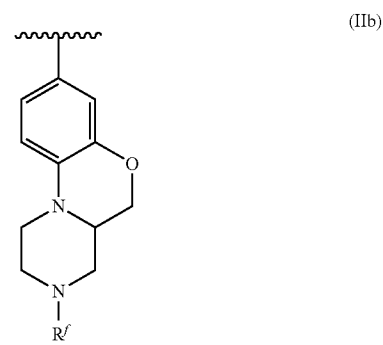

(IIb)

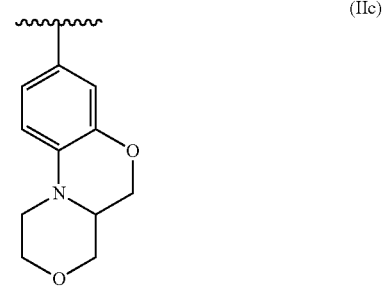

(IIc)

(IId)

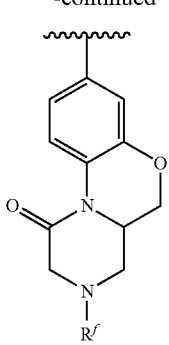

wherein R$^f$ is as defined in claim 1.

4. The compound of claim 1, or the optical isomers, pharmaceutically acceptable salts, prodrugs, deuterated forms, hydrates or solvates thereof, wherein in the formula (I), A is independently selected from group consisting of:

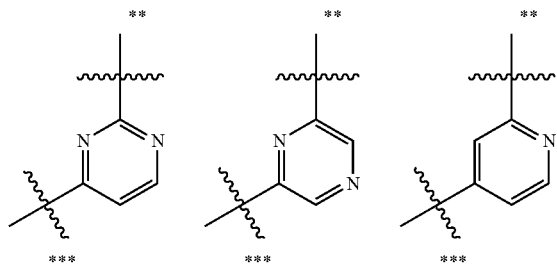 [SMILES: *c1ccnc(*)n1 ; *c1cncc(*)n1 ; *c1ccnc(*)c1]

wherein "" means connecting to U; "*" means connecting to B;
U is NR$^d$.

5. The compound of claim 1, or the optical isomers, pharmaceutically acceptable salts, prodrugs, deuterated forms, hydrates or solvates thereof, the formula (I) is:

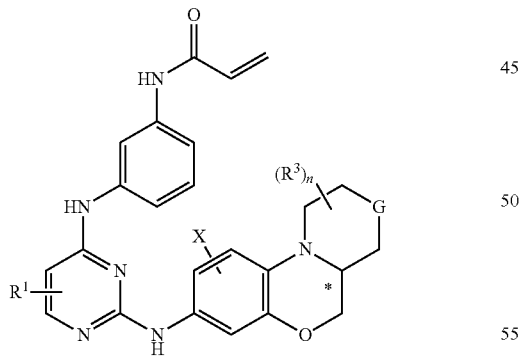

X is H;
G is NR$^f$ or O; wherein R$^f$ is as defined in claim 1;
R$^1$ is selected from the group consisting of hydrogen, halogen, or C$_{1-4}$ alkyl, wherein the alkyl group may be optionally substituted by one or more halogens;
each R$^3$ is independently hydrogen, or two R$^3$ link to the same carbon atom to form a carbonyl group (C=O);
n is 0, 1, or 2.

6. The compound of claim 5, or the optical isomers, pharmaceutically acceptable salts, prodrugs, deuterated forms, hydrates, or solvates thereof, wherein the M described is a group represented by the following formula (IIa):

(IIa)

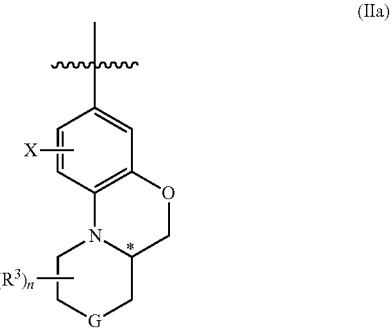

wherein X, R$^3$, G, and n are as defined in claim 5.

7. The compound of claim 5, or the optical isomers, pharmaceutically acceptable salts, prodrugs, deuterated forms, hydrates or solvates thereof, wherein the M is selected from the group consisting of formula (IIb), formula (IIc), and formula (IId):

(IIb)

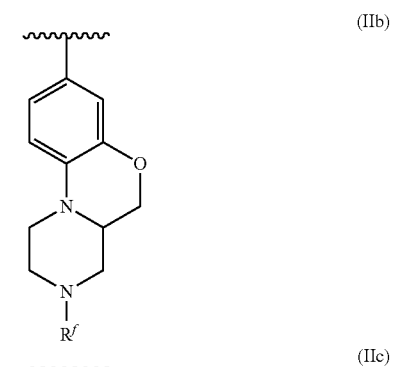

(IIc)

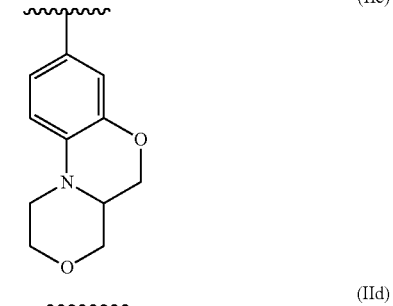

(IId)

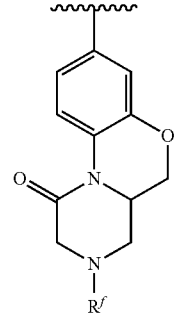

wherein R$^f$ is as defined in claim 5.

8. The compound of claim 1, or the optical isomers, pharmaceutically acceptable salts, prodrugs, deuterated forms, hydrates or solvates thereof, wherein the formula (I) is:

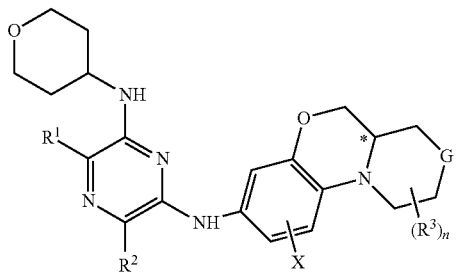

X is H;
G is NR$^f$ or O; wherein R$^f$ is as defined in claim 1;
R$^1$ is selected from hydrogen, or C$_{1-4}$ alkyl; R$^2$ is CONH$_2$;
each R$^3$ is independently hydrogen, or two R$^3$ link to the same carbon atom to form a carbonyl group (C=O);
n is 0, 1, or 2.

9. The compound of claim 8, or the optical isomers, pharmaceutically acceptable salts, prodrugs, deuterated forms, hydrates, or solvates thereof, wherein the M described is a group represented by the following formula (IIa):

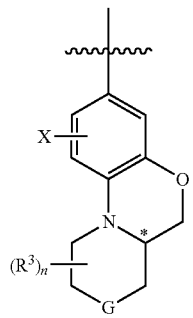

wherein X, R$^3$, G, and n are as defined in claim 8.

10. The compound of claim 8, or the optical isomers, pharmaceutically acceptable salts, prodrugs, deuterated forms, hydrates or solvates thereof, wherein the M is selected from the group consisting of formula (IIb), formula (IIc), and formula (IId):

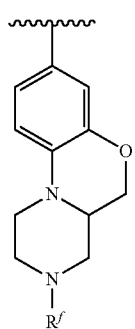

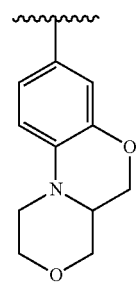

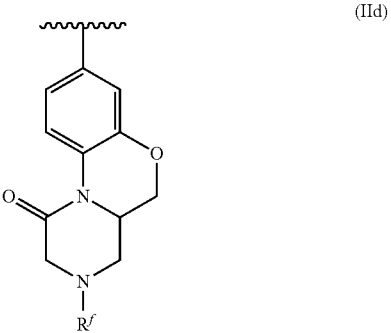

wherein R$^f$ is as defined in claim 8.

11. The compound of claim 1, or the optical isomers, pharmaceutically acceptable salts, prodrugs, deuterated forms, hydrates or solvates thereof, wherein the formula (I) is:

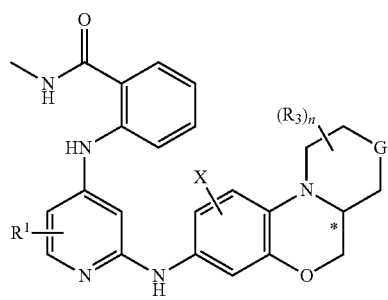

X is H;
G is NR$^f$ or O; wherein R$^f$ is as defined in claim 1;
R$^1$ is selected from hydrogen, halogen, or C$_{1-4}$ alkyl, wherein the alkyl group may be optionally substituted by one or more halogens;
each R$^3$ is independently hydrogen, or two R$^3$ link to the same carbon atom to form a carbonyl group (C=O);
n is 0, 1, or 2.

12. The compound of claim 11, or the optical isomers, pharmaceutically acceptable salts, prodrugs, deuterated forms, hydrates, or solvates thereof, wherein M is a group represented by the following formula (IIa):

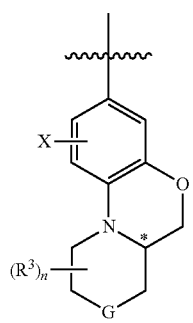

(IIa)

wherein X, $R^3$, G, and n are as defined in claim 11.

13. The compound of claim 11, or the optical isomers, pharmaceutically acceptable salts, prodrugs, deuterated forms, hydrates or solvates thereof, wherein M is selected from the group consisting of formula (IIb), formula (IIc), and formula (IId):

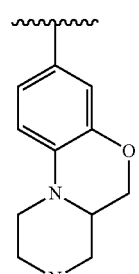

(IIb)

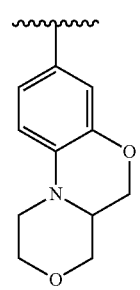

(IIc)

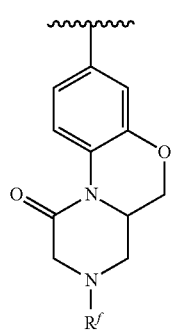

(IId)

wherein $R^f$ is as defined in claim 11.

14. The compound of claim 1, or the optical isomers, pharmaceutically acceptable salts, prodrugs, deuterated forms, hydrates or solvates thereof, which is selected from the group consisting of:

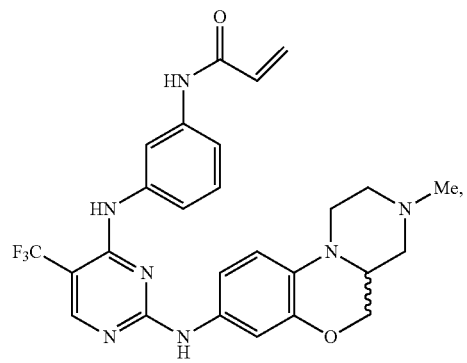

A1

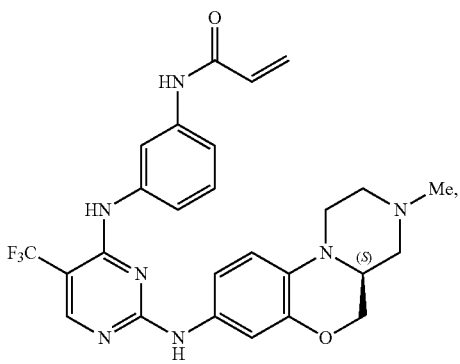

A1S

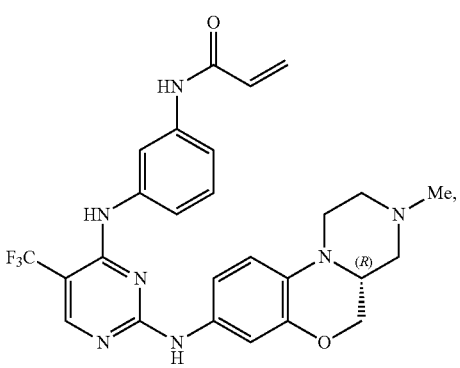

A1R

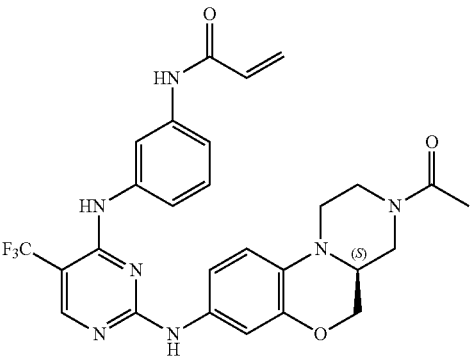

A2S

A2R
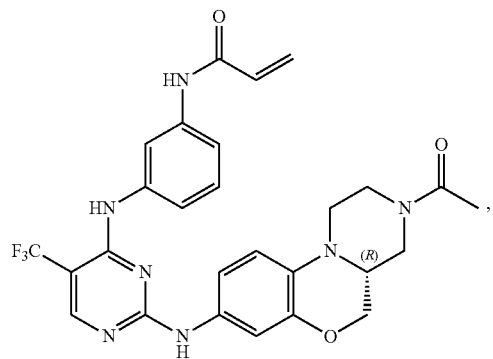
A5R
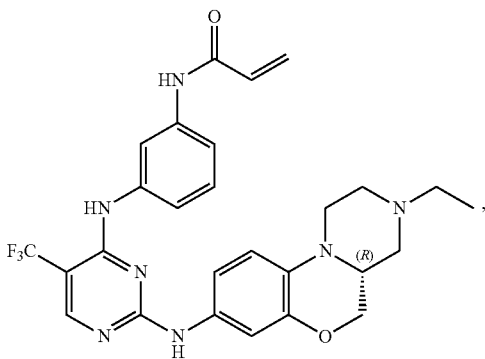
A3S
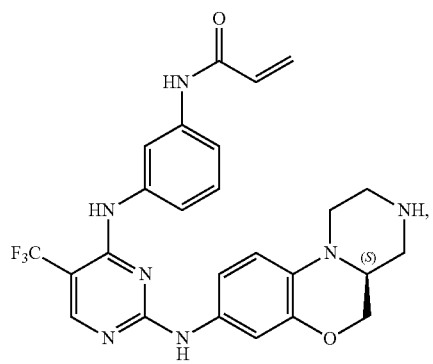
A6R
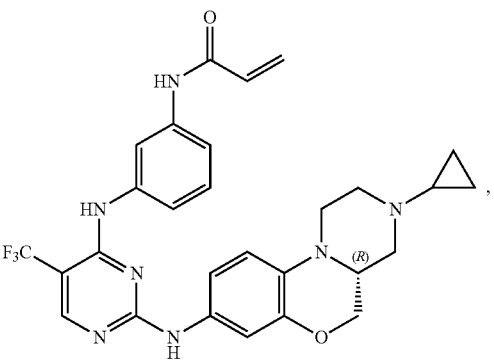
A3R
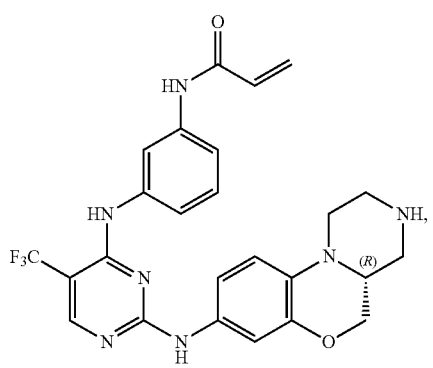
A7R
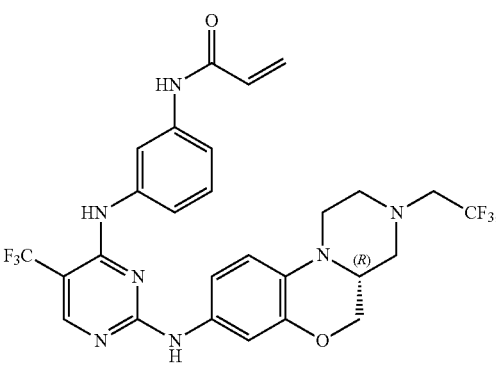
A4R
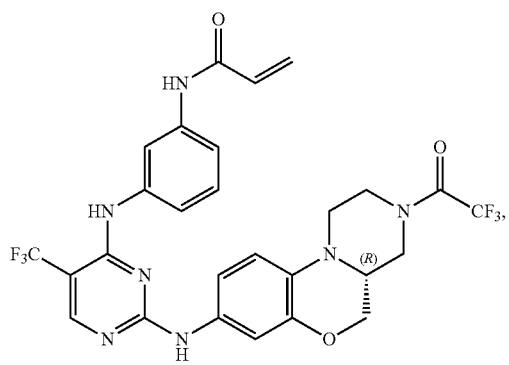
A8S
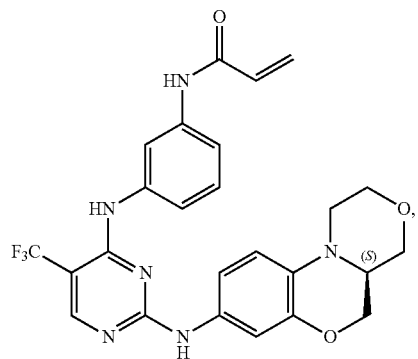

A8R 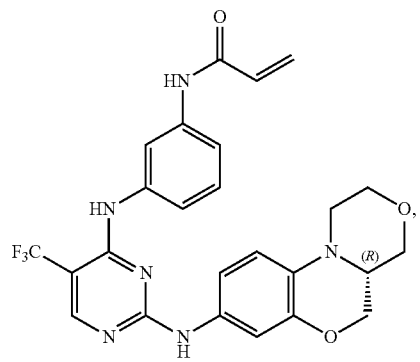
A9S 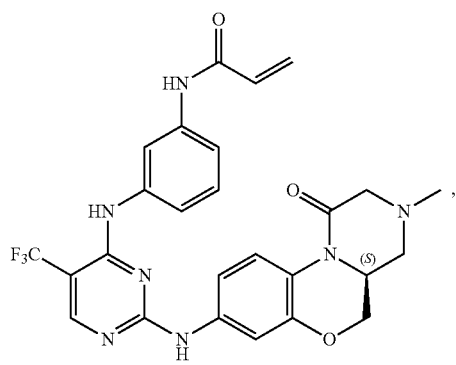
A9R 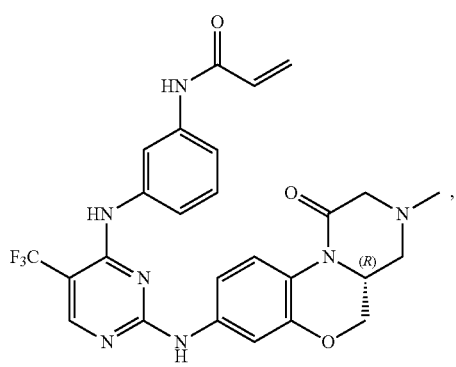
D1S 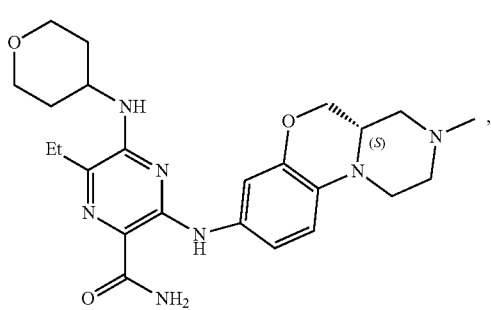
D1R 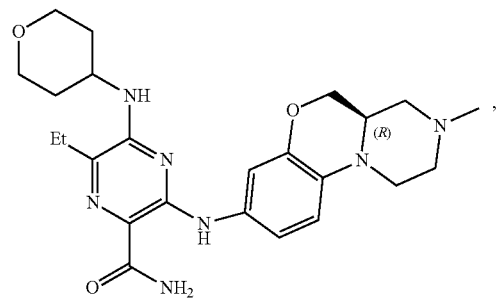
D2S 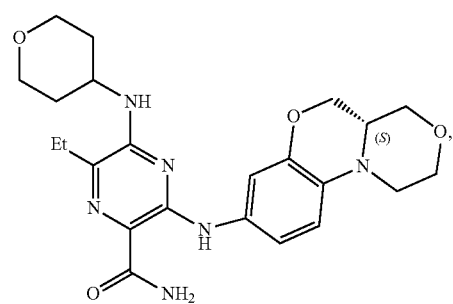
D2R 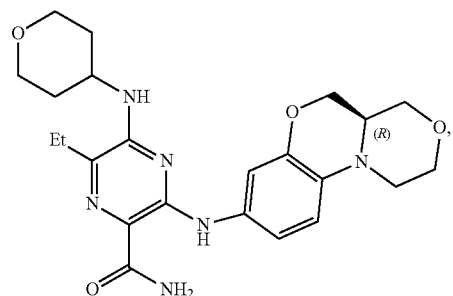
D3R 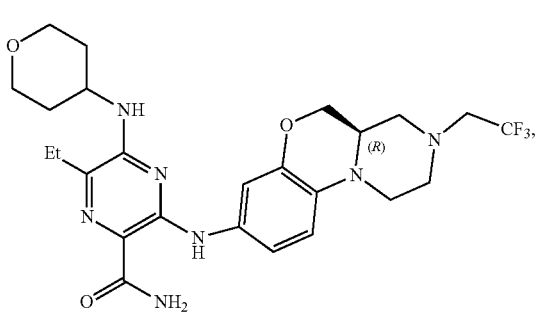
D4R 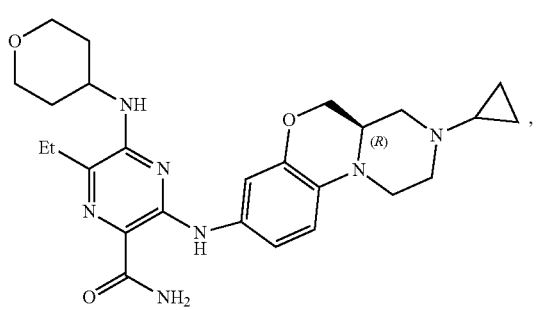

155
-continued
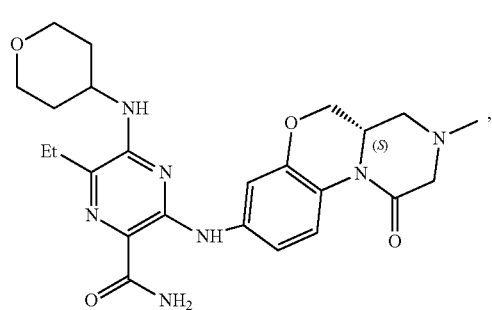
D5S
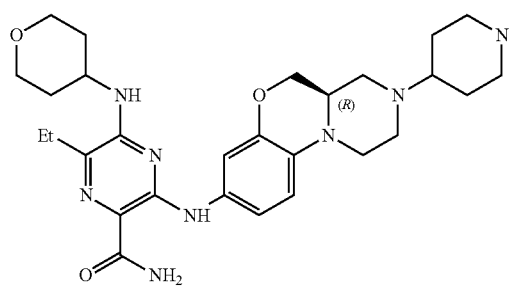
D6R
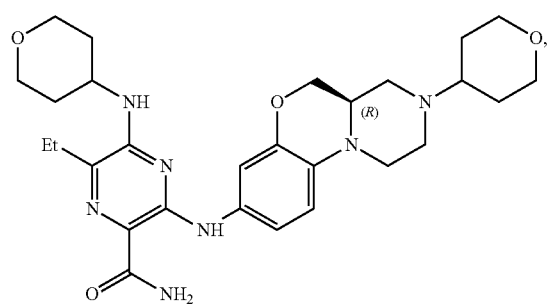
D7R
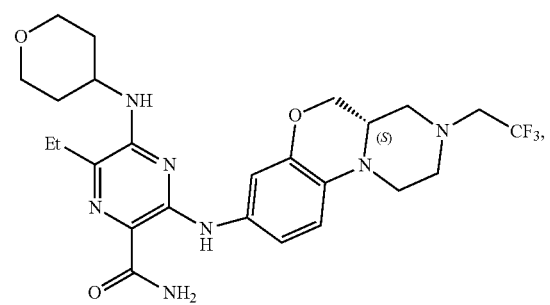
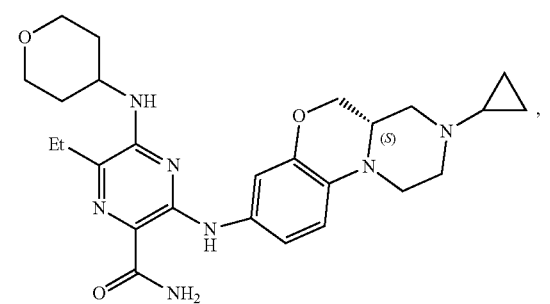
156
-continued
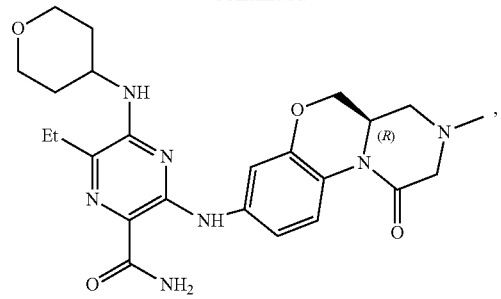
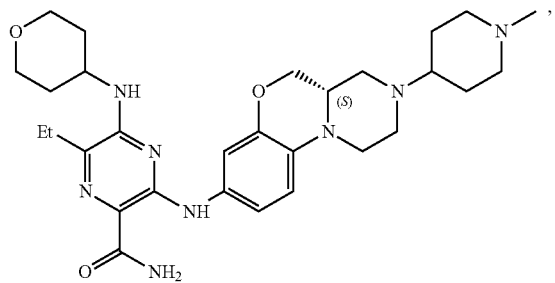
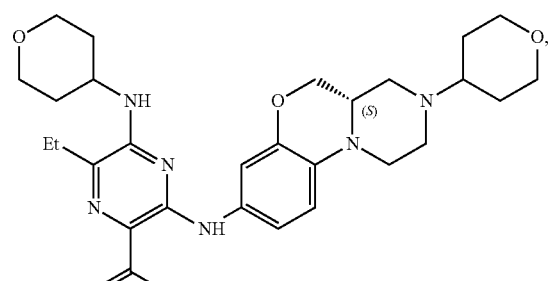
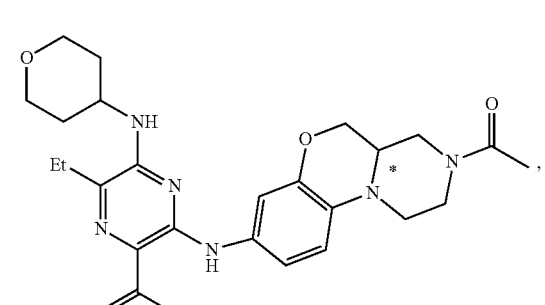
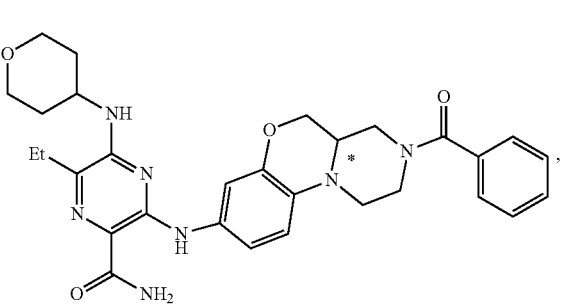

157
-continued
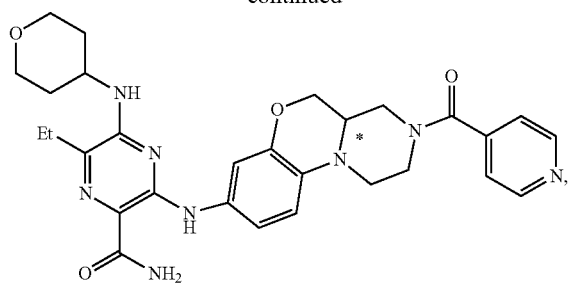
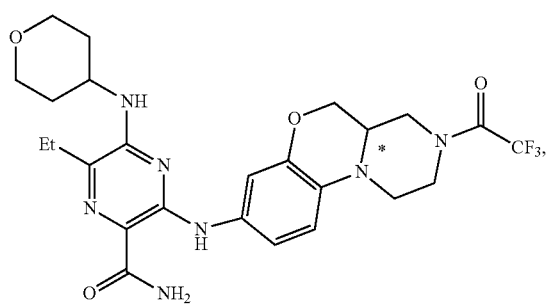
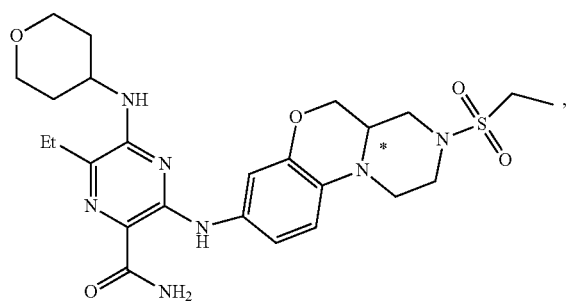
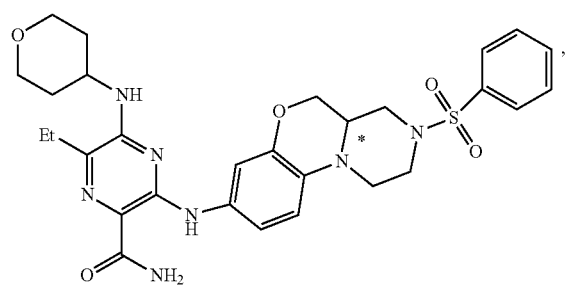
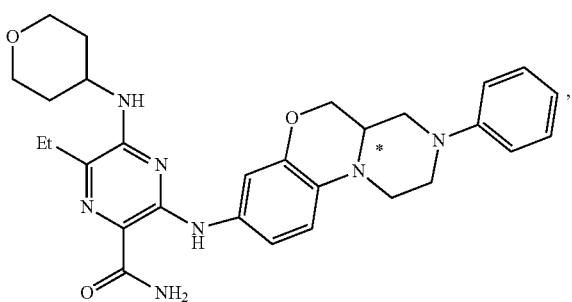
158
-continued
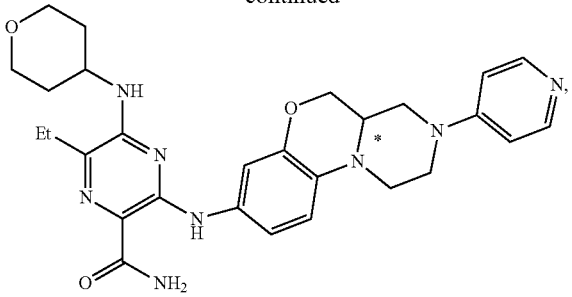
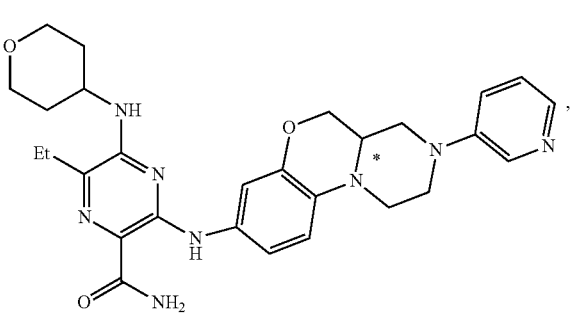
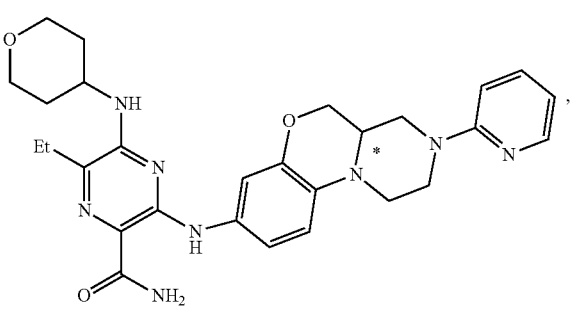
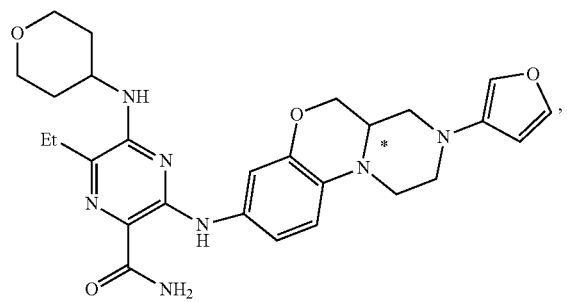
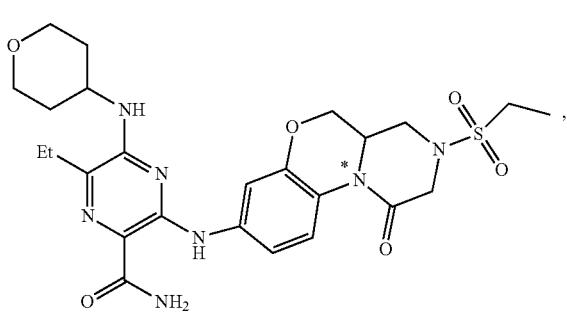

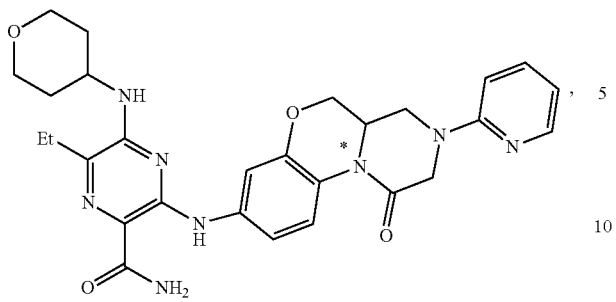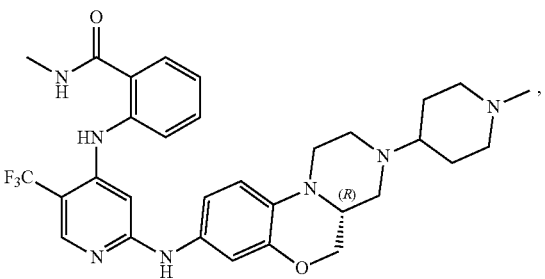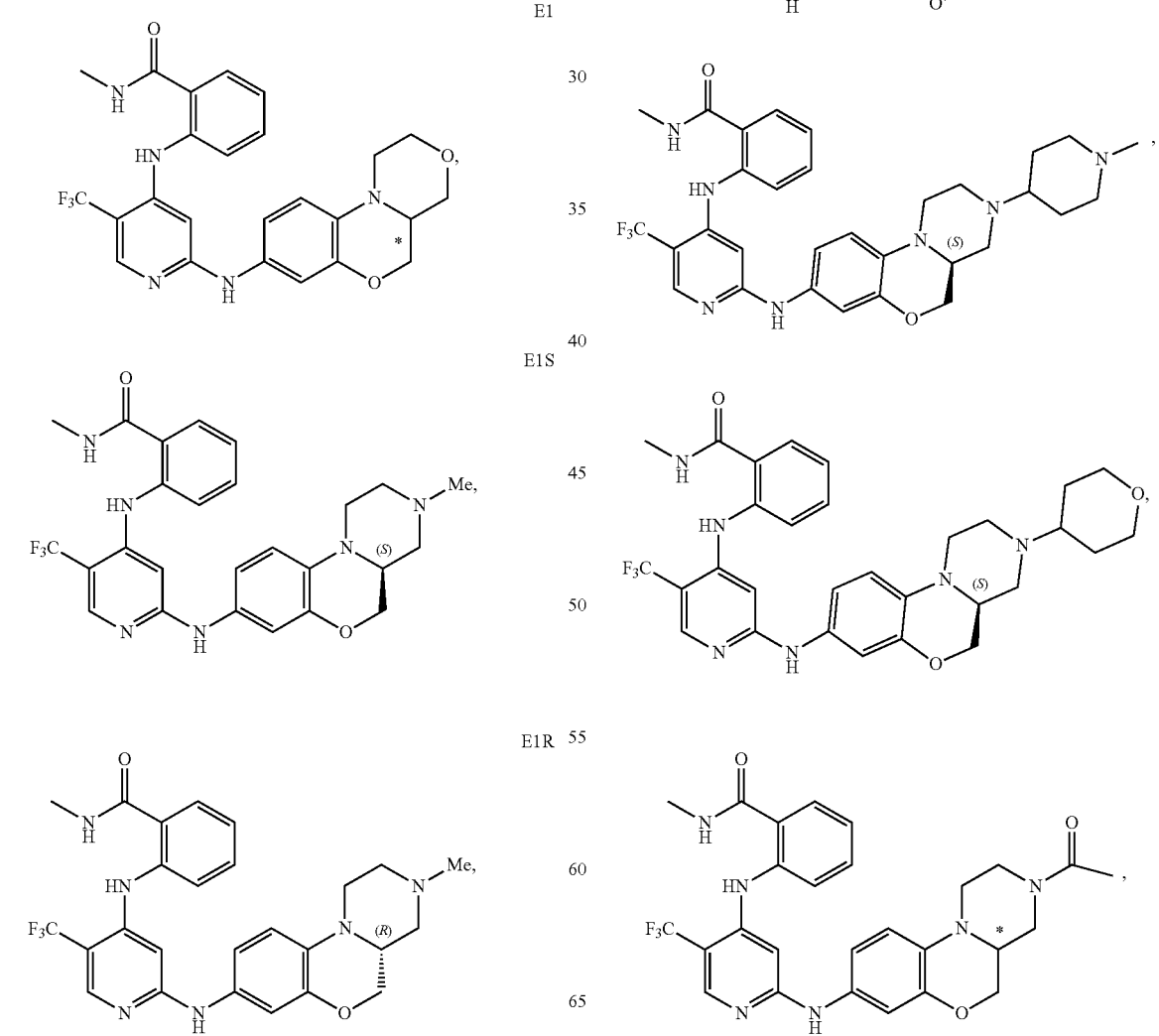

161
-continued
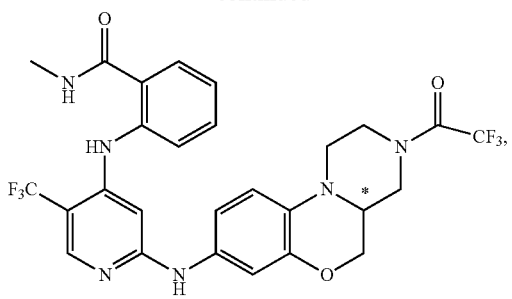
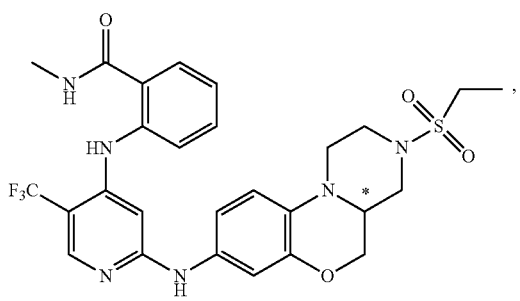
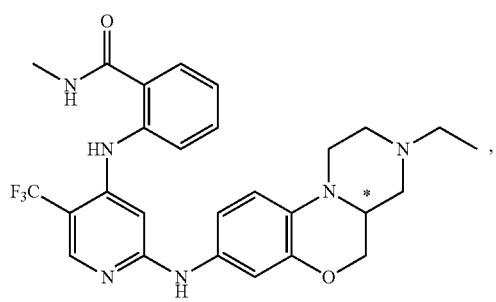
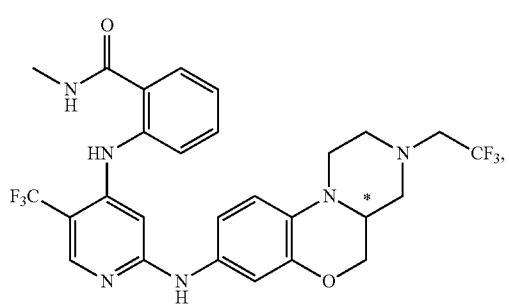
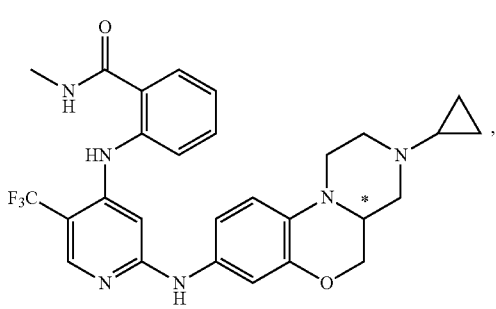
162
-continued
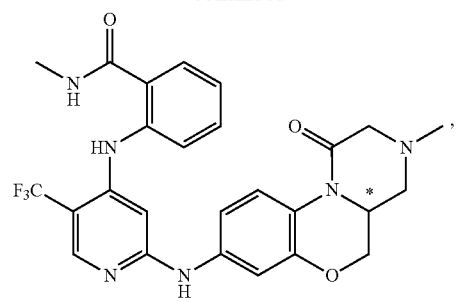
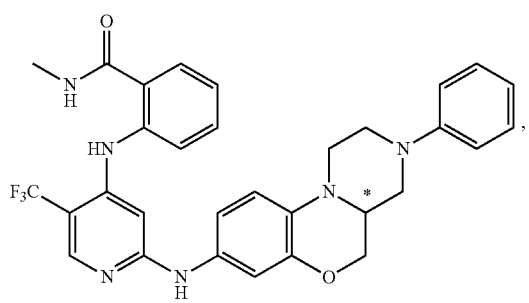
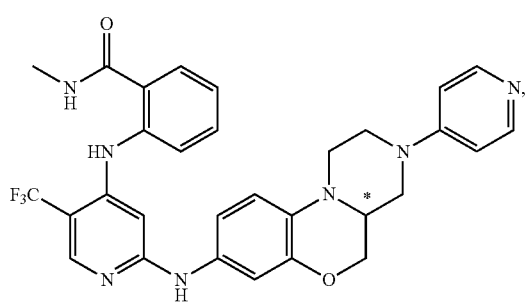
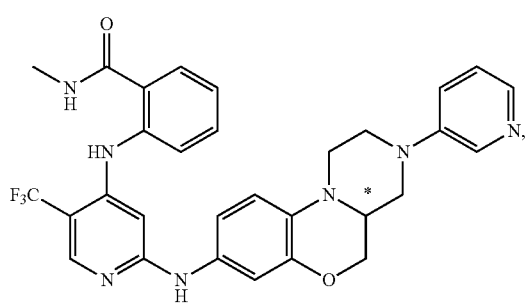
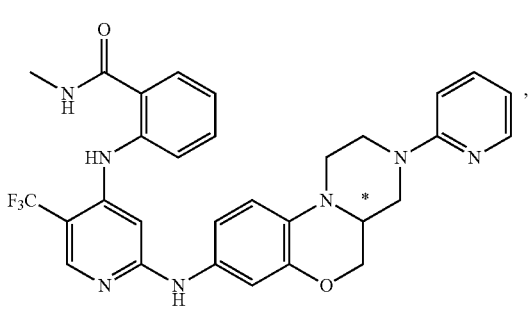

-continued

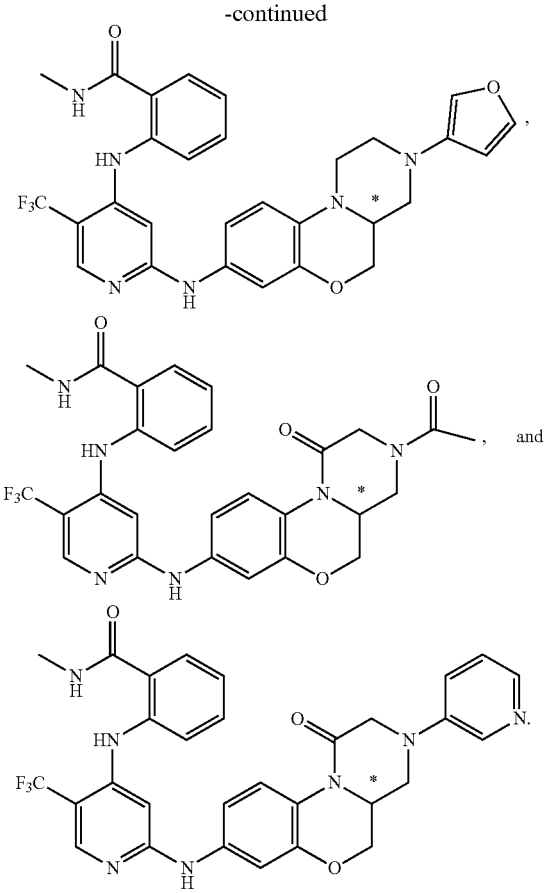

15. A method for treatment of diseases associated with protein kinase activity or expression amount, wherein the method comprises the step: administrating the compound (I) of claim 1, or the optical isomers, pharmaceutically acceptable salts, prodrugs, deuterated forms, hydrates or solvates thereof to a subject in need thereof; wherein, the protein kinase is selected from the group consisting of: EGFR, Flt-3, Axl, FAK, or the combinations thereof; and the diseases is selected from the group consisting of allergic asthma, myelofibrosis, rheumatoid arthritis, B-cell lymphoma, monocytic leukemia, splenomegaly, eosinophilic syndrome, primary thrombocytopenia, systemic Giant cell disease, liver cancer, rectal cancer, bladder cancer, throat cancer, non-small cell lung cancer, small cell lung cancer, lung adenocarcinoma, lung squamous cell carcinoma, breast cancer, prostate cancer, glioma, ovarian cancer, head and neck Squamous cell carcinoma, cervical cancer, esophageal cancer, kidney cancer, pancreatic cancer, colon cancer, skin cancer, lymphoma, gastric cancer, multiple myeloma and solid tumors.

16. The method of claim 15, wherein the disease is associated with high expression of EGFR.

17. The method of claim 15, wherein the disease is associated with high expression of Flt-3 and Axl.

18. The method of claim 15, wherein the disease is associated with high expression of FAK.

19. A pharmaceutical composition, comprising: (i) an effective amount of a compound of formula I according to claim 1, or the optical isomers, pharmaceutically acceptable salts, prodrugs, deuterated forms, hydrates or solvates thereof; and (ii) pharmaceutically acceptable carriers.

* * * * *